US009011866B2

(12) United States Patent
Wu et al.

(10) Patent No.: US 9,011,866 B2
(45) Date of Patent: Apr. 21, 2015

(54) RNA INTERFERENCE THAT BLOCKS EXPRESSION OF PRO-APOPTOTIC PROTEINS POTENTIATES IMMUNITY INDUCED BY DNA AND TRANSFECTED DENDRITIC CELL VACCINES

(75) Inventors: Tzyy-Choou Wu, Stevenson, MD (US); Chien-Fu Hung, Timonium, MD (US)

(73) Assignee: The Johns Hopkins University, Baltimore, MD (US)

( * ) Notice: Subject to any disclaimer, the term of this patent is extended or adjusted under 35 U.S.C. 154(b) by 662 days.

(21) Appl. No.: 11/773,162

(22) Filed: Jul. 3, 2007

(65) Prior Publication Data

US 2008/0069840 A1    Mar. 20, 2008

Related U.S. Application Data

(63) Continuation-in-part of application No. PCT/US2005/047200, filed on Dec. 30, 2005.

(60) Provisional application No. 60/641,901, filed on Jan. 6, 2005, provisional application No. 60/738,900, filed on Nov. 22, 2005.

(51) Int. Cl.
| *A61K 38/00* | (2006.01) |
| *C07H 21/04* | (2006.01) |
| *C12N 15/11* | (2006.01) |
| *A61K 31/7088* | (2006.01) |
| *C12N 15/113* | (2010.01) |

(52) U.S. Cl.
CPC .......... *C12N 15/111* (2013.01); *A61K 31/7088* (2013.01); *C12N 15/113* (2013.01); *C12N 2310/14* (2013.01); *C12N 2320/31* (2013.01)

(58) Field of Classification Search
USPC ...................................... 424/184.1; 536/24.5
See application file for complete search history.

(56) References Cited

U.S. PATENT DOCUMENTS

| 4,898,730 | A | 2/1990 | Levy et al. |
| 5,217,879 | A | 6/1993 | Huang et al. |
| 5,348,945 | A | 9/1994 | Berberian et al. |
| 5,426,097 | A | 6/1995 | Stern et al. |
| 5,547,846 | A | 8/1996 | Bartsch et al. |
| 5,582,831 | A | 12/1996 | Shinitzky |
| 5,591,716 | A | 1/1997 | Siebert et al. |
| 5,618,536 | A | 4/1997 | Lowy et al. |
| 5,629,161 | A | 5/1997 | Muller et al. |
| 5,674,486 | A | 10/1997 | Sobol et al. |
| 5,744,133 | A | 4/1998 | Lathe et al. |
| 5,750,119 | A | 5/1998 | Srivastava |
| 5,821,088 | A | 10/1998 | Darzins et al. |
| 5,830,464 | A | 11/1998 | Srivastava |
| 5,834,309 | A | 11/1998 | Thompson et al. |
| 5,837,251 | A | 11/1998 | Srivastava |
| 5,844,089 | A | 12/1998 | Hoffman et al. |
| 5,854,202 | A | 12/1998 | Dedhar |
| 5,855,891 | A | 1/1999 | Lowy et al. |
| 5,935,576 | A | 8/1999 | Srivastava |
| 5,948,646 | A | 9/1999 | Srivastava |
| 5,951,975 | A | 9/1999 | Falo, Jr. et al. |
| 5,962,318 | A | 10/1999 | Rooney et al. |
| 5,997,869 | A | 12/1999 | Goletz et al. |
| 6,007,821 | A | 12/1999 | Srivastava et al. |
| 6,013,262 | A | 1/2000 | Frazer et al. |
| 6,017,544 | A | 1/2000 | Srivastava |
| 6,017,735 | A | 1/2000 | O'Hare et al. |
| 6,020,309 | A | 2/2000 | Campo et al. |
| 6,030,618 | A | 2/2000 | Srivastava |
| 6,046,158 | A | 4/2000 | Ariizumi et al. |
| 6,066,716 | A | 5/2000 | Wallen et al. |
| 6,235,523 | B1 | 5/2001 | Gajewczyk et al. |
| 6,331,388 | B1 | 12/2001 | Malkovsky et al. |
| 6,399,070 | B1 | 6/2002 | Srivastava et al. |
| 6,403,080 | B1 | 6/2002 | Segal |
| 6,410,027 | B1 | 6/2002 | Srivastava |
| 6,410,028 | B1 | 6/2002 | Srivastava |
| 6,541,010 | B1 | 4/2003 | Johnston et al. |
| 6,734,173 | B1 | 5/2004 | Wu et al. |
| 7,001,995 | B1 | 2/2006 | Neeper et al. |
| 7,318,928 | B2 | 1/2008 | Wu et al. |
| 7,342,002 | B2 | 3/2008 | Wu et al. |
| 2001/0034042 | A1 | 10/2001 | Srivastava |

(Continued)

FOREIGN PATENT DOCUMENTS

| CA | 2413543 | 1/2002 |
| EP | 0 763 740 | 3/1997 |

(Continued)

OTHER PUBLICATIONS

Kim et al. (J. Immunol. 2003, 171:2970-2976).*
Kim et al., "Modification of Professional Antigen-Presenting Cells with Small Interfering RNA In vivo to Enhance Cancer Vaccine Potency," Cancer Research, 65(1):309-316 (2005).
Ray et al., "Apoptosis Induction in Prostate Cancer Cells and Xenografts by Combined Treatment with APO2 Ligand/Tumor Necrosis Factor-related apoptosis-inducing Ligand and CPT-11," Cancer Research, 63:4713-4723 (2003).
International Search Report dated Jul. 7, 2008 from PCT/US05/47200.
Aguiar et al., "Enhancement of the immune response in rabbits to a malaria DNA vaccine by immunization with a needle-free jet device," Vaccine, 20:275-280 (2001).
Alexander et al., "Development of High Potency Universal DR-Restricted Helper Epitopes by Modification of High Affinity DR-Blocking Peptides," Immunity, 1:751-761 (1994).
Anonymous: "E7 vaccine (NSC 723254)," Timeless Success Story, Online, XP002394109 (2002).

(Continued)

*Primary Examiner* — J E Angell
(74) *Attorney, Agent, or Firm* — Foley Hoag LLP

(57) ABSTRACT

An immunotherapeutic strategy is disclosed that combines antigen-encoding DNA vaccine compositions combined with siRNA directed to pro-apoptotic genes, primarily Bak and Bax, the products of which are known to lead to apoptotic death. Gene gun delivery (particle bombardment) of siRNA specific for Bak and/or Bax to antigen-expressing DCs prolongs the lives of such DCs and lead to enhanced generation of antigen-specific CD8+ T cell-mediated immune responses in vivo. Similarly, antigen-loaded DC's transfected with siRNA targeting Bak and/or Bax serve as improved immunogens and tumor immunotherapeutic agents.

31 Claims, 37 Drawing Sheets

(56) References Cited

U.S. PATENT DOCUMENTS

| | | | |
|---|---|---|---|
| 2002/0064771 A1 | 5/2002 | Zhong et al. | |
| 2002/0091246 A1 | 7/2002 | Pardoll et al. | |
| 2002/0182586 A1 | 12/2002 | Morris et al. | |
| 2004/0028693 A1 | 2/2004 | Wu et al. | |
| 2004/0086845 A1 | 5/2004 | Wu et al. | |
| 2004/0106128 A1 | 6/2004 | Majumdar et al. | |
| 2004/0259247 A1* | 12/2004 | Tuschl et al. | 435/375 |
| 2005/0048467 A1 | 3/2005 | Sastry et al. | |
| 2005/0054820 A1 | 3/2005 | Wu et al. | |
| 2005/0277605 A1 | 12/2005 | Wu et al. | |
| 2007/0026076 A1 | 2/2007 | Wu et al. | |

FOREIGN PATENT DOCUMENTS

| | | |
|---|---|---|
| WO | WO-89/12455 | 12/1989 |
| WO | WO-92/05248 | 4/1992 |
| WO | WO-93/20844 | 10/1993 |
| WO | WO-94/04696 | 3/1994 |
| WO | WO-94/29459 | 12/1994 |
| WO | WO-95/17212 | 6/1995 |
| WO | WO-96/36643 | 11/1996 |
| WO | WO-97/03703 | 2/1997 |
| WO | WO-97/06685 | 2/1997 |
| WO | WO-97/41440 | 11/1997 |
| WO | WO-98/20135 | 5/1998 |
| WO | WO-98/23735 | 6/1998 |
| WO | WO-98/32866 | 7/1998 |
| WO | WO-98/48003 | 10/1998 |
| WO | WO-99/07860 | 2/1999 |
| WO | WO-99/07869 | 2/1999 |
| WO | WO-99/42121 | 8/1999 |
| WO | WO-99/42472 | 8/1999 |
| WO | WO-99/58658 | 11/1999 |
| WO | WO-99/65940 | 12/1999 |
| WO | WO-01/29233 | 4/2001 |
| WO | WO-02/09645 | 2/2002 |
| WO | WO-02/12281 | 2/2002 |
| WO | WO-02/061113 | 8/2002 |
| WO | WO-02/074920 | 9/2002 |
| WO | WO 03008543 A2 * | 1/2003 |
| WO | WO-03/080111 | 10/2003 |
| WO | WO-03/085085 | 10/2003 |
| WO | WO 03083052 A2 * | 10/2003 |
| WO | WO-2004/030636 | 4/2004 |
| WO | WO-2004/060304 | 7/2004 |
| WO | WO-2004/098526 | 11/2004 |
| WO | WO-2005/047501 | 5/2005 |
| WO | WO-2005/081716 | 9/2005 |
| WO | WO-2006/073970 | 7/2006 |
| WO | WO-2006/081323 | 8/2006 |
| WO | WO-2006/120474 | 11/2006 |
| WO | WO-2007/027751 | 3/2007 |
| WO | WO-2007/071997 | 6/2007 |
| WO | WO-2009/007336 | 1/2009 |

OTHER PUBLICATIONS

Anthony et al., "Priming of CD8 CTL Effector Cells in Mice by Immunizationwith a Stress-Protein-Influenza Virus Nucleoprotein Fusion Molecule," Vaccine, 17(4):373-383 (1999).
Asea et al., "Novel Signal Transduction Pathway Utilized by Extracellular HSP70," Journal of Biological Chemistry, 277(7):15028-15034 (2002).
Ausbel, et al., Current Protocols in Molecular Biology, John Wiley & Sons (1989).
Babiuk et al., " Immunization of animals: from DNA to the dinner plate," Veterinary Immunology and Immunopathology, 72:189-202 (1999).
Bae et al., "Therapeutic Synergy of Human Papillomavirus E7 Subunit Vaccines plus Cisplatin in an Animal Tumor Model: Casual Involvement of Increased Sensitivity of Cisplatin-Treated Tumors to CTL-Mediated Killing in Therapeutic Synergy," Clin. Cancer Res., 13(1):341-349 (2007).
Banchereau, J., "Dendritic Cells: Therapeutic Potentials," Transfus Sci., 18(2):313-326 (1997).

Banu et al., "Modulation of Haematopoietic Progenitor Development by FLT-3 Ligand," Cytokine, 11(9):679-688 (1999).
Barrios et al., "Mycobacterial heat-shock proteins as carrier molecules. II: the use of the 70-kDa mycobacterial heat-shock protein as carrier for conjugated vaccines can circumvent the need for adjuvants and *Bacillus* Calmette Guerin priming," Eur. J. Immunol., 22:1365-1372 (1992).
Basu et al., "Calreticulin, A Peptide-Binding Chaperone of the Endoplasmic Reticulum, Elicits Tumor- and Peptide-Specific Immunity," Journal of Experimental Medicine, 189(5):797-802 (1999).
Becker et al., "CD40, an extracellular receptor for binding and uptake of Hsp70-peptide complexes," Journal of Cell Biology, 158(7):1277-1285 (2002).
Beissbarth et al., "Increased efficiency of folding and peptide loading of mutant MHC class I molecules," Eur. J. Immunol., 30:1203-1213 (2000).
Bennett et al., "Calnexin Association Is Not Sufficient to Protect T Cell Receptor α Proteins from Rapid Degradation in CD4+CD8+ Thymocytes," The Journal of Biological Chemistry 273(37):23674-23680 (1998).
Benton et al., "DNA Vaccine Strategies for the Treatment of Cancer," Curr Top Microbiol Immunol., 226:1-20 (1998).
Bhoola et al., "Diagnosis and management of epithelial ovarian cancer," Obstet. Gynecol., 107(6):1399-1410 (2006).
Biragyn et al., "Genetic fusion of chemokines to a self tumor antigen induces protective, T-Cell dependent antitumor immunity," Nature Biotechnology, 17:253-258 (1993) Abstract.
Blachere et al., "Heat shock Protein-peptide complexes, Reconstituted in vitro, Elicit Peptide-specific cytotoxic T Lymphocyte Response and Tumor Immunity," J. Exp. Med., 186(8):1315-1322 (1997).
Blachere et al. "Heat shock proteins against cancer," J. of Immunotherapy Emphasis Tumor Immunol., 14:352-356 (1993).
Bohm et al., "Routes of plasmid DNA vaccination that prime murine humoral and cellular immune responses," Vaccine, 16:949-954 (1998).
Boyle et al. "Enhanced responses to a DNA vaccine encoding a fusion antigen that is directed to sites of immune induction," Nature, 392:408-411 (1998).
Bredenbeek et al., "Sindbis Virus Expression Vectors: Packaging of RNA Replicons by Using Defective Helper RNAs," Journal of Virology, 67(11):6439-6446 (1993).
Breitburd et al., "Human papillomavirus vaccines," Cancer Biology, 9:431-445 (1999).
Brossart et al., "Identification of HLA-A2-Restricted T-Cell Epitopes Derived From the MUC1 Tumor Antigen for Broadly Applicable Vaccine Therapies," Blood, 93(12):4309-4317 (1999).
Buck et al., "Efficient Intracellular Assembly of Papillomaviral Vectors," Journal of Virology, 78(2):751-757 (2004).
Bueler et al., "Induction of Antigen-Specific Tumor Immunity by Genetic and Cellular Vaccines against MACE: Enhanced Tumor Protection by Coexpression of Granulocyte-Macrophage Colony-Stimulating Factor and B7-1," Molecular Medicine, 2(5):545-555 (1996).
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," The Journal of Cell Biology, 111:2129-2138 (1990).
Carbonetti et al., "Intracellular Delivery of a Cytolytic T-Lymphocyte Epitope Peptide by Pertussis Toxin to Major Histocompatibioity Complex Class I without Involvement of the Cytosolic Class I Antigen Processing Pathway," Infection and Immunity 67(2):602-607 (1999).
Cavill et al., "Generation of a Monoclonal Antibody Against Human Calreticulin by Immunization with a Recombinant Calreticulin Fusion Protein: Application in Paraffin-Embedded Sections," Appl. Immunohistochemistry & Molecular Morphology 7(2):150-155 (1999).
Celluzzi et al., "Peptide-pulsed Dendritic Cells Induce Antigen-specific, CTL-mediated Protective Tumor Immunity," J. Exp. Med. 183:283-287 (1996).

(56) References Cited

OTHER PUBLICATIONS

Chang et al., "Cancer Immunotherapy Using Irradiated Tumor Cells Secreting Heat Shock Protein 70," Cancer Res., 67(20):10047-10057 (2007).
Chang, C-L. et al., "Control of human mesothelin-expressing tumors by DNA vaccines." Gene Therapy 1-10 (2007).
Chavin, K. et al., "Obesity Induces Expression of Uncoupling Protein-2 in Hepatocytes and Promotes Liver ATP Depletion." J. Biol. Chem. 274(9):5692-5700 (1999).
Chen, C-H. et al., "Antigen-specific immunotherapy for human papillomavirus 16 E7-expressing tumors grown in the liver." Journal of Hepatology 33:91-98 (2000).
Chen, C.-H. et al., "Boosting with recombinant vaccinia increases HPV-16 E7-specific T cell precursor frequencies of HPV-16 E7-expressing DNA vaccines," Vaccine, 18:2015-2022 (2000).
Chen et al., Design of a genetic immunotoxin to eliminate toxin immunogenicity, Gene Therapy, 2:116-123 (1992).
Chen, C-H et al., "Enhancement of DNA Vaccine Potency by Linkage of Antigen Gene to an HSP70 Gene," Cancer Research, 60(4):1035-1042 (2000).
Chen, C.-H. et al., "Gene gun-mediated DNA vaccination induces antitumor immunity against human papillomavirus type 16 E7-expressing murine tumor metastases in the liver and lungs." Gene Therapy, 6:1972-1981 (1999).
Chen et al., "Human pappillomavirus type 16 nucleoprotein E7 is a tumor rejection antigen," PNAS, 88:110-114 (1991).
Chen et al., "Induction of Cytotoxic T Lymphocytes Specific for a Syngeneic Tumor Expressing the E6 Oncoprotein of Human Papillomavirus Type 16," Journal of Immunology, 148:2617-2621 (1992).
Chen, W. et al., "Modulatory Effects of the Human Heat Shock Protein 70 on DNA Vaccination," J. Biomed. Sci., 7(5):412-419 (2000).
Chen et al., "Mycobacterial heat shock protein 65 enhances antigen cross-presentation in dendritic cells independent of Toll-like receptor 4 signaling," Journal of Leukocyte Biology, 75:260-266 (2004).
Chen, C-H. et al. "Recombinant DNA vaccines protect against tumors that are resistant to recombinant vaccinia vaccines containing the same gene." Gene Therapy, 8:128-138 (2001).
Cheng et al., "Bax-independent inhibition of apoptosis by Bcl-$x_L$," Nature, 379(8):554-556 (1996).
Cheng, W-F. et al., "CD8+ T cells, NK cells and IFN-γ are important for control of tumor with downregulated MHC class I expression by DNA vaccination." Gene Therapy 10:1311-1320, (2003).
Cheng, W-F. et al., "Cancer Immunotherapy Using Sindbis Virus Replicon Particles Encoding a VP22-Antigen Fusion." Human Gene Therapy. 13:553-568 (2002).
Cheng, W.-F., et al.; "Characterization of DNA Vaccines Encoding the Domains of Calreticulin for Their Ability to Elicit Tumor-Specific Immunity and Antiangiogenesis," Vaccine, 23(29):3864-3874 (2005).
Cheng, W-F. et al. "Enhancement of Sindbis Virus Self-Replicating RNA Vaccine Potency by Linkage of Herpes Simplex Virus Type 1 VP22 Protein to Antigen." Journal of Virology, 75(5): 2368-2376 (2001).
Cheng, W-F. et al. "Enhancement of Sindbis Virus Self-Replicating RNA Vaccine Potency by Linkage of *Mycobacterium tuberculosis* Heat Shock Protein 70 Gene to an Antigen Gene." Journal of Immunology, 166:6218-6226 (2001).
Cheng, W-F. et al., "Enhancement of Sindbis Virus Self-Replicating RNA Vaccine Potency by Targeting Antigen to Endosomal/Lysosomal Compartments." Human Gene Therapy 12:235-252 (2001).
Cheng, W-F. et al., "Repeated DNA Vaccinations Elicited Qualitatively Different Cytotoxic T Lymphocytes and Improved Protective Antitumor Effects." J Biomed Sci 9:675-687 (2002).
Cheng et al. (Report on Results of Monographic Study # NSC91-2314-B-002-377, National Taiwan University, National Scientific Committee, available to public Oct. 31, 2003).

Cheng, W-F. et al., "Tumor-specific immunity and antiangiogenesis generated by a DNA vaccine encoding calreticulin linked to a tumor antigen." J. Clin. Invest. 108:669-678 (2001).
Cho et al., "Enhanced cellular immunity to hepatitis C virus nonstructural proteins by codelivery of granulocyte macrophage-colony stimulating factor gene in intramuscular DNA immunization," Vaccine, 17:1136-1144 (1999).
Chow et al., "Development of Thi1 and Th2 Populations and the Nature of Immune Responses to Hepatitis B Virus DNA Vaccines Can Be Modulated by Codelivery of Various Cytokine Genes," The Journal of Immunology, 160(3):1320-1329 (1998).
Chu et al., "Cancer Immunotherapy Using Adjuvant-Free, Fusion Protein Encoding M. Golvis BCG HSP65 and HPV16 E7," FASEB Journal 12(5), Mar. 20, 1998 Abstract XP000960840.
Chu et al., Immunotherapy of a human papillomavirus (HPV) type 16 E7-expressing tumour by administration of fusion protein comprising *Mycobacterium bovis* bacille Calmette-Guerin (BGG) hsp65 and HPV 16 E7, Clin. Exp. Immunol., 121(2):216-225 (2000).
Ciupitu et al., "Immunization with a Lymphocytec Choriomeningitis Virus Peptide Mixed Heat Sbcok Protein 70 Results in Protective Antiviral Immunity and Specific Cytotoxic T Lymphocytes," J. Exp. Med., 187(5):685-691 (1998).
Corr et al., "Costimulation Provided by DNA Immunization Enhances Antitumor Immunity," The Journal of Immunology, 159(10):4999-5004 (1997).
Coukos et al., "Immunotherapy for gynaecological malignancies," Expert Opin. Biol. Ther., 5(9):1193-1210 (2005).
Crum et al., "Vaccines for Cervical Cancer," Cancer Journal from Scientific American, 9(5):368-376 (2003).
Davidoff et al., "Immune Response to P53 is Dependent upon P53/HSP70 Complexes in Breast Cancers," Proceedings of the National Academy of Sciences of USA, 89(8):3442 (1992).
Debinsky et al., "A Wide Range of Human Cancers Express Interleukin 4 (IL-4) Receptors That Can Be Targeted with Chimeric Toxin Composed of IL-4 and *Pseudomonas* Exotoxin," The Journal of Biological Chemistry, 268(19):14065-14070 (1993).
de Jong et al., "Enhancement of human papillomavirus (HPV) type 16 E6 and E7-specific T-cell immunity in healthy volunteers through vaccination with TA-CIN, an HPV16 L2E7E6 fusion protein vaccine," Vaccine, 20:3456-3464 (2002).
Devaraj, K. et al., "Development of HPV Vaccines for HPV-Associated Head and Neck Squamous Cell Carcinoma," Crit. Rev. Oral Biol. Med. 14(5):345-362, (2003).
Dialynas et al., "Characterization of the Murine T Cell Surface Molecule Designated L3T4, Identified by Monocolonal Antibody GK1.5: Similarity of L3T4 to the Human Leu-3/T4 Molecule," J. Immunol., 131(5):2445-2451 (1983).
Donnelly et al., "DNA Vaccines," Annual Review of Immunology, 15:617-48 (1997).
Donnelly et al., "DNA Vaccines: Progress and Challenges," J. Immunol., 175:633-639 (2005).
Donnelly et al., "Targeted delivery of peptide epitopes to class I major histocompatibility molecules by a modified *Pseudomonas* exotoxin," Proc. Natl. Acad. Sci. USA 90:3530-3534 (1993).
Drake et al., "Assessing tumor growth and distribution in a model of prostate cancer metastasis using bioluminescence imaging," Clin. Exp. Metastasis, 22:674-684 (2005).
Eggleton, P. and Llewellyn, D.H., "Pathophysiological Roles of Calreticulin in Autoimmune Disease," Scand. J. Immunol. 49:466-473 (1999).
Eiben et al., "Establishment of an HLA-a*0201 Human Papillovavrus Type 16 Tumor Model to Determine the Efficacy of Vaccination Strategies in HLA-A*0201 Transgenic Mice," Cancer Research, 62:5792-5799 (2002).
Eisenbraun et al., "Examination of parameters affecting the elicitation of humoral immune responses by particle bombardment-mediated genetic immunization," DNA Cell Biol., 12(9):791-797 (1993).
Elliott et al., "Intercellular trafficking and protein delivery by a herpesvirus structural protein," Cell, 88(2):223-233 (1997).
Elsaghier et al., "Localisation of Linear Epitopes at the Carboxy-Terminal End of the Mycobacterial 71 KDA Heat Shock Protein," Molecular Immunology 29(9):1153-1156 (1992).

(56) References Cited

OTHER PUBLICATIONS

Feltkamp et al., "Vaccination with cytotoxic T lymphocyte epitope-containing peptide protects against a tumor induced by human papillomavirus type 16-transformed cells," Eur. J. Immunol., 23(9):2242-2249 (1993).
Fernando et al., "Expression, purification and immunological characterization of the transforming protein E7, from cervical cancer-associated human papilloma virus type 16," Clin. Exp. Immunol., 115:397-403 (1999).
Flohe et al., "Human Heat Shock Protein 60 Induces Maturation of Dendritic Cells Versus a Th1-Promoting Phenotype," The Journal of Immunology, 170:2340-2348 (2003).
Fominaya et al., "Target Cell-specific DNA Transfer Mediated by a Chimeric Multidomain Protein," the Journal of Biological Chemistry, 271(18):10560-10568 (1996).
Fomsgaard et al., "Improved Humoral and Cellular Immune Responses Against the gp120 V3 Loop of HIV-1 Following Genetic Immunization with a Chimeric DNA Vaccine Encoding the V3 Inserted into the Hepatitis B Surface Antigen," Scand J. Immunol., 47(4):289-95 (1998).
Forni et al., "Cytokine gene-engineered vaccines," Curr. Opin. Mol. Ther. Feb;1(1):34-38 (Abstract) (1999).
Frydman et al., "Folding of nascent polypeptide chains in a high molecular mass assembly with molecular chaperones," Nature, 370:111-117 (1994).
Galloway, D.A., "Papillomavirus vaccines in clinical trials," Lancet Infect. Dis., 3(8):469-475 (2003).
Gao et al., "Immune response to human papillomavirus type 16 E6 gene in a live vaccinia vector," Journal of General Virology, 75:157-164 (1994).
Gavarasana et al., "Prevention of Carcinoma of Cervix with Human Papillomavirus Vaccine," Indian Journal of Cancer, 37:57-66 (2000).
Geissler et al., "Enhancement of Cellular and Humoral Immune Responses to Hepatitis C Virus Protein Using DNA Based Vaccines Augmented with Cytokine-Expressing Plasmids," The Journal of Immunology, 158(3):1231-1237 (1997).
Georgopoulos et al., "Role of the Major Heat Shock Proteins as Molecular Chaperones," Annu. Rev. Cell. Bio., 9:601-634 (1993).
Goletz et al., "Delivery of Antigens to the MHC Class I Pathway Using Bacterial Toxins," Human Immunology, 54:129-136 (1997).
Grandis et al., "Head and Neck Cancer: Meeting Summary and Research Opportunities," Cancer Research, 64:8126-8129 (2004).
Graner et al., "Immunoprotective Activities of Multiple Chaperone Proteins Isolated from Murine B-Cell Leukemia/Lymphoma," Clinical Cancer Research, 6:909-915 (2000).
Haas et al., "cDNA cloning of the immunoglobulin heavy chain binding protein," Proc. Natl. Acad. Sci. USA, 85:2250-2254 (1988).
Hannum et al., "Ligand for FLT3/FLK2 Receptor Tyrosine Kinase Regulates Growth of Haematopoietic Stem Cells and is Encoded by Variant RNAs," Nature 368:643-8 (1994).
Hansen et al., "Structural features of MHC class I molecules that might facilitate alternative pathways of presentation," Immunology Today, 21(2):83-88 (2000).
Harris et al., "Calreticulin and Calnexin Interact with Different Protein and Glycan Determinants During the Assembly of MHC Class I," The Journal of Immunology 160:5404-5409 (1998).
Hartl, F., "Molecular chaperones in cellular protein folding," Nature, 381:571-579 (1996).
Hasan et al., "Nucleic acid immunization: concepts and techniques associated with third generation vaccines," Journal of Immunological Methods, 229:1-22 (1999).
Hauser et al., "Secretory heat-shock protein as a dendritic cell-targeting molecule: a new strategy to enhance the potency of genetic vaccines," Gene Therapy, 11:924-932 (2004).
He et al., "Viral Recombinant Vaccines to the E6 and E7 Antigens of HPV-16," Virology, 270:146-161 (2000).
Heikema et al., "Generation of heat shock protein-based vaccines by intracellular loading of gp96 with antigen peptides," Immunology Letters, 57(1-3):69-74 (1997).
Heller, J. et al., "Tetra-O-methyl Nordihydroguaiaretic Acid Induces G2 Arrest in Mammalian Cells and Exhibits Tumoricidal Activity in Vivo," Cancer Research 61:5499-5504, (2001).
Hendrick et al., "Molecular chaperone functions of heat-shock proteins," Annu. Rev. Biochem., 62:349-384 (1993).
Higgins et al., "Fast and Sensitive Multiple Sequence Alignments on a Microcomputer," Comput. Appl. Biosci. 5(2):151-153 (1989).
Hokey et al., "DNA vaccines for HIV: challenges and opportunities," Springer Semin. Immunopathol., 28(3):267-279 (2006).
Hope et al., "Flt-3 Ligand, in Combination with Bovine Granulocyte-Macrophage Colony-Stimulating Factor and Interleukin-4, Promotes the Growth of Bovine Bone Marrow Derived Dendritic Cells," Scand. J. Immunol., 51:60-66 (2000).
Hsieh, C-J. et al., "Enhancement of vaccinia vaccine potency by linkage of tumor antigen gene to gene encoding calreticulin," Vaccine, 22:3993-4001 (2004).
Hsu, K-F. et al., "Enhancement of suicidal DNA vaccine potency by linking *Mycobacterium tuberculosis* heat shock protein 70 to an antigen." Gene Therapy 8, 376-383 (2001).
Huang, C-H. et al. "Cancer Immunotherapy using a DNA vaccine encoding a single-chain trimer of MHC class I linked to an HPV-16 E6 immunodominant CTL epitope." Gene Therapy. 12:1180-1186 (2005).
Huang, C-C. et al., "Generation of Type-Specific Probes for the Detection of Single-Copy Human Papillomavirus by a Novel In Situ Hybridization Method," Mod. Pathol. 11(10):971-977 (1998).
Huang, C-C. et al., "HPV In Situ Hybridization with Catalyzed Signal Amplification and Polymerase Chain Reaction in Establishing Cerebellar Metastasis of a Cervical Carcinoma." Human Pathology, 30(5):587-591. (1999).
Huang, Q. et al., "In Vivo Cytotoxic T Lymphocyte Elicitation by Mycobacterial Heat Shock Protein 70 Fusion Proteins Maps to a Discrete Domain and Is CD4+ T Cell Independent," J. Exp. Med., 191(2):403-408 (2000).
Hung, C-F. et al. "A DNA vaccine encoding a single-chain trimer HLA-A2 linked to human mesothelin peptide generates anti-tumor effects against human mesothelin-expressing tumors." Vaccine 25:127-135 (2007).
Hung, C-F. et al., "Cancer Immunotherapy Using a DNA Vaccine Encoding the Translocation Domain of a Bacterial Toxin Linked to a Tumor Antigen." Cancer Research 61: 3698-3703 (2001).
Hung, C-F. et al., "Control of mesothelin-expressing ovarian cancer using adoptive transfer of mesothelin peptide-specific CD8+ T cells." Gene Therapy, pp. 1-9 (2007).
Hung et al., "Control of mesothelin-expressing ovarian cancer using adoptive transfer of mesothelin peptide-specific CD8+ T cells," Gene Therapy, 14(12):921-929 (2007).
Hung, C-F. et al., "DNA Vaccines Encoding Ii-PADRE Generates Potent PADRE-specific CD4+ T-Cell Immune Responses and Enhances Vaccine Potency." Mol. Ther. 15(6):1211-1219 (2007).
Hung, C-F. et al., "Enhancement of DNA Vaccine Potency by Linkage of Antigen Gene to a Gene Encoding the Extracellular Domain of Fms-like Tyrosine Kinase 3-Ligand." Cancer Research 61:1080-1088, (2001).
Hung, C-F. et al., "Enhancing Major Histocompatibility Complex Class I Antigen Presentation by Targeting Antigen to Centrosomes," Cancer Research, 63:2393-2398 (2003).
Hung, C-F., et al., "Improving DNA Vaccine Potency by Linking Marek's Disease Virus Type 1 VP22 to an Antigen," Journal of Virology, 76(6):2676-2682 (2002).
Hung, C-F. et al., "Improving DNA vaccine potency via modification of professional antigen presenting cells." Current Opinion in Molecular Therapeutics, 5(1):20-24 (2003).
Hung et al., "Improving vaccine potency through intercellular spreading and enhanced MHC class I presentation of antigen," J. Immunology, 166(9):5733-5740 (2001).
Hung, C-F. et al., "Modifying professional antigen-presenting cells to enhance DNA vaccine potency," Methods in Molecular Medicine, 127:199-220 (2006).
Hung, C-F. et al., "Vaccinia virus preferentially infects and controls human and murine ovarian tumors in mice." Gene Therapy. 14:20-29 (2007).

(56) References Cited

OTHER PUBLICATIONS

Hunt et al., "Characterization and sequence of a mouse hsp70 gene and its expression in mouse cell lines," Gene, 87(2):199-204 (1990).
Hunt et al., "Conserved features of eurkaryotic hsp70 genes revealed by comparison with the nucleotide sequence of human hsp70," Proc. Natl. Acad. Sci. USA, 82:6455-6459 (1985).
Indraccolo et al., "Generation of expression plasmids for angiostatin, endostatin and TIMP-2 for cancer gene therapy," Int. J. Biological Markers, 14(4):251-256 (1999) (Abstract).
Iwasaki et al., "Enhanced CTL Responses Mediated by Plasmid DNA Immunogens Encoding Costimulatory Molecules and Cytokines," The Journal of Immunology, 158(10):4591-4601 (1997).
Jaffee et al., "Novel allogeneic granulocyte-macrophage colony-stimulating factor-secreting tumor vaccine for pancreatic cancer: a phase I trial of safety and immune activation," J. Clin. Oncol., 19(1):145-156 (2001).
Jager et al., "Simultaneous Humoral and Cellular Immune Response against Cancer-Testis Antigen NY-ESO-1: Definition of Human Histocompatibility Leukocyte Antigen (HLA)-A2-binding Peptide Epitopes," J. Exp. Med., 187:265-270 (1998).
Janetzki et al., "Generation of Tumor-Specific Cytotoxic T Lymphocytes and Memory T Cells by Immunization with Tumor-Derived Heat Shock Protein gp96," Journal of Immunotherapy, 21(4):269-276 (1998).
Jenkins et al., "Bioluminescent Imaging (BLI) to Improve and Refine Traditional Murine Models of Tumor Growth and Metastasis," Clin. Exp. Metastatis, 20(8):733-744 (2003).
Ji, H et al., "Antigen-Specific Immunotherapy for Murine lung Metastatic Tumors Expressing Human Papillomavirus Type 16 E7 Oncoprotein." Int. J. Cancer: 78, 41-45 (1998).
Ji, H et al., "Targeting Human Papillomavirus Type 16 E7 to the Endosomal/Lysosomal Compartment Enhances the Antitumor Immunity of DNA Vaccines against Murine Human Papillomavirus Type 16 E7-Expressing Tumors," Human Gene Therapy 10:2727-2740 (1999).
Jinno et al., "Domain II Mutants of Pseudomonas Exotoxin Deficient in Translocation," J. Biol. Chem., 264(7):15953-15959 (1989).
Kadkol, S. et al., Chapter 5: "In Situ Hybridization in Cancer and Normal Tissue," Methods in Molecular Biology, Tumor Suppressor Genes, vol. II, Edited by W. Ei-Deiry, Humana Press Inc., Totowa, NJ., 223:51-72 (2003).
Kang, T. et al., "Enhancing dendritic cell vaccine potency by combining a BAK/BAX siRNA-mediated antiapoptotic strategy to prolong dendritic cell life with an intracellular strategy to target antigen to lysosomal compartments." Int. J. Cancer, 120:1696-1703 (2007).
Kerbel, Robert S., "Tumor angiogenesis: past, present and the near future," Carcinogenesis 21(3):505-515 (2000).
Kim et al., "Co-transfection with cDNA encoding the Bcl family of anti-apoptotic proteins improves the efficiency of transfection in primary fetal neural stem cells," J. Neuroscience Methods, 117(2):153-158 (2002).
Kim et al., "Cytokine Molecular Adjuvants Modulate Immune Responses Induced by DNA Vaccine Constructs for HIV-1 and SIV," Journal of Interferon and Cytokine Research, 19(1):77-84 (1999).
Kim, J. et al., "Comparison of HPV DNA vaccines employing intracellular targeting strategies." Gene Therapy, 11:1011-1018 (2004).
Kim, T. et al., "A DNA Vaccine Co-Expressing Antigen and an Anti-Apoptotic Molecule Further Enhances the Antigen-Specific CD8+ T-Cell Immune Response." J. Biomed. Sci. 11:493-499 (2004).
Kim, T. et al., "DNA Vaccines Employing Intracellular Targeting Strategies and a Strategy to Prolong Dendritic Cell Life Generate a Higher Number of CD8+ Memory T Cells and Better Long-Term Antitumor Effects Compared with a DNA Prime-Vaccinia Boost Regimin." Human Gene Therapy 16:26-34 (2005).
Kim, T. et al., "Enhancement of suicidal DNA vaccine potency by delaying suicidal DNA-induced cell death." Gene Therapy. 11:336-342. (2004).
Kim, T. et al., "Enhancement of DNA Vaccine Potency by Coadministration of a Tumor Antigen Gene and DNA Encoding Serine Protease Inhibitor-6." Cancer Research. 64:400-405 (2004).
Kim, T. et al., Enhancing DNA vaccine potency by coadministration of DNA encoding antiapoptotic proteins. J. Clin. Invest. 112:109-117 (2003).
Kim, T. et al., "Generation and Characterization of DNA Vaccines Targeting the Nucleocapsid Protein of Severe Acute Respiratory Syndrome Caronavirus." Journal of Virology, 78(9):4638-4645. (2004).
Kim, D. et al., "Monitoring the Trafficking of Adoptively Transferred Antigen-Specific CD8-Positive T Cells In Vivo, Using Noninvasive Luminescence Imaging." Human Gene Therapy. 18: 1-14 (2007).
Kim, T. et al., "Vaccination with a DNA Vaccine Encoding Herpes Simplex Type 1 VP22 Linked to Antigen Generates Long-Term Antigen-Specific CD8-Positive memory T Cells and Protective Immunity." Human Gene Therapy. 15:167-177. (2004).
King et al., "DNA vaccines with single-chain Fv fused to fragment C of tetanus toxin induce protective immunity against lymphoma and myeloma," Nature Medicine, 4(11):1281-1286 (1998).
Kita et al., "Frequent Gene Expression of Granulocyte Colony-Stimulating Factor (G-CSF) Receptor in CD7+ Surface CD3-Acute Lymphoblastic Leukaemia," Leukemia, 7(8):1184-1190 (1993).
Klinman et al., "Contribution of CpG Motifs to the Immunogenicity of DNA vaccines," The Journal of Immunology, 158(8):3635-3639 (1997).
Koch et al., "Hijacking a chaperone: manipulation of the MHC class II presentation pathway," Immunology Today, 21(11):546-550 (2000).
Konen-Waisman et al., "Self and Foreign 60-Kilodalton Heat Shock Protein T Cell Epitope Peptides Serve as Immunogenic Carriers for a T Cell-Independent Sugar Antigen," J. Immunology, 154:5977-5985 (1995).
Konishi et al., "Japanese encephalitis DNA vaccine candidates expressing premembrane and envelope genes induce virus-specific memory B cells and long-lasting antibodies in swine," Virology, 268(1):49-55 (2000).
Koo et al., "The NK-1.1(−) Mouse: A Model to Study Differentiation of Murine NK Cells," J. Immunol. 125:2665-2672 (1986).
Lafond-Walker, A. et al., "Inducible Nitric Oxide Synthase Expression in Coronary Arteries of Transplanted Human Hearts with Accelerated Graft Arteriosclerosis." American Journal of Pathology, 151(4): 919-925 (1997).
Larregina et al., "Pattern of cytokine receptors expressed by human dendritic cells migrated from dermal explants," Immunology, 91:303-313 (1997).
Lazar et al., "Transforming Growth Factor α: Mutation of Aspartic Acid 47 and Leucine 48 Results in Different Biological Activities," Mol. Cell Biol., 8(3):1247-1252 (1988).
Lee et al., "DNA inoculations with Hiv-1 recombinant genomes that express cytokine genes enbance HIV-1 specific immune responses," Vaccine, 17:473-479 (1999).
Lee et al., "Optimal Induction of Hepatitis C Virus Envelope-Specific Immunity by BiCistronic Plasmid DNA Inoculation with the Granulocyte-Macrophage Colony-Stimulating Factor Gene," Journal of Virology, 72(10):8430-8436 (1998).
Leitner et al., "DNA and RNA-Based Vaccines: Principles, Progress and Prospects," Vaccine 18(9-10):765-777 (1999).
Lemon et al., "Subcutaneous administration of inactivated hepatitis B vaccine by automatic jet injection," J. Med. Virol., 12(2):129-136 (1983).
Li et al., "Roles of heat-shock proteins in antigen presentation and cross-presentation," Curr. Opin. Immunol., 14(1):45-51 (2002).
Liaw, K. et al., "Human papillomavirus and cervical neoplasia: a case-control study in Taiwan." Int. J. Cancer. 62(5):565-71 (1995).
Lim et al., "Vaccination with an ovalbumin/interleukin-4 fusion DNA efficiently induces Th2 cell-mediated immune responses in an ovalbumin-specific manner," Arch. Pharm. Res., 21(5):537-542 (Abstract) (1998).
Lin, C-T. et al., "Boosting with Recombinant Vaccinia Increases HPV-16 E7-Specific T Cell Precursor Frequencies and Antitumor Effects of HPV-16 E7-Expressing Sindbis Virus Replicon Particles." Molecular Therapy. 8(4):559-566 (2003).

(56) References Cited

OTHER PUBLICATIONS

Lin, K.Y. et al., "Coinfection of HPV-11 and HPV-16 in a case of Laryngeal Squamous Papillomas With severe Dysplasia." Laryngoscope. 107(7):942-947 (1997).

Lin, K.-Y. et al., "Ectopic Expression of Vascular Cell Adhesion Molecule-1 as a New Mechanism for Tumor Immune Evasion." Cancer. Res. 67(4):1832-1841 (2007).

Lin, K-Y. et al., "Treatment of Established Tumors with a Novel Vaccine That Enhances Major Histocompatibility Class II Presentation of Tumor Antigen," Cancer Research 56:21-26 (1996).

Lin, Y-Y. et al., "Vaccines against human papillomavirus." Frontiers in Bioscience. 12:246-264 (2007).

Ling, M. et al., "Preventive and Therapeutic Vaccines for Human Papillomavirus-Associated Cervical Cancers." J Biomed Sci 7:341-356 (2000).

Liu et al., "The emerging role of IL-15 in NK-cell development," Immunology Today, 21(3):113-116 (2000).

Liu et al., "Recombinant Adeno-Associated Virus Expressing Human Papillomavirus Type 16 E7 Peptide DNA Fused with Heat Shock Protein DNA as a Potential Vaccine for Cervical Cancer," Journal of Virology, 2888-2894 (2000).

Luke et al., "An OspA-based DNA vaccine protects mice against infection with *Borrelia burgdorferi*," J. Infect. Dis., 175(1):91-97 (1997).

Lyras and Rood, "Genetic Organization and Distribution of Tetracycline Resistance Determinants in *Clostridium perfringens*," Antimicrobial Agents and Chemotherapy 40:2500-2504 (1996).

Maecker et al., "DNA vaccination with cytokine fusion constructs biases the immune response to ovalbumin," Vaccine, 15(15):1687-1696 (Abstract) (1997).

Maki et al., "Human homologue of murine tumor rejection antigen pg96: 5'-Regulatory and coding regions and relationship to stress-induced proteins," Proc. Natl. Acad. Sci. USA, 87:5658-5662 (1990).

Mao, C-P. et al., "Immunological research using RNA interference technology." Immunology, 121:295-307 (2007).

Mao, C-P. et al. "Immunotherapeutic strategies employing RNA interference technology for the control of cancers." Journal of Biomedical Science 14:15-29 (2007).

Maraskovsky et al., "Dramatic Increase in the Nos. Of Funtionally Mature Dendritic Cells in Flt-3 Ligand-treated Mice: Multiple Dendritie Cell Subpopulations Identified," J. Exp. Med., 184:1953-1962 (1996).

Massa et al., "Enhanced Efficacy of Tumor Cell Vaccines Transfected with Secretable hsp70," Cancer Research, 64:1502-1508 (2004).

McCluskie, et al., "Route and Method of Delivery of DNA Vaccine Influence Immune Responses in Mice and Non-Human Primates," Mol. Med. 5:287-300 (1999).

McKenzie et al., "Sequence and Immunogenicity of the 70-kDa Heat Shock Protein of *Mycobacterium leprae*," J. Immunol., 147(1):312-319 (1991).

Meinkoth et al., "Hybridization of nucleic acids immobilized on solid supports," Anal. Biochem., 138(2):267-284 (1984).

Meneguzzi et al., "Immunization against Human Papillomavirus Type 16 Tumor Cells with Recombinant Vaccinia Viruses Expressing E6 and E7," Virology, 181:62-69 (1991).

MHC Class-I Binding Peptide Prediction Results for the Maltose Binding Protein of Vector pMAL used in D8, using ProPred-I (http://www.imtech.res.In/raghava/propredl/) (2007).

Michel, N., et al., "Enhanced Immunogenicity of HPV 16 E7 Fusion Proteins in DNA Vaccination," Virology, 294:47-59 (2002) XP002201708.

Michel, N. et al., "Improved Immunogenicity of Human Papillomavirus Type 16 E7 DNA After Fusion to the Herpes Simplex Virus 1 VP22 Gene"; Barcelona, Spain, Jul. 23-28, 2000, Abstract, 458, XP002201712.

Mikayama et al., "Molecular cloning and functional expression of a cDNA encoding glycosylation-inhibiting factor," PNAS, 90:10056-10060 (1993).

Mold, D. et al., "Four Classes of HERV-K Long Terminal Repeats and Their Relative Promoter Strengths for Transcription." J Biomed Sci 4:78-82 (1997).

Molinari and Helenius, "Chaperone Selection During Glycoprotein Translocation into the Endoplasmic Reticulum," Science, 288(5464):331 (2000).

Moniz, M. et al., "HPV DNA Vaccines," Frontiers in Bioscience 8, d55-68, (2003).

More et al., "Activation of cytotoxic T cells in vitro by recombinant gp96 fusion proteins irrespective of the 'fused' antigenic peptide sequence," Immunol. Lett., 69(2):275-282 (1999).

Mrsny et al., "Mucosal administration of a chimera composed of Pseudomonas exotoxin and the gp120 loop sequence of HIV-1 induces both salivary and serum antibody responses," Vaccine, 17:1425-1433 (1999).

Nair et al., "Calreticulin Displays in Vivo Peptide-Binding Activity and Can Elicit TL1 Responses Against Bound Peptides," Journal of Immunology 162(11):6426-5432 (1999).

Nakano et al., "Immunization with Plasmid DNA Encoding Hepatitis C Virus Envelope E2 Antigenic Domains Induces Antibodies Whose Immune Reactivity Is Linked to the Injection Mode," Journal of Virology 71:7101-7109 (1997).

Nawrocki, S. and Mackiewicz, A., "Genetically modified tumour vaccines—where we are today," Cancer Treatment Reviews 25:29-46 (1999).

Nguyen et al., "A Mutant of Human Papillomavirus Type 16 E6 Deficient in Bindong α-Helix Partners Displays Reduced Oncogenic Potential In Vivo," Journal of Virology, 76(24):13039-13048 (2002).

Nicchitta, C.V. and Reed, R.C., "The immunological properties of endoplasmic reticulum chaperones: a conflict of interest?," Essays in Biochemistry 36:15-25 (2000).

Noessner et al., "Tumor-Derived Heat Shock Protein 70 Peptide Complexes Are Cross-Presented by Human Dendritic Cells," The Journal of Immunology, 169:5424-5432 (2002).

Ockert et al., "Advances in Cancer Immunotherapy Symposium, Dresden, Germany," Immunology Today 20(2):63-65 (1999). Abstract.

Ohtsuka, K., "Cloning of a cDNA for heat-shock protein hsp40, a human homologue of bacterial DnaJ," Biochem. Biophys. Res. Commun., 197(1):235-240 (1993).

Okada et al., "Intranasal Immunization of a DNA Vaccine with IL-12- and Granulocyte-Macrophage Colony-Stimulating Factor (GM-CSF)-Expressing Plasmids in Lipsomes Induces Strong Mucosal and Cell Mediated Immune Responses Against HIV-1 Antigens," The Journal of Immunology, 159(7):3638-3647 (1997).

Operschall et al., "Enhanced protection against viral infection by co-administration of plasmid DNA coding for viral antigen and cytokines in mice," Journal of Clinical Virology, 13:17-27 (1999).

Ozols, RF., "Systemic therapy for ovarian cancer: current status and new treatments," Semin. Oncol., 33:53-11 (2006).

Pai, S I et al., "Prospects of RNA interference therapy for cancer." Gene Therapy. 13:464-477 (2006).

Pan et al., "A recombinant Listeria Monocytogenes Vaccine Expressing a Model Tumour Antigen Protects Mice Against Lethal Tumour Cell Challenge and Causes Regression of Established Tumours," Nature Medicine, 1(5):471-7 (1995).

Pan et al., "Regression of Established Tumors in Mice Mediated by the Oral Administration of a Recombinant Listeria monocytogenes Vaccine," Cancer Research, 55(21):4776-4779 (1995).

Pardoll et al., "Exposing the Immunology of Naked DNA Vaccines," Immunity, 3:165-169 (1995).

Pejawar-Gaddy et al., "Cancer vaccines: accomplishments and challenges," Crit. Rev. Oncol. Hematol., 67(2):93-102 (2008).

Peng et al., "A combination of DNA vaccines targeting human papillomavirus type 16 E6 and E7 generates potent antitumor effects." Gene Therapy. 13:257-265 (2006).

Peng, S. et al., "Characterization of HLA-A2-restricted HPV-16 E7-specific CD8+ T-cell immune responses induced by DNA vaccines in HLA-A2 transgenic mice." Gene Therapy. 13:67-77 (2006).

Peng, S., et al.; "Characterization of HPV16-E6 DNA vaccines employing intracellular targeting and intercellular spreading strategies;" Journal of Biomedical Science, 12:689-700 (2005).

(56) References Cited

OTHER PUBLICATIONS

Peng, S. et al., "Development of a DNA Vaccine targeting Human Papillomavirus Type 16 Oncoprotein E6." Journal of Virology. 78(16):8468-8476. (2004).
Peng et al., "Efficient delivery of DNA vaccines using human papillomavirus pseudovirions," Gene Therapy, 17(12):1453-1464 (2010).
Peng, S. et al., "HLA-DQB1*02- restricted HPV-16 E7 Peptide-Specific CD4+ T-Cell Immune Responses Correlate with Regression of HPV-16-Associated High-Grade Squamous Intraepithelial Lesions." Clin. Cancer Res. 13(8):2479-2487 (2007).
Peng, S. et al., "Vaccination with Dendritic Cells Transgected with BAK and BAX siRNA Enhances Antigen-Specific Immune Responses by Prolonging Dendritic Cell Life." Human Gene Therapy 16:584-593 (2005).
Peoples et al., "Vaccine Implications of Folate Binding Protein, a Novel Cytotoxic T Lymphocyte-recognized Antigen System in Epithelial Cancers," Clinical Cancer Research, 5:4214-4223 (1999).
Pfisterer et al., "Management of platinum-sensitive recurrent ovarian cancer," Semin. Oncol., 33:512-516 (2006).
Przepiorka et al., "Heat shock protein peptide complexes as Immunotherapy for human cancer," Molecular Medicine Today (Reviews), 4(11):478-484 (1998).
Ramos-Soriano, A. et al., "Enteric pathogens associated with gastrointestinal dysfunction in children with HIV infection." Molecular and Cellular Probes 10: 67-73 (1996).
Rashid, A. et al., "Mitochondrial Proteins That Regulate Apoptosis and Necrosis Are Induced in Mouse Fatty Liver." Hepatology 29:1131-1138 (1999).
Robinson et al., "DNA Vaccines," Seminars in Immunology, 9(5):271-283 (1997).
Roby et al., "Development of a syngeneic mouse model for events related to ovarian cancer," Carcinogenesis, 21(4):585-591 (2000).
Roden, R. et al. "The impact of preventative HPV Vaccination," Discovery Medicine, 6(35):175-181 (2006).
Roden, R. et al., "Vaccination to Prevent and Treat Cervical Cancer." Human Pathology. 35(8): 971-982. (2004).
Roden and Wu, "How will HPV vaccines affect cervical cancer?" Nature Reviews, 6:753-763 (2006).
Rodriguez et al., "DNA Immunization with Minigenes: Low Frequency of Memory Cytotoxic T Lymphocytes and Inefficient Antiviral Protection Are Rectified by Ubiquitination," Journal of Virology, 72(6):5174-5181 (1998).
Rogers et al., "Multistage Multiantigen Heterologous Prime Boost Vaccine for *Plasmodium knowlesi* Malaria Provides Partial Protection in Rhesus Macaques," Infection and Immunity, 69(9):5565-5572 (2001).
Rouse et al., "Induction in Vitro of Primary Cytotoxic T-Lymphocyte Responses with DNA Encoding Herpes Simplex Virus Proteins," Journal of Virology, 68(9):5685-5689 (1994).
Sanchez-Perez et al., "Killing of Normal Melanocytes, Combined with Heat Shock Protein 70 and CD4OL Expression, Cures Large Established Melanomas," The Journal of Immunology, 177:4168-4177 (2006).
Sarmiento et al., "IgCx or IgM Monoclonal Antibodies Reactive with Different Determinants of the Molecular Complex Bearing LYT 2 Antigen Block T Cell Mediated Cytolysis in the Absence of Complement," J. Immunol., 125(6):2665-2672 (1980).
Sasaki et al., "Adjuvant formulations and delivery systems for DNA vaccines," Methods, 31(3):243-254 (2003).
Schultes et al., "Monitoring of immune responses to CA125 with IFN-gamma ELISPOT assay," J. Immunol. Methods, 279:1-15 (2003).
Schutze-Redelmeier et al., "Introduction of Exogenous Antigens into the MHC Class I Processing and Presentation Pathway by *Drosophila* Antennapedia Homeodomain Primes Cytotoxic T Cells In Vivo," Journal of Immunology 157:650-655 (1996).
Serody et al., "T Cell Activity After Dendritic Cell Vaccination Is Dependent on Both the Type of Antigen and the Mode of Delivery," J. Immunology, 164(9):4961-4967 (2000).

Shalinsky et al., "Marked Antiangiogenic and Antitumor Efficacy of AG3340 in Chemoresistant Human Non-Small Cell Lung Cancer Tumors: Single Agent and Combination Chemotherapy Studies," Clincal Cancer Research 5:1905-1917 (1999).
Sheikh et al., "Guns, genes, and spleen: a coming of age for rational vaccine design," Methods, 31(3):183-192 (2003).
Sin et al., "Enhancement of protective humoral (Th2) and cell mediated (Th1) immune responses against herpes simplex virus-2 co-delivery of granulocyte-macrophage colony-stimulating factor expression cassettes," Eur. J. Immunol., 28:3530-3540 (1998).
Sin, J.I., "Human papillomavirus vaccines for the treatment of cervical cancer," Expert Review Vaccines, 5(6):783-792 (2006).
Smahel et al., "DNA vaccine against oncogenic hamster cells transformed by HPV16 E6/E7 oncogenes and the activated *ras* oncogene," Oncology Reports, 6:211-215 (1999).
Smahel et al., "Immunisation with modified HPV16 E7 genes against mouse oncogenic TC-1 cell sublines with downregulated expression of MHC class I molecules," Vaccine, 21:1125-1136 (2003).
Srivastava et al., "Evidence for Peptide-Chaperoning by the Endoplasmic Reticular Heat Shock Protein GP96: Implications for Vaccination Against Cancer and Infectious Diseases," J. Cell. Biochem. Suppl. 17D:94 (Abstract NZ 014) (1993).
Srivastava et al., "Heat Shock Proteins Come of Age: Primitive Functions Acquire New Roles in an Adaptive World," Immunity, 8:657-665 (1998).
Srivastava, P., "Interaction of heat shock proteins with peptides and antigen presenting cells: chaperoning of the innate and adaptive immune responses," Annu. Rev. Immunol., 20:395-425 (2002).
Srivastava et al., "5'-Structural analysis of genes encoding polymorphic antigens of chemically induced tumors," Proc. Natl. Acad. Sci. USA, 84:3807-3811 (1987).
Srivastava et al., "The Serologically Unique Cell Surface Antigen of Zajdela Ascitic Heptoma is also its Tumor-Associated Transplantation Antigen," Int. J. Cancer, 33:417-422 (1984).
Srivastava et al., "Tumor rejection antigens of chemically induced sarcomas of inbred mice," Proc. Natl.-Acad. Sci. USA, 83:3407-3411 (1986).
Steinman et al., "The Sensitization Phase of T-Cell-mediated Immunity," Annals of the New York Academy of Sciences, 546:80-90 (1988).
Stevenson et al., "Idiotypic DNA Vaccines Against B-cell Lymphoma," Immunological Reviews, 145:211-228 (1995).
Suto et al., "A Mechanism for the Specific Immunogenicity of Heat Shcck Protein-Chaperoned Peptides," Science, 269:1585-1588 (1995).
Suzue et al., "Adjuvant-Free HSP70 Fusion Protein System Elicits Humoral and Cellular Immune Responses to HIV-1," Journal of Immunology 156:873-879 (1996).
Suzue et al., "Heat shock fusion proteins as vehicles for antigen delivery into the major histocompatibility complex class I presentation pathway," Proc. Natl. Acad. Sci. USA 94:13146-13151 (1997).
Syrengelas et al., "DNA immunization induces protective immunity against B-cell lymphoma," Nature Medicine, 2( 9):1038-1041 (1996).
Szymczak et al., "Correction of multi-gene deficiency in vivo using a single 'self-cleaving' 2A peptide-based retroviral vector," Nat. Biotechnol., 22(5):589-594 (2004).
Tamura et al., "Immunotherapy of Tumors with Autologous Tumor-Derived Heat Shock Protein Preparations," Science, 278:117-120 (1997).
Theriault et al., "Extracellular HSP70 binding to surface receptors present on antigen presenting cells and endothelial/epithelial cells," FEBS Lett., 579(9):1951-1960 (2005).
Thomas et al., "Mesothelin-specific CD8+ T Cell Responses Provide Evidence of In Vivo Cross-Priming by Antigen-Presenting Cells in Vaccinated Pancreatic Cancer Patients," J. Exp. Med., 200(3):297-306 (2004).
Thornburg et al., "Induction of Cytotoxic T Lymphocytes With Dendritic Cells Transfected With Human Papillomavirus E6 and E7 RNA: Implications for Cervical Cancer Immunotherapy," Journal of Immunotherapy, 23(4):412-418 (2000).

(56) References Cited

OTHER PUBLICATIONS

Ting et al., "Human gene encoding the 78,000-dalton glucose-regulated protein and its pseudogene: structure, conservation, and regulation," DNA, 7(4):275-286 (1988).
Tobery et al., "Targeting of HIV-1 antigen for rapid intracellular degradation enhances cytotoxic T lymphocyte (CTL) recognition and the induction of De Novo CTL responses in Vivo after immunization," J. Exp. Med., 185(5):909-920 (1997).
Tomson, T. et al. "Human papillomavirus vaccines for the prevention and treatment of cervical cancer." Current Opinion in Investigational Drugs, 5(12):1247-1261. (2004).
Torres et al., "Differential Dependence on Target Site Tissue for Gene Gun and Intramuscular DNA Immunizations," The Journal of Immunology 158:4529-4532 (1997).
Trimble, C. et al., "Comparison of the CD8+ T cell responses and antitumor effects generated by DNA vaccine administered through gen gun, biojector and syringe," Vaccine. 21:4036-4042 (2003).
Trimble C, et al., "Spontaneous Regression of High-Grade Cervical Dysplasia: Effects of Human Papillomavirus Type and HLA Phenotype." Clin. Cancer Res. 11(13):4717-4723 (2005).
Trompeter, Hans-Ingo et al., "Variable Nuclear Cytoplasmic Distribution of the 11.5-kDa Zinc-binding Protein (Parathymosin-α) and Identification of a Bipartite Nuclear Localization Signal," The Journal of Biological Chemistry 271(2):1187-1193 (1996).
Trujillo, J. et al., "Characterization of human papillomavirus type 57b: transforming activity and comparative sequence analysis as probes for biological determinants associated with high-risk oncogenic viruses." Virus genes. 12(2):165-78 (1996).
Tsen, S-W. et al., "Enhancing DNA Vaccine Potency by Modifying the Properties of Antigen-Presenting Cells," Expert Review of Vaccines, 6(2):227-239 (2007).
Tseng et al., "Systemic tumor targeting and killing by Sindbis viral vectors," Nature Biotechnology, 22(1):70-77 (2004).
Tseng et al., "Using Sindbis Viral Vectors for Specific Detection and Suppression of Advanced Ovarian Cancer in Animal Models," Cancer Research, 64:6684-6692 (2004).
Tuting et al., "Autologous Human Monocyte-Derived Dendritic Cells Genetically Modified to Express Melanoma Antigens Elicit Primary Cytotoxic T Cell Responses In Vitro: Enhancement by Cotransfection of Genes Encoding the Th1-Biasing Cytokines IL-12 and IFN-$\alpha^1$," Journal of Immunology 160:1139-1147 (1998).
Udono et al., "Cellular requirements for tumor-specific immunity elicited by hear shock proteins: Tumor rejection antigen gp96 primes CD8+ T cells in vivo," Proc. Natl. Acad. Sci. USA, 91:3077-3081 (1994).
Udono et al., "Comparison of Tumor specific immunogenicities of stress-induced proteins gp96, hsp90, and hsp70'," The Journal of Immunology, 152(11):5398-5403 (1994).
Udono et al., "Heat Shock Protein 70-associated Peptides Elicit Specific Cancer Immunity," J. Exp. Med., 178:1391-1396 (1993).
Ulmer et al., "Presentation of an exogenous antigen by major histocompatibility complex class I molecules," Eur. J. Immunol., 24:1590-1596 (1994).
van der Burg et al., "Pre-clinical safety and efficacy of TA-CIN, a recombinant HPV16 L2E6E7 fusion protein vaccine, in homologous and heterologous prime-boost regimens," Vaccine, 19:3652-3660 (2001).
van Bergen et al., "Superior Tumor Protection Induced by a Cellular Vaccine Carrying a Tumor-specific T Helper Epitope by Genetic Exchange of the Class II-associated Invariant Chain Peptide," Cancer Research, 60(22):6427-6433 (2000).
van Tienhoven et al., "Induction of antigen specific CD4 + T cell responses by invariant chain based DNA vaccines," Vaccine, 19:1515-1519 (2001).
Vu, K. et al., "Cellular Proliferation, Estrogen Receptor, Progesterone Receptor, and bcl-2 Expression in GnRH Agonist-Treated Uterine Leiomyomas." Human Pathology 29:359-363 (1998).

Wang et al., "CD40 Is a Cellular Receptor Mediating Mycobacterial Heat Shock Protein 70 Stimulation of CC-Chemokines," Immunity, 15:971-983 (2001).
Wang et al., "A Single Amino Acid Determines Lysophospholipid Specificity of the $S1P_1$ (EDG1) and $LPA_1$ (EDG2) Phospholipid Growth Factor Receptors," The Journal of Biological Chemistry, 276(52):49213-49220 (2001).
Wang, T-L. et al., "Intramuscular administration of E7-transfected dendritic cells generates the most potent E7-specific anti-tumor immunity." Gene Therapy 7:726-733 (2000).
Weiss et al., "A plasmid encoding murine granulocyte-macrophage colony-stimulating factor increases protection conferred by a malaria DNA vaccine," The Journal of Immunology, 161(5):2325-2332 (1998).
Whisstock et al., "Prediction of protein function from protein sequence and structure," Quarterly Reviews of Biophysics, 3:307-340 (2003).
Whittall et al., "Interaction between the CCR5 chemokine receptors and microbial HSP70," Eur. J. Immunol., 36(9):2304-2314 (2006).
Wu, T-C. et al., "A Reassessment of the Role of B7-1 Expression in Tumor Rejection." J. Exp. Med. 182:1415-1421 (1995).
Wu, T-C. et al., "Demonstration of human papillomavirus (HPV) genomic amplification and viral-like particles from CaSki cell line in SCID mice." Journal of Virological Methods 65:287-298 (1997).
Wu, T-C. et al., "Detection of the Human Cytomegalovirus 2.0-kb Immediate Early Gene I Transcripts in Permissive and Nonpermissive Infections by RNA in situ Hybridization." J Biomed Sci 4:19-27 (1997).
Wu, T-C, et al., "Engineering an intracellular pathway for major histocompatibility complex class II presentation of antigens." Proc. Natl. Acad. Sci. 92:11671-11675 (1995).
Wu, T-C. "Therapeutic human papillomavirus DNA vaccination strategies to control cervical cancer." European Journal of immunology. 37:310-314 (2007).
Yen, M. et al., "Diffuse Mesothelin Expression Correlates with Prolonged Patient Survival in Ovarian Serous Carcinoma." Clin. Cancer. Res. 12(3):827-831 (2006).
Yokokawa et al., "Identification of Novel Human CTL Epitopes and Their Agonist Epitopes of Mesotheliin," Clin. Cancer Res., 11(17):6342-6351 (2005).
International Search Report dated Oct. 15, 2001 from PCT/US2000/41422.
International Search Report dated Nov. 13, 2007 from PCT/US2003/10235.
International Search Report dated Dec. 3, 2002 from PCT/US2001/24134.
International Search Report dated Sep. 20, 2002 from PCT/US2002/02598.
International Search Report dated Jun. 28, 2002 from PCT/US2001/23966.
International Search Report dated Mar. 25, 2005 from PCT/US2004/05292.
International Search Report dated Apr. 1, 2005 from PCT/US2004/13756.
International Search Report dated Mar. 22, 2007 from PCT/US2006/02707.
International Search Report dated Aug. 13, 2008 from PCT/US2007/76525.
Supplementary EP Search Report dated Mar. 6, 2006 from EP 02 70 7618.
Supplementary EP Search Report dated Sep. 28, 2006 from EP 04 75 1244.
Supplementary EP Search Report dated May 30, 2008 from EP 06 73 3904.
Oltersdorf et al., "Identification of Human Papillomavirus Type 16 E7 Protein by Monoclonal Antibodies," J. Gen. Virol., 68:2933-2938 (1987).
Ballard et al., "Anthrax toxin-mediated delivery of a cytotoxic T-cell epitope in vivo," Proc. Natl. Acad. Sci., 93:12531-12534 (1996).
Bennett et al., "Induction of CD8+ Cytotoxic T Lymphocyte Response by Cross-priming Requires Cognate CD4+ T Cell Help," J. Exp. Med, 186(1):65-70 (1997).

(56) References Cited

OTHER PUBLICATIONS

Cassetti et al., "Antitumor efficacy of Venezuelan equine encephalitis virus replicon particles encoding mutated HPV16 *E6* and *E7* genes," Vaccine, 22:520-527 (2004).

Demierre et al., "Chemoprevention of Melanoma," Current Oncology Reports, 6:406-413 (2004).

Diaz, Rosa Maria, et al. "Oncolytic Immunovirotherapy for Melanoma Using Vesicular Stomatitis Virus," Cancer Research, 67(6): 2840-2848 (2007).

Fayolle et al., "In Vivo Induction of CTL Responses by Recombinant Adenylate Cyclase of *Bordetella pertussis* Carrying Viral CD8+ T Cell Epitopesl," J. Immunol., 156:4697-4706 (1996).

Galbraith et al., "Effects of 5,6-Dimethylxanthenone-4-Acetic Acid on Human Tumor Microcirculation Assessed by Dynamic Contrast-Enhanced Magnetic Resonance Imaging," Journal of Clinical Oncology, 20(18):3826-3840 (2002).

Gambhira et al., "Vaccination of Healthy Volunteers with Human Papillomavirus Type 16 L2E7E6 Fusion Protein Induces Serum Antibody that Neutralizes across Papillomavirus Species," Cancer Reseach, 66:11120-11124 (2006).

Kinoshita et al., "Spreading of the immune response from 52 kDaRo and 60 kDaRo to calreticulin in experimental autoimmunity," Lupus, 7:7-11 (1998).

Mandavi et al., "Vaccines Against Human Papillomavirus and Cervical Cancer: Promises and Challenges," The Oncologist, 10:528-538 (2005).

Pike et al., "Calreticulin and Calreticulin Fragments Are Endothelial Cell Inhibitors That Suppress Tumor Growth," Blood, 94:2461-2468 (1999).

Roitt et al., Immunology (textbook), 5th Edition, p. 128 (1998).

Tagawa et al., "Phase I Study of Intranodal Delivery of a Plasmid DNA Vaccine for Patients with Stage IV Melanoma," Cancer, 98:144-154 (2003).

Xiang et al., "A New Dynamic Model of CD8+ T Effector Cell Responses via CD4+ T Helper-Antigen-Presenting Cells1," J. Immunol., 174:7497-7505 (2005).

Extended European Search Report dated Apr. 15, 2013, from EP 10772568.1.

International Search Report dated Jan. 13, 2011 from PCT/US2010/032779.

Chuang et al., "Combination of Viral Oncolysis and Tumor-Specific Immunity to Control Established Tumors," Clinical Cancer Research, 15(14):4581-4588 (2009).

Edmonds et al., "A Point Mutational Analysis of Human Papillomavirus Type 16 E7 Protein," Journal of Virology, 63(6):2650-2656 (1989).

Ye et al., "Cytokine Transgene Expression and Promoter Usage in Primary CD34+ Cells Using Particle-Mediated Gene Delivery," Human Gene Therapy, 9:2197-2205 (1998).

\* cited by examiner

Figure 34
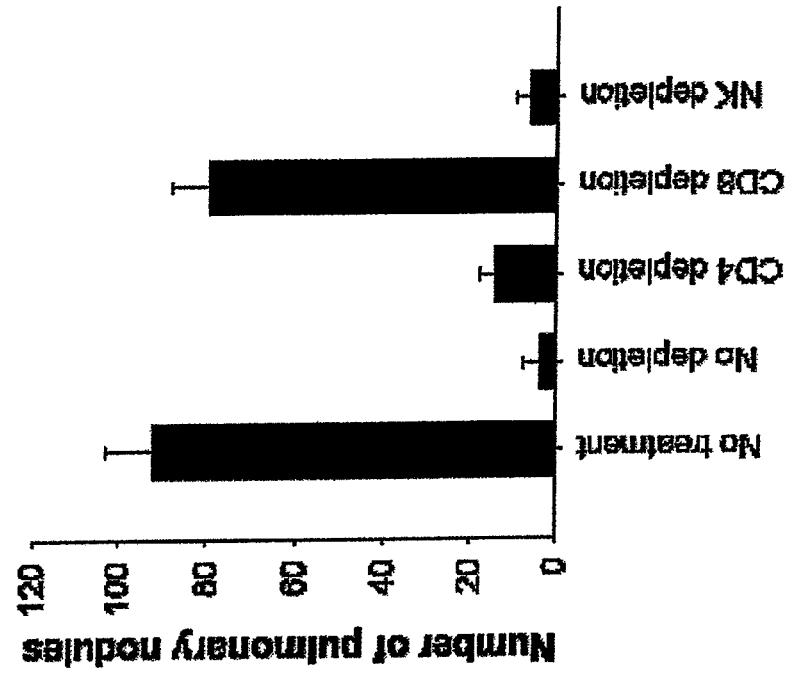
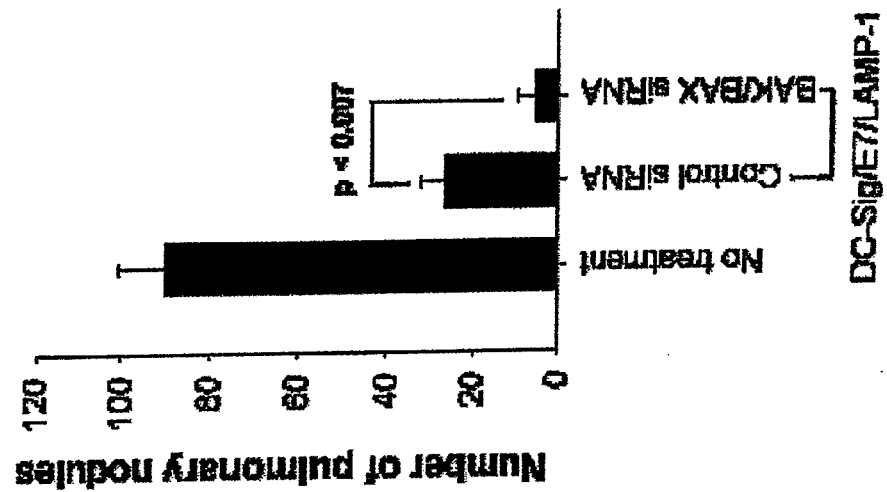

Figure 36

```
gacggatcgg gagattcccc gatcccctat ggtcgactct cagtacaatc tgctctgatg ccgcatagtt aagcagtat ctgcccctg cttgtgtgtt ggagtcgct
gagtgtgcg cgagcaaaat ttaagctaca acaaggcaag gcttgaccga caattgcatg aaggattacg aggagttag agcccatata cggttttgcg ctgcttcgcg atgacgggc
cagatacg cgttgacatt gattattgac tagtattaa gtctgaccatc aatagttcat agccatata tttccccaata acgccaata ggagttcg gttacataa cttacgtaa
atgcccgcc tgctgaccg ccaatgacc cgccccatt gacgtaata atgacgtag acgccaaata gggactttc gcctgttttc atgactgca atggtggac
tatttacggt aaactgcca cttgcagta catcaagtgt atcatatgcc aagtagcc cctattacg cggttttggc taaatgccc gctagcatt atgccagta
catgacctta tggactttc ctacttggca gtacatctac gtattgtca tcgctattac catggtgatg aaaatcacg ggactttcca agtacatcaa tgggcgtga taggcgtttg
actcacggg atttcagt tttgaattcaa gcagagctct ctttggcact agagaacca gcttatcga ggacttcca attaatcgc cccattgacg
caaatgggcg gtaaggcgt acgtggcgt gtctatataa gcagagcct ctggcacct agagaacca gcttatcga attaataga ctcactacg
ggagaccca gctggctagc gtttaaacg gccctctaga ctgaccggc cgcactgtg ctggatatct gcagaattcc accactgg actagtgat ccgagctcgg
taccaagctt aagttttaaаc cgtgatcag atggtcctagt gcctctagt taggtctgag tctgtgtttg cccctcctcc gtccttcct tgacctgga aggtgccact
cccactgctc tttcctaata aatgaggaa attgtctgag taggtctgag tctattctgag gggtcggag gggcaggaa agcaggggg aggattgga
agacaatagc aggcatgctg ggatgcgcgt cctgactgt gttctggag cggaagaaac tctaggggt atctcccaaagc gccctgtagc ggcgcattaa
gccgcgggg tgtggttggt acgcagcgg tgtaccgtac gcctcagcc ggtcttct cgcctttt cctctcttc tcgccacgtt cgccggcttt
cccgtagc ctctaaatcg gggatcctt ttaggttcc gcagtatgcc ctcgaccaa aaaaactcca ttagagtgag gtattcagt gttggcaga gtgggcatc
gccctgata ccggttttc gccctttgac attggagtcc gtgagtcc actagtcaga atagtgtgga gaaagtcca cactcaacc tatcggtt tatttttttg
atttataagg gattttggg attcgcctt aggcagaagt cccgaggca aatgacct acctttt gaccaactg cattaaaga aatctaata cggaggcaaa
tttattacg agaggcgag gcgctctg cctcgggct tgaggatcgt tcgcatgat tgtgagagag gggctctgg aggagagc gtgagaagga tattggca
tccattttcg gatctgata agcagaagt agagacagga tgatgccagc gttcttagccg tgacaaagga caggtcctcc ggccgcttg gtgatgacg gccctgaatg
tgactgggca caacagacaa tcgccgctg tgtttccgc gtgtttcaga gggccgcga actccgcc agtccgcgct gtcttttgt ctgtccggt gccctgatg
aactgcagga cgagcagcg cgggctctg ggctggccac gacgggcgtt cctgtgcga gtacatc gttggtcact cgttgtcagg gggactggct gctattggcg
gaagtgcggg gcaggatct cctgtcatct catcaatga ctgccgaa agtgcatgt tgtgatccag agcagggtc cttgatccgg ttaccttgcc
attcgaccac caagaagac atcgcatcgc gcgagccag acctggatgg aagcctgtg gtgaccatg aagcctctg gatgtgctg tcagggctc cgccaagcc
aactgttcgc caagctcaag gcgcatgc ccgacggca cgagctctg gtgacccatg gcgaatgctg atcatgggt caactgcg ctttctcgga
tcatgact gtgccgcgct ggtgtgggcg aacgcctatc ttccccccgg aggacatagc gttgctaca gtgaagct cgtgaactct gctctctgt
gctctacgt atcgagagtt tcgatcga cgattcgca ttccccccgg tcagttcgt tctttcctg gtcggactct ggggtcgaa atgaacgcg ggggatccgc
caacctgcc tcgagatt cctcgccac cccaactgt cgcgcctc cgcgtctcca ggggcttc aatcgttttc cgtgatgat cattttttct actgcattct
tgctggagtt ctcgccac acaactag ttattcgagc ttattcgagc tacacataa acaattc caccaataaa atggcatag ctgttcttcg tgtgaaattg
agtgtggtt tgtccaaact catcatcatg accgggaag tctgtatacc gtcgaccct tggcgtaatc aatggggga aaatgcatag tgctcttcgt tactaccg
ttatccagc acaatccag acacatacg agcggaagc ataaagtgta aagctgggg cgccaataga gtaagctaa cgctattggg tgcggttt cactgactcg
ctttccagtc gggaacctg tcgtccagc tgcatttaatg gtatcagtcc acccaagc cgcgcggga ggtaatacgg ttatccaacg aatgacagga gacacaaagg
ctgctcgg tgctcggct gggcgagcg gtatcagcagcg ggcgttttcc gcgttttctc atgggcctc gtgcagat taacgcagga ctcaagtcag agtggccgaa
ccgaaaca gccaaaagg gttaaaagc ccgtttttcc cccccccggg aagcctccctc gtggccgctt cccgcgctct gaagatcca accggatacc tgtgccctt tctctctctcg
accgacag actataaaga ctactcacg ttcctgtact tcagttcaa ttgttggcaa gcagcagatt ttgttgtta acgcgagga gttacctcg ccgacctgg ccgacctg
ggaagcgtgg gcttctacga atgctcagc cgtcgtagc tgtaaggttt ggagttcgt cagtgtgctc aaaaggtcc gcacgaacc cccgttacg ccagcgcctg
cgctatactc ggtaactatc gtcttgagtc caaccgggta aaacatacga gagaccaggc actggtaa aggactctg gatttagcag agcgaggtg gtagcctttg
ctacagagt cttgaagctg tgcctcact acgctaacg ttggagggtat tgttttgctg ctgaagaatg ttgttttgtta ctgagcaa aggagtcct cagtatgatc ttcggaccgt
tgatcccgca aacaaccac cgtcgtatgc acttgttgta acagttacca agtcatgcca gattgtta ggctcccac agggtctcat gacatcgtt gttttcctt taggcagcga
gtctgagcgt cagtgaaacg cgtcgtatac ttaacctctg gcccgctt taccatcctg tcagtatgt accattggtt ctcattggta accatcagta atgcagtcaa taaccagtcg
gtcgtgtag taactacgat acggacgcga aaactaag acttgtcta acggttcc gggccctgca tctgtatgta gatcaatgt tttgtgggg gccaactg ctactactcc
agcggaagg gccgagcgca gaagtggctc ccctggagct cgactccagt aactcgcaga agtgggggc aaaaagacag cacgaagcta gatcagagcg ctgcatatat cccgtttcc
ttgtcaaaa agcgtatag ctccttcgtt tttctctgcac tgtcagtag tcaacgtagt atctcaggg gcagtggcc cgatgcatg gcccgtgta gatcaaacccc cgacaatgcc
catgccatc gtaagatgct cccattgctt acttttaaag acttactcat cagttcaga catttgcc gcagttccag cggttcacag gtagtggtga ttgcacaggg atcaatgt
atcgtgcac acataagtagc ccaactggtc gttatctgac tgtgagtgac cctgggccg gagtgagca acaacagaa ctcaacttg cggacaacgc ggaataagcg atacggaatg
atgtgaata gtctcatatct tccttttcat atattatga cccggcactct aaaaaagaga aatacagga gacaatatat aagtttcatag agctaaag taccatacagat ccggaaataag
gggttcccgcg cacattcccc cgaaaagtgc cacctgacgt c                                                                                       5431
```

Figure 37

```
tggccattgc atacgttgta tccatatcat aatatgtaca tttatattgg ctcatgtcca acattaccgc catgttgaca ttgattattg actagttatt aatagtaatc
aattacggg  tcattagttc atagcccata tatgagttc  cggttacat  cgcttacgt  aacttacgt  cctggctgac cctgacga  cgccaacga  cccgccca  ttgacgtcaa
taatgacgta tgttcccata gtaacgccaa tagggactt  ccattgacgt caatgggcag agtattacg  gtaaactgcc cactggcag tacatcagt  tatcatatg
ccaagtacgc ccctattga  cgtcaatgac cgcctggctg  ccgctggca  aatgggcggt tgactcacgg  ggatttccaa tatgggactt tcctactgg  cagtacatct acgtattagt
catcgctatt accatggtga tgcggttttg gcagtacatc aatgggcgtg gatagcggtt tgactcacgg ggatttccaa gtctccacc catttgacgtc aatgggagtt
tgtttggca  ccaaaatcaa acggcctgga taacactcc  taacatgcc  gctgtttga  cgacaaatgg cgtaggcgt  gtacggtgg  gaggtcatat aagcagagct
gcggattcc  acgtccaga  cgccatccac cgccatccat cgccttata  cctccatga  agacaccg   acgacgtg   acgagcggg  tggctggg   tcatcgaac
cccgcttcct catgttatag gtgatgtgtat agcttagcct ataggtgtgg gttattgacc actccaacgg ctgtcgtcga atactgttt  tggctgga   tctatacg
ttgctgccgc gcgcgccacc agacataata gctgacagac ttccttttca ctgcagtcac cgtcgtcgac ggtatcgata gccttgaga  gcagtactg
cgaattcacg tgggcccgt  acgtatact  ctagacgac  cgcgatca   gatctttttc ctccgccaaa aattatgggg acatcatgaa gccctttgag agcttgata
ctggctaata aaggaaattt atttcattgc aataagtgtgt tggaattttt tgtgtctctc actcggaagg gcgcaaatca aatatggga  gccctttgag tttaaaacat cagaatcagt
atttggttta gagtttgcca acatatgcca ttcttcgcta ctgactcgct gcgctcggtc acctcggtac cacttcac   atcagctcac tcaaaggcg  gttttccat
taatacggtt atccacagaa tcaggggata acgcaggaa  gaacatgtga gcaaatggcc caggaaaaagc aaaagccg   cgttgctggc gttttctga   agtccctcgt
aggctccgcc ccctgacga  gcatccacaa aatcgacgta caagtcgaga gtgtggaaa  acgagtgcg  agcagaacgat tgctcattca  tggttatcgt ctggcttcac  agttcggttg
gcgctctcct gttccgacc  cgcttaac   cggatccttg acgaaccccc tcccttcggg gacgctgcg  atccgcaaa  ttatcactca  gcactcaat  taggttatct  agttcggttt
agtcgttcg  ctccaagctg ggctgtgtgc acgtgtgc   gttcagccc  cgtcagcc   gacccggcg  acagagttct gacgtggtg  gcctaactac ggctacacta gaaggacagt
tcgcagtgt  cagcagccac tggtaacagg atagcagag  cgagtatgt  aggcggtgct agttgtatta ataggttgt  caaaccaaaa caaaccaaa  cggtttttttt gtttgcaagc
atttggtatc tgcgctctgc tgaagccagt taccttcgga gtagctcgtc atcgccaaa  atcgccaaa  gtggaacgaa aactcacgtt aagggattt  ggtcagcc
agcagattac gcgcagaaaa aaagagctc ctagacctct tttgatcttt aatgaagttt ctgactgct  taagtatat  atgagtaaac ttggtctgac agttaccaat gcttaatcag
ttatcaaaaa gatcttcac ctagatccttt ttaaattaaa tgaagttttaa atcaatggggggg cggtcgttgg aagtgttgc  tactcatac
caggcaacg  atctcagcga tcgtctcatt tcgttcatcc atagttgcct gactccgggg gtttggtata gcttcattca ccaacgatca  ggcgagtta  catgatcccc
catgttgtgc aaaaagcgg  ttagctccta tgctcctcg  atcgttgtca gaagtaagtt ggccgcagtg gcttattggc agcactcaat  agcacgcat  aattctctta
ctgtcatgcc atccgtaaga tgcttttctg tgactggtga gtactcaac  aagtcattct gagaatagtg tatgcggcga ccgagttgct ctgacccggc tcttggagca gtcaatacgg
gataatacgg cgcacata   cagaactttta aaagtgctca tcattgaaa  agttcctttg ggcgaaaac  cgttgagata  tcctaccctg ttgagatcca gttgatcca  gtcgatgta
ccaccgcgt  ggacctgaat caaactgaac aagtgaggga gccacgttg  atgcaacaaa agcgcgtcc  tgttgtaggt attccattt  ggacagttg  cgtcaagtca gcttttgctt
tgccacggga cggtctgcgt atgctgcgct tcccggaag   atgcgtga   actcagcaaa agtcgattt  attcaacaa  atttattgct ttattcatat aataccatat  actttgaaaa
ctgcagtgt  tacaccaat  tgatttagaa tgattagaaa acctcatcga gcatcaaatg aaactgcaat ttattcatat gagattccg  actcgtccaa catcaataca acctattaat
ttcccctgt  taatgagga  gaaaactcac ccaatggat  gaagcagtt  cgacttactggt gtagaatg   gactgaatcc  tgcaaacctt  atgcattctc ttcagactcc gttcaacagg
cacgccatta cgcctgtcat cacaatcact gttatcaacc cgcatcaaca aacgttgtac tcattgtga  gccgcctaga acatatcgg   gcaaagcttc gctgttaaa   ctgtaacatc
aaaacagaaa cgcaatgcaa cggcgcagga cgcgaatgcaa acactgaaca ccatatttca  atgctgcttc ctgaatcagg ataattttca   ataccctgga   atgctgttt   cggggttac
caggtggtga gtacctgcga cattcagga  gtacgtgaa  atgcgtgat  ggtgcgaaga gacattaagg caatgatga  gtttagtctg accattcctg atgctgtttt ctgtaacatc
attggcagc  gtaacttgc  catgtttgc  aatttaatcg gcgcttcgg  ctcccatta  cagcttcata atgctgaat  cgcagacaaa cctggggctg atgtggccc  gcacccctg  tatgttaagca
tataccata  taaattatgt cctgatttgg ttatctctg  gcttccata  caatagaag  caatgtaaa  tcagagattt cccgtgaa   caacacaa   cgggcttttt  cccccccc  tatttattatca
gacagttta  ttgtttcatga tctcatgagcg gatacattttt ttatctctggt gaatgtatttt tgaaatatgg ttcacgcga  tgagacaca  cgttgcgtttc acatttccc  catttattgt
gggtattgt  ctcatgagcg gatacatattt gataaatattt tataaaatta gggtatcac  tagaaatta  ggcctgcctttt gagcccttttt gcaagcgt  tggtcggtg  cgtcagcaga  tcccgagac
ggtcacagct tgtctgtaag cggatgccgg gcagacaca  acccgctgg  aggagacaa  cgtcaggcg  gccgtcagc  ggggcttgg  gggtcgacgc cacatgcagc  tcccgagac
ttgtactgag agtgcaccat atgcggtgtg aaataccgca cagatgcgta aggagaaaat accgcatcag attgtgaaca ttggcgtat   atttggctat
                                                                                                                          4479
```

Figure 38 Cont.

```
taacaaaaat ttaacgcgaa ttaattctgt ggaatgtgtg tcagttaggg tgtgaaagt cccaggctc cccaggcagg cagaagtatg
caaagcatgc atctcaatta gtcagcaacc agtgtgaaa agtcccagg ctcccagca ggcagaagta tgcaaagcat gcatctcaat
tagtcagcaa ccatagtccc gccctaact cgcccatcc cgccctaac tcgcccagt tcgcccatt ctcgcccca tgctgacta
attttttta tttatgcaga gccgagcgc gcctctgcct ctgagctgct ctgagctatt ccagaagtag tgaggagct tttttggagg cctaggcttt
tgcaaaagc tccggagc ttgtatatcc attttcggat ctgatcaaga gacaggatga ggatcgtttc gcatgattga acaagatga
ttgcacgcag gttctccggc cgcttgggtg gagaggctat tccgcagtca agaccgacct gtccggtgcc gcataaatcg gtgctctga tgccgcgtg
ttccggctgt cagcgcaggg gcgccggtt ggcgttcct tgcgcagctg tgtcagctgt gtcactgaa tgtcactgaa tgcaggacga ggcagcgcgg
ctatcggtgg tggccacgac gggcgttcct tgcgcacgt tgtcagcagt gcggaagg actgcttgct attggggcaa gtgccgggc
tggccacgac gggcgttcct tgcgcacgt tgtcagcagt atccatatg gctgatgaa ccgtcttgt cgatcaggat gatctgagcg
aggatctcct gtcatctcac cttgctcctg ccagaaagt agcagagcg gcatcgagcg cggatctctgt cgatcaggat gatctgagcg
cctgcccatt cgaccaccaa gcgaaacatc gcatcgagcg cgtcagccgt atcgacctgt cgtcgtgg accatgcg
agagcaatca gggctgcgc gggcgtgaaa atgtggaaa atgccgctt tctgattc aacgctgtg gcggctggga ccatgcg
atgcctgctt gccgaatatc atgtggaaa atgccgctt tctgattc cgcgaatg gctgaccgct tcctcgtgct tacgtatc gcgctccg
acatagcgtt gccaacccgt gatattgctg aagagctgg cggcgaatgg gctgaccgct tcctcgtgct tacgtatc gcgctccg
attcgagcg catcgcttc tatcgcttc ttgacgagtt cttctgagcg gactctggg gttcgaaatg gttcgacg cgacgccaa
cctgccatca cgagattcg atccacgc cgcttctat gaaaggtgg cttcgacg cttcgacg cttgacg cgaccaag cgacgccaa
ccagcgcggg gatctcatcg tggagtcct cgccaccc ctagagtat cttgagctg ggaggcgct ggatgatct
aaatttcaca aataaagcat ttttcat gcattctagt tgtggtttgt ccaaactcat caatgatac tatcatgtct gtataccgtc
gacctctagc tagagcttgg cgtaatcatg gtcatagctg tttctgtgt gaaattgta tccgctaca attccacaca acatcgagc
cggaagcata aagttgtaaag cctgggtgc ctaatgagtg agctaactca cattaattgc gttgcgctca ctgcccgctt tccagctcgg
aacctgtcg tgcagctgc attaatgaat cggccaacgc gcgggagag gcggtttgg tattgggcgc tcttccgctt cctgctcac
tgactcgctg cgctcggtcg ttcggctgcg gcgagcgta tcagctcact caaaggcgg aatacggtta tccacagaat caggatga
cgcggaaagc aacagtgag caaaaggcca gcaaaaggcc aggaaccgta aaaaggccgc gttgctgcg catcacaaaa atcgacgctc
aagtcagagg tggcgaaacc cgacaggact ataaagatac caggcgttc cccctgaag gcccctgaag ctccctcgtg cgctctcctg ttcgaccct
gcgctttacc ggataccgt cccgctttct cccttcggga agcgtggcgc ttcgcccgc accgctgcgc ctacgctgt gttcgtgta
ggtcgttcgc tccaagctgg gctgtgcac gccactggc agcagccact gtaacagga ttagcagagc gaggttagta ggcggtgcta ttgagtcaa
ccggtaaga cacgacttat gctactacg aaggacagta tttgtatct gacctgctt gagcctgct gaagcagtt acctgggaa cagagtctt
gaagtggtgg cctaactacg gctacactag aaggacagta tttgttttg tttgcaagca acctcactta agggattttg gtcatgagat tatcaaaag
tagctcttga tccggcaac aaaccaccgc tggtagcgt tgagctgcag tggaacgaaa actcagctta agtatata tgagtaaact tgtctgaca gttaccaatg
agaagatcct ttgatctttt ctacgggtc tgacgctcag tggaacgaaa actcactct gttaatcatc caacaggatt actccgaagg ctagtagtaa
ctaatcaagt gagcacta tctcagcat ctgtctatt cgttccatca cgagaccca gctacagcgt ctagagctat ctcgacgg ccatccaga gatgctttagt atgcttcat tcagctccgg
ggagggctta gcatctgcgc ccagtgctgc aatgatacg cgagaccca gctacagcgt ctagagttc gccgttcga tgggatata cggatacgc
cggaaggcc gagccagaaa gtggcagaa agttgttgc cattgctcaa ggcatcgtgg tgtcagctc tgtctggt gtggtttggt atgcttcat tcagctccgg
gccagtttaat agttggca acgttgttgc cattgctcaa ggcatcgtgg tgtcagctc cggttagctc cttcggtcct ccgatcgtg tcagaatgaa
ttcccaacga tcaagggag ttacatgatc cccatgttg tgcaaaaag cggttagctc ttactgtcat gccatccgta agatgcttt ctgtgactgg
gttgccgca gtgttatcac atggttat ggcagcactg cataattctc ttactgtcat gccatccgta agatgcttt cggatatata ccgcgcaca
tagtactca accagtcat tctgagaata gtgtatgcgg cgaccgatt gctcttgcc gctcttgcc gctcttgcc gctcttgcc gctcttgcc acacagcg
tagcagaact ttaaagtgc tcatcattgg aaaacgttct tcggggcgaa aactctcaag gatcttaccg ctgttgaga cagggccaaaa aaatgccgc
gtaacccact cgtgcaccca actgatcttc agcatctttt actttcacca gcgtttctgg gtgagcaaa acaggaaggc aaatgccgc
aaaaaggga ataagggcga cacgaaatg ttgaatactc atactctttc ctttttcaat attattgaag catttatcag ggttattgtc
catgagcgga tacatatttg aatgtattta gaaaatata tctccccga atttcccgac aaagtgcca ctgacgtc
```

```
          10         20         30         40         50         60         70         80         90
gacggatcgg gagatctccc gatcccctat ggtcgactct cagtacaatc tgctctgatg cgcatagtt aagccagtat ctgtccctg
cttgtgtgtt ggaggtcgct gagtagtgcg cgagcaaaat ttaagctaca acaaggcaag gcttgaccga cattgcatg aagaatctgc
ttagggtag gcgttttgcg ctgcttgcgg atgtacgggc cagatatacg cgttgacatt gattattgac tagttattaa tagtaatcaa
ttacggggtc attagttcat agcccatatca tggagttccg ccttacataa cttacgtaa atgcccgcc tgctgaccg cccaacgacc
ccgcccatt gacgtcaata atgacgtatg ttcccatagt aacgccaata gggacttcc attgacgtca atggtggac tattacgt
aaactgccca cttggcagta catcaagtgt atcatatgcc aagtacgccc cctattgacg tcaatgacgg taaatgccc gcctgcatt
atgccagta catgaccta tgggcactttc ctacttggca gtacatctac gtattagtca tcgctattac catggtgatg cggttttggc
agtacatcaa tgggcgtgga tagcggttg actcacgggg atttccaagt ctccacccca ttgacgtcaa tgggagttg tttgcacc
aaaatcaacg ggactttcca aaatgtgta acaactccgc cccattgacg caaatgggcg gtaggcgtgt acgtgggag gtctataa
gcagagctct ctggctaact agagaaccca ctgcttactg gcttatcgaa attaatacga ctcactatag ggagacccaa gctgctagc
gtttaaacgg gccctctaga ctcgagcggc cgccactgtg cgcactgtg ctggatatct gcagaattcA TGCGCCTGCA CTTCCCGAG GGCGGGCAGCC
TGGCGCGCGT GACCGCGCAC CAGGCTTGCC ACCTGCGCT GGAGACTTTC ACCCGTCATC GCCAGCCGCG CGGCTGGGAA CAACTGGAGC
AGTGCGGCTA TCCGGTGCAG CGGCTGGTCG CGGCTGGTCG CCCTCTACCT GGCGGCGCGG CTGTCGTCGA CCAGGTGA CCAGGTGATC CCGAACGCCC
TGGCCAGCCC CGGCAGCGGC GGCGACCTGG GCGAAGCGAT CCGCGAGCAG CCGGAGCAGG CCGGTCTGGC CCTGACCCTG GCCGCCGCCG
AGAGCGAGCG CTTCGTCCGG CAGGGCCACG GCAACGACGA GGCCGGGCGC GCCAACGCCG ACGTGGTGAG CCTGACCTGC CCGGTCGCCG
CCGGTGAATG CGCGGGCCCG GCGACACGAGG GCGACACGCG GCTGGAGCGC AACTATCCCA CTGGCGCGGA GTTCCTCGGC GACGGCGGCG
ACGTCAGCTT CAGCACCCGC GGCACACGCA ACGAATTCAT GCATGGAGAT ACACCTACAT TGCATGGAAA TATGTTAGAT TTGCAACCAG
AGACAACTGA TCTCTACTGT TATGAGCAAT TAAATGACAG CTCAGAGGAG GAGGATGAAA TAGAGGTCC AGCTGGACAA GCAGAACCGG
ACAGAGCCCA TTACAATATT GTAACCTTTT GTTGCAAGTG TGACTCTACG CTTCGGTTGT GCCTACAAAG CACACACGTA GACATTCGTA
CTTTGAAGA CCTGTTAATG GGCACACTAG GAATTGTGTG CCCCATCTGT TCTCAAggat ccgagctcgg taccaagctt aagtttaaac
cgctgatcag cctcgactgt gccttcagt tgccagcat aaatgaggaa attgcatcgc attgtccgag ggcttgtcat taggtgtcat tgacccctga agtgccact
cccactgtcc tttcctaata aaatgaggaa attgcatcgc attgtccgag ggcctctatc gttctgagg gggtgggggt gggcaggaac
agcaaggggg agattggga agacaatagc aggcatgctg gggatgcggt gggctcttatg gcttctgagg cggaaagaac cagctgggc
tctagggggt atcccccacgc gccctgtage ggcgcattaa cctcctttc tcgccaacgt gtggtgtt gcccgcagcg tgaccgctac acttgccagc
gcctagcgc cggtctttc cgctttcttc cctaaatcg gtggccatc gtggccata gcccatcct
ttaggttcc gatttagtgc tttacggcac ctcgacccca aaaaacttga ttaggtgat gttcacgta gtggccatc gcctgatag
acggttttt gcccttgac gttggagtcc agtcttta atagtggact ctggttccaa actgaacaa cactccacc tatctggtc
tattcttttg atttataagg gatttgggg atttcgcgt agtcccagg ctcccatgc gtatgcaaag catgcatctc aattaacaa aatttaacgc gaattaatc
tgtggaatgt gtgtcagtta gggtgtgaa agtccgcaga gccaggcaga gtatgcaaag catgcatctc aataagtcag caaccatag cccgcccta
accaggtgtg gaaagtcccc agctccgccc agttgccgc atttcctgga gtcctga ctaatttttt ttatttatgc agaggccgag
actccgccca tcccgcccct aactccgccc atttcctgat ttgcatgat gttcaaaa agctcccggg agcttgtata
gcctctg cctctgagct attccagaag tagtgaggag aggcttttttg gcttttttgg ttgcaaa aggctcacg caggttctcc ggccgcttgg
tccattttcg gatcgatca agagacagga caacgacaa tcggctctc gatgccgcc gtgtccggc tgtcagcgca gggcgcccg
gtggagagc tattcggcta tgactgggca caacagacaa cggcagga aactgcagga cggcagcg cggcctatcgt ggctggccac gacgggcgtt
```

Figure 40

```
gctcgcccc cctgacgagc atcacaaaaa tcgacgctca agtcagaggt ggcgaaaccc gacaggacta taaagatacc aggcgttcc
ccctgaagc tccctcgtgc gctcctcgt tccgaccctg ccgcttaccg gatacctgtc cgcctttctc cttcggaa gcgtgcgct
ttctcatagc tcacgctgta ggtatctcag ttcggtgtag gtcgttcgct ccaagctggg ctgtgtgcac cacccccg ttcagccga
ccgctcgcc ttatccggta actatcgtct tgagtccaac ccgtaagac acgacttatc gccactggca gcagccactg gtaacaggat
tagcagagcg aggtatgtag gcggtgctac agagttcttg aagtggtggc ctaactacgg ctacactaga agaacagtat ttggtatctg
cgctctgctg aagccagtta ccttcggaaa aagagttggt agctcttgat agctcttgat cggcaaaca aaccacccgct ggtagcggtg gttttttgt
ttgcaagcag cagattacgc gcagaaaaaa ggatctcaa gaagatcctt tgatcttttc tacgggtct gacgctcagt ggaacgaaaa
ctcacgttaa gggattttgg tcatgagatt atcaaaaagg atcttcacct agatccttt aaattaaaaa tgaagtttta aatcaatcta
aagtatatat gagtaaactt ggtctgacag ttaccaatgc ttaatcagtg aggcacctat ctcagcgatc tgtctatttc gttcatccat
agttgcctga ctcggggggg gagtcgcctg aggtctgcct cgtgaagaag gtgttgctga ctcataccag ggcaacgttg ttgccattgc
tacaggcatc gtgtgtcac gtcgtcgttt tggtatgct tcattcagct cggttccca acgatcaagg cgagttacat gatccccat
gttgtgcaaa aaagcggtta gctcttccgg tctccgatc gttgtcagaa gtaagttggc cgcagtgtta tcactcatgg ttatggcago
actgcataat tctcttactg tcatgccatc cgtaagatgc ttttctgtga ctgtgagta ctcaaccaag tcattctgag aatagtgtat
gcggcgaccg agttgctctt gccggcgtc aatacggat aataccgcgc cacatagcag aactttaaaa gtgctcatca ttggaaaacg
ttcttcgggg cgaaaactct caagatctt accgctgttg agatccagtt cgatgtaacc cactcgtgca cctgaatcgc cccatcatcc
agccagaaag tgaggagcc acggttgatg agagctttgt tgtaggttgt ccagttggtg atttttgaact tttgctttgc cacggaacgg
tctgcgttgt cgggaagatg cgtagatcga tcctcaact cagcaaaagt tcgatttatt caacaaagcc gcgtcccgt caagtcagcg
taatgctctg ccagtgttac aaccaattaa ccaattctga ttagaaaaac tcatcgagaa tcaaatgaaa ctgcaattta ttcatatcag
gattatcaat accatatttt tgaaaaagc gtttctgtaa aactcaccga ggcagttcca taggatgca agatcctggt
atcggtctgc gattccgact cgtccaacat cattaattc ccctcgtcaa aaataaggtt atcaagtgag aaatcaccat
gagtgacgac tgaatccggt gagaatggca aaagcttatg cattctttcc cagacttgtt caacaggcca gccattacgc tgtcatcaa
aatcactcgc atcaaccaaa ccgttattca ttcgtgattg cgcctgagcg agacgaaata ttttcacctg cgcgatcgct gttaaaagga caattacaaa
caggaatcga atgcaaccgg cgcaggaaca ctgccagcgc atcaacaata atcaggagta tttcacctg aatcaggata ttcttctaat acctgaatg
ctgtttccc gggatcgca gtggtgagta accatgcatc atcatcatt ggcaacgcta attatcgga ggataaaat gcttgatggt cggaagaggc ataaattccg
tcagccagtt tagtctgacc atctcatctg taacatcatt gccaacgcta attatcgcga gctttgccat gtttcagaaa caactctggc gcatcggggct
tcccataaa tcgatagatt gtcgcacctg attgccccga gttgaatatg gctcataaca gagattttga gacacaagt accatataa atcagcatcc atgttggaat
tttaatcgcgg cctcgagcaa gacgtttccc gttgtgcaa tctttgtcaa tgtaacatca gagattttga gacacaagt tactgtttat gtaagcagac agttttattg
ttcatgatga tatattttta tcttgtctc atgagcggat tgtaacatca atattttga atgtatttag aaaataaaac ggcttccccc ccccccccat tattgaagca
aagtgccaaaa ttatgtctc gaaaccatta ctctgacaca ttatcatgac attaacctat aaaatatagc aataggggt tccgcgcaca tttcccgaa
tcggtgatga cggtgaaaac ctctgacaca tgcagctcccc ggagacggtc acagcttgct aaatagggt gtatcacgag gcctttcgt ctcgcgcgtt
gtcagggggg gtcagcgggt ttcggcgggt gtcggggctg gcttaactat gggcatcag agcagtgcag tgcgggagc tgcgggggc agacaagccc
gggtgaaat accgcacaga tcgtaagga gaaataccg catcagattg gctattggcc attgcatacg ttgtatccat atcataatat
gtacattat attggctcat gtccaacatt accgccatgt tgcattgat tattgactag ttattaatag taataatta cgggtcatt
```

```
agttcatagc ccatatatgg agttccgcgt tacataactt acggtaaatg gcccgcctgg ctgaccgccc aacgacccc gcccattgac
gtcaataatg acgtatgttc ccatagtaac gccaataggg acttccatt gacgtcaatg ggtggagtat ttacggtaaa ctgcccactt
ggcagtacat caagtgtatc atatgccaag tacgccccct attgacgtca atgacgtaa atggcccgcc tggcattatg ccagtacat
gacctatgg gactttccta cttggcagta catctacgta ttagtcatcg ctattaccat ggtgatgcgg ttttggcagt acatcaatgg
gcgtggatag cggtttgact cacgggatt tccaagtctc caccccattg acgtcaatgg gagtttgttt tggcaccaaa atcaacggga
ctttccaaaa tgtcgtaaca actccgcccc attgacgcaa atgggcggta ggcgtgtacg gtgggaggtc tatataagca gagctgttt
agtgaaccgt cagatcgcct ggagacgcca tccacgctgt tttgacctcc ataagcaga ccgggaccga tccagcctcc gcggccgga
acggtgcatt ggaacgcgga ttccccgtgc caagagtgac gtaagtaccg cctatagact ctataggcac accccttgg ctcttatgca
tgctatactg ttttggctt gggcctata cacccccgct tcctatgct atagtgatg gtatagctta gcctataggt gtgggttatt
gaccattatt gaccactcca acggtggagg gcagtgagt ctgagcagta ctcgttgctg cgcgcgcgc caccagacat aatagctgac
agactaacag actgttcctt tccatggtc ttttctgcag tcacgtcgt cgacATGCTG CTATCCGTGC CGCTGCTGCT CGGCCTCCTC
GGCCTGGCCG TCGCCGAGCC TGCCGTCTAC TTCAAGGAGC AGTTCCTGA CGGGGACGGG CGAGAGAAA GATAAAGGTT TGCAGACAAG CCAGGATGCA
AAGTCAGATT TTGGCAAATT CGTTCTCAGT TCCGGCAAGT TCTACGGTGA ACAAAGGCCA GACGCTGGTG GTGCAGTTCA CGGTGAAACA TGAGCAGAAC
CGCTTTTATG CTCTGTCGGC CAGTTTCGAG CCTTTCAGCA GTTTCCTAATA GTTTGGACCA CACGAGACT CAGAATACAA CATCATGTTT
ATCGACTGTG GGGGCGGCTA TGTGAAGCTG TGTGAAGCTG TTTCCTAATA GTTTGGACCA CACGAGACT CAGAATACAA CATCATGTTT
GGTCCCGACA TCTGTGGCCC TGGCACCAAG AAGGTTCATG TCATCTTCAA CTACAAGGGC AAGAACGTGC TGATCAACAA GGACATCCGT
TGCAAGGATG ATGAGTTTAC ACACCTGTAC TGCGGCCAGA AACACCTAT GAGGTGAAGA TTGACAACAG CCAGGTGGAG
TCCGGCTCCT TGGAAGACGA TTGGGACTTC CTGCCACCCA AGAAGATAAA GGATCCTGAT GCTTCAAAAC TGGAAGACTG CCAGGTGGAG
GCCAAGATCG ATGATCCCAC AGATCCCAAG CCTGAGGACT GGGACAAGCC CGAGCATATC CCTGACCCTG ATGCTAAGAA GCCGAGGAC
TGGGATGAAG AGATGACGG AGAGTGGGAA CCCCCAGTGA TTCAGAACCC TGAGTACAAG GGTGAGTGGGA AGCCCCGGCA GATCGACAAC
CCAGATTACA AGGGCACTTG GATCCACCCA GAAATTGACA ACCCCGAGTA TTCTCCCGAT CTTCCTCATC ACCAGTATCT ATGCCTATGA TAACTTTGGC
GTGCTGGGCC TGGACTCTG GCAGTTCAAG TCTGGCACCA TCTTTGACAA CAAACAGGAC CAAACAGGAC ATGCCATAGC TGAGGAGTTT
GGCAACGAGA CGTGGGGCGT AACAAAGGCA GCAGAGAAC GAGGAGGACA GAGGAGGAGA GGCTTAAGGA GGAGGAAGAA
GACAAGAAAC GCAAGAGAGA GGAGGAGGCA GAGGACAAGG GAGGATGATGA GGACAAAGAT GAGGATGAGG AGGATGAGGA GGACAAGGAG
GAAGATGAGG AGGAAGATGT CCCCGGCCAG GCCAAGGACG AGCTGgaatt cATGCATGGA CATGCATGA GATACACCTA CATTGCATGA ATATATGTTA
GATTTGCAAC CAGAGACAAC TGATCTCTAC GGTTATGGGC AATTAAATGA CAGCTCAGAG GTGTGACTCT ACGCTTCGGT TGTGCGTACA TCCAGCTGGA
CAAGCAGAAC CGGACAGAGC CCATTACAAT ATTGTAACCT TTTGTTGCAA GTGTGACTCT ACGCTTCGGT TGTGCGTACA AAGCACACAC
GTAGACATTC GTACTTTGGA AGACCTGTTA ATGGGCACAC TAGGAATTGT GTGCCCCATC TGTTCTCAGA AACCATAAgg atccagatct
ttttccctct gccaaaaatt atgggacat catgaagcc cttgagcatc tgacttctgg ctaataagg aaatttattt tcattgcaat
agtgtgttgg aatttttgt gtctctcact cggaaggg tatgggaggg caaatcattt aaaacatcag aagtagtatt tggtttagag
tttggcaaca tatgccatt cctccgttc ctgctcact gactcgctgc gctcggtcgt tcggctgcgg cgagcgtat cagctcactc
aaaggcggta atacgttat ccacagaatc aggggataac gcaggaaaga acatgtgagc aaaaggcca aaaggccag gaaccgtaa
aaaggccgcg ttgctggcgt ttttccatag
          5970
```

Figure 40 Cont.

RNA INTERFERENCE THAT BLOCKS EXPRESSION OF PRO-APOPTOTIC PROTEINS POTENTIATES IMMUNITY INDUCED BY DNA AND TRANSFECTED DENDRITIC CELL VACCINES

CROSS-REFERENCE TO RELATED APPLICATIONS

This application is a continuation-in-part of Application No. PCT/US2005/047200, filed Dec. 30, 2005, which claims the benefit of U.S. Provisional Application No. 60/641,901, filed Jan. 6, 2005, and U.S. Provisional Application No. 60/738,900, filed Nov. 22, 2005, the contents of all of which are specifically incorporated by reference herein.

BACKGROUND OF THE INVENTION

1. Field of the Invention

The present invention in the fields of molecular biology, immunology and medicine relates to combinations or mixtures of nucleic acid molecules and chimeric nucleic acid molecules that encode an antigen and a small interfering RNA (siRNA). The expression of the siRNA blocks expression of one or more an anti-apoptotic protein in vivo. This results in prolonging the life of important antigen presenting cells, dendritic cells (DCs), and as a consequence, the more potent induction and enhancement immune responses, primarily cytotoxic T lymphocyte (CTL) responses to specific antigens such as tumor or viral antigens.

2. Description of the Background Art

Cytotoxic T lymphocytes (CTL) are critical effectors of anti-viral and antitumor responses (reviewed in Chen, C H et al., J Biomed Sci. 5: 231-252, 1998; Pardoll, D M. Nat Med. 4: 525-531, 1998; Wang, R F et al., Immunol Rev. 170: 85-100, 1999). Activated CTL are effector cells that mediate antitumor immunity by direct lysis of their target tumor cells or virus-infected cells and by releasing of cytokines that orchestrate immune and inflammatory responses that interfere with tumor growth or metastasis, or viral spread. Depletion of CD8$^+$ CTL leads to the loss of antitumor effects of several cancer vaccines (Lin, K-Y et al., Canc Res 56: 21-26, 1996; Chen, C-H et al., Canc Res. 60: 1035-42, 2000). Therefore, the enhancement of antigen presentation through the MHC class I pathway to CD8$^+$ T cells has been a primary focus of cancer immunotherapy.

Naked DNA vaccines have emerged recently as attractive approaches for vaccine development (reviewed in Hoffman, S L et al., Ann NY Acad Sci 772: 88-94, 1995; Robinson, H L. Vaccine 15: 785-787, 1997; Donnelly, J J et al., Annu Rev Immunol 15: 617-648, 1997; Klinman, D M et al., Immunity 11: 123-129, 1999; Restifo, N P et al., Gene Ther 7: 89-92, 2000; Gurunathan, S et al., Annu Rev Immunol 18: 927-974, 2000). DNA vaccines generated long-term cell-mediated immunity (reviewed in Gurunathan, S et al., Curr Opin Immunol 12: 442-447, 2000) and can generate CD8$^+$ T cell responses in vaccinated humans (Wang, R et al. Science 282: 476-480, 1998).

However, one limitation of these vaccines is their lack of potency, since the DNA vaccine vectors generally do not have the intrinsic ability to be amplified and to spread in vivo as do some replicating viral vaccine vectors. Furthermore, some tumor antigens such as the E7 and E6 proteins of human papillomavirus-16 ("HPV-16") are weak immunogens (Chen et al., 2000, supra). Therefore, there is a need in the art for strategies to enhance DNA vaccine potency, particularly for more effective cancer and viral immunotherapy.

The present inventors and their colleagues demonstrated that linkage of HPV-16 E7 antigen to a number of immunogenicity-potentiating polypeptides (Kim J W et al., Gene Ther. 11:1011-18, 2004,), such as Mycobacterium tuberculosis (Mtb) heat shock protein 70 (Hsp70) (Chen et al., supra; Wu et al., WO 01/29233) and CRT (Cheng W F et al., J Clin Invest, 2001, 108:669-78; WO/0212281) result in the enhancement of DNA vaccine potency. See, also Cheng W F et al., Vaccine 23:3864-74, 2005; Peng S et al., J Biomed Sci. 12:689-700, 2005; Peng S et al., J Virol. 2004, 78:8468-76; Peng S et al., Gene Ther. 2005 (Sep. 22; Epublished ahead of print)

Others have shown, using protein vaccines, as distinct from DNA immunogens, that immunization with HSP complexes isolated from tumor or virus-infected cells potentiated antitumor immunity (Janetzki, S et al., J Immunother 21:269-7, 1998) or antiviral immunity (Heikema, A et al., Immunol Lett 57:69-74, 1997). Immunogenic HSP-peptide complexes could be reconstituted in vitro by mixing the peptides with HSPs (Ciupitu, A M et al., 1998. J Exp Med 187:685-9, 1998). HSP-based protein vaccines have been created by fusing antigens to HSPs (Suzue, K et al., J Immunol 156:873-79, 1996). However, prior to the discoveries of the present inventors and their colleagues since about 1999 with DNA immunogens, HSP vaccines (and those employing other intracellular transport proteins or intercellular spreading proteins) were limited to peptide/protein molecules that were typically produced bacteria using bacterial expression vectors and purified therefrom. The present inventors and their colleagues were the first to provide naked DNA and self-replicating RNA vaccines that incorporated HSP70 and other immunogenicity-potentiating polypeptides. The present inventors and their colleagues were also the first to demonstrate that linking antigen to intracellular targeting moieties calreticulin (CRT), domain II of Pseudomonas aeruginosa exotoxin A (ETA(dII)), or the sorting signal of the lysosome-associated membrane protein type 1 (Sig/LAMP-1) enhanced DNA vaccine potency compared to compositions comprising only DNA encoding the antigen of interest. To enhance MHC class II antigen processing, one of the present inventors and colleagues (Lin, K Y et al., 1996, Canc Res 56: 21-26) linked the sorting signals of the lysosome-associated membrane protein (LAMP-1) to the cytoplasmic/nuclear human papilloma virus (HPV-16) E7 antigen, creating a chimera (Sig/E7/LAMP-1). Expression of this chimera in vitro and in vivo with a recombinant vaccinia vector had targeted E7 to endosomal and lysosomal compartments and enhanced MHC class II presentation to CD4+ T cells. This vector was found to induce in vivo protection against an E7+ tumor, TC-1 so that 80% of mice vaccinated with the chimeric Sig/E7/LAMP1 vaccinia remained tumor free 3 months after tumor injection. Treatment with the Sig/E7/LAMP-1 vaccinia vaccine cured mice with small established TC-1 tumors, whereas the wild-type E7-vaccinia showed no effect on this established tumor burden. These findings point to the importance of adding an immunopotentiating "element" (in the form of DNA encoding that "element") to DNA encoding an antigen to enhance in vivo potency of a recombinant DNA vaccine for antigens that are presented as either MHC class I- or MHC class II-antigen complexes, such as by rerouting a cytosolic tumor antigen to the endosomal/lysosomal compartment.

Intradermal administration of DNA vaccines via gene gun can efficiently deliver genes of interest into professional antigen presenting cells (APCs) in vivo (Condon C et al., Nat Med, 2: 1122-28, 1996). The skin contains numerous bone marrow-derived APCs (called Langerhans cells) that are able to move through the lymphatic system from the site of injection to draining lymph nodes (LNs), where they can prime antigen-specific T cells (Porgador A et al., *J Exp Med* 188: 1075-1082, 1998). Powerful APCs in other sites, particularly in lymphatic tissue are dendritic cells (DC). Gene gun immunization therefore provides the opportunity to test vaccine strategies that require direct delivery of DNA or RNA to APCs.

Antigen presentation by DCs is a critical element for the induction of the cellular immune responses that mediate various types of immunotherapy, particularly tumor immunotherapy. Several studies demonstrated that immunization with tumor antigen-pulsed DCs could break the tolerance of the immune system against antigens expressed by tumor cells and in some cases generate appreciable clinical responses. Thus, DC-based vaccines represent a promising method for the treatment of malignancies. See, for example, Gunzer, M et al., *Crit Rev Immunol* 21: 133-45, 2001; Engleman, E G Dendritic cell-based cancer immunotherapy. *Semin Oncol* 30:23-29, 2003; Schuler, G et al., *Curr Opin Immunol* 15:138-147, 2003; Cerundolo, V et al., Dendritic cells: a journey from laboratory to clinic. *Nat Immunol* 5:7-10, 2004; Figdor, C G et al., *Nat Med* 10:475-480, 2004; Markiewicz, M A et al., *Cancer Invest* 22:417-434, 2004; Turtle, C J et al., *Curr Drug Targets* 5:17-39, 2004).

Dendritic cell-based vaccines have become an important approach for the treatment of malignancies. Numerous techniques have recently been designed to optimize dendritic cell activation, tumor antigen delivery to dendritic cells, and induction of tumor-specific immune responses in vivo. Dendritic cells, however, have a limited life span because they are subject to apoptotic cell death mediated by T cells, hindering their long-term ability to prime antigen-specific T cells.

DCs, however, have a limited life span that hinders their long-term ability to prime antigen-specific T cells (see Ronchese, F et al. *J Exp Med* 194:F23-26, 2001). A principal contributor to the shortened lifespan of DCs is CTL-induced apoptosis. After activation by DCs, CTLs that recognize epitopes can kill target cells expressing these epitopes, typically presented by MHC Class I proteins. Because DCs express MHC-I:antigen peptide complexes, newly primed CTLs can kill the very DCs that activated them (Medema, J P et al., *J Exp Med* 194:657-667, 2001). Thus, DC-based vaccination should be enhanced by inhibiting apoptosis and prolong survival of antigen-expressing DCs in vivo (Kim, T W et al., *J Immunol* 171:2970-2976, 2003a; Kim, T W et al., *J Clin Invest* 112:109-17, 2003(b); and a patent application by the present inventors and colleagues WO05/047501 (26 May 2005) incorporated herein by reference in its entirety.

The present inventors and their colleagues have used gene gun immunization of DNA compositions to test vaccine strategies that involve intracellular targeting strategies that direct delivery of DNA or RNA to APCs. The targeting molecules (using coding DNA linked to DNA encoding an antigen) that have shown potent effects include *Mycobacterium tuberculosis* heat shock protein 70 (HSP70) (Chen C H et al., 2000, *Cancer Res* 60:1035-42, 2000), calreticulin (CRT; Cheng W F, 2001, supra), and the sorting signal of the lysosome-associated membrane protein 1 (LAMP-1; Ji H et al., *Hum Gene Therapy*, 10:2727-40, 1999).

Vaccination with DNA vectors that encode such fusion proteins are able to route an antigen (generally exemplified with HPV-16 E6 and E7) to desired subcellular compartments, and enhance antigen processing and presentation to T cells. Therefore, direct delivery of DNA vaccines into DCs via gene gun provides an opportunity to modify the quality and quantity of DNA-transfected DCs and influence vaccine potency.

T cell-mediated apoptotic cell death can occur through two major pathways, the intrinsic and the extrinsic pathways. See, for example, Russell, J H et al., *Annu Rev Immunol* 20:323-370, 2002). In general, death domain-containing receptors such as CD95 (APO-1/Fas) can sense the external signal (such as Fas ligand) and activate the extrinsic apoptotic pathway through the Fas-associated death domain (Fadd). This pathway is mediated by recruitment and activation of caspase-8, an initiator caspase, in the death-inducing signaling complex (DISC) followed by direct cleavage of downstream effector caspases.

The intrinsic pathway (granzyme B/perforin-mediated apoptosis), important for T cell-mediated induction of apoptotic DC death, initiates from within the cell. The pore-forming protein perforin and the serine protease granzyme B secreted into cells by antigen-specific $CD8^+$ T cells induce intracellular changes, such as DNA damage, resulting in the release of a number of pro-apoptotic factors from mitochondria, such as cytochrome c, leading to the activation of another initiator caspase, caspase-9 (Jacotot, E et al., *Ann NY Acad Sci* 887:18-30, 1999; Korsmeyer, S J et al., *Cell Death Differ* 7:1166-73, 2000; Degli Esposti, M et al., Dive, C. *Biochem Biophys Res Commun* 304:455-61, 2003; Opferman J T et al., *Nat Immunol* 4: 410-15, 2003). 5-61, 2003; Opferman J T et al., *Nat Immunol* 4: 410-15, 2003). Activated caspase-9 leads to the activation of effector caspases (caspase-3, -6, and -7) in a protein complex called the apoptosome (for review, see Johnson, C R et al., *Apoptosis* 9:423-27, 2004) leading to proteolysis of a cascade of substrates and apoptotic death.

Thus Bak, Bax, and caspase 9 are clearly important pro-apoptotic proteins for the intrinsic apoptotic pathway and caspases-8 and -3 are is an important pro-apoptotic proteins in the extrinsic apoptotic pathway. Because of the role of Bak and Bax as gatekeepers in the intrinsic apoptotic pathway, the present inventors have conceived of targeting these genes for inhibition by RNA interference (RNAi) to diminish DC apoptosis. This is disclosed in detail and exemplified below. However, the present inventors conception includes a similar targeting of caspase-9, caspase-3 and caspase-8.

RNA interference (RNAi) is a recently reported phenomenon that has developed into a new approach for elucidating and regulating gene function. RNAi is a sequence-specific, post-transcriptional, gene-silencing mechanism that is effected through double-stranded RNA (dsRNA) molecules homologous to a sequence of the target gene (Elbashir, S M et al., *Nature* 411:494-498, 2001; Fire, A et al., *Nature* 391:806-811, 1998; Tuschl, T et al., *Genes Dev* 13:3191-3197, 1999). Fragments of the dsRNA called "small interfering" RNAs (siRNAs) can rapidly induce loss of function, and only a few molecules are required in a cell to produce the effect (Fire et al., supra) through hybrid formation between a homologous siRNA and mRNA (Lin, S L et al., *Curr Cancer Drug Targets* 1:241-247, 2001). A member of the RNase III family of nucleases named dicer has been identified as being involved in processing (Bernstein, E et al., *Nature* 409:363-366, 2001). DNA vector-mediated RNAi technology has made it possible to develop therapeutic applications for use in mammalian cells (Sui, G et al., *Proc Natl Acad Sci USA* 99:5515-5520, 2002; McCaffrey, A P et al., *Nature* 418:38-39, 2002; Lee, N S et al., *Nat Biotechnol* 20:500-505, 2002). There have been several reports of delivery of siRNA by retroviral vectors for stable expression (Barton, G. M et al., *Proc Natl Acad Sci USA* 99:14943-14945, 2002; Paddison, P J et al., *Cancer Cell* 2:17-23, 2002; Rubinson, D A et al., *Nat Genet* 33:401-406, 2003; Tiscornia, G et al., *Proc Natl Acad Sci USA* 100:1844-1848, 2003) or by adenoviral vectors for transient expression (Xia, H et al., *Nat Biotechnol* 20:1006-1010, 2002). RNAi may be effected by small interfering RNA molecules (siRNA) that induce sequence-specific degradation of mRNA or by inhibiting translation of its complementary mRNA (see, for example, Mittal V. *Nat Rev Genetics* 5:355-65, 2004). Use of this approach to prolong the life of DCs by targeting pro-apoptotic proteins with the appropriate siRNAs is one of the objects of the present invention.

SUMMARY OF THE INVENTION

Partial List of Abbreviations Used

APC, antigen presenting cell; BM, bone marrow; BM-DC, BM-derived dendritic cells; CMV, cytomegalovirus; CTL, cytotoxic T lymphocyte; CRT, calreticulin; DC, dendritic cell; E6, HPV oncoprotein E6; E7, HPV oncoprotein E7; ELISA, enzyme-linked immunosorbent assay; GFP, green fluorescent protein; HPV, human papillomavirus; HSP, heat shock protein; Hsp70, mycobacterial heat shock protein 70; IFNγ, interferon-γ; i.m., intramuscular(ly); i.v., intravenous; IPP, immunogenicity-potentiating (or -promoting) polypeptide; LN, lymph node; MHC, major histocompatibility complex; PBS, phosphate-buffered saline; PCR, polymerase chain reaction; RNAi, RNA interference or interfering RNA; siRNA, small interfering RNA; siNA, small interfering nucleic acid; β-gal, β-galactosidase.

The present inventors have designed and disclose herein an immunotherapeutic strategy that combines antigen-encoding DNA vaccine compositions with siRNAs directed to pro-apoptotic genes, primarily Bak and Bax, the products of which are known to lead to apoptotic death of, inter alia, DCs. The present inventors conceived that gene gun delivery (particle bombardment) or delivery by other appropriate routes of siRNA specific for Bak and/or Bax to antigen-expressing (antigen-presenting) DCs would prolong the lives of such transfected DCs and lead to enhanced generation of antigen-specific T cell-mediated immune responses in vivo.

The present disclosure shows the impact of intradermal (gene gun) coadministration of DNA vaccines encoding HPV-16 E7 antigen with Bak and/or Bax siRNA. The present inventors chose HPV-16 E7 as a model antigen because HPVs, particularly HPV-16, are associated with a majority of cervical cancers, and E7 (and E6) is essential for oncogenic cell transformation. Use of constructs comprising DNA encoding HPV protein E6 would be expected to have the same activity (as supported by comparisons between the two using the present inventors' other immunopotentiating strategies). Minimally genetically modified E7 or E6 proteins ("detox") which have been rendered incapable of oncogenic activity by between 1 and 3 point mutations may be used in place of wild-type E7 and E6, and are safer for human subjects.

Effective vaccines against E7 (and/or E6) can be used to control HPV infections and HPV-associated lesions. As disclosed herein, evaluation of E7-specific immune responses, antitumor effects, and survival of DNA-transfected DCs, confirmed the present inventors' conception that co-administration of (i) a DNA vaccine or immunogen comprising sequences encoding an antigen with Bak- and/or Bax-specific siRNA (which term is used interchangeably with "Bak- or Bax siRNA") is a successful and innovative strategy for enhancing DNA vaccine potency.

As disclosed in herein (see Examples 8 et seq.) in DCs that are transfected with Bak/Bax siRNA Bak and Bax protein expression is abolished. According to the present invention, DCs transfected with Bak and Bax siRNA that are pulsed (loaded) with an antigenic peptide, so that they present that peptide, induce more potent antigen-specific $CD8^+$ T cell immune responses and antitumor effects in vaccinated subject mice, compared to peptide-pulsed DCs transfected with control siRNA. Bak/Bax siRNA-transfected DCs survive better in vivo than do antigenic peptide-loaded DCs transfected with a control siRNA in mice into which antigen-specific $CD8^+$ T cells (able to kill the antigen-presenting DCs) have been adoptively transferred. Bone marrow-derived DCs (BM-DCs) and long-term DC cell lines as shown to be useful cellular immunogens.

The foregoing conceptions and discoveries provide a basis for clinical therapy of pathologies associated with any antigen, such as an antigen from a pathogenic microorganism (virus, bacterium, parasite), and pathogenic "endogenous" cells such as a tumor or cancer cells. Examples of viral antigens against which this strategy is exemplified herein are the two oncoprotein antigens from HPV-16, namely E6 and E7.

The invention exploits siRNA-based strategies to manipulate the functions, primarily to promote the survival, of DCs exposed to the siRNA ex vivo and/or in vivo. The siRNA-encoding constructs described can be used in combination with the strategy of enhancing the presentation of antigen through the MHC class I pathway to $CD8^+$ T cells by exploiting the features of certain polypeptides to target or translocate the antigenic polypeptide to which they are fused. Such polypeptide are referred to collectively herein as "immunogenicity-potentiating (or -promoting) polypeptide" or "IPP" to reflect this general property, even though these IPP's may act by any of a number of cellular and molecular mechanisms that may or may not share common steps. This designation is intended to be interchangeable with the term "targeting polypeptide." Inclusion of nucleic acid sequences that encode polypeptides that modify the way the antigen encoded by molecular vaccine is "received" or "handled" by the immune system serve as a basis for enhancing vaccine potency. All of these polypeptides in some way, contribute to the augmentation of the specific immune response to an antigen to which they are linked by one or another means that these molecules "employ" to effect the way in which the cells of the immune system handle the antigen or respond with cell proliferation and/or survival. IPP's may be produced as fusion or chimeric polypeptides with the antigen, or may be expressed from the same nucleic acid vector but produced as distinct expression products.

In addition to the strategy of including DNA encoding such IPPs in their vaccine constructs, the present invention harnesses the additional biological mechanism of inhibiting apoptosis by employing the RNAi approach significantly enhances T cell responses to DNA vaccine comprising antigen-coding sequences (with or without linked sequences encoding such IPPs).

Intradermal vaccination by gene gun efficiently delivers a DNA vaccine into DCs of the skin, resulting in the activation and priming of antigen-specific T cells in vivo. DCs, however, have a limited life span, hindering their long-term ability to prime antigen-specific T cells. According to the present invention, a strategy that prolongs the survival of DNA-transduced DCs enhances priming of antigen-specific T cells and thereby, increase DNA vaccine potency. As described herein co-delivery of siRNA that suppresses the expression of apoptotic pathways via Bak and Bax, prolongs the survival of transduced DCs. More importantly, vaccinated subjects exhibited significant enhancement in antigen-specific CD8+ T cell immune responses, resulting in a potent antitumor effect against antigen-expressing tumors. In another embodiment, instead of delivering the siRNA directly via gene gun, DNA encoding the siRNA is delivered either as part of the same vector that encodes the antigen, or as a separate vector that is co-administered.

The combination of a strategy to prolong DC life (via siRNA) with intracellular targeting strategies afforded by certain IPPs produces a more effective DNA vaccine against E7, E6 or any antigen. Co-administration of siRNA (or DNA encoding siRNA) directed to Bak and/or Bax with DNA encoding antigen (exemplified as E7) linked to DNA encoding HSP70, CRT, or Sig/LAMP-1 results in further enhancement of the antigen (here E7)-specific CD8+ T cell response for all three types of constructs. This combination increases CD8+ T cell functional avidity, and increases the E7-specific CD4+ Th1 cell response, enhances tumor therapeutic effect, and will yield more durable tumor protection when compared with mice vaccinated without the siRNA. Therefore, DNA vaccines that combine strategies to enhance intracellular antigen processing and prolong DC life have clinical utility for control of viral infection and neoplasia, among other forms of pathology where immunotherapy is useful as an ameliorative or curative therapy.

Thus, the present invention is directed to a nucleic acid composition useful as an immunogen, comprising a combination of:
(a) a first nucleic acid molecule comprising a first sequence encoding an epitope of an antigenic polypeptide or peptide; and optionally, linked to the first sequence, directly or via a linker, a second sequence that encodes an immunogenicity-potentiating polypeptide (IPP); and
(c) a second nucleic acid molecule the activity or expression of which stimulates development of an immune response to the epitope, which second nucleic molecule is (i) a siNA or (ii) DNA that encodes the siNA, wherein the siNA has a sequence that is sufficiently complementary to, and thus targets, the sequence of mRNA that encodes a pro-apoptotic protein expressed in a dendritic cell (DC), such that the activity or expression of the siNA in the cell results in inhibition of or loss of expression of the mRNA, resulting in inhibition of apoptosis and increased survival of DCs, wherein the development of the immune response is stimulated.

The IPP above is preferably fused in frame to the first sequence such that the first and the second sequences encode a fusion protein comprising the antigenic epitope and the IPP. The IPP acts in potentiating an immune response preferably by promoting:
(a) processing of the linked antigenic polypeptide via the MHC class I pathway or targeting of a cellular compartment that increases the processing;
(b) development, accumulation or activity of antigen presenting cells or targeting of antigen to compartments of the antigen presenting cells leading to enhanced antigen presentation;
(c) intercellular transport and spreading of the antigen; or
(d) any combination of (a)-(c).

In the above composition, the IPP is: preferably
(a) the sorting signal of the lysosome-associated membrane protein type 1 (Sig/LAMP-1)
(b) a mycobacterial HSP70 polypeptide, the C-terminal domain thereof, or a functional homologue or derivative of the polypeptide or domain;
(c) a viral intercellular spreading protein selected from the group of herpes simplex virus-1 VP22 protein, Marek's disease virus UL49 protein or a functional homologue or derivative thereof;
(d) an endoplasmic reticulum chaperone polypeptide selected from the group of calreticulin or a domain thereof, ER60, GRP94, gp96, or a functional homologue or derivative thereof.
(e) domain II of *Pseudomonas* exotoxin ETA or a functional homologue or derivative thereof;
(f) a polypeptide that targets the centrosome compartment of a cell selected from γ-tubulin or a functional homologue or derivative thereof; or
(g) a polypeptide that stimulates DC precursors or activates DC activity selected from the group consisting of GM-CSF, Flt3-ligand extracellular domain, or a functional homologue or derivative thereof.

In the above composition the pro-apoptotic protein is preferably selected from the group consisting of one or more of (a) Bak, (b) Bax, (c) caspase-8, (d) caspase-9 and (e) caspase-3. Most preferably the siNA targets the encoding mRNA of anti-apoptotic protein Bak and/or Bax.

Preferably the siNA is an siRNA. The siRNA preferably targets SEQ ID NO:4 of Bak and/or SEQ ID NO:8 of Bax. The preferred siRNA is selected from the group consisting of (a) SEQ ID NO:1/SEQ ID NO:2; and (b) SEQ ID NO:5/SEQ ID NO:6.

The antigenic polypeptide or peptide of the above composition preferably comprises an epitope that binds to and is presented on surfaces of antigen-presenting cells by MHC class I proteins. The epitope may be between about 8 and about 11 amino acid residues in length.

The antigenic polypeptide or peptide of the above composition preferably (i) is derived from a pathogen such as a mammalian cell (e.g., specific or tumor-associated antigen), a microorganism or a virus; or (ii) cross-reacts with an antigen of the pathogen; or (iii) is expressed on the surface of a pathogenic cell. Preferred antigens are from a human papilloma virus, primarily the E7 and E6 polypeptide, including the "detox" forms of these polypeptides.

In the above composition, the first nucleic acid molecule is preferably an expression vector comprising a promoter operatively linked to the first and/or the second sequence; the promoter is preferably one that is expressed in an APC, most preferably in a DC.

Also provided herein are particles comprising a material suitable for introduction into a cell or an animal by particle bombardment to which particles is bound the above composition. Also intended is a combination of first and second particles each comprising a material is suitable for introduction into a cell or an animal by particle bombardment, and to which particles is bound the above composition. Wherein (a) the first nucleic acid molecules are bound to a first set of particles; and (b) the second nucleic acids (the siNA, preferably siRNA) are bound to a second set of particles. The preferred particles are gold particles.

This invention includes a pharmaceutical composition capable of inducing or enhancing an antigen specific immune response, comprising any of the above compositions or particles and a pharmaceutically acceptable carrier or excipient.

In another embodiment, the invention is directed to a method of inducing or enhancing an antigen specific immune response in a subject comprising administering to the subject an effective amount of the above composition or particles thereby inducing or enhancing the antigen specific immune response. The antigen specific immune response is preferably one mediated at least in part by $CD8^+$ cytotoxic T lymphocytes (CTL). The method is preferably carried out on a mammalian, most preferably a human subject. In the method, the composition or particles are preferably administered intradermally by particle bombardment (gene gun). The composition may also be administered intratumorally or peritumorally.

One embodiment is directed to a method of increasing the numbers of CD8+ CTLs specific for a selected desired antigen in a subject comprising administering an effective amount of the above composition, particles or pharmaceutical compositions, wherein the antigenic peptide or polypeptide comprises an epitope that binds to and is presented on surfaces of APCs by MHC class I proteins.

Also provided is a method of inhibiting the growth of a tumor in a subject comprising administering an effective amount of the above composition, particles or pharmaceutical compositions, wherein the antigenic epitopes are those expressed by the tumor or ones cross reactive with those expressed by the tumor.

This invention is further directed to an immunogenic cellular composition, including a pharmaceutical composition thereof, comprising DCs which have been modified by:
(a) loading the DCs with an antigen so that the antigen is expressed on the DC surface, or transducing or transfecting the DCs with DNA that encodes an antigen fused to an IPP; and
(b) transfecting the DCs with a nucleic acid molecule that is (i) a siNA or (ii) DNA that encodes the siNA, preferably siRNA, wherein the siNA has a sequence that is sufficiently complementary to the sequence of, and thus targets, mRNA that encodes a pro-apoptotic protein expressed in the DC, such that expression or activity the siNA in the cell results in diminution or loss of expression of the mRNA, resulting in inhibition of apoptosis and prolonged survival of the DC.

The pro-apoptotic protein target is preferably one or more of (a) Bak, (b) Bax, (c) caspase-8, (d) caspase-9 and (e) caspase-3. Preferably, the siRNA targets Bak and/or Bax; preferred targeted sequences are SEQ ID NO:4 of Bak and SEQ ID NO:8 of Bax. Preferred siRNA is selected is (a) SEQ ID NO:1/SEQ ID NO:2; or b) SEQ ID NO:5/SEQ ID NO:6.

A method of inducing or enhancing an antigen specific immune response in a subject comprises administering to the subject an effective amount of the above DC composition thereby inducing or enhancing the antigen specific immune response.

A method of increasing the numbers of CD8+ CTLs specific for a selected desired antigen in a subject comprises administering an effective amount of the DC composition wherein the loaded antigen or the antigen expressed from the transduced DNA comprises an epitope that binds to and is presented on the DC surface by MHC class I proteins, thereby increasing the numbers of antigen-specific CD8+ CTLs.

A method of inhibiting the tumor growth in a subject comprises administering an effective amount of the DC composition, wherein the antigenic epitopes are those expressed by the tumor or ones cross reactive with those expressed by the tumor, thereby inhibiting growth of the tumor.

The invention is directed to use of a nucleic acid composition as defined above or particles as defined above or a DC composition as defined above in the manufacture of a medicament, preferably a vaccine, for inducing or enhancing an antigen specific immune response in a subject.

Also included is the use of a nucleic acid composition as defined above, particles as defined above, or a DC composition as defined above in the manufacture of a medicament for inhibiting the growth of a tumor or treating cancer in a subject wherein the antigenic epitopes are those expressed by the tumor or ones cross-reactive with those expressed by the tumor.

BRIEF DESCRIPTION OF THE DRAWINGS

FIGS. 1-3. Detection of Bak and Bax expression and evaluation of resistance to apoptotic cell death after delivery of Bak and/or Bax siRNA. FIG. 1 is a Western blot analysis demonstrating expression of Bak and/or Bax protein in transfected cells. FIG. 2 is a Western blot demonstrating kinetics of Bak and Bax expression in siRNA-transfected DC-1 cells. β-actin was used as an internal control for quantification of protein expression.

FIGS. 4 and 5 show results of mice vaccinated with pcDNA3-E7. FIGS. 6 and 7 shows results of mice vaccinated with pcDNA3-HA or -OVA. pcDNA3 encoding Bak+Bax siRNA served as a negative control. FIG. 4 shows representative flow cytometry results. FIG. 5 represents the number of IFN-γ-expressing E7-specific CD8+ T cells in a population of spleen cells from vaccinated mice. FIG. 6 shows representative flow cytometric data. FIG. 7 represents the number of IFN-γ-expressing HA- or OVA-specific CD8+ T cells in a spleen cell population from vaccinated mice.

FIG. 8 shows results of an in vivo tumor protection experiment. pcDNA3 encoding Bak+Bax siRNA was used as a negative control. FIG. 9 shows results of an in vivo antibody depletion experiments indicating the contribution of lymphocyte subsets to the observed protective effect above. FIG. 10 shows results of an in vivo tumor therapy experiment using the hematogenous spread lung metastasis model. pcDNA3 encoding Bak+Bax siRNA was used as a negative control.

FIG. 13 is a representative example of a flow cytometric analysis. FIG. 12, represents the number of IFN-γ-expressing E7-specific CD8+ T cells in a spleen cell population from vaccinated mice. FIG. 13 represents the number of IFN-γ-expressing E7-specific CD4+ Th1 cells in a spleen cell population from vaccinated mice. FIG. 14 represents the number of IL-4-expressing E7-specific CD4+ Th2 cells in the spleen cell population from vaccinated mice.

FIG. 15, is a representative sample of a flow cytometry analysis 2 and 5 days after intradermal administration of pcDNA3-E7/GFP. The numbers indicate the percentage of GFP-expressing cells out of the total of CD11c+ cells. FIG. 16 shows percentages of GFP-expressing cells out of the total of CD11c+ cells. FIG. 17 shows results of a representative in vivo antibody depletion experiment. FIG. 18 shows percentages of GFP+ cells (out of total CD11c+ cells) after antibody depletion.

FIG. 19 shows representative flow cytometric results. FIG. 20 shows the numbers of IFN-γ-expressing E7-specific CD8+ T cells in the spleen cell population from vaccinated mice.

FIG. 22 shows representative flow cytometric results for pooled spleen cells harvested from vaccinated mice that were either (i) stimulated with E7 aa49-57 peptide or (ii) unstimulated in culture. FIG. 23 shows the numbers of IFN-γ-secreting E7-specific CD8+ T cell precursors (per $3\times10^5$ spleen cells) from mice vaccinated with E7 peptide-loaded DCs that were transfected with (i) control siRNA, (i) Bak/Bax siRNA or (iii) untransfected. Results shown are means±SD; p<0.001; Student's t test).

FIG. 25 represents the number of IFN-γ-secreting E7-specific CD8+ T cell precursors (per $3\times10^5$ spleen cells) after immunization with E7 peptide-loaded BM-DCs transfected with siRNA or from non-immunized mice (mean±SD; p<0.001; Student's t-test).

FIG. 26 shows results of a tumor protection experiment in which mice (5/group) were immunized with E7 peptide-loaded DCs transfected with either (i) control siRNA or (ii) Bak/Bax siRNA and boosted after 1 week. 7 days after the last immunization, each mouse was challenged with $5\times10^4$ TC-1 tumor cells (see Example I). Tumors were monitored twice a week. Unvaccinated mice served as negative controls. FIG. 27 shows results of an in vivo tumor therapy experiment in which mice were given E7 peptide-loaded DCs transfected with (i) Bak/Bax siRNA or (ii) control siRNA, three days after TC-1 tumor cell challenge ($5\times10^4$ tumor cells). Mice were boosted with the same dose and regimen of E7 peptide-loaded DCs one week later and sacrificed 28 days after tumor challenge. Lung nodules (experimental metastases) were evaluated and the results expressed as the mean number of lung nodules±SD (p<0.001; Student's t-test).

FIG. 28A presents flow cytometric results showing the different level of carboxyfluorescein (CFSE)-labeled E7 peptide-loaded BM-DCs transfected with either (i) Bak/Bax siRNA ("low CFSE") or (ii) control siRNA ("high CFSE"). Bak/Bax-transfected BM-DCs were labeled with a lower concentration (0.5 μM) of CF SE, whereas control BM-DCs (transfected with control siRNA) were labeled with a higher concentration (5 μM) of CFSE. A representative graph shows the presence of similar numbers of "low CFSE"-labeled E7 peptide-loaded BM-DCs transfected with Bak/Bax siRNA and "high CFSE"-labeled E7 peptide-loaded control BM-DCs before i.v. injection. FIG. 28B shows flow cytometric results demonstrating the ratio of "low CFSE" to "high CFSE" E7 peptide-loaded BM-DCs that have localized to the spleen and lungs of mice 16 hrs after i.v. injection of a mixture equal numbers ($2.5\times10^5$/mouse) of "low CFSE" E7 peptide-loaded BM-DCs transfected with Bak/Bax siRNA and "high CFSE" E7 peptide-loaded control BM-DCs. These CFSE-labeled BM-DCs were injected into mice 3 days after the administration of $10^6$ E7-specific T cells/mouse. Contact with these T cells are the basis for DC apoptosis in this study. Note that the number of "low CFSE" cells was significantly higher than the number of "high CFSE" cells.

FIG. 34. In vivo tumor treatment experiments in mice vaccinated with DCs expressing E7 or Sig/E7/LAMP-1. An in vivo tumor treatment experiment was performed using a hematogenous spread lung model. Mice were inoculated with 5×10⁵ TC-1 tumor cells via tail vein injection and then treated with DC-Sig/E7/LAMP-1 cells transfected with control or BAK/BAX siRNAs 3 days after inoculation. No treatment served as a negative control (A). In vivo antibody depletion experiments to determine the contribution of subsets of lymphocytes to the observed protective anti-tumor effect (B). Mice were challenged and vaccinated as described in (A). CD4, CD8, or NK1.1 depletion was initiated 1 week after the second vaccination. Mice were sacrificed 28 days after tumor challenge to examine the growth of pulmonary nodules. Data are expressed as the mean number of lung nodules. The data presented in this figure are from one representative experiment of two performed.

FIG. 36 shows the sequence of the pcDNA3 plasmid vector (SEQ ID NO:14).

FIG. 37 shows the sequence of the pNGVL4a plasmid vector (SEQ ID NO:15).

FIG. 40 shows the nucleotide sequence of plasmid pNGVL4a-CRT/E7(detox) (SEQ ID NO:44). The sequence is annotated to show plasmid-derived sequences (lower case), CRT-derived (bold, upper case) and HPV-E7-derived (detoxified by two amino acid substitutions as described above (upper case, italicized, underlined)) sequences.

DETAILED DESCRIPTION

Figure 1:
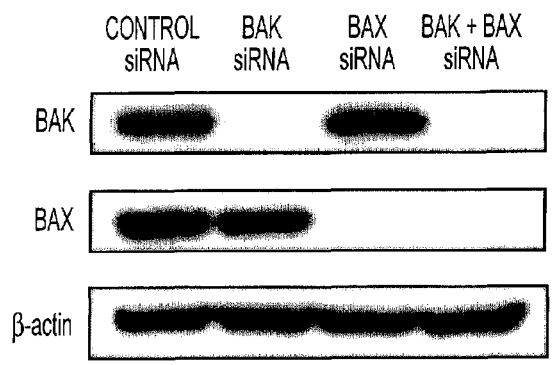

The present invention is directed to one of two fundamental approaches to the improvement of molecular vaccine potency. As the present inventors discovered, in addition to DNA encoding an antigen, the concomitant administration of a second DNA molecule encoding an siRNA specific for an apoptotic protein, preferably Bak and/or Bax, termed "anti-apoptotic siRNA DNA" for simplicity), enhances the magnitude and/or duration of a T cell mediated immune response, and potentiates a desired clinical effect—such as eradication of an existing tumor or prevention of the spread or metastasis of a tumor.

The anti-apoptotic siRNA DNA may be physically linked to the antigen-encoding DNA. Alternatively, and preferably, the anti-apoptotic siRNA DNA may be administered separately from, but in combination with the antigen-encoding DNA molecule. Examples of the co-administration of these two types of vectors is provided.

This strategy may be combined with an additional strategy pioneered by the present inventors and colleagues, that involve linking DNA encoding another protein, generically termed a "immunogenicity-potentiating polypeptide" or "IPP" to the antigen-encoding DNA. Again, for the sake of simplicity, the DNA encoding such a targeting polypeptide will be referred to herein as a "IPP DNA." That strategy has been shown to be effective in enhancing the potency of the vectors carrying only antigen-encoding DNA. See for example: Wu et al., WO 01/29233; Wu et al., WO 02/009645; Wu et al., WO 02/061113; Wu et al., WO 02/074920; Wu et al., WO 02/12281, all of which are incorporated by reference in their entirety.

The details of the various targeting polypeptide strategies will not be discussed in detail herein, although several such vectors are useful in the present invention and their sequences are provided below. The preferred IPPs include Sig/LAMP-1, the translocation domain, which is domain II (dII) of *Pseudomonas aeruginosa* exotoxin A (ETA(dII)) or from similar toxins from Diptheria, *Clostridium, Botulinum, Bacillus, Yersinia, Vibrio cholerae*, or *Bordetella*), an endoplasmic reticulum chaperone polypeptide exemplified by calreticulin (CRT) but also including ER60, GRP94 or gp96, well-characterized ER chaperone polypeptide that representatives of the HSP90 family of stress-induced proteins (see WO 02/012281), VP22 protein from herpes simplex virus and its homologues from other herpes viruses such as Marek's disease virus (see WO 02/09645), mycobacterial heat shock protein HSP70 (WO0129233, U.S. Pat. No. 6,734,173; WO02061113), and γ-tubulin (Hung C F et al., *Canc Res* 63:2393-98, 2003)

DNA encoding each of these polypeptides, or fragments or variants thereof with substantially the same biological activity, when linked to an antigen-encoding or epitope-encoding DNA molecule, result in more potent T cell mediate responses to the antigen compared to immunization with the antigen-encoding DNA alone. These polypeptide can be considered as "molecular adjuvants." These effects are manifest primarily with CD8+ T cells, although some of these approaches induce potent CD4+ T cell mediated effects as well.

The results presented herein prove that molecular vaccination with
(a) a combination of an antigen-encoding DNA and an anti-apoptotic siRNA DNA; or (b) a combination of a chimeric DNA encoding (i) antigen plus (ii) an IPP and an anti-apoptotic siRNA or a combination of (a) and (b) above, will results in a stronger and more durable immune response which can be protective and/or therapeutic. A related embodiment that is expected to give similar results is:

(c) a combination of a chimeric DNA comprising an antigen-encoding DNA sequence optionally linked to an IPP-encoding DNA and a DNA composition encoding an anti-apoptotic siRNA.

Also included within the scope of this invention (compositions and methods for inducing more potent immune responses, is a DC that is (i) loaded with, and therefore presenting, an antigen, and (ii) transfected with siRNA or with DNA encoding siRNA directed to Bak/Bax that suppress or reverse Bak/Bax protein expression. Such transfected DCs are preferably "pulsed" (or "loaded") with an antigenic peptide. The DCs may be transfected ex vivo with anti-apoptotic siRNA or siRNA DNA, and loaded with antigen ex vivo. Alternatively, the transfection or loading or both may take place in vivo. If transfection or loading takes place ex vivo, the other may be conducted in vivo, either prior to removing the cells for ex vivo treatment or after the ex vivo treated cells have been administered to the subject.

Any one of the types of vectors may also comprise DNA encoding an immunostimulatory cytokine, preferably those that target APCs, preferably DC's, such as granulocyte macrophage colony stimulating factor (GM-CSF), or active fragments or domains thereof, and/or DNA encoding a costimulatory signal, such as a B7 family protein, including B7-DC (see U.S. patent application Ser. No. 09/794,210), B7.1, B7.2, soluble CD40, etc.).

The vectors used to deliver the foregoing DNA sequences include naked DNA vectors (plasmids), DNA-based alphaviral RNA replicons ("suicidal DNA vectors") and self replicating RNA replicons.

The order in which the two (or more) components of a chimeric DNA vaccine construct (antigen and IPP) are arranged, and therefore, the order of the encoding nucleic acid fragments in the nucleic acid vector, can be altered without affecting immunogenicity of the fusion polypeptides proteins and the utility of the composition. As has been disclosed by the present inventors and their colleagues in other published patent applications cited herein, for some combinations of antigen/IPP, one order is preferred, e.g. E7 . . . HSP70 and CRT . . . E7 (indicating N- to C-terminal in the polypeptide).

The experiments described herein demonstrate that the methods of the invention can enhance a cellular immune response, particularly, tumor-destructive CTL reactivity, induced by a DNA vaccine encoding an epitope of a human pathogen. Human HPV-16 E7 was used as a model antigen for vaccine development because human papillomaviruses (HPVs), particularly HPV-16, are associated with most human cervical cancers. The oncogenic HPV proteins E7 and E6 are important in the induction and maintenance of cellular transformation and co-expressed in most HPV-containing cervical cancers and their precursor lesions. Therefore, cancer vaccines, such as the compositions of the invention, that target E7 can be used to control of HPV-associated neoplasms (Wu (1994) *Curr. Opin. Immunol.* 6:746-754). Similar DNA vaccines encoding E6 are also included herein and studies with E6 using the IPPs disclosed herein have shown successful potentiation of E6-specific immune responses.

Based on studies of simultaneous vaccination with both CRT/E6 and CRT/E7 DNA vaccines generated significant E6- and E7-specific T-cell immune responses and significantly better therapeutic antitumor effects against E6- and E7-expressing tumors than vaccination with either CRT/E6 DNA or CRT/E7 DNA alone.

In one embodiment, the present invention is directed to simultaneous vaccination with both E6 and E7 DNA immunogens, or IPP/E6 and IPP/E7 DNA immunogens, in combination with delivery of siRNA targeting mRNA encoding pro-apoptotic proteins, preferably Bak and/or Bax.

The present invention is not limited to the exemplified antigen(s). Rather, one of skill in the art will appreciate that the same results are expected for any antigen (and epitopes thereof) for which a T cell-mediated response is desired. The response so generated will be effective in providing protective or therapeutic immunity, or both, directed to an organism or disease in which the epitope or antigenic determinant is involved—for example as a cell surface antigen of a pathogenic cell or an envelope or other antigen of a pathogenic virus, or a bacterial antigen, or an antigen expressed as or as part of a pathogenic molecule.

Thus, in one embodiment, the antigen (e.g., the MHC class I-binding peptide epitope) is one that is derived from a pathogen, e.g., a peptide expressed by a pathogen. The pathogen can be a virus, such as, e.g., a papilloma virus, a herpesvirus, a retrovirus (including an immunodeficiency virus, such as HIV-1), an adenovirus, and the like. The papilloma virus can be a human papilloma virus, for which a preferred antigen (e.g., a MHC class I-binding peptide) can be the HPV-16 E6 or E7 polypeptide or an immunogenic fragment thereof. In one embodiment employing E6 and/or E7, the polypeptide is rendered substantially non-oncogenic by about 1 to about 3 amino acid substitutions that maintain immunogenicity while destroying oncogenicity, for example, by destroying the ability of the polypeptide to bind retinoblastoma polypeptide (pRB) or substantially lowering the affinity for pRB. As a result, the E7 polypeptide is effectively non-oncogenic when expressed in vivo or delivered in vivo.

In alternative embodiments, the pathogen is a bacteria, such as *Bordetella pertussis; Ehrlichia chaffeensis; Staphylococcus aureus; Toxoplasma gondii; Legionella pneumophila; Brucella suis; Salmonella enterica; Mycobacterium avium; Mycobacterium tuberculosis; Listeria monocytogenes; Chlamydia trachomatis; Chlamydia pnemoniae; Rickettsia rickettsii*; or, a fungus, such as, e.g., *Paracoccidioides brasiliensis*; or other pathogen, e.g., *Plasmodium falciparum*.

In another embodiment, the MHC class I-binding peptide epitope is derived from a tumor cell. The tumor cell-derived peptide epitope can comprise a tumor associated antigen, e.g., a tumor specific antigen, such as, e.g., a HER-2/neu antigen, or one of a number of known melanoma antigens, etc.

In one embodiment, the isolated or recombinant nucleic acid molecule is operatively linked to a promoter, such as, e.g., a constitutive, an inducible or a tissue-specific promoter. The promoter can be expressed in any cell, including cells of the immune system, including, e.g., antigen presenting cells (APCs), e.g., in a constitutive, an inducible or a tissue-specific manner.

In alternative embodiments, the APCs are DCs, keratinocytes, astrocytes, monocytes, macrophages, B lymphocytes, a microglial cell, or activated endothelial cells, and the like.

Unless defined otherwise, all technical and scientific terms used herein have the meaning commonly understood by a person skilled in the art of this invention. As used herein, the following terms have the meanings ascribed to them unless specified otherwise.

The term "antigen" or "immunogen" as used herein refers to a compound or composition or cell comprising a peptide, polypeptide or protein which is "antigenic" or "immunogenic" when administered in an appropriate amount (an "immunogenically effective amount"), i.e., capable of inducing, eliciting, augmenting or boosting a cellular and/or humoral immune response and of being recognized by the products of that response (T cells, antibodies). A nucleic acid such as DNA that encodes an immunogen and is used as a vaccine is referred to as a "DNA immunogen" as the encoded polypeptide is expressed in vivo after administration of the DNA. An immunogen may be effective when given alone or in combination, or linked to, or fused to, another substance (which can be administered at one time or over several intervals). An immunogenic composition can comprise an antigenic peptide/polypeptide of at least about 5, or about 10 or about 15, or about 20 amino acids, etc. Smaller antigens may require presence of a "carrier" polypeptide e.g., as a fusion protein, aggregate, conjugate or mixture, preferably linked (chemically or otherwise) to the antigen to be immunogenic. The immunogen can be recombinantly expressed from a vaccine vector, which can be naked DNA which comprises the polypeptide immunogen's coding sequence operably linked to a promoter, e.g., an expression vector or cassette as described herein. The immunogen includes one or more antigenic determinants or epitopes which may vary in size from about 3 to about 15 amino acids.

The term "epitope" as used herein refers to an antigenic determinant or antigenic site that interacts with an antibody or a T cell receptor (TCR), e.g., the MHC class I-binding peptide compositions (or expressed products of the nucleic acid compositions of the invention) used in the methods of the invention. An "antigen" is a molecule or chemical structure that either induces an immune response or is specifically recognized or bound by the product or mediator of an immune response, such as an antibody or a CTL. The specific conformational or stereochemical "domain" to which an antibody or a TCR bind is an "antigenic determinant" or "epitope." TCRs bind to peptide epitopes which are physically associated with a third molecule, a major histocompatibility complex (MHC) class I or class II protein.

The term "recombinant" refers to (1) a nucleic acid or polynucleotide synthesized or otherwise manipulated in vitro, (2) methods of using recombinant DNA technology to produce gene products in cells or other biological systems, or (3) a polypeptide encoded by a recombinant nucleic acid. For example, the ETA(dII)-encoding nucleic acid or polypeptide, the nucleic acid encoding an MHC class I-binding peptide epitope (antigen) or the peptide itself can be recombinant. "Recombinant means" includes ligation of nucleic acids having various coding regions or domains or promoter sequences from different sources into a single unit in the form of an expression cassette or vector for expression of the coding sequences in the vectors resulting in production of the encoded polypeptide.

The term "self-replicating RNA replicon" refers to a construct based on an RNA viruses, such as alphavirus genome RNAs (e.g., Sindbis virus, Semliki Forest virus, etc.) that have been engineered to allow expression of heterologous RNAs and proteins. These recombinant vectors are self-replicating ("replicons") which can be introduced into cells as naked RNA or DNA, as described in detail in co-pending, commonly assigned U.S. and PCT patent applications by the present inventors (U.S. Ser. No. 10/060,274 and WO 02/061113).

siRNAs

The present inventors designed siRNA sequences that hybridize to, and block expression of the activation of Bak and Bax proteins that are central players in the apoptosis signalling pathway. The present invention is directed to the siRNA molecules (sequences), vectors containing or encoding the siRNA, expression vectors with a promoter operably linked to the siRNA coding sequence that drives transcription of siRNA sequences that are "specific" for sequences Bak and Bax nucleic acid. siRNAs may include single stranded "hairpin" sequences because of their stability and binding to the target mRNA.

Since Bak and Bax are involved, among other death proteins, in apoptosis of APCs, particularly DCs, the present siRNA sequences may be used in conjunction with a broad range of DNA vaccine constructs encoding antigens to enhance and promote the immune response induced by such DNA vaccine constructs, particularly CD8+ T cell mediated immune responses typified by CTL activation and action. This is believed to occur as a result of the effect of the siRNA in prolonging the life of antigen-presenting DCs which may otherwise be killed in the course of a developing immune response by the very same CTLs that the DCs are responsible for inducing.

In addition to Bak and Bax, additional targets for siRNAs designed in an analogous manner include caspase 8, caspase 9 and caspase 3. These proteins and their role in apoptosis was described above. The present invention includes compositions and methods in which siRNAs targeting any two or more of Bak, Bax, caspase 8, caspase 9 and caspase 3 are used in combination, optionally simultaneously (along with a DNA immunogen that encodes an antigen), to administer to a subject. Such combinations of siRNAs may also be used to transfect DCs (along with antigen loading) to improve the immunogenicity of the DCs as cellular vaccines by rendering them resistant to apoptosis.

siRNAs suppress gene expression through a highly regulated enzyme-mediated process called RNA interference (RNAi) (Sharp, P. A., Genes Dev. 15:485-90, 2001; Bernstein, E et al., Nature 409:363-66, 2001; Nykanen, A et al., Cell 107:309-21, 2001; Elbashir et al., Genes Dev. 15:188-200, 2001). RNA interference is the sequence-specific degradation of homologues in an mRNA of a targeting sequence in an siNA. As used herein, the term siNA (small, or short, interfering nucleic acid) is meant to be equivalent to other terms used to describe nucleic acid molecules that are capable of mediating sequence specific RNAi (RNA interference), for example short (or small) interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), translational silencing, and others. RNAi involves multiple RNA-protein interactions characterized by four major steps: assembly of siRNA with the RNA-induced silencing complex (RISC), activation of the RISC, target recognition and target cleavage. These interactions may bias strand selection during siRNA-RISC assembly and activation, and contribute to the overall efficiency of RNAi (Khvorova, A et al., Cell 115:209-216 (2003); Schwarz, D S et al. 115:199-208 (2003)))

Considerations to be taken into account when designing an RNAi molecule include, among others, the sequence to be targeted, secondary structure of the RNA target and binding of RNA binding proteins. Methods of optimizing siRNA sequences will be evident to the skilled worker. Typical algorithms and methods are described in Vickers et al. (2003) *J Biol Chem* 278:7108-7118; Yang et al. (2003) *Proc Natl Acad Sci USA* 99:9942-9947; Far et al. (2003) *Nuc. Acids Res.*

31:4417-4424; and Reynolds et al. (2004) *Nature Biotechnology* 22:326-330, all of which are incorporated by reference in their entirety.

The methods described in Far et al., supra, and Reynolds et al., supra, may be used by those of ordinary skill in the art to select targeted sequences and design siRNA sequences that are effective at silencing the transcription of the relevant mRNA. Far et al. suggests options for assessing target accessibility for siRNA and supports the design of active siRNA constructs. This approach can be automated, adapted to high throughput and is open to include additional parameters relevant to the biological activity of siRNA. To identify siRNA-specific features likely to contribute to efficient processing at each of the steps of RNAi noted above. Reynolds et al., supra, present a systematic analysis of 180 siRNAs targeting the mRNA of two genes. Eight characteristics associated with siRNA functionality were identified: low G/C content, a bias towards low internal stability at the sense strand 3'-terminus, lack of inverted repeats, and sense strand base preferences (positions 3, 10, 13 and 19). Application of an algorithm incorporating all eight criteria significantly improves potent siRNA selection. This highlights the utility of rational design for selecting potent siRNAs that facilitate functional gene knockdown.

Candidate siRNA sequences against mouse and human Bax and Bak are selected using a process that involves running a BLAST search against the sequence of Bax or Bak (or any other target) and selecting sequences that "survive" to ensure that these sequences will not be cross matched with any other genes.

siRNA sequences selected according to such a process and algorithm may be cloned into an expression plasmid and tested for their activity in abrogating Bak/Bax function cells of the appropriate animal species. Those sequences that show RNAi activity may be used by direct administration bound to particles, or recloned into a viral vector such as a replication-defective human adenovirus serotype 5 (Ad5).

One advantage of this viral vector is the high titer obtainable (in the range of $10^{10}$) and therefore the high multiplicities-of infection that can be attained. For example, infection with 100 infectious units/cell ensures all cells are infected. Another advantage of this virus is the high susceptibility and infectivity and the host range (with respect to cell types). Even if expression is transient, cells would survive, possibly replicate, and continue to function before Bak/Bax activity would recover and lead to cell death. Preferred constructs described in the Examples are the following:

```
For Bak:
                                        (SEQ ID NO:1)
   5' P-UGCCUACGAACUCUUCACCdTdT-3' (sense)

(SEQ ID NO:2)
   5' P-GGUGAAGAGUUCGUAGGCAdTdT-3' (antisense),
```

The nucleotide sequence encoding the Bak protein (including the stop codon) (GenBank accession No. NM_007523 is shown below (SEQ ID NO:3) with the targeted sequence in upper case, underscored.

```
atggcatctggacaaggaccaggtccccgaaggtgggctgcgatgagtc cccgtcccttctgaacagcaggttgcccaggacacagaggaggtctttc gaagctacgttttttacctccaccagcaggaacaggagacccaggggcgg ccgcctgccaacccgagatggacaacttgccccctggaacccaacagcat
``` cttgggtcaggtgggtcggcagcttgctctcatcggagatgatattaacc ggcgctacgacacagagttccagaatttactagaacagcttcagcccaca gccgggaaTGCCTACGAACTCTTCACCaagatcgcctccagcctatttaa gagtggcatcagctggggccgcgtggtggctctcctgggctttggctacc gtctggccctgtacgtctaccagcgtggtttgaccggcttcctgggccag gtgacctgcttttggctgatatcatactgcatcattacatcgccagatg gatcgcacagagaggcggttgggtggcagccctgaatttgcgtagagacc ccatcctgaccgtaatggtgattttggtgtggttctgttgggccaattc gtggtacacagattcttcagatcatga 637

The targeted sequence of Bak, TGCCTACGAACTCT-TCACC is SEQ ID NO:4

```
For Bax:
                                        (SEQ ID NO:5)
   5' P-UAUGGAGCUGCAGAGGAUGdTdT-3' (sense)

(SEQ ID NO:6)
   5' P-CAUCCUCUGCAGCUCCAUAdTdT-3' (antisense)
```

The nucleotide sequence encoding Bax (including the stop codon) (GenBank accession No. L22472 is shown below (SEQ ID NO:7) with the targeted sequence shown in upper case and underscored atggacgggtccggggagcagcttgggagcggcgggcccaccagctctga acagatcatgaagacaggggccttttgctacagggtttcatccaggatc gagcagggaggatggctggggagacacctgagctgaccttggagcagccg ccccaggatgcgtccaccaagaagctgagcgagtgtctccggcgaattgg agatgaactggatagcaaTATGGAGCTGCAGAGGATGattgctgacgtgg acacggactcccccgagaggtcttcttccgggtggcagctgacatgttt gctgatggcaacttcaactggggccgcgtggttgccctcttctactttgc tagcaaactggtgctcaaggccctgtgcactaaagtgcccgagctgatca gaaccatcatgggctggacactggacttcctccgtgagcggctgcttgtc tggatccaagaccagggtggctgggaaggcctcctctcctacttcgggac ccccacatggcagacagtgaccatctttgtggctggagtcctcaccgcct cgctcaccatctggaagaagatgggctga 589

The targeted sequence of Bax, TATGGAGCTGCAGAG-GATG is SEQ ID NO:8

In a preferred embodiment, the inhibitory molecule is a double stranded nucleic acid (preferably an RNA), used in a method of RNA interference. The following show the "paired" 19 nucleotide structures of the siRNA sequences shown above, where the symbol ↕:

```
Bak:5'P-     UGCCUACGAACUCUUCACCdTdT-3'   (sense)      (SEQ ID NO: 1)
             !!!!!!!!!!!!!!!!!!!!!
     3'P-dTdtACGGAUGCUUGAGAAGUGG       -5'  (antisense) (SEQ ID NO: 2)

BaX:5'P-     UAUGGAGCUGCAGAGGAUGdTdT-3'   (sense)      (SEQ ID NO: 5)
             !!!!!!!!!!!!!!!!!!!!!
     3'P-dTdTAUACCUCGACGUCUCCUAC       -5'  (antisense) (SEQ ID NO: 6)
```

Other Pro-Apoptotic Proteins to be Targeted

1. Caspase 8: The nucleotide sequence of human caspase-8 is shown below (SEQ ID NO:9). GenBank Access. #NM_001228. One target sequence for RNAi is underscored. Others may be identified using methods such as those described herein (and in reference cited herein, primarily Far et al., supra and Reynolds et al., supra).

```
atg gac ttc agc aga aat ctt tat gat att ggg gaa
caa ctg gac agt gaa gat ctg gcc tcc ctc aag ttc
ctg agc ctg gac tac att ccg caa agg aag caa gaa
ccc atc aag gat gcc ttg atg tta ttc cag aga ctc
cag gaa aag aga atg ttg gag gaa agc aat ctg tcc
ttc ctg aag gag ctg ctc ttc cga att aat aga ctg
gat ttg ctg att acc tac cta aac act aga aag gag
gag atg gaa agg gaa ctt cag aca cca ggc agg gct
caa att tct gcc tac agg ttc cac ttc tgc cgc atg
agc tgg gct gaa gca aac agc cag tgc cag aca cag
tct gta cct ttc tgg cgg agg gtc gat cat cta tta
ata agg gtc atg ctc tat cag att tca gaa gaa gtg
agc aga tca gaa ttg agg tct ttt aag ttt ctt ttg
caa gag gaa atc tcc aaa tgc aaa ctg gat gat gac
atg aac ctg ctg gat att ttc ata gag atg gag aag
agg gtc atc ctg gga gaa gga aag ttg gac atc ctg
aaa aga gtc tgt gcc caa atc aac aag agc ctg ctg
aag ata atc aac gac tat gaa gaa ttc agc aaa ggg
gag gag ttg tgt ggg gta atg aca atc tcg gac tct
cca aga gaa cag gat agt gaa tca cag act ttg gac
aaa gtt tac caa atg aaa agc aaa cct cgg gga tac
tgt ctg atc atc aac aat cac aat ttt gca aaa gca
cgg gag aaa gtg ccc aaa ctt cac agc att agg gac
agg aat gga aca cac ttg gat gca ggg gct ttg acc
acg acc ttt gaa gag ctt cat ttt gag atc aag ccc
cac gat gac tgc aca gta gag caa atc tat gag att
ttg aaa atc tac caa ctc atg gac cac agt aac atg
gac tgc ttc atc tgc tgt atc ctc tcc cat gga gac
aag ggc atc atc tat ggc act gat gga cag gag gcc
ccc atc tat gag ctg aca tct cag ttc act ggt ttg
aag tgc cct tcc ctt gct gga aaa ccc aaa gtg ttt
ttt att cag gct tgt cag ggg gat aac tac cag aaa
ggt ata cct gtt gag act gat tca gag gag caa ccc
tat tta gaa atg gat tta tca tca cct caa acg aga
tat atc ccg gat gag gct gac ttt ctg ctg ggg atg
gcc act gtg aat aac tgt gtt tcc tac cga aac cct
gca gag gga acc tgg tac atc cag tca ctt tgc cag
agc ctg aga gag cga tgt cct cga ggc gat gat att
ctc acc atc ctg act gaa gtg aac tat gaa gta agc
aac aag gat gac aag aaa aac atg ggg aaa cag atg
cct cag cct act ttc aca cta aga aaa aaa ctt gtc
ttc cct tct gat tga 1491
```

The sequences of sense and antisense siRNA strands for targeting this sequence (including dTdT 3' overhangs, are:

```
                                            (SEQ ID NO:10)
5'-AACCUCGGGGAUACUGUCUGAdTdT-3' (sense)

5'-UCAGACAGUAUCCCCGAGGUUdTdT-3' (antisense)
```

2. Caspase 9: The nucleotide sequence of human caspase-9 is shown below (SEQ ID NO:12). See GenBank Access. #NM_001229. The sequence below is of "variant α" which is longer than a second alternatively spliced variant β, which lacks the underscored part of the sequence shown below (and which is anti-apoptotic). Target sequences for RNAi, expected to fall in the underscored segment, are identified using known methods such as those described herein and in Far et al., supra and Reynolds et al., supra). and siNAs, such as siRNAs, are designed accordingly.

```
atg gac gaa gcg gat cgg cgg ctc ctg cgg cgg tgc
cgg ctg cgg ctg gtg gaa gag ctg cag gtg gac cag
ctc tgg gac gcc ctg ctg agc cgc gag ctg ttc agg
ccc cat atg atc gag gac atc cag cgg gca ggc tct
gga tct cgg cgg gat cag gcc agg cag ctg atc ata
gat ctg gag act cga ggg agt cag gct ctt cct ttg
ttc atc tcc tgc tta gag gac aca ggc cag gac atg
ctg gct tcg ttt ctg cga act aac agg caa gca gca
aag ttg tcg aag cca acc cta gaa aac ttg acc cca
gtg gtg ctc aga cca gag att cgc aaa cca gag gtt
ctc aga ccg gaa aca ccc aga cca gtg gac att ggt
```

-continued

```
tct gga gga ttt ggt gat gtc ggt gct ctt gag agt ttg agg gga aat gca gat ttg gct tac atc ctg agc atg gag ccc tgt ggc cac tgc ctc att atc aac aat gtg aac ttc tgc cgt gag tcc ggg ctc cgc acc cgc act ggc tcc aac atc gac tgt gag aag ttg cgg cgt cgc ttc tcc tcg ctg cat ttc atg gtg gag gtg aag ggc gac ctg act gcc aag aaa atg gtg ctg gct ttg ctg gag ctg gcg cag cag gac cac ggt gct ctg gac tgc tgc gtg gtg gtc att ctc tct cac ggc tgt cag gcc agc cac ctg cag ttc cca ggg gct gtc tac ggc aca gat gga tgc cct gtg tcg gtc gag aag att gtg aac atc ttc aat ggg acc agc tgc ccc agc ctg gga ggg aag ccc aag ctc ttt ttc atc cag gcc tgt ggt ggg gag cag aaa gac cat ggg ttt gag gtg gcc tcc act tcc cct gaa gac gag tcc cct ggc agt aac ccc gag cca gat gcc acc ccg ttc cag gaa ggt ttg agg acc ttc gac cag ctg gac gcc ata tct agt ttg ccc aca ccc agt gac atc ttt gtg tcc tac tct act ttc cca ggt ttt gtt tcc tgg agg gac ccc aag agt ggc tcc tgg tac gtt gag acc ctg gac gac atc ttt gag cag tgg gct cac tct gaa gac ctg cag tcc ctc ctg ctt agg gtc gct aat gct gtt tcg gtg aaa ggg att tat aaa cag atg cct ggt tgc ttt aat ttc ctc cgg aaa aaa ctt ttc ttt aaa aca tca taa 1191
```

3. Caspase 3: The nucleotide sequence of human caspase-3 is shown below (SEQ ID NO:13). See GenBank Access. #NM_004346. The sequence below is of "variant α" which is the longer of two alternatively spliced variants, all of which encode the full protein. Target sequences for RNAi are identified using known methods such as those described herein and in Far et al., supra and Reynolds et al., supra) and siNAs, such as siRNAs, are designed accordingly.

```
atg gag aac act gaa aac tca gtg gat tca aaa tcc att aaa aat ttg gaa cca aag atc ata cat gga agc gaa tca atg gac tct gga ata tcc ctg gac aac agt tat aaa atg gat tat cct gag atg ggt tta tgt ata ata att aat aat aag aat ttt cat aaa agc act gga atg aca tct cgg tct ggt aca gat gtc gat gca gca aac ctc agg gaa aca ttc aga aac ttg aaa tat gaa gtc agg aat aaa aat gat ctt aca cgt gaa gaa att gtg gaa ttg atg cgt gat gtt tct aaa gaa gat cac agc aaa agg agc agt ttt gtt tgt gtg ctt ctg agc
```

```
cat ggt gaa gaa gga ata att ttt gga aca aat gga cct gtt gac ctg aaa aaa ata aca aac ttt tca aga ggg gat cgt tgt aga agt cta act gga aaa ccc aaa ctt ttc att att cag gcc tgc cgt ggt aca gaa ctg gac tgt ggc att gag aca gac agt ggt gtt gat gat gac atg gcg tgt cat aaa ata cca gtg gag gcc gac ttc ttg tat gca tac tcc aca gca cct ggt tat tat tct tgg cga aat tca aag gat ggc tcc tgg ttc atc cag tcg ctt tgt gcc atg ctg aaa cag tat gcc gac aag ctt gaa ttt atg cac att ctt acc cgg gtt aac cga aag gtg gca aca gaa ttt gag tcc ttt tcc ttt gac gct act ttt cat gca aag aaa cag att cca tgt att gtt tcc atg ctc aca aaa gaa ctc tat ttt tat cac taa 834
```

Long double stranded interfering RNAs, such a miRNAs, appear to tolerate mismatches more readily than do short double stranded RNAs. In addition, as used herein, the term RNAi is meant to be equivalent to other terms used to describe sequence specific RNA interference, such as post transcriptional gene silencing, or an epigenetic phenomenon. For example, siNA molecules of the invention can be used to epigenetically silence genes at both the post-transcriptional level or the pre-transcriptional level. In a non-limiting example, epigenetic regulation of gene expression by siNA molecules of the invention can result from siNA mediated modification of chromatin structure and thereby alter gene expression (see, for example, Allshire Science 297:1818-19, 2002; Volpe et al., Science 297:1833-37, 2002; Jenuwein, Science 297:2215-18, 2002; and Hall et al., Science 297, 2232-2237, 2002.)

An siNA can be designed to target any region of the coding or non-coding sequence of an mRNA. An siNA is a double-stranded polynucleotide molecule comprising self-complementary sense and antisense regions, wherein the antisense region comprises nucleotide sequence that is complementary to nucleotide sequence in a target nucleic acid molecule or a portion thereof and the sense region has a nucleotide sequence corresponding to the target nucleic acid sequence or a portion thereof. The siNA can be assembled from two separate oligonucleotides, where one strand is the sense strand and the other is the antisense strand, wherein the antisense and sense strands are self-complementary. The siNA can be assembled from a single oligonucleotide, where the self-complementary sense and antisense regions of the siNA are linked by means of a nucleic acid based or non-nucleic acid-based linker(s). The siNA can be a polynucleotide with a hairpin secondary structure, having self-complementary sense and antisense regions. The siNA can be a circular single-stranded polynucleotide having two or more loop structures and a stem comprising self-complementary sense and antisense regions, wherein the circular polynucleotide can be processed either in vivo or in vitro to generate an active siNA molecule capable of mediating RNAi. The siNA can also comprise a single stranded polynucleotide having nucleotide sequence complementary to nucleotide sequence in a target nucleic acid molecule or a portion thereof (or can be an siNA molecule that does not require the presence within the siNA molecule of nucleotide sequence corresponding to the target nucleic acid sequence or a portion thereof), wherein the single stranded polynucleotide can further comprise a terminal phosphate group, such as a 5'-phosphate (see for example Martinez et al. (2002) *Cell* 110, 563-574 and Schwarz et al. (2002) *Molecular Cell* 10, 537-568), or 5',3'-diphosphate.

In certain embodiments, the siNA molecule of the invention comprises separate sense and antisense sequences or regions, wherein the sense and antisense regions are covalently linked by nucleotide or non-nucleotide linkers molecules as is known in the art, or are alternately non-covalently linked by ionic interactions, hydrogen bonding, Van der Waal's interactions, hydrophobic interactions, and/or stacking interactions. Some preferred siRNAs are discussed above and in the Examples.

As used herein, siNA molecules need not be limited to those molecules containing only ribonucleotides but may also further encompass deoxyribonucleotides (as in the preferred siRNAs which each include a dTdT dinucleotide) chemically-modified nucleotides, and non-nucleotides. In certain embodiments, the siNA molecules of the invention lack 2'-hydroxy (2'-OH) containing nucleotides. In certain embodiments, siNAs do not require the presence of nucleotides having a 2'-hydroxy group for mediating RNAi and as such, siNAs of the invention optionally do not include any ribonucleotides (e.g., nucleotides having a 2'-OH group). Such siNA molecules that do not require the presence of ribonucleotides within the siNA molecule to support RNAi can however have an attached linker or linkers or other attached or associated groups, moieties, or chains containing one or more nucleotides with 2'-OH groups. Optionally, siNA molecules can comprise ribonucleotides at about 5, 10, 20, 30, 40, or 50% of the nucleotide positions. If modified, the siNAs of the invention can also be referred to as "short interfering modified oligonucleotides" or "siMON." Other chemical modifications, e.g., as described in Int'l Patent Publications WO 03/070918 and WO 03/074654, can be applied to any siNA sequence of the invention.

Preferably a molecule mediating RNAi has a 2 nucleotide 3' overhang (dTdT in the preferred sequences disclosed herein). If the RNAi molecule is expressed in a cell from a construct, for example from a hairpin molecule or from an inverted repeat of the desired sequence, then the endogenous cellular machinery will create the overhangs.

Methods of making siRNAs are conventional. In vitro methods include processing the polyribonucleotide sequence in a cell-free system (e.g., digesting long dsRNAs with RNAse III or Dicer), transcribing recombinant double stranded DNA in vitro, and, preferably, chemical synthesis of nucleotide sequences homologous to Bak or Bax sequences. See, e.g., Tuschl et al., *Genes & Dev.* 13:3191-3197, 1999. In vivo methods include (1) transfecting DNA vectors into a cell such that a substrate is converted into siRNA in vivo. See, for example, Kawasaki et al., *Nucleic Acids Res* 31:700-07, 2003; Miyagishi et al., *Nature Biotechnol* 20:497-500, 2003; Lee et al., *Nature Biotechnol* 20:500-05, 2002; Brummelkamp et al., *Science* 296:550-53, 2002; McManus et al., *RNA* 8:842-50, 2002; Paddison et al., *Genes Dev* 16:948-58, 2002; Paddison et al., *Proc Natl Acad Sci USA* 99:1443-48, 2002; Paul et al., *Nature Biotechnol* 20:505-08, 2002; Sui et al., *Proc Natl Acad Sci USA* 99:5515-20, 2002; Yu et al., *Proc Natl Acad Sci USA* 99:6047-52, 2002)

(2) expressing short hairpin RNAs from plasmid systems using RNA polymerase III (pol III) promoters. See, for example, Kawasaki et al., supra; Miyagishi et al., supra; Lee et al., supra; Brummelkamp et al., supra; McManus et al., supra), Paddison et al., supra (both); Paul et al., supra, Sui et al., supra; and Yu et al., supra; and/or (3) expressing short RNA from tandem promoters. See, for example, Miyagishi et al., supra; Lee et al., supra).

When synthesized in vitro, a typical micromolar scale RNA synthesis provides about 1 mg of siRNA, which is sufficient for about 1000 transfection experiments using a 24-well tissue culture plate format. In general, to inhibit Bak or Bax expression in cells in culture, one or more siRNAs can be added to cells in culture media, typically at about 1 ng/ml to about 10 µg siRNA/ml.

For reviews and more general description of inhibitory RNAs, see Lau et al., *Sci Amer* August 2003: 34-41; McManus et al., *Nature Rev Genetics* 3, 737-47, 2002; and Dykxhoom et al., *Nature Rev Mol Cell Bio* 4:457-467, 2003. For further guidance regarding methods of designing and preparing siRNAs, testing them for efficacy, and using them in methods of RNA interference (both in vitro and in vivo), see, e.g., Allshire, *Science* 297:1818-19, 2002; Volpe et al., *Science* 297:1833-37, 2002; Jenuwein, *Science* 297:2215-18, 2002; Hall et al., *Science* 2972232-37, 2002; Hutvagner et al., *Science* 297:2056-60, 2002; McManus et al. *RNA* 8:842-850, 2002; Reinhart et al., *Genes Dev.* 16:1616-26, 2002; Reinhart et al., *Science* 297:1831, 2002; Fire et al. (1998) *Nature* 391:806-11, 2002; Moss, *Curr Biol* 11:R772-5, 2002: Brummelkamp et al., supra; Bass, *Nature* 411 428-9, 2001; Elbashir et al., *Nature* 411:494-8; U.S. Pat. No. 6,506,559; Published US Pat App. 20030206887; and PCT applications WO99/07409, WO99/32619, WO 00/01846, WO 00/44914, WO00/44895, WO01/29058, WO01/36646, WO01/75164, WO01/92513, WO 01/29058, WO01/89304, WO01/90401, WO02/16620, and WO02/29858.

Ribozymes and siNAs can take any of the forms, including modified versions, described for antisense nucleic acid molecules; and they can be introduced into cells as oligonucleotides (single or double stranded), or in the form of an expression vector.

In a preferred embodiment, an antisense nucleic acid, siNA (e.g., siRNA) or ribozyme comprises a single stranded polynucleotide comprising a sequence that is at least about 90% (e.g., at least about 93%, 95%, 97%, 98% or 99%) identical to a target segment (such as those indicted for Bak and Bax above) or a complement thereof. As used herein, a DNA and an RNA encoded by it are said to contain the same "sequence," taking into account that the thymine bases in DNA are replaced by uracil bases in RNA.

Active variants (e.g., length variants, including fragments; and sequence variants) of the nucleic acid-based inhibitors discussed herein are also within the scope of the invention. An "active" variant is one that retains an activity of the inhibitor from which it is derived (preferably the ability to inhibit expression). It is routine to test a variant to determine for its activity using conventional procedures.

As for length variants, an antisense nucleic acid or siRNA may be of any length that is effective for inhibition of a gene of interest. Typically, an antisense nucleic acid is between about 6 and about 50 nucleotides (e.g., at least about 12, 15, 20, 25, 30, 35, 40, 45 or 50 nt), and may be as long as about 100 to about 200 nucleotides or more. Antisense nucleic acids having about the same length as the gene or coding sequence to be inhibited may be used. When referring to length, the terms bases and base pairs (bp) are used interchangeably, and will be understood to correspond to single stranded (ss) and double stranded (ds) nucleic acids. The length of an effective siNA is generally between about 15 bp and about 29 bp in length, preferably between about 19 and about 29 bp (e.g., about 15, 17, 19, 21, 23, 25, 27 or 29 bp), with shorter and longer sequences being acceptable. Generally, siNAs are shorter than about 30 bases to prevent eliciting interferon effects. For example, an active variant of an siRNA having, for one of its strands, the 19 nucleotide sequence of any of SEQ ID NO: 1, 2, 5 and 6 herein can lack base pairs from either, or both, of ends of the dsRNA; or can comprise additional base pairs at either, or both, ends of the ds RNA, provided that the total of length of the siRNA is between about 19 and about 29 bp, inclusive. One embodiment of the invention is an siRNA that "consists essentially of" sequences represented by SEQ ID NO:1, 2, 5 or 6 or complements of these sequence. The term "consists essentially of" is an intermediate transitional phrase, and in this case excludes, for example, sequences that are long enough to induce a significant interferon response. An siRNA of the invention may consist essentially of between about 19 and about 29 bp in length.

As for sequence variants, it is generally preferred that an inhibitory nucleic acid, whether an antisense molecule, a ribozyme (the recognition sequences), or an siNA, comprise a strand that is complementary (100% identical in sequence) to a sequence of a gene that it is designed to inhibit. However, 100% sequence identity is not required to practice the present invention. Thus, the invention has the advantage of being able to tolerate naturally occurring sequence variations, for example, in human c-met, that might be expected due to genetic mutation, polymorphism, or evolutionary divergence. Alternatively, the variant sequences may be artificially generated. Nucleic acid sequences with small insertions, deletions, or single point mutations relative to the target sequence can be effective inhibitors.

The degree of sequence identity may be optimized by sequence comparison and alignment algorithms well-known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). At least about 90% sequence identity is preferred (e.g., at least about 92%, 95%, 98% or 99%), or even 100% sequence identity, between the inhibitory nucleic acid and the targeted sequence of targeted gene.

Alternatively, an active variant of an inhibitory nucleic acid of the invention is one that hybridizes to the sequence it is intended to inhibit under conditions of high stringency. For example, the duplex region of an siRNA may be defined functionally as a nucleotide sequence that is capable of hybridizing with a portion of the target gene transcript under high stringency conditions (e.g., 400 mM NaCl, 40 mM PIPES pH 6.4, 1 mM EDTA, 50° C. or 70° C., hybridization for 12-16 hours), followed generally by washing.

DC-1 cells or BM-DCs presenting a given antigen X, when not treated with the siRNAs of the invention, respond to sufficient numbers X-specific CD8+ CTL by apoptotic cell death. In contrast, the same cells transfected with the siRNA or infected with a viral vector encoding the present siRNA sequences survive better despite the delivery of killing signals.

Delivery and expression of the siRNA compositions of the present invention inhibit the death of DCs in vivo in the process of a developing T cell response, and thereby promote and stimulate the generation of an immune response induced by immunization with an antigen-encoding DNA vaccine vector. These capabilities have been exemplified by showing that:

(1) co-administration of DNA vaccines encoding HPV-16 E7 with siRNA targeted to Bak and Bax prolongs the lives of antigen-presenting DCs in the draining lymph nodes, thereby enhancing antigen-specific $CD8^+$ T cell responses, and eliciting potent antitumor effects against an E7-expressing tumor in vaccinated subjects.

(2) DCs transfected with siRNA targeting Bak and Bax resist killing by T cells in vivo. E7-loaded DCs transfected with Bak/Bax siRNA so that Bak and Bax protein expression is down-regulated resist apoptotic death induced by T cells in vivo. When administered to subjects, these DCs generate stronger antigen-specific immune responses and manifest therapeutic effects (compared to DCs transfected with control siRNA).

Thus the siRNA constructs of the present invention are useful as a part of nucleic acid vaccination and immunotherapy regimen.

Vectors, Antigen, and IPP Nucleic Acids and Polypeptides

Plasmid Sequences

The sequence of the pcDNA3 plasmid vector (SEQ ID NO:14) is shown in FIG. 36, and the sequence of the pNGVL4a plasmid vector (SEQ ID NO:15) is shown in FIG. 37.

pNGVL4a, a preferred plasmid backbone for the present invention was originally derived from the pNGVL3 vector, which has been approved for human vaccine trials. The pNGVL4a vector includes two immunostimulatory sequences (tandem repeats of CpG dinucleotides) in the non-coding region. Whereas any other plasmid DNA that can transform either APCs, preferably DC's or other cells which, via cross-priming, transfer the antigenic moiety to DCs, is useful in the present invention, pNGFVLA4a is preferred because of the fact that it has already been approved for human therapeutic use.

Antigen Polypeptide Sequences

Thus using either CRT or any of the other IPPs, the present invention includes a combined DNA vaccine composition that includes a DNA immunogen encoding E6 with a DNA immunogen encoding E7 along with the delivery of siRNA targeting Bak and/or Bak (or several other pro-apoptotic proteins as described above). The siRNA may be delivered directly (e.g., bound to particles delivered via gene gun) or in the form of a DNA vector that encodes this siRNA.

The E7 nucleic acid sequence (SEQ ID NO:16) and amino acid sequence (SEQ ID NO:17) from HPV-16 are shown below (see Accession Number NC_001526)

```
atg cat gga gat aca cct aca ttg cat gaa tat atg tta gat ttg caa cca gag aca act    60
Met His Gly Asp Thr Pro Thr Leu His Glu Tyr Met Leu Asp Leu Gln Pro Glu Thr Thr    20 gat ctc tac tgt tat gag caa tta aat gac agc tca gag gag gag gat gaa ata gat ggt   120
Asp Leu Tyr Cys Tyr Glu Gln Leu Asn Asp Ser Ser Glu Glu Glu Asp Glu Ile Asp Gly    40 cca gct gga caa gca gaa ccg gac aga gcc cat tac aat att gta acc ttt tgt tgc aag   180
Pro Ala Gly Gln Ala Glu Pro Asp Arg Ala His Tyr Asn Ile Val Thr Phe Cys Cys Lys    60
```

-continued

```
tgt gac tct acg ctt cgg ttg tgc gta caa agc aca cac gta gac att cgt act ttg gaa   240
Cys Asp Ser Thr Leu Arg Leu Cys Val Gln Ser Thr His Val Asp Ile Arg Thr Leu Glu    80 gac ctg tta atg ggc aca cta gga att gtg tgc ccc atc tgt tct cag gat aag ctt       297
Asp Leu Leu Met Gly Thr Leu Gly Ile Val Cys Pro Ile Cys Ser Gln Asp Lys Leu        99
```

In single letter code, the wild type E7 amino acid sequence is (SEQ ID NO:17 above))
MHGDTPTLHE YMLDLQPETT DLYCYEQLND SSEEEDEIDG

PAGQAEPDRA HYNIVTFCCK CDSTLRLCVQ STHVDIRTLE

DLLMGTLGIV CPICSQDKL 99

In another embodiment (See GenBank Accession No. AF125673, nucleotides 562-858 and the E7 amino acid sequence) the C-terminal four amino acids QDKL (and their codons) above are replaced with the three amino acids QKP (and the codons cag aaa cca yielding a protein of 98 residues.

When an oncoprotein or an epitope thereof is the immunizing moiety, it is preferable to reduce the tumorigenic risk of the vaccine itself. Because of the potential oncogenicity of the HPV E7 protein, the E7 protein is preferably used in a "detoxified" form To reduce oncogenic potential of E7 in a construct of this invention, one or more of the following positions of E7 is mutated:

| Original residue | Mutant residue | Preferred codon mutation | nt Position (in SEQ ID NO:16) | Amino acid (in SEQ ID NO:17) |
|---|---|---|---|---|
| Cys | Gly (or Ala) | TGT→GGT | 70 | 24 |
| Glu | Gly (or Ala) | GAG→GGG (or GCG) | 77 | 26 |
| Cys | Gly (or Ala) | TGC→GGC | 271 | 91 |

The preferred E7 (detox) mutant sequence has the following two mutations:
a TGT→GGT mutation resulting in a Cys→Gly substitution at position 24 of SEQ ID NO:17 a and GAG→GGG mutation resulting in a Glu→Gly substitution at position 26 of SEQ ID NO:17. This mutated amino acid sequence is shown below with the replacement residues underscored.

(SEQ ID NO:18)
MHGDTPTLHE YMLDLQPETT DLYGYEGLND SSEEEDEIDG

PAGQAEPDRA HYNIVTFCCK CDSTLRLCVQ STHVDIRTLE

DLLMGTLGIV CPICSQKP 97

These substitutions completely eliminate the capacity of the E7 to binding capacity to Rb, and thereby nullify its transforming activity.

Any nucleotide sequence that encodes encoding the above E7 or E7(detox) polypeptide, or an antigenic fragment or epitope thereof, can be used in the present compositions and methods, though the preferred E7 and E7(detox) sequences are shown above.

E6 Protein from HPV-16

The wild type HPV E6 amino acid sequence (see GenBank Accession Number NC_001526) (SEQ ID NO:4) is shown below. This sequence has 158 amino acids.

The wild type E6 nucleotide (SEQ ID NO:19) and amino acid (SEQ ID NO:20) sequences are shown below (see GenBank accession #'s K02718 and NC_001526)):

```
atg cac caa aag aga act gca atg ttt cag gac cca cag gag cga ccc aga aag tta cca   60
Met His Gln Lys Arg Thr Ala Met Phe Gln Asp Pro Gln Glu Arg Pro Arg Lys Leu Pro    20 cag tta tgc aca gag ctg caa aca act ata cat gat ata ata tta gaa tgt gtg tac tgc   120
Gln Leu Cys Thr Glu Leu Gln Thr Thr Ile His Asp Ile Ile Leu Glu Cys Val Tyr Cys    40 aag caa cag tta ctg cga cgt gag gta tat gac ttt gct ttt cgg gat tta tgc ata gta   180
Lys Gln Gln Leu Leu Arg Arg Glu Val Tyr Asp Phe Ala Phe Arg Asp Leu Cys Ile Val    60 tat aga gat ggg aat cca tat gct gta tgt gat aaa tgt tta aag ttt tat tct aaa att   240
Tyr Arg Asp Gly Asn Pro Tyr Ala Val Cys Asp Lys Cys Leu Lys Phe Tyr Ser Lys Ile    80 agt gag tat aga cat tat tgt tat agt ttg tat gga aca aca tta gaa cag caa tac aac   300
Ser Glu Tyr Arg His Tyr Cys Tyr Ser Leu Tyr Gly Thr Thr Leu Glu Gln Gln Tyr Asn   100 aaa ccg ttg tgt gat ttg tta att agg tgt att aac tgt caa aag cca ctg tgt cct gaa   360
Lys Pro Leu Cys Asp Leu Leu Ile Arg Cys Ile Asn Cys Gln Lys Pro Leu Cys Pro Glu   120 gaa aag caa aga cat ctg gac aaa aag caa aga ttc cat aat ata agg ggt cgg tgg acc   420
```

-continued

```
Glu Lys Gln Arg His Leu Asp Lys Lys Gln Arg Phe His Asn Ile Arg Gly Arg Trp Thr      140 ggt cga tgt atg tct tgt tgc aga tca tca aga aca cgt aga gaa acc cag ctg taa          474

Gly Arg Cys Met Ser Cys Cys Arg Ser Ser Arg Thr Arg Glu Thr Gln Leu stop             158
```

This polypeptide has 158 amino acids and is shown below in single letter code:

```
                                            [SEQ ID NO:20, above]
MHQKRTAMFQ DPQERPRKLP QLCTELQTTI HDIILECVYC

KQQLLRREVY DFAFRDLCIV YRDGNPYAVC DKCLKFYSKI

SEYRHYCYSL YGTTLEQQYN KPLCDLLIRC INCQKPLCPE

EKQRHLDKKQ RFHNIRGRWT GRCMSCCRSS RTRRETQL 158
```

E6 proteins from cervical cancer-associated HPV types such as HPV-16 induce proteolysis of the p53 tumor suppressor protein through interaction with E6-AP. Human mammary epithelial cells (MECs) immortalized by E6 display low levels of p53. HPV-16 E6 as well as other cancer-related papillomavirus E6 proteins also binds the cellular protein E6BP (ERC-55). As with E7, it is preferred to used a non-oncogenic mutated form of E6, referred to as "E6(detox)." Several different E6 mutations and publications describing them are discussed below.

The preferred amino acid residues to be mutated are underscored in the E6 amino acid sequence above. Some studies of E6 mutants are based upon a shorter E6 protein of 151 nucleic acids, wherein the N-terminal residue was considered to be the Met at position 8 in SEQ ID NO:20 above. That shorter version of E6 is shown below as SEQ ID NO:21.

```
MFQDPQERPR KLPQLCTELQ TTIHDIILEC VYCKQQLLRR

EVYDFAFRDL CIVYRDGNPY AVCDKCLKFY SKISEYRHYC

YSLYGTTLEQ QYNKPLCDLL IRCINCQKPL CPEEKQRHLD

KKQRFHNIRG RWTGRCMSCC RSSRTRRETQ L
```

To reduce oncogenic potential of E6 in a construct of this invention, one or more of the following positions of E6 is mutated:

| Original residue | Mutant residue | aa position in SEQ ID NO:20 | aa position in SEQ ID NO:21 |
|---|---|---|---|
| Cys | Gly (or Ala) | 70 | 63 |
| Cys | Gly (or Ala) | 113 | 106 |
| Ile | Thr | 135 | 128 |

Nguyen M et al., *J Virol.* 6:13039-48, 2002, described a mutant of HPV-16 E6 deficient in binding α-helix partners which displays reduced oncogenic potential in vivo. This mutant, that involves a replacement of Ile with Thr as position 128 (of SEQ ID NO:21), may be used in accordance with the present invention to make an E6 DNA vaccine that has a lower risk of being oncogenic. This E6($I^{128}$T) mutant is defective in its ability to bind at least a subset of α-helix partners, including E6AP, the ubiquitin ligase that mediates E6-dependent degradation of the p53 protein, Cassetti M C et al., *Vaccine* 22:520-52, 2004, examined the effects of mutations four or five amino acid positions in E6 and E7 to inactivate their oncogenic potential. The following mutations were examined: E6-$C^{63}$G and E6 $C^{106}$G (positions based on SEQ ID NO:21); E7-$C^{24}$G, E7-$E^{26}$G, and E7 $C^{91}$G (positions based on SEQ ID NO:17). Venezuelan equine encephalitis virus replicon particle (VRP) vaccines encoding mutant or wild type E6 and E7 proteins elicited comparable CTL responses and generated comparable antitumor responses in several HPV16 E6(+)E7(+) tumor challenge models: protection from either C3 or TC-1 tumor challenge was observed in 100% of vaccinated mice. Eradication of C3 tumors was observed in approximately 90% of the mice. The predicted inactivation of E6 and E7 oncogenic potential was confirmed by demonstrating normal levels of both p53 and Rb proteins in human mammary epithelial cells infected with VRPs expressing mutant E6 and E7 genes.

The HPV16 E6 protein contains two zinc fingers important for structure and function; one cysteine (C) amino acid position in each pair of C-X-X-C (where X is any amino acid) zinc finger motifs are preferably was mutated at E6 positions 63 and 106 (based on SEQ ID NO:21). Mutants are created, for example, using the Quick Change Site-Directed Mutagenesis Kit (Stratagene, La Jolla, Calif.). HPV16 E6 containing a single point mutation in the codon for $Cys^{106}$ in SEQ ID NO:21 (=Cys 113 in SEQ ID NO:20). $Cys^{106}$ neither binds nor facilitates degradation of p53 and is incapable of immortalizing human mammary epithelial cells (MEC), a phenotype dependent upon p53 degradation. A single amino acid substitution at position $Cys^{63}$ of SEQ ID NO:21 (=$Cys^{70}$ in SEQ ID NO:20) destroys several HPV16 E6 functions: p53 degradation, E6TP-1 degradation, activation of telomerase, and, consequently, immortalization of primary epithelial cells.

Any nucleotide sequence that encodes this E6 polypeptide, or preferably, one of the mutants thereof discussed below, or an antigenic fragment or epitope thereof, can be used in the present invention. Other mutations can be tested and used in accordance with the methods described herein including those described in Cassetti et al., supra. These mutations can be produced from any appropriate starting sequences by mutation of the coding DNA.

The present invention also includes the use of a tandem E6-E7 vaccine, using one or more of the mutations described herein to render the oncoproteins inactive with respect to their oncogenic potential in vivo. VRP vaccines (described in Cassetti et al., supra) comprised fused E6 and E7 genes in one open reading frame which were mutated at four or five amino acid positions (see below). Thus, the present constructs may include one or more epitopes of E6 and E7, which may be arranged in their native order or shuffled in any way that permits the expressed protein to bear the E6 and E7 antigenic epitopes in an immunogenic form. DNA encoding amino acid spacers between E6 and E7 or between individual epitopes of these proteins may be introduced into the vector, provided again, that the spacers permit the expression or presentation of the epitopes in an immunogenic manner after they have been expressed by transduced host cells.

Influenza Hemagglutinin (HA)

A nucleic acid sequence encoding HA [SEQ ID NO:22] is shown below.

```
atgaaggcaaacctactggtcctgttaagtgcacttgcagctgcagatgc
agacacaatatgtataggctaccatgcgaacaattcaaccgacactgttg
acacagtactcgagaagaatgtgacagtgacacactctgttaacctgctc
gaagacagccacaacggaaaactatgtagattaaaaggaatagccccact
acaattggggaaatgtaacatcgccggatggctcttgggaaacccagaat
gcgacccactgcttccagtgagatcatggtcctacattgtagaaacacca
aactctgagaatggaatatgttatccaggagatttcatcgactatgagga
gctgagggagcaattgagctcagtgtcatcattcgaaagattcgaaatat
ttcccaaagaaagctcatggcccaaccacaacacaaacggagtaacggca
gcatgctcccatgaggggaaaagcagtttttacagaaatttgctatggct
gacggagaaggagggctcatacccaaagctgaaaaattcttatgtgaaca
aaaaagggaaagaagtccttgtactgtggggtattcatcacccgcctaac
agtaaggaacaacagaatatctatcagaatgaaaatgcttatgtctctgt
agtgacttcaaattataacaggagatttaccccggaaatagcagaaagac
ccaaagtaagagatcaagctgggaggatgaactattactggaccttgcta
aaacccggagacacaataatatttgaggcaaatggaaatctaatagcacc
aatgtatgctttcgcactgagtagaggctttgggtccggcatcatcacct
caaacgcatcaatgcatgagtgtaacacgaagtgtcaaacacccctggga
gctataaacagcagtctcccttaccagaatatacacccagtcacaatagg
agagtgcccaaaatacgtcaggagtgccaaattgaggatggttacaggac
taaggaacactccgtccattcaatccagaggtctatttggagccattgcc
ggttttattgaaggggggatggactggaatgatagatggatggtatggtta
tcatcatcagaatgaacagggatcaggctatgcagcggatcaaaaaagca
cacaaaatgccattaacgggattacaaacaaggtgaacactgttatcgag
aaaatgaacattcaattcacagctgtgggtaaagaattcaacaaattaga
aaaaaggatggaaaatttaaataaaaaagttgatgatggatttctggaca
tttggacatataatgcagaattgttagttctactggaaaatgaaaggact
ctggatttccatgactcaaatgtgaagaatctgtatgagaaagtaaaaag
ccaattaaagaataatgccaaagaaatcggaaatggatgttttgagttct
accacaagtgtgacaatgaatgcatggaaagtgtaagaaatgggacttat
gattatcccaaatattcagaagagtcaaagttgaacagggaaaaggtaga
tggagtgaaattggaatcaatggggatctatcagattctggcgatctact
caactgtcgccagttcactggtgcttttggtctccctgggggcaatcagt
ttctggatgtgttctaatggatctttgcagtgcagaatatgcatctga
```

The amino acid sequence of HA [SEQ ID NO:23; immunodominant epitope underscored, is:

```
MKANLLVLLS ALAAADADTI CIGYHANNST DTVDTVLEKN
VTVTHSVNLL EDSHNGKLCR LKGIAPLQLG KCNIAGWLLG
```

-continued

```
NPECDPLLPV RSWSYIVETP NSENGICYPG DFIDYEELRE
QLSSVSSFER FEIFPKESSW PNHNTNGVTA ACSHEGKSSF
YRNLLWLTEK EGSYPKLKNS YVNKKGKEVL VLWGIHHPPN
SKEQQNIYQN ENAYVSVVTS NYNRRFTPEI AERPKVRDQA
GRMNYYWTLL KPGDTIIFEA NGNLIAPMYA FALSRGFGSG
IITSNASMHE CNTKCQTPLG AINSSLPYQN IHPVTIGECP
KYVRSAKLRM VTGLRNTPSI QSRGLFGAIA GFIEGGWTGM
IDGWYGYHHQ NEQGSGYAAD QKSTQNAING ITNKVNTVIE
KMNIQFTAVG KEFNKLEKRM ENLNKKVDDG FLDIWTYNAE
LLVLLENERT LDFHDSNVKN LYEKVKSQLK NNAKEIGNGC
FEFYHKCDNE CMESVRNGTY DYPKYSEESK LNREKVDGVK
LESMGIYQIL AIYSTVASSL VLLVSLGAIS FWMCSNGSLQ
CRICI
```

Other Antigens Associated with Pathogens

A major use for the present invention is as a therapeutic vaccine for cancer and for major chronic viral infections that cause morbidity and mortality worldwide. Such vaccines are designed to eliminate infected cells—this requires T cell responses as antibodies are often ineffective. The vaccines of the present invention are designed to meet these needs.

Preferred antigens are epitopes of pathogenic microorganisms against which the host is defended by effector T cells responses, including CTL and delayed type hypersensitivity. These typically include viruses, intracellular parasites such as malaria, and bacteria that grow intracellularly such as *Mycobacteria* and *Listeria* species. Thus, the types of antigens included in the vaccine compositions of this invention are any of those associated with such pathogens (in addition, of course, to tumor-specific antigens). It is noteworthy that some viral antigens are also tumor antigens in the case where the virus is a causative factor in cancer.

In fact, the two most common cancers worldwide, hepatoma and cervical cancer, are associated with viral infection. Hepatitis B virus (HBV) (Beasley, R. P. et al., *Lancet* 2:1129-1133 (1981) has been implicated as etiologic agent of hepatomas. 80-90% of cervical cancers express the E6 and E7 antigens (discussed above and exemplified herein) from one of four "high risk" human papillomavirus types: HPV-16, HPV-18, HPV-31 and HPV-45 (Gissmann, L. et al., *Ciba Found Symp.* 120:190-207, 1986; Beaudenon, S., et al. *Nature* 321:246-9, 1986). The HPV E6 and E7 antigens are the most promising targets for virus associated cancers in immunocompetent individuals because of their ubiquitous expression in cervical cancer. In addition to their importance as targets for therapeutic cancer vaccines, virus associated tumor antigens are also ideal candidates for prophylactic vaccines. Indeed, introduction of prophylactic HBV vaccines in Asia have decreased the incidence of hepatoma (Chang, M H et al. *New Engl. J. Med.* 336, 1855-1859 (1997), representing a great impact on cancer prevention.

Among the most important viruses in chronic human viral infections are HPV, HBV, hepatitis C Virus (HCV), human immunodeficiency virus (HIV-1 and HIV-2), herpesviruses such as Epstein Barr Virus (EBV), cytomegalovirus (CMV) and HSV-1 and HSV-2 and influenza virus. Useful antigens include HBV surface antigen or HBV core antigen; ppUL83 or pp89 of CMV; antigens of gp120, gp41 or p24 proteins of HIV-1; ICP27, gD2, gB of HSV; or influenza hemagglutinin or nucleoprotein (Anthony, L S et al., *Vaccine* 1999; 17:373-83). Other antigens associated with pathogens that can be utilized as described herein are antigens of various parasites, includes malaria, preferably malaria peptide based on repeats of NANP.

In addition to its applicability to human cancer and infectious diseases, the present invention is also intended for use in treating animal diseases in the veterinary medicine context. Thus, the approaches described herein may be readily applied by one skilled in the art to treatment of veterinary herpesvirus infections including equine herpesviruses, bovine viruses such as bovine viral diarrhea virus (for example, the E2 antigen), bovine herpesviruses, Marek's disease virus in chickens and other fowl; animal retroviral and lentiviral diseases (e.g., feline leukemia, feline immunodeficiency, simian immunodeficiency viruses, etc.); pseudorabies and rabies; and the like.

As for tumor antigens, any tumor-associated or tumor-specific antigen that can be recognized by T cells, preferably by CTL, can be used. These include, without limitation, mutant p53, HER2/neu or a peptide thereof, or any of a number of melanoma-associated antigens such as MAGE-1, MAGE-3, MART-1/Melan-A, tyrosinase, gp75, gp100, BAGE, GAGE-1, GAGE-2, GnT-V, and p15 (see, for example, U.S. Pat. No. 6,187,306).

DNA Encoding Immunogenicity-Potentiating Polypeptides (IPPs)

The present inventors and their colleagues have described a number of IPPs and their use in DNA vaccines, in the following publications, all of which are incorporated by reference in their entirety: Kim T W et al., *J Clin Invest* 112: 109-117, 2003; Cheng W F et al., *J Clin Invest* 108: 669-678, 2001; Hung C F et al., *Cancer Res* 61:3698-3703, 2001; Chen C H et al., 2000, supra; U.S. Pat. No. 6,734,173; published patent applications WO05/081716, WO05/047501, WO03/085085, WO02/12281, WO02/074920, WO02/061113, WO02/09645, and WO01/29233. Recently, they have described comparative studies of these IPPs using HPV E6 as the antigen in Peng, S. et al., *J Biomed Sci.* 12:689-700 2005

The DNA sequence encoding the E7 protein fused to the translocation Signal sequence and LAMP-1 domain (Sig-E7-L1) [SEQ ID NO:24] is:

```
ATGGCGGCCCCCGGCGCCCGGCGGCCGCTGCTCCTGCTGCTGCTGGCAGG

CCTTGCACATGGCGCCTCAGCACTCTTTGAGGATCTAATCATGCATGGAG

ATACACCTACATTGCATGAATATATGTTAGATTTGCAACCAGAGACAACT

GATCTCTACTGTTATGAGCAATTAAATGACAGCTCAGAGGAGGAGGATGA

AATAGATGGTCCAGCTGGACAAGCAGAACCGGACAGAGCCCATTACAATA

TTGTTACCTTTTGTTGCAAGTGTGACTCTACGCTTCGGTTGTGCGTACAA

AGCACACACGTAGACATTCGTACTTTGGAAGACCTGTTAATGGGCACACT

AGGAATTGTGTGCCCCATCTGTTCTCAGGATCTTAACAACATGTTGATCC

CCATTGCTGTGGGCGGTGCCCTGGCAGGGCTGGTCCTCATCGTCCTCATT

GCCTACCTCATTGGCAGGAAGAGGAGTCACGCCGGCTATCAGACCATCTA

G
```

The amino acid sequence of Sig-E7-L1 [SEQ ID NO:25] is:

```
MAAPGARRPL LLLLLAGLAH GASALFEDLI MHGDTPTLHE

YMLDLQPETT DLYCYEQLND SSEEEDEIDG PAGQAEPDRA

HYNIVTFCCK CDSTLRLCVQ STHVDIRTLE DLLMGTLGIV

CPICSQDLNN MLIPIAVGGA LAGLVLIVLI AYLIGRKRSH

AGYQTI
```

The nucleotide sequence of the immunogenic vector pcDNA3-sigE7-L1 [SEQ ID NO:26] is shown below with the SigE7-L1 coding sequence in lower case and underscored:

```
GACGGATCGGGAGATCTCCCGATCCCCTATGGTCGACTCTCAGTACAATC

TGCTCTGATGCCGCATAGTTAAGCCAGTATCTGCTCCCTGCTTGTGTGTT

GGAGGTCGCTGAGTAGTGCGCGAGCAAAATTTAAGCTACAACAAGGCAAG

GCTTGACCGACAATTGCATGAAGAATCTGCTTAGGGTTAGGCGTTTTGCG

CTGCTTCGCGATGTACGGGCCAGATATACGCGTTGACATTGATTATTGAC

TAGTTATTAATAGTAATCAATTACGGGGTCATTAGTTCATAGCCCATATA

TGGAGTTCCGCGTTACATAACTTACGGTAAATGGCCCGCCTGGCTGACCG

CCCAACGACCCCCGCCCATTGACGTCAATAATGACGTATGTTCCCATAGT

AACGCCAATAGGGACTTTCCATTGACGTCAATGGGTGGACTATTTACGGT

AAACTGCCCACTTGGCAGTACATCAAGTGTATCATATGCCAAGTACGCCC

CCTATTGACGTCAATGACGGTAAATGGCCCGCCTGGCATTATGCCCAGTA

CATGACCTTATGGGACTTTCCTACTTGGCAGTACATCTACGTATTAGTCA

TCGCTATTACCATGGTGATGCGGTTTTGGCAGTACATCAATGGGCGTGGA

TAGCGGTTTGACTCACGGGGATTTCCAAGTCTCCACCCCATTGACGTCAA

TGGGAGTTTGTTTTGGCACCAAAATCAACGGGACTTTCCAAAATGTCGTA

ACAACTCCGCCCCATTGACGCAAATGGGCGGTAGGCGTGTACGGTGGGAG

GTCTATATAAGCAGAGCTCTCTGGCTAACTAGAGAACCCACTGCTTACTG

GCTTATCGAAATTAATACGACTCACTATAGGGAGACCCAAGCTGGCTAGC

GTTTAAACGGGCCCTCTAGACTCGAGCGGCCGCCACTGTGCTGGATATCT

GCAGAATTCatggcggcccccggcgcccggcggccgctgctcctgctgct gctggcaggccttgcacatggcgcctcagcactctttgaggatctaatca tgcatggagatacacctacattgcatgaatatatgttagatttgcaacca gagacaactgatctctactgttatgagcaattaaatgacagctcagagga ggaggatgaaatagatggtccagctggacaagcagaaccggacagagccc attacaatattgttaccttttgttgcaagtgtgactctacgcttcggttg tgcgtacaaagcacacacgtagacattcgtactttggaagacctgttaat gggcacactaggaattgtgtgccccatctgttctcaggatcttaacaaca tgttgatcccattgctgtgggcggtgccctggcagggctggtcctcatc gtcctcattgcctacctcattggcaggaagaggagtcacgccggctatca gaccatctagGGATCCGAGCTCGGTACCAAGCTTAAGTTTAAACCGCTGA

TCAGCCTCGACTGTGCCTTCTAGTTGCCAGCCATCTGTTGTTTGCCCCTC
```

CCCCGTGCCTTCCTTGACCCTGGAAGGTGCCACTCCCACTGTCCTTTCCT
AATAAAATGAGGAAATTGCATCGCATTGTCTGAGTAGGTGTCATTCTATT
CTGGGGGGTGGGGTGGGGCAGGACAGCAAGGGGGAGGATTGGGAAGACAA
TAGCAGGCATGCTGGGGATGCGGTGGGCTCTATGGCTTCTGAGGCGGAAA
GAACCAGCTGGGGCTCTAGGGGGTATCCCCACGCGCCCTGTAGCGGCGCA
TTAAGCGCGGCGGGTGTGGTGGTTACGCGCAGCGTGACCGCTACACTTGC
CAGCGCCCTAGCGCCCGCTCCTTTCGCTTTCTTCCCTTCCTTTCTCGCCA
CGTTCGCCGGCTTTCCCCGTCAAGCTCTAAATCGGGGCATCCCTTTAGGG
TTCCGATTTAGTGCTTTACGGCACCTCGACCCCAAAAAACTTGATTAGGG
TGATGGTTCACGTAGTGGGCCATCGCCCTGATAGACGGTTTTTCGCCCTT
TGACGTTGGAGTCCACGTTCTTTAATAGTGGACTCTTGTTCCAAACTGGA
ACAACACTCAACCCTATCTCGGTCTATTCTTTTGATTTATAAGGGATTTT
GGGGATTTCGGCCTATTGGTTAAAAAATGAGCTGATTTAACAAAAATTTA
ACGCGAATTAATTCTGTGGAATGTGTGTCAGTTAGGGTGTGGAAAGTCCC
CAGGCTCCCAGGCAGGCAGAAGTATGCAAAGCATGCATCTCAATTAGTC
AGCAACCAGGTGTGGAAAGTCCCCAGGCTCCCCAGCAGGCAGAAGTATGC
AAAGCATGCATCTCAATTAGTCAGCAACCATAGTCCCGCCCCTAACTCCG
CCCATCCCGCCCCTAACTCCGCCCAGTTCCGCCCATTCTCCGCCCCATGG
CTGACTAATTTTTTTATTTATGCAGAGGCCGAGGCCGCCTCTGCCTCTG
AGCTATTCCAGAAGTAGTGAGGAGGCTTTTTTGGAGGCCTAGGCTTTTGC
AAAAAGCTCCCGGGAGCTTGTATATCCATTTTCGGATCTGATCAAGAGAC
AGGATGAGGATCGTTTCGCATGATTGAACAAGATGGATTGCACGCAGGTT
CTCCGGCCGCTTGGGTGGAGAGGCTATTCGGCTATGACTGGGCACAACAG
ACAATCGGCTGCTCTGATGCCGCCGTGTTCCGGCTGTCAGCGCAGGGGCG
CCCGGTTCTTTTTGTCAAGACCGACCTGTCCGGTGCCCTGAATGAACTGC
AGGACGAGGCAGCGCGGCTATCGTGGCTGGCCACGACGGGCGTTCCTTGC
GCAGCTGTGCTCGACGTTGTCACTGAAGCGGGAAGGGACTGGCTGCTATT
GGGCGAAGTGCCGGGGCAGGATCTCCTGTCATCTCACCTTGCTCCTGCCG
AGAAAGTATCCATCATGGCTGATGCAATGCGGCGGCTGCATACGCTTGAT
CCGGCTACCTGCCCATTCGACCACCAAGCGAAACATCGCATCGAGCGAGC
ACGTACTCGGATGGAAGCCGGTCTTGTCGATCAGGATGATCTGGACGAAG
AGCATCAGGGGCTCGCGCCAGCCGAACTGTTCGCCAGGCTCAAGGCGCGC
ATGCCCGACGGCGAGGATCTCGTCGTGACCCATGGCGATGCCTGCTTGCC
GAATATCATGGTGGAAAATGGCCGCTTTTCTGGATTCATCGACTGTGGCC
GGCTGGGTGTGGCGGACCGCTATCAGGACATAGCGTTGGCTACCCGTGAT
ATTGCTGAAGAGCTTGGCGGCGAATGGGCTGACCGCTTCCTCGTGCTTTA
CGGTATCGCCGCTCCCGATTCGCAGCGCATCGCCTTCTATCGCCTTCTTG
ACGAGTTCTTCTGAGCGGGACTCTGGGGTTCGAAATGACCGACCAAGCGA
CGCCCAACCTGCCATCACGAGATTTCGATTCCACCGCCGCCTTCTATGAA
AGGTTGGGCTTCGGAATCGTTTTCCGGGACGCCGGCTGGATGATCCTCCA
GCGCGGGGATCTCATGCTGGAGTTCTTCGCCCACCCCAACTTGTTTATTG

CAGCTTATAATGGTTACAAATAAAGCAATAGCATCACAAATTTCACAAAT
AAAGCATTTTTTTCACTGCATTCTAGTTGTGGTTTGTCCAAACTCATCAA
TGTATCTTATCATGTCTGTATACCGTCGACCTCTAGCTAGAGCTTGGCGT
AATCATGGTCATAGCTGTTTCCTGTGTGAAATTGTTATCCGCTCACAATT
CCACACAACATACGAGCCGGAAGCATAAAGTGTAAAGCCTGGGGTGCCTA
ATGAGTGAGCTAACTCACATTAATTGCGTTGCGCTCACTGCCCGCTTTCC
AGTCGGGAAACCTGTCGTGCCAGCTGCATTAATGAATCGGCCAACGCGCG
GGGAGAGGCGGTTTGCGTATTGGGCGCTCTTCCGCTTCCTCGCTCACTGA
CTCGCTGCGCTCGGTCGTTCGGCTGCGGCGAGCGGTATCAGCTCACTCAA
AGGCGGTAATACGGTTATCCACAGAATCAGGGGATAACGCAGGAAAGAAC
ATGTGAGCAAAAGGCCAGCAAAAGGCCAGGAACCGTAAAAAGGCCGCGTT
GCTGGCGTTTTTCCATAGGCTCCGCCCCCCTGACGAGCATCACAAAAATC
GACGCTCAAGTCAGAGGTGGCGAAACCCGACAGGACTATAAAGATACCAG
GCGTTTCCCCCTGGAAGCTCCCTCGTGCGCTCTCCTGTTCCGACCCTGCC
GCTTACCGGATACCTGTCCGCCTTTCTCCCTTCGGGAAGCGTGGCGCTTT
CTCAATGCTCACGCTGTAGGTATCTCAGTTCGGTGTAGGTCGTTCGCTCC
AAGCTGGGCTGTGTGCACGAACCCCCCGTTCAGCCCGACCGCTGCGCCTT
ATCCGGTAACTATCGTCTTGAGTCCAACCCGGTAAGACACGACTTATCGC
CACTGGCAGCAGCCACTGGTAACAGGATTAGCAGAGCGAGGTATGTAGGC
GGTGCTACAGAGTTCTTGAAGTGGTGGCCTAACTACGGCTACACTAGAAG
GACAGTATTTGGTATCTGCGCTCTGCTGAAGCCAGTTACCTTCGGAAAAA
GAGTTGGTAGCTCTTGATCCGGCAAACAAACCACCGCTGGTAGCGGTGGT
TTTTTTGTTTGCAAGCAGCAGATTACGCGCAGAAAAAAAGGATCTCAAGA
AGATCCTTTGATCTTTTCTACGGGGTCTGACGCTCAGTGGAACGAAAACT
CACGTTAAGGGATTTTGGTCATGAGATTATCAAAAAGGATCTTCACCTAG
ATCCTTTTAAATTAAAAATGAAGTTTTAAATCAATCTAAAGTATATATGA
GTAAACTTGGTCTGACAGTTACCAATGCTTAATCAGTGAGGCACCTATCT
CAGCGATCTGTCTATTTCGTTCATCCATAGTTGCCTGACTCCCCGTCGTG
TAGATAACTACGATACGGGAGGGCTTACCATCTGGCCCCAGTGCTGCAAT
GATACCGCGAGACCCACGCTCACCGGCTCCAGATTTATCAGCAATAAACC
AGCCAGCCGGAAGGGCCGAGCGCAGAAGTGGTCCTGCAACTTTATCCGCC
TCCATCCAGTCTATTAATTGTTGCCGGGAAGCTAGAGTAAGTAGTTCGCC
AGTTAATAGTTTGCGCAACGTTGTTGCCATTGCTACAGGCATCGTGGTGT
CACGCTCGTCGTTTGGTATGGCTTCATTCAGCTCCGGTTCCCAACGATCA
AGGCGAGTTACATGATCCCCCATGTTGTGCAAAAAAGCGGTTAGCTCCTT
CGGTCCTCCGATCGTTGTCAGAAGTAAGTTGGCCGCAGTGTTATCACTCA
TGGTTATGGCAGCACTGCATAATTCTCTTACTGTCATGCCATCCGTAAGA
TGCTTTTCTGTGACTGGTGAGTACTCAACCAAGTCATTCTGAGAATAGTG
TATGCGGCGACCGAGTTGCTCTTGCCCGGCGTCAATACGGGATAATACCG
CGCCACATAGCAGAACTTTAAAAGTGCTCATCATTGGAAAACGTTCTTCG

```
GGGCGAAAACTCTCAAGGATCTTACCGCTGTTGAGATCCAGTTCGATGTA
ACCCACTCGTGCACCCAACTGATCTTCAGCATCTTTTACTTTCACCAGCG
TTTCTGGGTGAGCAAAAACAGGAAGGCAAAATGCCGCAAAAAAGGGAATA
AGGGCGACACGGAAATGTTGAATACTCATACTCTTCCTTTTTCAATATTA
TTGAAGCATTTATCAGGGTTATTGTCTCATGAGCGGATACATATTTGAAT
GTATTTAGAAAAATAAACAAATAGGGGTTCCGCGCACATTTCCCCGAAAA
GTGCCACCTGACGTC
```

HSP70 from *M. tuberculosis*

The nucleotide sequence encoding HSP70 (SEQ ID NO:27) is shown below (nucleotides 10633-12510 of the *M. tuberculosis* genome in GenBank NC_000962);

```
atggctcg tgcggtcggg atcgacctcg ggaccaccaa
ctccgtcgtc tcggttctgg aaggtggcga cccggtcgtc
gtcgccaact ccgagggctc caggaccacc ccgtcaattg
tcgcgttcgc ccgcaacggt gaggtgctgg tcgccagcc
cgccaagaac caggcagtga ccaacgtcga tcgcaccgtg
cgctcggtca agcgacacat gggcagcgac tggtccatag
agattgacgg caagaaatac accgcgccgg agatcagcgc
ccgcattctg atgaagctga gcgcgacgc cgaggcctac
ctcggtgagg acattaccga cgcggttatc acgacgcccg
cctacttcaa tgacgcccag cgtcaggcca ccaaggacgc
cggccagatc gccggcctca acgtgctgcg gatcgtcaac
gagccgaccg cggccgcgct ggcctacggc ctcgacaagg
gcgagaagga gcagcgaatc ctggtcttcg acttgggtgg
tggcactttc gacgttccc tgctggagat cggcgagggt
gtggttgagg tccgtgccac ttcgggtgac aaccacctcg
gcggcgacga ctgggaccag cgggtcgtcg attggctggt
ggacaagttc aagggcacca gcggcatcga tctgaccaag
gacaagatgg cgatgcagcg gctgcgggaa gccgccgaga
aggcaaagat cgagctgagt tcgagtcagt ccacctcgat
caacctgccc tacatcaccg tcgacgccga caagaacccg
ttgttcttag acgagcagct gaccgcgcg gagttccaac
ggatcactca ggacctgctg gaccgcactc gcaagccgtt
ccagtcggtg atcgctgaca ccggcatttc ggtgtcggag
atcgatcacg ttgtgctcgt gggtggttcg acccggatgc
ccgcggtgac cgatctggtc aaggaactca ccggcggcaa
ggaacccaac aagggcgtca accccgatga ggttgtcgcg
gtgggagccg ctctgcaggc cggcgtcctc aagggcgagg
tgaaagacgt tctgctgctt gatgttaccc cgctgagcct
gggtatcgag accaaggcg gggtgatgac caggctcatc
gagcgcaaca ccacgatccc caccaagcgg tcggagactt
tcaccaccgc cgacgacaac caaccgtcgg tgcagatcca
ggtctatcag ggggagcgtg agatcgccgc gcacaacaag
ttgctcgggt ccttcgagct gaccggcatc ccgccggcgc
cgcgggggat tccgcagatc gaggtcactt tcgacatcga
cgccaacggc attgtgcacg tcaccgccaa ggacaagggc
accggcaagg agaacacgat ccgaatccag gaaggctcgg
gcctgtccaa ggaagacatt gaccgcatga tcaaggacgc
cgaagcgcac gccgaggagg atcgcaagcg tcgcgaggag
gccgatgttc gtaatcaagc cgagacattg gtctaccaga
cggagaagtt cgtcaaagaa cagcgtgagg ccgagggtgg
ttcgaaggta cctgaagaca cgctgaacaa ggttgatgcc
gcggtggcgg aagcgaaggc ggcacttggc ggatcggata
tttcggccat caagtcggcg atggagaagc tgggccagga
gtcgcaggct ctggggcaag cgatctacga agcagctcag
gctgcgtcac aggccactgg cgctgcccac cccggcggcg
agccgggcgg tgcccacccc ggctcggctg atgacgttgt
ggacgcggag gtggtcgacg acggccggga ggccaagtga
```

The amino acid sequence of HSP70 [SEQ ID NO:28] is:

```
MARAVGIDLG TTNSVVSVLE GGDPVVVANS EGSRTTPSIV
AFARNGEVLV GQPAKNQAVT NVDRTVRSVK RHMGSDWSIE
IDGKKYTAPE ISARILMKLK RDAEAYLGED ITDAVITTPA
YFNDAQRQAT KDAGQIAGLN VLRIVNEPTA AALAYGLDKG
EKEQRILVFD LGGGTFDVSL LEIGEGVVEV RATSGDNHLG
GDDWDQRVVD WLVDKFKGTS GIDLTKDKMA MQRLREAAEK
AKIELSSSQS TSINLPYITV DADKNPLFLD EQLTRAEFQR
ITQDLLDRTR KPFQSVIADT GISVSEIDHV VLVGGSTRMP
AVTDLVKELT GGKEPNKGVN PDEVVAVGAA LQAGVLKGEV
KDVLLLDVTP LSLGIETKGG VMTRLIERNT TIPTKRSETF
TTADDNQPSV QIQVYQGERE IAAHNKLLGS FELTGIPPAP
RGIPQIEVTF DIDANGIVHV TAKDKGTGKE NTIRIQEGSG
LSKEDIDRMI KDAEAHAEED RKRREEADVR NQAETLVYQT
EKFVKEQREA EGGSKVPEDT LNKVDAAVAE AKAALGGSDI
SAIKSAMEKL GQESQALGQA IYEAAQAASQ ATGAAHPGGE
PGGAHPGSAD DVVDAEVVDD GREAK
```

The E7-Hsp70 Chimera/Fusion Polypeptide (Nucleotide sequence SEQ ID NO:29 and amino acid sequence SEQ ID NO:30) are provided below. The E7 coding sequence is shown in upper case and underscored.

```
1/1                                   31/11
ATG CAT GGA GAT ACA CCT ACA TTG CAT GAA TAT ATG TTA GAT TTG CAA CCA GAG ACA ACT
Met His Gly Asp Thr Pro Thr Leu His Glu Tyr Met Leu Asp Leu Gln Pro Glu Thr Thr

61/21                                 91/31
GAT CTC TAC TGT TAT GAG CAA TTA AAT GAC AGC TCA GAG GAG GAG GAT GAA ATA GAT GGT
Asp Leu Tyr Cys Tyr Glu Gln Leu Asn Asp Ser Ser Glu Glu Glu Asp Glu Ile Asp Gly

121/41                                151/51
CCA GCT GGA CAA GCA GAA CCG GAC AGA GCC CAT TAC AAT ATT GTA ACC TTT TGT TGC AAG
Pro Ala Gly Gln Ala Glu Pro Asp Arg Ala His Tyr Asn Ile Val Thr Phe Cys Cys Lys

181/61                                211/71
TGT GAC TCT ACG CTT CGG TTG TGC GTA CAA AGC ACA CAC GTA GAC ATT CGT ACT TTG GAA
Cys Asp Ser Thr Leu Arg Leu Cys Val Gln Ser Thr His Val Asp Ile Arg Thr Leu Glu

241/81                                271/91
GAC CTG TTA ATG GGC ACA CTA GGA ATT GTG TGC CCC ATC TGT TCT CAA GGA TCC atg gct
Asp Leu Leu Met Gly Thr Leu Gly Ile Val Cys Pro Ile Cys Ser Gln Gly Ser Met Ala 301/101                               331/111
cgt gcg gtc ggg atc gac ctc ggg acc acc aac tcc gtc gtc tcg gtt ctg gaa ggt ggc
Arg Ala Val Gly Ile Asp Leu Gly Thr Thr Asn Ser Val Val Ser Val Leu Glu Gly Gly 361/121                               391/131
gac ccg gtc gtc gtc gcc aac tcc gag ggc tcc agg acc acc ccg tca att gtc gcg ttc
Asp Pro Val Val Val Ala Asn Ser Glu Gly Ser Arg Thr Thr Pro Ser Ile Val Ala Phe 421/141                               451/151
gcc cgc aac ggt gag gtg ctg gtc ggc cag ccc gcc aag aac cag gca gtg acc aac gtc
Ala Arg Asn Gly Glu Val Leu Val Gly Gln Pro Ala Lys Asn Gln Ala Val Thr Asn Val 481/161                               511/171
gat cgc acc gtg cgc tcg gtc aag cga cac atg ggc agc gac tgg tcc ata gag att gac
Asp Arg Thr Val Arg Ser Val Lys Arg His Met Gly Ser Asp Trp Ser Ile Glu Ile Asp 541/181                               571/191
ggc aag aaa tac acc gcg ccg gag atc agc gcc cgc att ctg atg aag ctg aag cgc gac
Gly Lys Lys Tyr Thr Ala Pro Glu Ile Ser Ala Arg Ile Leu Met Lys Leu Lys Arg Asp 601/201                               631/211
gcc gag gcc tac ctc ggt gag gac att acc gac gcg gtt atc acg acg ccc gcc tac ttc
Ala Glu Ala Tyr Leu Gly Glu Asp Ile Thr Asp Ala Val Ile Thr Thr Pro Ala Tyr Phe 661/221                               691/231
aat gac gcc cag cgt cag gcc acc aag gac gcc ggc cag atc gcc ggc ctc aac gtg ctg
Asn Asp Ala Gln Arg Gln Ala Thr Lys Asp Ala Gly Gln Ile Ala Gly Leu Asn Val Leu 721/241                               751/251
cgg atc gtc aac gag ccg acc gcg gcc gcg ctg gcc tac ggc ctc gac aag ggc gag aag
Arg Ile Val Asn Glu Pro Thr Ala Ala Ala Leu Ala Tyr Gly Leu Asp Lys Gly Glu Lys 781/261                               811/271
gag cag cga atc ctg gtc ttc gac ttg ggt ggt ggc act ttc gac gtt tcc ctg ctg gag
Glu Gln Arg Ile Leu Val Phe Asp Leu Gly Gly Gly Thr Phe Asp Val Ser Leu Leu Glu 841/281                               871/291
atc ggc gag ggt gtg gtt gag gtc cgt gcc act tcg ggt gac aac cac ctc ggc ggc gac
Ile Gly Glu Gly Val Val Glu Val Arg Ala Thr Ser Gly Asp Asn His Leu Gly Gly Asp 901/301                               931/311
gac tgg gac cag cgg gtc gtc gat tgg ctg gtg gac aag ttc aag ggc acc agc ggc atc
Asp Trp Asp Gln Arg Val Val Asp Trp Leu Val Asp Lys Phe Lys Gly Thr Ser Gly Ile 961/321                               991/331
gat ctg acc aag gac aag atg gcg atg cag cgg ctg cgg gaa gcc gcc gag aag gca aag
Asp Leu Thr Lys Asp Lys Met Ala Met Gln Arg Leu Arg Glu Ala Ala Glu Lys Ala Lys 1021/341                              1051/351
atc gag ctg agt tcg agt cag tcc acc tcg atc aac ctg ccc tac atc acc gtc gac gcc
Ile Glu Leu Ser Ser Ser Gln Ser Thr Ser Ile Asn Leu Pro Tyr Ile Thr Val Asp Ala 1081/361                              1111/371
gac aag aac ccg ttg ttc tta gac gag cag ctg acc cgc gcg gag ttc caa cgg atc act
Asp Lys Asn Pro Leu Phe Leu Asp Glu Gln Leu Thr Arg Ala Glu Phe Gln Arg Ile Thr 1141/381                              1171/391
cag gac ctg ctg gac cgc act cgc aag ccg ttc cag tcg gtg atc gct gac acc ggc att
Gln Asp Leu Leu Asp Arg Thr Arg Lys Pro Phe Gln Ser Val Ile Ala Asp Thr Gly Ile
```

```
1201/401                              1231/411
tcg gtg tcg gag atc gat cac gtt gtg ctc gtg ggt ggt tcg acc cgg atg ccc gcg gtg
Ser Val Ser Glu Ile Asp His Val Val Leu Val Gly Gly Ser Thr Arg Met Pro Ala Val 1261/421                              1291/431
acc gat ctg gtc aag gaa ctc acc ggc ggc aag gaa ccc aac aag ggc gtc aac ccc gat
Thr Asp Leu Val Lys Glu Leu Thr Gly Gly Lys Glu Pro Asn Lys Gly Val Asn Pro Asp 1321/441                              1351/451
gag gtt gtc gcg gtg gga gcc gct ctg cag gcc ggc gtc ctc aag ggc gag gtg aaa gac
Glu Val Val Ala Val Gly Ala Ala Leu Gln Ala Gly Val Leu Lys Gly Glu Val Lys Asp 1381/461                              1411/471
gtt ctg ctg ctt gat gtt acc ccg ctg agc ctg ggt atc gag acc aag ggc ggg gtg atg
Val Leu Leu Leu Asp Val Thr Pro Leu Ser Leu Gly Ile Glu Thr Lys Gly Gly Val Met 1441/481                              1471/491
acc agg ctc atc gag cgc aac acc acg atc ccc acc aag cgg tcg gag act ttc acc acc
Thr Arg Leu Ile Glu Arg Asn Thr Thr Ile Pro Thr Lys Arg Ser Glu Thr Phe Thr Thr 1501/501                              1531/511
gcc gac gac aac caa ccg tcg gtg cag atc cag gtc tat cag ggg gag cgt gag atc gcc
Ala Asp Asp Asn Gln Pro Ser Val Gln Ile Gln Val Tyr Gln Gly Glu Arg Glu Ile Ala 1561/521                              1591/531
gcg cac aac aag ttg ctc ggg tcc ttc gag ctg acc ggc atc ccg ccg gcg ccg cgg ggg
Ala His Asn Lys Leu Leu Gly Ser Phe Glu Leu Thr Gly Ile Pro Pro Ala Pro Arg Gly 1621/541                              1651/551
att ccg cag atc gag gtc act ttc gac atc gac gcc aac ggc att gtg cac gtc acc gcc
Ile Pro Gln Ile Glu Val Thr Phe Asp Ile Asp Ala Asn Gly Ile Val His Val Thr Ala 1681/561                              1711/571
aag gac aag ggc acc ggc aag gag aac acg atc cga atc cag gaa ggc tcg ggc ctg tcc
Lys Asp Lys Gly Thr Gly Lys Glu Asn Thr Ile Arg Ile Gln Glu Gly Ser Gly Leu Ser 1741/581                              1771/591
aag gaa gac att gac cgc atg atc aag gac gcg cac gcc gag gag gat cgc aag
Lys Glu Asp Ile Asp Arg Met Ile Lys Asp Ala His Ala Glu Glu Asp Arg Lys 1801/601                              1831/611
cgt cgc gag gag gcc gat gtt cgt aat caa gcc gag aca ttg gtc tac cag acg gag aag
Arg Arg Glu Glu Ala Asp Val Arg Asn Gln Ala Glu Thr Leu Val Tyr Gln Thr Glu Lys 1861/621                              1891/631
ttc gtc aaa gaa cag cgt gag gcc gag ggt ggt tcg aag gta cct gaa gac acg ctg aac
Phe Val Lys Glu Gln Arg Glu Ala Glu Gly Gly Ser Lys Val Pro Glu Asp Thr Leu Asn 1921/641                              1951/651
aag gtt gat gcc gcg gtg gcg gaa gcg aag gcg gca ctt ggc gga tcg gat att tcg gcc
Lys Val Asp Ala Ala Val Ala Glu Ala Lys Ala Ala Leu Gly Gly Ser Asp Ile Ser Ala 1981/661                              2011/671
atc aag tcg gcg atg gag aag ctg ggc cag gag tcg cag gct ctg ggg caa gcg atc tac
Ile Lys Ser Ala Met Glu Lys Leu Gly Gln Glu Ser Gln Ala Leu Gly Gln Ala Ile Tyr 2041/681                              2071/691
gaa gca gct cag gct gcg tca cag gcc act ggc gct gcc cac ccc ggc tcg gct gat gaA
GLU ALA ALA GLN ALA ALA SER GLN ALA THR GLY ALA ALA HIS PRO GLY SER ALA ASP GLU 2101/701
AGC a
Ser
```

ETA(dII) from *Pseudomonas aeruginosa*

The complete coding sequence for *Pseudomonas aeruginosa* exotoxin type A (ETA)-SEQ ID NO:31-GenBank Accession No. K01397, is shown below:

```
ctgcagctgg tcaggccgtt tccgcaacgc ttgaagtcct
ggccgatata ccggcagggc cagccatcgt tcgacgaata
aagccacctc agccatgatg ccctttccat ccccagcgga
accccgacat ggacgccaaa gccctgctcc tcggcagcct
ctgcctggcc gccccattcg ccgacgcggc gacgctcgac
aatgctctct ccgcctgcct cgccgcccgg ctcggtgcac
cgcacacggc ggagggccag ttgcacctgc cactcaccct
tgaggcccgg cgctccaccg gcgaatgcgc ctgtacctcg
gcgctggtgc gatatcggct gctggccagg ggcgccagcg
ccgacagcct cgtgcttcaa gagggctgct cgatagtcgc
```

-continued

```
caggacacgc cgcgcacgct gaccctggcg gcggacgccg
gcttggcgag cggccgcgaa ctggtcgtca ccctggggttg
tcaggcgcct gactgacagg ccgggctgcc accaccaggc
cgagatggac gccctgcatg tatcctccga tcggcaagcc
tcccgttcgc acattcacca ctctgcaatc cagttcataa
atcccataaa agccctcttc cgctccccgc cagcctcccc
gcatcccgca ccctagacgc cccgccgctc tccgccggct
cgcccgacaa gaaaaaccaa ccgctcgatc agcctcatcc
ttcacccatc acaggagcca tcgcgatgca cctgataccc
cattggatcc ccctggtcgc cagcctcggc ctgctcgccg
gcggctcgtc cgcgtccgcc gccgaggaag ccttcgacct
ctggaacgaa tgcgccaaag cctgcgtgct cgacctcaag
gacggcgtgc gttccagccg catgagcgtc gacccggcca
tcgccgacac caacggccag ggcgtgctgc actactccat
ggtcctggag ggcggcaacg acgcgctcaa gctggccatc
gacaacgccc tcagcatcac cagcgacggc ctgaccatcc
gcctcgaagg cggcgtcgag ccgaacaagc cggtgcgcta
cagctacacg cgccaggcgc gcggcagttg gtcgctgaac
tggctggtac cgatcggcca cgagaagccc tcgaacatca
aggtgttcat ccacgaactg aacgccggca accagctcag
ccacatgtcg ccgatctaca ccatcgagat gggcgacgag
ttgctggcga agctggcgcg cgatgccacc ttcttcgtca
gggcgcacga gagcaacgag atgcagccga cgctcgccat
cagccatgcc ggggtcagcg tggtcatggc ccagacccag
ccgccgcggg aaaagcgctg gagcgaatgg gccagcggca
aggtgttgtg cctgctcgac ccgctggacg gggtctacaa
ctacctcgcc cagcaacgct gcaacctcga cgatacctgg
gaaggcaaga tctaccgggt gctcgccggc aacccggcga
agcatgacct ggacatcaaa cccacggtca tcagtcatcg
cctgcacttt cccgagggcg gcagcctggc cgcgctgacc
gcgcaccagg cttgccacct gccgctggag actttcaccc
gtcatcgcca gccgcgcggc tgggaacaac tggagcagtg
cggctatccg gtgcagcggc tggtcgccct ctacctggcg
gcgcggctgt cgtggaacca ggtcgaccag gtgatccgca
acgccctggc cagccccggc agcggcggcg acctgggcga
agcgatccgc gagcagccgg agcaggcccg tctggccctg
accctggccg ccgccgagag cgagcgcttc gtccggcagg
gcaccggcaa cgacgaggcc ggcgcggcca acgccgacgt
ggtgagcctg acctgccgg tcgccgccgg tgaatgcgcg
ggcccggcg acagcggcga cgccctgctg gagcgcaact
atcccactgg cgcggagttc ctcggcgacg gcggcgcgt
```

-continued

```
cagcttcagc acccgcggca cgcagaactg gacggtggag
cggctgctcc aggcgcaccg ccaactggag gagcgcggct
atgtgttcgt cggctaccac ggcaccttcc tcgaagcggc
gcaaagcatc gtcttcggcg gggtgcgcgc gcgcagccag
gacctcgacg cgatctggcg cggtttctat atcgccggcg
atccggcgct ggcctacggc tacgcccagg accaggaacc
cgacgcacgc ggccggatcc gcaacggtgc cctgctgcgg
gtctatgtgc cgcgctcgag cctgccgggc ttctaccgca
ccagcctgac cctggccgcg ccggaggcgg cgggcgaggt
cgaacggctg atcggccatc cgctgccgct gcgcctggac
gccatcaccg gccccgagga ggaaggcggg cgcctggaga
ccattctcgg ctggccgctg ccgagcgca ccgtggtgat
tccctcggcg atccccaccg acccgcgcaa cgtcggcggc
gacctcgacc cgtccagcat ccccgacaag gaacaggcga
tcagcgccct gccggactac gccagccagc ccggcaaacc
gccgcgcgag gacctgaagt aactgccgcg accggccggc
tcccttcgca ggagccggcc ttctcggggc ctggccatac
atcaggtttt cctgatgcca gcccaatcga atatgaattc 2760
```

The amino acid sequence of ETA (SEQ ID NO:32), GenBank Accession No. K01397, is:

```
MHLIPHWIPL VASLGLLAGG SSASAAEEAF DLWNECAKAC
VLDLKDGVRS SRMSVDPAIA DTNGQGVLHY SMVLEGGNDA
LKLAIDNALS ITSDGLTIRL EGGVEPNKPV RYSYTRQARG
SWSLNWLVPI GHEKPSNIKV FIHELNAGNQ LSHMSPIYTI
EMGDELLAKL ARDATFFVRA HESNEMQPTL AISHAGVSVV
MAQTQPRREK RWSEWASGKV LCLLDPLDGV YNYLAQQRCN
LDDTWEGKIY RVLAGNPAKH DLDIKPTVIS HRLHFPEGGS
LAALTAHQAC HLPLETFTRH RQPRGWEQLE QCGYPVQRLV
ALYLAARLSW NQVDQVIRNA LASPGSGGDL GEAIREQPEQ
ARLALTLAAA ESERFVRQGT GNDEAGAANA DVVSLTCPVA
AGECAGPADS GDALLERNYP TGAEFLGDGG DVSFSTRGTQ
NWTVERLLQA HRQLEERGYV FVGYHGTFLE AAQSIVFGGV
RARSQDLDAI WRGFYIAGDP ALAYGYAQDQ EPDARGRIRN
GALLRVYVPR SSLPGFYRTS LTLAAPEAAG EVERLIGHPL
PLRLDAITGP EEEGGRLETI LGWPLAERTV VIPSAIPTDP
RNVGGDLDPS SIPDKEQAIS ALPDYASQPG KPPREDLK 638
```

Residues 1-25 (italicized) above represent the signal peptide. The first residue of the mature polypeptide, Ala, is bolded/underscored. The mature polypeptide is residues 26-638 of SEQ ID NO:32.

Domain II (ETA(II)), translocation domain (underscored above) spans residues 247-417 of the mature polypeptide (corresponding to residues 272-442 of SEQ ID NO:32) and is presented below separately as SEQ ID NO:33.

RLHFPEGGSL AALTAHQACH LPLETFTRHR QPRGWEQLEQ

CGYPVQRLVA LYLAARLSWN QVDQVIRNAL ASPGSGGDLG

EAIREQPEQA RLALTLAAAE SERFVRQGTG NDEAGAANAD

VVSLTCPVAA GECAGPADSG DALLERNYPT GAEFLGDGGD

VSFSTRGTQN W 171

The construct in which ETA(dII) is fused to HPV-16 E7 is shown below (nucleotides; SEQ ID NO:34 and amino acids; SEQ ID NO:35). The ETA(dII) sequence appears in plain font, extra codons from plasmid pcDNA3 are italicized. Nucleotides between ETA(dII) and E7 are also bolded (and result in the interposition of two amino acids between ETA (dII) and E7). The E7 amino acid sequence is underscored (ends with Gln at position 269).

The nucleotide sequence of the pcDNA3 vector encoding E7 and HSP70 (pcDNA3-E7-Hsp70) (SEQ ID NO:36) is shown in FIG. 38. The E7-Hsp70 fusion sequence is shown in upper case, underscored. Plasmid sequences are in lower case.

The nucleic acid sequence of plasmid construct pcDNA3-ETA(dII)/E7 (SEQ ID NO:37) is shown in FIG. 39. ETA(dII)/E7 is ligated into the EcoRI/BamHI sites of pcDNA3 vector. The nucleotides encoding ETA(dII)/E7 are shown in upper case and underscored. Plasmid sequence is lower case.

Calreticulin (CRT)

"Calreticulin" or "CRT" describes the well-characterized ~46 kDa resident protein of the ER lumen that has lectin activity and participates in the folding and assembly of nascent glycoproteins. CRT acts as a "chaperone" polypeptide and a member of the MHC class I transporter TAP complex; CRT associates with TAP1 and TAP2 transporters, tapa- 1/1 31/11
atg cgc ctg cac ttt ccc gag ggc ggc agc ctg gcc gcg ctg acc gcg cac cag gct tgc
Met arg leu his phe pro glu gly gly ser leu ala ala leu thr ala his gln ala cys 61/21 91/31
cac ctg ccg ctg gag act ttc acc cgt cat cgc cag ccg cgc ggc tgg gaa caa ctg gag
His Leu Pro Leu Glu Thr Phe Thr Arg His Arg Gln Pro Arg Gly Trp Glu Gln Leu Glu 121/41 151/51
cag tgc ggc tat ccg gtg cag cgg ctg gtc gcc ctc tac ctg gcg gcg cgg ctg tcg tgg
Gln Cys Gly Tyr Pro Val Gln Arg Leu Val Ala Leu Tyr Leu Ala Ala Arg Leu Ser Trp 181/61 211/71
aac cag gtc gac cag gtg atc cgc aac gcc ctg gcc agc ccc ggc agc ggc ggc gac ctg
Asn Gln Val Asp Gln Val Ile Arg Asn Ala Leu Ala Ser Pro Gly Ser Gly Gly Asp Leu 241/81 271/91
ggc gaa gcg atc cgc gag cag ccg gag cag gcc cgt ctg gcc ctg acc ctg gcc gcc gcc
Gly Glu Ala Ile Arg Glu Gln Pro Glu Gln Ala Arg Leu Ala Leu Thr Leu Ala Ala Ala 301/101 331/111
gag agc gag cgc ttc gtc cgg cag ggc acc ggc aac gac gag gcc ggc gcg gcc aac gcc
Glu Ser Glu Arg Phe Val Arg Gln Gly Thr Gly Asn Asp Glu Ala Gly Ala Ala Asn Ala 361/121 391/131
gac gtg gtg agc ctg acc tgc ccg gtc gcc gcc ggt gaa tgc gcg ggc ccg gcg gac agc
Asp Val Val Ser Leu Thr Cys Pro Val Ala Ala Gly Glu Cys Ala Gly Pro Ala Asp Ser 421/141 451/151
ggc gac gcc ctg ctg gag cgc aac tat ccc act ggc gcg gag ttc ctc ggc gac ggc ggc
Gly Asp Ala Leu Leu Glu Arg Asn Tyr Pro Thr Gly Ala Glu Phe Leu Gly Asp Gly Gly 481/161 511/171
gac gtc agc ttc agc acc cgc ggc acg cag aac gaa ttc atg cat gga gat aca cct aca
Asp Val Ser Phe Ser Thr Arg Gly Thr Gln Asn Glu Phe Met His Gly Asp Thr Pro Thr 541/181 571/191
ttg cat gaa tat atg tta gat ttg caa cca gag aca act gat ctc tac tgt tat gag caa
Leu His Glu Tyr Met Leu Asp Leu Gln Pro Glu Thr Thr Asp Leu Tyr Cys Tyr Glu Gln 601/201 631/211
tta aat gac agc tca gag gag gag gat gaa ata gat ggt cca gct gga caa gca gaa ccg
Leu Asn Asp Ser Ser Glu Glu Glu Asp Glu Ile Asp Gly Pro Ala Gly Gln Ala Glu Pro 661/221 691/231
gac aga gcc cat tac aat att gta acc ttt tgt tgc aag tgt gac tct acg ctt cgg ttg
Asp Arg Ala His Tyr Asn Ile Val Thr Phe Cys Cys Lys Cys Asp Ser Thr Leu Arg Leu 721/241 751/251
tgc gta caa agc aca cac gta gac att cgt act ttg gaa gac ctg tta atg ggc aca cta
Cys Val Gln Ser Thr His Val Asp Ile Arg Thr Leu Glu Asp Leu Leu Met Gly Thr Leu 781/261 811/271
gga att gtg tgc ccc atc tgt tct caa gga tcc gag ctc ggt acc aag ctt aag ttt aaa
Gly Ile Val Cys Pro Ile Cys Ser Gln *Gly Ser Glu Leu Gly Thr Lys Leu Lys Phe Lys*

841/281
ccg ctg atc agc ctc gac tgt gcc ttc tag
*Pro Leu Ile Ser Leu Asp Cys Ala Phe AMB* sin, MHC Class I heavy chain polypeptide and β2 microglobulin to function in the loading of peptide epitopes onto nascent MHC class I molecules (Jorgensen, *Eur. J. Biochem.* 267:2945-54, 2002. The term "calreticulin" or "CRT" refers to polypeptides and nucleic acids molecules having substantial identity (defined herein) to the exemplary CRT sequences as described herein. A CRT polypeptide is a polypeptides comprising a sequence identical to or substantially identical (defined herein) to the amino acid sequence of CRT. An exemplary nucleotide and amino acid sequence for a CRT used in the present compositions and methods are presented below. The terms "calreticulin" or "CRT" encompass native proteins as well as recombinantly produced modified proteins that induce an immune response, including a CTL response. The terms "calreticulin" or "CRT" encompass homologues and allelic variants of CRT, including variants of native proteins constructed by in vitro techniques, and proteins isolated from natural sources. The CRT polypeptides of the invention, and sequences encoding them, also include fusion proteins comprising non-CRT sequences, particularly MHC class I-binding peptides; and also further comprising other domains, e.g., epitope tags, enzyme cleavage recognition sequences, signal sequences, secretion signals and the like.

The term "endoplasmic reticulum chaperone polypeptide" as used herein means any polypeptide having substantially the same ER chaperone function as the exemplary chaperone proteins CRT, tapasin, ER60 or calnexin. Thus, the term includes all functional fragments or variants or mimics thereof. A polypeptide or peptide can be routinely screened for its activity as an ER chaperone using assays known in the art, such as that set forth in Example 1. While the invention is not limited by any particular mechanism of action, in vivo chaperones promote the correct folding and oligomerization of many glycoproteins in the ER, including the assembly of the MHC class I heterotrimeric molecule (heavy (H) chain, β2m, and peptide). They also retain incompletely assembled MHC class I heterotrimeric complexes in the ER (Hauri FEBS Lett. 476:32-37, 2000).

The sequences of CRT, including human CRT, are well known in the art (McCauliffe, *J. Clin. Invest.* 86:332-5, 1990; Burns, *Nature* 367:476-80, 1994; Coppolino, *Int. J. Biochem. Cell Biol.* 30:553-8, 2000). The nucleic acid sequence appears as GenBank Accession No. NM 004343 and is SEQ ID NO:38.

```
   1 gtccgtactg cagagccgct gccggagggt cgttttaaag ggccgcgttg ccgccccctc
  61 ggcccgccat gctgctatcc gtgccgctgc tgctcggcct cctcggcctg gccgtcgccg
 121 agcccgccgt ctacttcaag gagcagtttc tggacggaga cgggtggact tcccgctgga
 181 tcgaatccaa acacaagtca gattttggca aattcgttct cagttccggc aagttctacg
 241 gtgacgagga gaaagataaa ggtttgcaga caagccagga tgcacgcttt tatgctctgt
 301 cggccagttt cgagcctttc agcaacaaag gccagacgct ggtggtgcag ttcacggtga
 361 aacatgagca gaacatcgac tgtgggggcg gctatgtgaa gctgtttcct aatagtttgg
 421 accagacaga catgcacgga gactcagaat acaacatcat gtttggtccc gacatctgtg
 481 gccctggcac caagaaggtt catgtcatct tcaactacaa gggcaagaac gtgctgatca
 541 acaaggacat ccgttgcaag gatgatgagt ttacacacct gtacacactg attgtgcggc
 601 cagacaacac ctatgaggtg aagattgaca cagccaggt ggagtccggc tccttggaag
 661 acgattggga cttcctgcca cccaagaaga taaaggatcc tgatgcttca aaaccggaag
 721 actgggatga gcgggccaag atcgatgatc ccacagactc caagcctgag gactgggaca
 781 agcccgagca tatccctgac cctgatgcta agaagcccga ggactgggat gaagagatgg
 841 acggagagtg ggaacccca gtgattcaga cccctgagta caagggtgag tggaagcccc
 901 ggcagatcga caacccagat tacaagggca cttggatcca cccagaaatt gacaacccg
 961 agtattctcc cgatcccagt atctatgcct atgataactt tggcgtgctg ggcctggacc
1021 tctggcaggt caagtctggc accatctttg acaacttcct catcaccaac gatgaggcat
1081 acgctgagga gtttggcaac gagacgtggg gcgtaacaaa ggcagcagag aaacaaatga
1141 aggacaaaca ggacgaggag cagaggctta aggaggagga agaagacaag aaacgcaaag
1201 aggaggagga ggcagaggac aaggaggatg atgaggacaa agatgaggat gaggaggatg
1261 aggaggacaa ggaggaagat gaggaggaag atgtccccgg ccaggccaag gacgagctgt
1321 agagaggcct gcctccaggg ctggactgag gcctgagcgc tcctgccgca gagcttgccg
1381 cgccaaataa tgtctctgtg agactcgaga acttttcattt ttttccaggc tggttcggat
1441 ttggggtgga ttttggtttt gttccctcc tccactctcc cccacccct ccccgcctt
1501 ttttttttt tttttaaact ggtattttat cctttgattc tccttcagcc ctcacccctg
```

-continued

```
1561 gttctcatct ttcttgatca acatctttc ttgcctctgt gccccttctc tcatctctta 1621 gctcccctcc aacctggggg gcagtggtgt ggagaagcca caggcctgag atttcatctg 1681 ctctccttcc tggagcccag aggagggcag cagaaggggg tggtgtctcc aacccccag 1741 cactgaggaa gaacggggct cttctcatt cacccctccc tttctccct gcccccagga 1801 ctgggccact tctgggtggg gcagtgggtc ccagattggc tcacactgag aatgtaagaa 1861 ctacaaacaa aatttctatt aaattaaatt ttgtgtctc 1899
```

Human CRT protein (GenBank Accession No. NM 004343), (SEQ ID NO:39) is shown below:

```
  1 MLLSVPLLLG LLGLAVAEPA VYFKEQFLDG DGWTSRWIES KHKSDFGKFV LSSGKFYGDE

61 EKDKGLQTSQ DARFYALSAS FEPFSNKGQT LVVQFTVKHE QNIDCGGGYV KLFPNSLDQT

121 DMHGDSEYNI MFGPDICGPG TKKVHVIFNY KGKNVLINKD IRCKDDEFTH LYTLIVRPDN

181 TYEVKIDNSQ VESGSLEDDW DFLPPKKIKD PDASKPEDWD ERAKIDDPTD SKPEDWDKPE

241 HIPDPDAKKP EDWDEEMDGE WEPPVIQNPE YKGEWKPRQI DNPDYKGTWI HPEIDNPEYS

301 PDPSIYAYDN FGVLGLDLWQ VKSGTIFDNF LITNDEAYAE EFGNETWGVT KAAEKQMKDK

361 QDEEQRLKEE EEDKKRKEEE EAEDKEDDED KDEDEEDEED KEEDEEEDVP GQAKDEL 417
```

For the generation of plasmid encoding the full length of rabbit calreticulin (there is more than 90% homology between rabbit, human, mouse, and rat calreticulin), pcDNA3-CRT, the DNA fragment encoding this protein was first amplified with PCR using conditions as described in Chen, *Cancer Res.*, 2000, supra, using rabbit calreticulin cDNA template (Michalak, *Biochem J.* 344 Pt 2:281-292, 1999), provided by Dr. Marek Michalak, University of Alberta, Edmonton, Canada, and a set of the following primers:

```
5'-ccggtctagaatgctgctccctgtgccgct-3'  (SEQ ID NO:40)
and

5'-ccggagatctcagctcgtccttggcctggc-3'  (SEQ ID NO:41)
```

The amplified product was then digested with the restriction digest enzymes XbaI and BamHI and further cloned into the XbaI and BamHI cloning sites of pcDNA3 vector (Invitrogen, Carlsbad, Calif.). For the generation of pcDNA3-CRT/E7, the E7 DNA was amplified by PCR using pcDNA3-E7 as a DNA template and a set of primers:

```
5'-ggggaattcatggagatacaccta-3'   (SEQ ID NO:42)
and

5'-ggtggatccttgagaacagatgg-3'    (SEQ ID NO:43)
```

The amplified E7 DNA fragment was then digested with BamHI and further cloned into the BamHI cloning sites of pcDNA3-CRT vector. The orientation and accuracy of these constructs was confirmed by DNA sequencing.

Plasmid DNA with CRT, E7 or CRT/E7 gene insert and the "empty" plasmid vector were transfected into subcloning-efficient DH5 ™ cells (Life Technologies, USA). The DNA was then amplified and purified using double CsCl purification (BioServe Biotechnologies, Laurel, Md.). The integrity of plasmid DNA and the absence of *E. coli* DNA or RNA were verified by agarose gel electrophoresis, and the presence of the inserted E7 fragment was confirmed by restriction enzyme digestion and gel electrophoresis.

The present inventors and their colleagues have found that DNA vaccines encoding CRT linked either to E6 or to E7 both of generate significant antitumor effects against E6- and E7-expressing tumors, respectively. Moreover, simultaneous vaccination with both CRT/E6 and CRT/E7 DNA vaccines generated significant E6- and E7-specific T-cell immune responses and significantly better therapeutic antitumor effects against E6- and E7-expressing tumors than vaccination with either CRT/E6 DNA or CRT/E7 DNA alone.

The three domains of CRT also produce E7-specific antitumor immunity and antiangiogenic effects (Cheng W F et al., *Vaccine.* 23:3864-74, 2005). DNA vaccines encoding each of N, P, and C domains of CRT linked to E7 antigen produced significant stimulation of E7-specific CD8+ T cell precursors and antitumor effects against E7-expressing tumors. The N domain of CRT also showed antiangiogenic properties that might have contributed to the antitumor effect. Thus, the present invention includes DNA immunogens in which the IPP is the N, P, or C domain of CRT.

The nucleotide sequence of plasmid pNGVL4a-CRT/E7 (detox) (SEQ ID NO:44) is shown in FIG. 40. The sequence is annotated to show plasmid-derived sequences (lower case), CRT-derived (bold, upper case) and HPV-E7-derived (detoxified by two amino acid substitutions as described above (upper case, italicized, underlined) sequences.

General Recombinant DNA Methods

Basic texts disclosing general methods of molecular biology, all of which are incorporated by reference, include: Sambrook, J et al., *Molecular Cloning: A Laboratory Manual*, 2nd Edition, Cold Spring Harbor Press, Cold Spring Harbor, N.Y., 1989; Ausubel, F M et al. *Current Protocols in Molecular Biology*, Vol. 2, Wiley-Interscience, New York, (current edition); Kriegler, *Gene Transfer and Expression: A Laboratory Manual* (1990); Glover, D M, ed, *DNA Cloning: A Practical Approach*, vol. I & II, IRL Press, 1985; Albers, B. et al., *Molecular Biology of the Cell*, 2nd Ed., Garland Publishing, Inc., New York, N.Y. (1989); Watson, J D et al., *Recombinant DNA*, 2nd Ed., Scientific American Books, New York, 1992; and Old, R W et al., *Principles of Gene Manipu-*

*lation: An Introduction to Genetic Engineering*, 2nd Ed., University of California Press, Berkeley, Calif. (1981).

Techniques for the manipulation of nucleic acids, such as, e.g., generating mutations in sequences, subcloning, labeling probes, sequencing, hybridization and the like are well described in the scientific and patent literature. See, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Tijssen, ed. Elsevier, N.Y. (1993).

Nucleic acids, vectors, capsids, polypeptides, and the like can be analyzed and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, e.g. fluid or gel precipitin reactions, immunodiffusion, immuno-electrophoresis, radioimmunoassays (RIAs), enzyme-linked immunosorbent assays (ELISAs), immunofluorescence assays, Southern analysis, Northern analysis, dot-blot analysis, gel electrophoresis (e.g., SDS-PAGE), RT-PCR, quantitative PCR, other nucleic acid or target or signal amplification methods, radiolabeling, scintillation counting, and affinity chromatography.

Amplification of Nucleic Acids

Oligonucleotide primers can be used to amplify nucleic acids to generate fusion protein coding sequences used to practice the invention, to monitor levels of vaccine after in vivo administration (e.g., levels of a plasmid or virus), to confirm the presence and phenotype of activated CTLs, and the like. The skilled artisan can select and design suitable oligonucleotide amplification primers using known sequences. Amplification methods are also well known in the art, and include, e.g., polymerase chain reaction, PCR (*PCR Protocols, A Guide to Methods and Applications*, ed. Innis, Academic Press, N.Y. (1990) and *PCR Strategies* (1995), ed. Innis, Academic Press, Inc., N.Y., ligase chain reaction (LCR) (Wu (1989) *Genomics* 4:560; Landegren (1988) *Science* 241: 1077; Barringer (1990) *Gene* 89:117); transcription amplification (Kwoh (1989) *Proc. Natl. Acad. Sci. USA* 86:1173); and, self-sustained sequence replication (Guatelli (1990) *Proc. Natl. Acad. Sci. USA* 87:1874); Qβ replicase amplification (Smith (1997) *J. Clin. Microbiol.* 35:1477-1491; Burg (1996) *Mol. Cell. Probes* 10:257-271) and other RNA polymerase mediated techniques (NASBA, Cangene, Mississauga, Ontario; Berger (1987) *Methods Enzymol.* 152:307-316; U.S. Pat. Nos. 4,683,195 and 4,683,202; Sooknanan (1995) *Biotechnology* 13:563-564).

Unless otherwise indicated, a particular nucleic acid sequence is intended to encompasses conservative substitution variants thereof (e.g., degenerate codon substitutions) and a complementary sequence. The term "nucleic acid" is synonymous with "polynucleotide" and is intended to include a gene, a cDNA molecule, an mRNA molecule, as well as a fragment of any of these such as an oligonucleotide, and further, equivalents thereof (explained more fully below). Sizes of nucleic acids are stated either as kilobases (kb) or base pairs (bp). These are estimates derived from agarose or polyacrylamide gel electrophoresis (PAGE), from nucleic acid sequences which are determined by the user or published. Protein size is stated as molecular mass in kilodaltons (kDa) or as length (number of amino acid residues). Protein size is estimated from PAGE, from sequencing, from presumptive amino acid sequences based on the coding nucleic acid sequence or from published amino acid sequences.

Specifically, cDNA molecules encoding the amino acid sequence corresponding to the fusion polypeptide of the present invention or fragments or derivatives thereof can be synthesized by the polymerase chain reaction (PCR) (see, for example, U.S. Pat. No. 4,683,202) using primers derived the sequence of the protein disclosed herein. These cDNA sequences can then be assembled into a eukaryotic or prokaryotic expression vector and the resulting vector can be used to direct the synthesis of the fusion polypeptide or its fragment or derivative by appropriate host cells, for example COS or CHO cells.

This invention includes isolated nucleic acids having a nucleotide sequence encoding the novel fusion polypeptides that comprise a translocation polypeptide and an antigen, fragments thereof or equivalents thereof. The term nucleic acid as used herein is intended to include such fragments or equivalents. The nucleic acid sequences of this invention can be DNA or RNA.

A cDNA nucleotide sequence the fusion polypeptide can be obtained by isolating total mRNA from an appropriate cell line. Double stranded cDNA is prepared from total mRNA. cDNA can be inserted into a suitable plasmid, bacteriophage or viral vector using any one of a number of known techniques.

In reference to a nucleotide sequence, the term "equivalent" is intended to include sequences encoding structurally homologous and/or a functionally equivalent proteins. For example, a natural polymorphism in a nucleotide sequence encoding an anti-apoptotic polypeptide according to the present invention (especially at the third base of a codon) may be manifest as "silent" mutations which do not change the amino acid sequence. Furthermore, there may be one or more naturally occurring isoforms or related, immunologically cross-reactive family members of these proteins. Such isoforms or family members are defined as proteins that share function amino acid sequence similarity to the reference polypeptide.

Fragment of Nucleic Acid

A fragment of the nucleic acid sequence is defined as a nucleotide sequence having fewer nucleotides than the nucleotide sequence encoding the full length translocation polypeptide, antigenic polypeptide or the fusion thereof. This invention includes such nucleic acid fragments that encode polypeptides which retain (1) the ability of the fusion polypeptide to induce increases in frequency or reactivity of T cells, preferably CD8+ T cells, that are specific for the antigen part of the fusion polypeptide.

For example, a nucleic acid fragment as intended herein encodes an antigen or an IPP that that retains the ability to improve the immunogenicity of an antigen vaccine when administered as a chimeric DNA with antigen-encoding sequence, or when co-administered therewith.

Generally, the nucleic acid sequence encoding a fragment of an anti-apoptotic polypeptide comprises of nucleotides from the sequence encoding the mature protein (or an active fragment thereof).

Nucleic acid sequences of this invention may also include linker sequences, natural or modified restriction endonuclease sites and other sequences that are useful for manipulations related to cloning, expression or purification of encoded protein or fragments. These and other modifications of nucleic acid sequences are described herein or are well-known in the art.

The techniques for assembling and expressing DNA coding sequences for translocation types of proteins, and DNA coding sequences for antigenic polypeptides, include synthesis of oligonucleotides, PCR, transforming cells, constructing vectors, expression systems, and the like; these are well-established in the art such that those of ordinary skill are familiar with standard resource materials, specific conditions and procedures.

Expression Vectors and Host Cells

This invention includes an expression vector comprising a nucleic acid sequence encoding (a) an antigen, optionally linked to (b) an IPP or (c) an siRNA operably linked to at least one regulatory sequence, which includes a promoter that is expressable in a eukaryotic cell, preferably in a mammalian cells, more preferably in a human cell.

The term "expression vector" or "expression cassette" as used herein refers to a nucleotide sequence which is capable of affecting expression of a protein coding sequence in a host compatible with such sequences. Expression cassettes include at least a promoter operably linked with the polypeptide coding sequence; and, optionally, with other sequences, e.g., transcription termination signals. Additional factors necessary or helpful in effecting expression may also be included, e.g., enhancers.

"Operably linked" means that the coding sequence is linked to a regulatory sequence in a manner that allows expression of the coding sequence. Known regulatory sequences are selected to direct expression of the desired protein in an appropriate host cell. Accordingly, the term "regulatory sequence" includes promoters, enhancers and other expression control elements. Such regulatory sequences are described in, for example, Goeddel, *Gene Expression Technology. Methods in Enzymology*, vol. 185, Academic Press, San Diego, Calif. (1990)).

Thus, expression cassettes include plasmids, recombinant viruses, any form of a recombinant "naked DNA" vector, and the like. A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors include replicons (e.g., RNA replicons), bacteriophages) to which fragments of DNA may be attached and become replicated. Vectors thus include, but are not limited to RNA, autonomous self-replicating circular or linear DNA or RNA, e.g., plasmids, viruses, and the like (U.S. Pat. No. 5,217,879), and includes both the expression and nonexpression plasmids. Where a recombinant cell or culture is described as hosting an "expression vector" this includes both extrachromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

Those skilled in the art appreciate that the particular design of an expression vector of this invention depends on considerations such as the host cell to be transfected and/or the type of protein to be expressed.

The present expression vectors comprise the full range of nucleic acid molecules encoding the various embodiments of the fusion polypeptide and its functional derivatives (defined herein) including polypeptide fragments, variants, etc., as well as those encoding siRNA or other siNAs of the present invention.

Such expression vectors are used to transfect host cells (in vitro, ex vivo or in vivo) for expression of the DNA and production of the encoded proteins which include fusion proteins or peptides. It will be understood that a genetically modified cell expressing the fusion polypeptide may transiently express the exogenous DNA for a time sufficient for the cell to be useful for its stated purpose.

The present in invention provides methods for producing the fusion polypeptides, fragments and derivatives. For example, a host cell transfected with a nucleic acid vector that encodes the fusion polypeptide or an siRNA is cultured under appropriate conditions to allow expression of the polypeptide or siRNA.

Host cells may also be transfected with one or more expression vectors that singly or in combination comprise (a) DNA encoding at least a portion of the fusion polypeptide and (b) DNA encoding at least a portion of a second protein, preferably an antigen, or (c) DNA encoding an siRNA, so that the host cells produce yet further fusion polypeptides or siRNAs A culture typically includes host cells, appropriate growth media and other byproducts. Suitable culture media are well known in the art. The fusion polypeptide can be isolated from medium or cell lysates using conventional techniques for purifying proteins and peptides, including ammonium sulfate precipitation, fractionation column chromatography (e.g. ion exchange, gel filtration, affinity chromatography, etc.) and/or electrophoresis (see generally, "Enzyme Purification and Related Techniques", *Meth Enzymol*, 22:233-577 (1971)). Once purified, partially or to homogeneity, the recombinant polypeptides or siRNAs of the invention can be utilized in pharmaceutical compositions as described in more detail herein.

The term "isolated" as used herein, when referring to a molecule or composition, such as a translocation polypeptide or a nucleic acid coding therefor, means that the molecule or composition is separated from at least one other compound (protein, other nucleic acid, etc.) or from other contaminants with which it is natively associated or becomes associated during processing. An isolated composition can also be substantially pure. An isolated composition can be in a homogeneous state and can be dry or in aqueous solution. Purity and homogeneity can be determined, for example, using analytical chemical techniques such as polyacrylamide gel electrophoresis (PAGE) or high performance liquid chromatography (HPLC). Even where a protein has been isolated so as to appear as a homogenous or dominant band in a gel pattern, there are trace contaminants which co-purify with it.

Host cells transformed or transfected to express the fusion polypeptide or a homologue or functional derivative thereof are within the scope of the invention. For example, the fusion polypeptide may be expressed in yeast, or mammalian cells such as Chinese hamster ovary cells (CHO) or, preferably human cells. Preferred cells for expression of the siRNA of the present invention are APCs most preferably, DCs. Other suitable host cells are known to those skilled in the art.

Expression in eukaryotic cells leads to partial or complete glycosylation and/or formation of relevant inter- or intra-chain disulfide bonds of the recombinant protein.

Although preferred vectors are described in the Examples, other examples of expression vectors are provided here. Examples of vectors for expression in yeast *S. cerevisiae* include pYepSec1 (Baldari et al., *EMBO J*. 6:229-34, 1987), pMFa (Kurjan et al., *Cell* 30:933-43, 1982), pJRY88 (Schultz et al., *Gene* 54:113-23, 1987), and pYES2 (Invitrogen Corp.). Baculovirus vectors available for expression of proteins in cultured insect cells (SF 9 cells) include the pAc series (Smith et al., *Mol. Cell Biol*. 3:2156-65, 1983) and the pVL series (Lucklow, V A et al., *Virology* 170:31-9, 1989). Generally, COS cells (Gluzman, Y., *Cell* 23:175-82, 1981) are used in conjunction with such vectors as pCDM 8 (Aruffo A et al., supra, for transient amplification/expression in mammalian cells, while CHO (dhfr-negative CHO) cells are used with vectors such as pMT2PC (Kaufman et al. *EMBO J.* 6:187-95, 1987) for stable amplification/expression in mammalian cells. The NS0 myeloma cell line (a glutamine synthetase expression system.) is available from Celltech Ltd.

Often, in fusion expression vectors, a proteolytic cleavage site is introduced at the junction of the reporter group and the target protein to enable separation of the target protein from the reporter group subsequent to purification of the fusion protein. Proteolytic enzymes for such cleavage and their recognition sequences include Factor Xa, thrombin and enterokinase. Typical fusion expression vectors include pGEX (Amrad Corp., Melbourne, Australia), pMAL (New England Biolabs) and pRIT5 (Pharmacia, Piscataway, N.J.) which fuse glutathione S-transferase, maltose E binding protein, or protein A, respectively, to the target recombinant protein. Inducible non-fusion expression vectors include pTrc (Amann et al., *Gene* 69:301-15, 1988) and pET 11d (Studier et al., *Gene Expression Technology: Meth Enzymol* 185:60-89, Academic Press, 1990).

Vector Construction

Construction of suitable vectors comprising the desired coding and control sequences employs standard ligation and restriction techniques which are well understood in the art. Isolated plasmids, DNA sequences, or synthesized oligonucleotides are cleaved, tailored, and re-ligated in the form desired. The sequences of several preferred plasmid vectors, with and without inserted coding sequences, have been disclosed above.

The DNA sequences which form the vectors are available from a number of sources. Backbone vectors and control systems are generally found on available "host" vectors which are used for the bulk of the sequences in construction. For the pertinent coding sequence, initial construction may be, and usually is, a matter of retrieving the appropriate sequences from cDNA or genomic DNA libraries. However, once the sequence is disclosed it is possible to synthesize the entire gene sequence in vitro starting from the individual nucleotide derivatives. The entire gene sequence for genes of sizeable length, e.g., 500-1000 bp may be prepared by synthesizing individual overlapping complementary oligonucleotides and filling in single stranded nonoverlapping portions using DNA polymerase in the presence of the deoxyribonucleotide triphosphates. This approach has been used successfully in the construction of several genes of known sequence. See, for example, Edge, Md., *Nature* 292:756, 1981; Nambair, K P, et al., *Science* 223:1299, 1984; Jay, E, *J Biol Chem* 259:6311, 1984).

Synthetic oligonucleotides are prepared by either the phosphotriester method as described by references cited above or the phosphoramidite method (Beaucage, S L et al., *Tet Lett* 22:1859, 1981; Matteucci, M D et al., *J Am Chem Soc* 103: 3185, 1981) and can be prepared using commercially available automated oligonucleotide synthesizers. Kinase treatment of single strands prior to annealing or for labeling is by conventional methods.

Once the components of the desired vectors are thus available, they can be excised and ligated using standard restriction and ligation procedures. Site-specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. A general description of size separations is found in *Methods in Enzymology* (1980) 65:499-560.

Restriction cleaved fragments may be blunt ended by treating with the large fragment of *E. coli* DNA polymerase I (Klenow) in the presence of the four deoxynucleotide triphosphates (dNTPs) using conventional methods and conditions. Ligations are performed using conventional methods. In vector construction employing "vector fragments", the fragment is commonly treated with bacterial or mammalian alkaline phosphatase to remove the 5' phosphate and prevent self-ligation. Alternatively, re-ligation can be prevented in vectors which have been double digested by additional restriction enzyme and separation of the unwanted fragments.

Any of a number of methods are used to introduce mutations into the coding sequence to generate the variants of the invention. These mutations include simple deletions or insertions, systematic deletions, insertions or substitutions of clusters of bases or substitutions of single bases.

For example, modifications of DNA sequences are created by site-directed mutagenesis, a well-known technique for which protocols and reagents are commercially available (Zoller, M J et al., *Nucleic Acids Res* 10:6487-500, 1982; Adelman, J P et al., *DNA* 2:183-193, 1983). Using conventional methods, transformants are selected based on the presence of the ampicillin-, tetracycline-, or other antibiotic resistance gene (or other selectable marker) depending on the mode of plasmid construction. Plasmids are then prepared from the transformants with optional chloramphenicol amplification (Clewell, D B et al., *Proc Natl Acad Sci USA* 62:1159, 1969); Clewell, D B, *J Bacteriol* 110:667, 1969)). Several mini DNA preps are commonly used. See, e.g., *Anal Biochem* 114:193-7, 1981; *Nucleic Acids Res* 7:1513-23, 1979). The isolated DNA is analyzed by restriction and/or sequenced by the dideoxy nucleotide method of Sanger (*Proc Natl Acad Sci USA* 74:5463, 1977; Messing, et al., *Nucleic Acids Res* 9:309, 1981), or by the method of Maxam et al., *Meth Enzymology* 65:499, 1980.

Vector DNA can be introduced into mammalian cells via conventional techniques such as calcium phosphate or calcium chloride co-precipitation, DEAE-dextran-mediated transfection, lipofection, or electroporation. Suitable methods for transforming host cells can be found in Sambrook et al. supra and other standard texts. In fusion expression vectors, a proteolytic cleavage site may be introduced at the junction of two sequences (such as a reporter group and the target protein to enable separation of the target protein from the reporter group subsequent to purification of the fusion protein). Proteolytic enzymes for such cleavage and their recognition sequences include Factor Xa, thrombin and enterokinase.

Promoters and Enhancers

A promoter region of a DNA or RNA molecule binds RNA polymerase and promotes the transcription of an "operably linked" nucleic acid sequence. As used herein, a "promoter sequence" is the nucleotide sequence of the promoter which is found on that strand of the DNA or RNA which is transcribed by the RNA polymerase. Two sequences of a nucleic acid molecule, such as a promoter and a coding sequence, are "operably linked" when they are linked to each other in a manner which permits both sequences to be transcribed onto the same RNA transcript or permits an RNA transcript begun in one sequence to be extended into the second sequence. Thus, two sequences, such as a promoter sequence and a coding sequence of DNA or RNA are operably linked if transcription commencing in the promoter sequence will produce an RNA transcript of the operably linked coding sequence. In order to be "operably linked" it is not necessary that two sequences be immediately adjacent to one another in the linear sequence.

The preferred promoter sequences of the present invention must be operable in mammalian cells and may be either eukaryotic or viral promoters. Although preferred promoters are described in the Examples, other useful promoters and regulatory elements are discussed below. Suitable promoters may be inducible, repressible or constitutive. A "constitutive" promoter is one which is active under most conditions encountered in the cell's environmental and throughout development. An "inducible" promoter is one which is under environmental or developmental regulation. A "tissue specific" promoter is active in certain tissue types of an organism. An example of a constitutive promoter is the viral promoter MSV-LTR, which is efficient and active in a variety of cell types, and, in contrast to most other promoters, has the same enhancing activity in arrested and growing cells. Other preferred viral promoters include that present in the CMV-LTR (from cytomegalovirus) (Bashart, M. et al., Cell 41:521, 1985) or in the RSV-LTR (from Rous sarcoma virus) (Gorman, C. M., Proc. Natl. Acad. Sci. USA 79:6777, 1982). Also useful are the promoter of the mouse metallothionein I gene (Hamer, D, et al., J. Mol. Appl. Gen. 1:273-88, 1982; the TK promoter of Herpes virus (McKnight, S, Cell 31:355-65, 1982); the SV40 early promoter (Benoist, C., et al., Nature 290:304-10, 1981); and the yeast gal4 gene promoter (Johnston, S A et al., Proc. Natl. Acad. Sci. USA 79:6971-5, 1982); Silver, P A, et al., Proc. Natl. Acad. Sci. (USA) 81:5951-5, 1984)). Other illustrative descriptions of transcriptional factor association with promoter regions and the separate activation and DNA binding of transcription factors include: Keegan et al., Nature 231:699, 1986; Fields et al., Nature 340:245, 1989; Jones, Cell 61:9, 1990; Lewin, Cell 61:1161, 1990; Ptashne et al., Nature 346:329, 1990; Adams et al., Cell 72:306, 1993. The relevant disclosure of all of these above-listed references is hereby incorporated by reference.

The promoter region may further include an octamer region which may also function as a tissue specific enhancer, by interacting with certain proteins found in the specific tissue. The enhancer domain of the DNA construct of the present invention is one which is specific for the target cells to be transfected, or is highly activated by cellular factors of such target cells. Examples of vectors (plasmid or retrovirus) are disclosed in (Roy-Burman et al., U.S. Pat. No. 5,112,767). For a general discussion of enhancers and their actions in transcription, see, Lewin, B M, Genes IV, Oxford University Press pp. 552-576, 1990 (or later edition). Particularly useful are retroviral enhancers (e.g., viral LTR) that is preferably placed upstream from the promoter with which it interacts to stimulate gene expression. For use with retroviral vectors, the endogenous viral LTR may be rendered enhancer-less and substituted with other desired enhancer sequences which confer tissue specificity or other desirable properties such as transcriptional efficiency.

Nucleic acids of the invention can also be chemically synthesized using standard techniques, including solid-phase synthesis which, like peptide synthesis, has been fully automated with commercially available DNA synthesizers (Itakura U.S. Pat. Nos. 4,598,049, 4,401,796 and 4,373,071; Caruthers et al. U.S. Pat. No. 4,458,066.

Proteins and Polypeptides

The terms "polypeptide," "protein," and "peptide" when referring to compositions of the invention are meant to include variants, analogues, and mimetics with structures and/or activity that substantially correspond to the polypeptide or peptide from which the variant, etc., was derived.

The present invention includes an "isolated" fusion polypeptide comprising a targeting polypeptide linked to an antigenic polypeptide.

The term "chimeric" or "fusion" polypeptide or protein refers to a composition comprising at least one polypeptide or peptide sequence or domain that is chemically bound in a linear fashion with a second polypeptide or peptide domain. One embodiment of this invention is an isolated or recombinant nucleic acid molecule encoding a fusion protein comprising at least two domains, wherein the first domain comprises an IPP and the second domain comprises an antigenic epitope, e.g., an MHC class I-binding peptide epitope. The "fusion" can be an association generated by a peptide bond, a chemical linking, a charge interaction (e.g., electrostatic attractions, such as salt bridges, H-bonding, etc.) or the like. If the polypeptides are recombinant, the "fusion protein" can be translated from a common mRNA. Alternatively, the compositions of the domains can be linked by any chemical or electrostatic means. The chimeric molecules of the invention (e.g., targeting polypeptide fusion proteins) can also include additional sequences, e.g., linkers, epitope tags, enzyme cleavage recognition sequences, signal sequences, secretion signals, and the like. Alternatively, a peptide can be linked to a carrier simply to facilitate manipulation or identification/location of the peptide.

Also included is a "functional derivative" of an IPP (or of its coding sequence) which refers to an amino acid substitution variant, a "fragment," or a "chemical derivative" of the protein, which terms are defined below. A functional derivative of an IPP retains measurable activity, preferably that is manifest as promoting immunogenicity of one or more antigenic epitopes fused thereto or co-administered therewith. "Functional derivatives" encompass "variants" and "fragments" regardless of whether the terms are used in the conjunctive or the alternative herein.

A functional homologue must possess the above biochemical and biological activity. In view of this functional characterization, use of homologous proteins including proteins not yet discovered, fall within the scope of the invention if these proteins have sequence similarity and the recited biochemical and biological activity.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred method of alignment, Cys residues are aligned.

In a preferred embodiment, the length of a sequence being compared is at least 30%, preferably at least 40%, more preferably at least 50%, even more preferably at least 60%, and even more preferably at least 70%, 80%, or 90% of the length of the reference sequence. The amino acid residues (or nucleotides) at corresponding amino acid (or nucleotide) positions are then compared. When a position in the first sequence is occupied by the same amino acid residue (or nucleotide) as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* 48:444-453 (1970) algorithm which has been incorporated into the GAP program in the GCG software package (available at the GCG website on the world wide web), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at the GCG website on the world wide web), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against public databases, for example, to identify other family members or related sequences. Such searches can be performed using the NBLAST and XBLAST programs (version 2.0) of Altschul et al. (1990) *J. Mol. Biol.* 215:403-10. BLAST nucleotide searches can be performed with the NBLAST program, score=100, wordlength=12 to obtain nucleotide sequences homologous to a reference nucleic acid molecules. BLAST protein searches can be performed with the XBLAST program, score=50, wordlength=3 to obtain amino acid sequences homologous to HVP22 protein molecules. To obtain gapped alignments for comparison purposes, Gapped BLAST can be utilized as described in Altschul et al. (1997) *Nucleic Acids Res.* 25:3389-3402. When utilizing BLAST and Gapped BLAST programs, the default parameters of the respective programs (e.g., XBLAST and NBLAST) can be used. See the NCBI website on the world wide web.

Thus, a homologue of a particular IPP as described herein is characterized as having (a) functional activity of the native IPP and (b) sequence similarity to a native IPP when determined as above, of at least about 20% (at the amino acid level), preferably at least about 40%, more preferably at least about 70%, even more preferably at least about 90%, 95%, 97%, 98% or 99%.

It is within the skill in the art to obtain and express such a protein using DNA probes based on the disclosed sequences.

Then, the chimeric DNA construct or fusion protein's biological activity can be tested readily using art-recognized methods such as those described herein in the Examples. A biological assay of the stimulation of antigen-specific T cell reactivity will indicate whether the homologue has the requisite activity to qualify as a "functional" homologue.

A "variant" of a protein, e.g., an antigen or an IPP, refers to a molecule substantially identical to either the full protein or to a fragment thereof in which one or more amino acid residues have been replaced (substitution variant) or which has one or several residues deleted (deletion variant) or added (addition variant). A "fragment" of the IPP refers to any subset of the molecule, that is, a shorter polypeptide of the full-length protein.

A preferred group of conservative variants are those in which at least one amino acid residue and preferably, only one, has been substituted by different residue. For a detailed description of protein chemistry and structure, see Schulz, G E et al., *Principles of Protein Structure*, Springer-Verlag, New York, 1978, and Creighton, T. E., *Proteins: Structure and Molecular Properties*, W.H. Freeman & Co., San Francisco, 1983, which are hereby incorporated by reference. The types of substitutions that may be made in the protein molecule may be based on analysis of the frequencies of amino acid changes between a homologous protein of different species, such as those presented in Table 1-2 of Schulz et al. (supra) and FIG. 3-9 of Creighton (supra). Based on such an analysis, conservative substitutions are defined herein as exchanges within one of the following five groups:

| 1 | Small aliphatic, nonpolar or slightly polar residues | Ala, Ser, Thr (Pro, Gly); |
|---|---|---|
| 2 | Polar, negatively charged residues and their amides | Asp, Asn, Glu, Gln; |
| 3 | Polar, positively charged residues | His, Arg, Lys; |
| 4 | Large aliphatic, nonpolar residues | Met, Leu, Ile, Val (Cys) |
| 5 | Large aromatic residues | Phe, Tyr, Trp. |

The three amino acid residues in parentheses above have special roles in protein architecture. Gly is the only residue lacking a side chain and thus imparts flexibility to the chain. Pro, because of its unusual geometry, tightly constrains the chain. Cys can participate in disulfide bond formation, which is important in protein folding.

More substantial changes in biochemical, functional (or immunological) properties are made by selecting substitutions that are less conservative, such as between, rather than within, the above five groups. Such changes will differ more significantly in their effect on maintaining (a) the structure of the peptide backbone in the area of the substitution, for example, as a sheet or helical conformation, (b) the charge or hydrophobicity of the molecule at the target site, or (c) the bulk of the side chain. Examples of such substitutions are (i) substitution of Gly and/or Pro by another amino acid or deletion or insertion of Gly or Pro; (ii) substitution of a hydrophilic residue, e.g., Ser or Thr, for (or by) a hydrophobic residue, e.g., Leu, Ile, Phe, Val or Ala; (iii) substitution of a Cys residue for (or by) any other residue; (iv) substitution of a residue having an electropositive side chain, e.g., Lys, Arg or H is, for (or by) a residue having an electronegative charge, e.g., Glu or Asp; or (v) substitution of a residue having a bulky side chain, e.g., Phe, for (or by) a residue not having such a side chain, e.g., Gly.

Most acceptable deletions, insertions and substitutions according to the present invention are those that do not produce radical changes in the characteristics of the wild-type or native IPP in terms of its intracellular processing, intercellular translocation, or other activity that is responsible for its ability to stimulate antigen specific T cell reactivity to an antigenic epitope or epitopes that are fused to the IPP. However, when it is difficult to predict the exact effect of the substitution, deletion or insertion in advance of doing so, one skilled in the art will appreciate that the effect can be evaluated by routine screening assays such as those described here, without requiring undue experimentation.

The term "chemically linked" refers to any chemical bonding of two moieties, e.g., as in one embodiment of the invention, where a translocation polypeptide is chemically linked to an antigenic peptide. Such chemical linking includes the peptide bonds of a recombinantly or in vivo generated fusion protein.

Therapeutic Compositions and their Administration

A vaccine composition comprising the nucleic acid encoding the antigen or the antigen in a fusion polypeptide with an IPP, a particle comprising the nucleic acid or a cell expressing this nucleic acid, is administered to a mammalian subject, preferably a human together with an siNA, preferably an siRNA, that targets mRNA for a pro-apoptotic protein, preferably Bak and/or Bax. Another embodiment is a vaccine composition comprising DCs that are loaded with the antigen and transfected with the above siNA. The vaccine composition and siNA or the modified DCs are administered in a pharmaceutically acceptable carrier in a biologically effective or a therapeutically effective amount.

Certain preferred conditions are disclosed in the Examples. The composition may be given alone or in combination with another protein or peptide such as an immunostimulatory molecule. Treatment may include administration of an adjuvant, used in its broadest sense to include any nonspecific immune stimulating compound such as an interferon. Adjuvants contemplated herein include resorcinols, non-ionic surfactants such as polyoxyethylene oleyl ether and n-hexadecyl polyethylene ether.

A therapeutically effective amount is a dosage that, when given for an effective period of time, achieves the desired immunological or clinical effect.

A therapeutically active amount of a nucleic acid encoding the fusion polypeptide may vary according to factors such as the disease state, age, sex, and weight of the individual, and the ability of the peptide to elicit a desired response in the individual. Dosage regimes may be adjusted to provide the optimum therapeutic response. For example, several divided doses may be administered daily or the dose may be proportionally reduced as indicated by the exigencies of the therapeutic situation. A therapeutically effective amounts of the protein, in cell associated form may be stated in terms of the protein or cell equivalents.

Thus an effective amount of the vaccine and the siNA are between about 1 nanogram and about 1 gram per kilogram of body weight of the recipient, more preferably between about 0.1 μg/kg and about 10 mg/kg, more preferably between about 1 μg/kg and about 1 mg/kg. Dosage forms suitable for internal administration preferably contain (for the latter dose range) from about 0.1 μg to 100 μg of active ingredient per unit. The active ingredient may vary from 0.5 to 95% by weight based on the total weight of the composition. Alternatively, an effective dose of DCs loaded with the antigen and expressing siRNA is between about $10^4$ and $10^8$ cells. Those skilled in the art of immunotherapy will be able to adjust these doses without undue experimentation.

The composition may be administered in a convenient manner, e.g., injection by a convenient and effective route. Preferred routes for the DNA/siRNA combination include intradermal "gene gun" delivery or intramuscular injection. The modified DCs are preferably administered by subcutaneous, intravenous or intramuscular routes. Other possible routes include oral administration, intrathecal, inhalation, transdermal application, or rectal administration. For the treatment of existing tumors which have not been completely resected or which have recurred, direct intratumoral injection is also intended.

Depending on the route of administration, the composition may be coated in a material to protect the compound from the action of enzymes, acids and other natural conditions which may inactivate the compound. Thus it may be necessary to coat the composition with, or co-administer the composition with, a material to prevent its inactivation. For example, an enzyme inhibitors of nucleases or proteases (e.g., pancreatic trypsin inhibitor, diisopropylfluorophosphate and trasylol) or in an appropriate carrier such as liposomes (including water-in-oil-in-water emulsions as well as conventional liposomes (Strejan et al., *J. Neuroimmunol* 7:27, 1984).

As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

Preferred pharmaceutically acceptable diluents include saline and aqueous buffer solutions. Pharmaceutical compositions suitable for injection include sterile aqueous solutions (where water soluble) or dispersions and sterile powders for the extemporaneous preparation of sterile injectable solutions or dispersion. Isotonic agents, for example, sugars, polyalcohols such as mannitol, sorbitol, sodium chloride may be included in the pharmaceutical composition. In all cases, the composition should be sterile and should be fluid. It should be stable under the conditions of manufacture and storage and must include preservatives that prevent contamination with microorganisms such as bacteria and fungi. Dispersions can also be prepared in glycerol, liquid polyethylene glycols, and mixtures thereof and in oils. Under ordinary conditions of storage and use, these preparations may contain a preservative to prevent the growth of microorganisms.

The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Prevention of the action of microorganisms in the pharmaceutical composition can be achieved by various antibacterial and antifungal agents, for example, parabens, chlorobutanol, phenol, ascorbic acid, thimerosal, and the like.

Compositions are preferably formulated in dosage unit form for ease of administration and uniformity of dosage. Dosage unit form refers to physically discrete units suited as unitary dosages for a mammalian subject; each unit contains a predetermined quantity of active material (e.g., the nucleic acid vaccine) calculated to produce the desired therapeutic effect, in association with the required pharmaceutical carrier. The specification for the dosage unit forms of the invention are dictated by and directly dependent on (a) the unique characteristics of the active material and the particular therapeutic effect to be achieved, and (b) the limitations inherent in the art of compounding such an active compound for the treatment of, and sensitivity of, individual subjects For lung instillation, aerosolized solutions are used. In a sprayable aerosol preparations, the active protein may be in combination with a solid or liquid inert carrier material. This may also be packaged in a squeeze bottle or in admixture with a pressurized volatile, normally gaseous propellant. The aerosol preparations can contain solvents, buffers, surfactants, and antioxidants in addition to the protein of the invention.

Other pharmaceutically acceptable carriers for the nucleic acid vaccine compositions according to the present invention are liposomes, pharmaceutical compositions in which the active protein is contained either dispersed or variously present in corpuscles consisting of aqueous concentric layers adherent to lipidic layers. The active protein is preferably present in the aqueous layer and in the lipidic layer, inside or outside, or, in any event, in the non-homogeneous system generally known as a liposomic suspension. The hydrophobic layer, or lipidic layer, generally, but not exclusively, comprises phospholipids such as lecithin and sphingomyelin, steroids such as cholesterol, more or less ionic surface active substances such as dicetylphosphate, stearylamine or phosphatidic acid, and/or other materials of a hydrophobic nature. Those skilled in the art will appreciate other suitable embodiments of the present liposomal formulations.

Delivery of Vaccine Nucleic Acid to Cells and Animals

The following references set forth principles and current information in the field of basic, medical and veterinary virology and are incorporated by reference: *Fields Virology*, Fields, B N et al., eds., Lippincott Williams & Wilkins, NY, 1996; *Principles of Virology: Molecular Biology, Pathogenesis, and Control*, Flint, S. J. et al., eds., Amer Soc Microbiol, Washington D.C., 1999; *Principles and Practice of Clinical Virology*, 4th Edition, Zuckerman. A. J. et al., eds, John Wiley & Sons, NY, 1999; *The Hepatitis C Viruses*, by Hagedorn, C H et al., eds., Springer Verlag, 1999; *Hepatitis B Virus: Molecular Mechanisms in Disease and Novel Strategies for Therapy*, Koshy, R. et al., eds, World Scientific Pub Co, 1998; *Veterinary Virology*, Murphy, F. A. et al., eds., Academic Press, NY, 1999; *Avian Viruses: Function and Control*, Ritchie, B. W., Iowa State University Press, Ames, 2000; *Virus Taxonomy: Classification and Nomenclature of Viruses: Seventh Report of the International Committee on Taxonomy of Viruses*, by M. H. V. Van Regenmortel, M H V et al., eds., Academic Press; NY, 2000.

The Examples below describe certain preferred approaches to delivery of the vaccines and combinations of the present invention. A broader description of other approaches including viral and nonviral vectors and delivery mechanisms follow.

DNA delivery involves introduction of a "foreign" DNA into a cell ex vivo and ultimately, into a live animal or directly into the animal. Several general strategies for gene delivery (=delivery of nucleic acid vectors) for purposes that include "gene therapy" have been studied and reviewed extensively (Yang, N-S., *Crit. Rev. Biotechnol.* 12:335-356 (1992); Anderson, W F, *Science* 256:808-13, 1992; Miller, A S, *Nature* 357:455-60, 1992; Crystal, R G, *Amer. J. Med.* 92(suppl 6A):44-52S, 1992; Zwiebel, J A et al., *Ann NY Acad Sc.* 618:394-404, 1991; McLachlin, J R et al., *Prog. Nucl. Acid Res. Molec. Biol.* 38:91-135, 1990; Kohn, D B et al., *Cancer Invest.* 7:179-92, 1989), which references are herein incorporated by reference in their entirety).

One approach comprises nucleic acid transfer into primary cells in culture followed by autologous transplantation of the ex vivo transformed cells into the host, either systemically or into a particular organ or tissue.

The term "systemic administration" refers to administration of a composition or agent such as a molecular vaccine as described herein, in a manner that results in the introduction of the composition into the subject's circulatory system or otherwise permits its spread throughout the body. "Regional" administration refers to administration into a specific, and somewhat more limited, anatomical space, such as intraperitoneal, intrathecal, subdural, or to a specific organ. The term "local administration" refers to administration of a composition or drug into a limited, or circumscribed, anatomic space, such as intratumoral injection into a tumor mass, subcutaneous injections, intramuscular injections. One of skill in the art would understand that local administration or regional administration may also result in entry of a composition into the circulatory system.

For accomplishing the objectives of the present invention, nucleic acid therapy would be accomplished by direct transfer of a the functionally active DNA into mammalian somatic tissue or organ in vivo. DNA transfer can be achieved using a number of approaches described below. These systems can be tested for successful expression in vitro by use of a selectable marker (e.g., G418 resistance) to select transfected clones expressing the DNA, followed by detection of the presence of the antigen-containing expression product (after treatment with the inducer in the case of an inducible system) using an antibody to the product in an appropriate immunoassay. Efficiency of the procedure, including DNA uptake, plasmid integration and stability of integrated plasmids, can be improved by linearizing the plasmid DNA using known methods, and co-transfection using high molecular weight mammalian DNA as a "carrier".

The DNA molecules encoding the fusion polypeptides of the present invention may be packaged into retrovirus vectors using packaging cell lines that produce replication-defective retroviruses, as is well-known in the art (see, for example, Cone, R. D. et al., *Proc. Natl. Acad. Sci. USA* 81:6349-6353 (1984); Mann, R. F. et al., *Cell* 33:153-159 (1983); Miller, A. D. et al., *Molec. Cell. Biol.* 5:431-437 (1985),; Sorge, J., et al., *Molec. Cell. Biol.* 4:1730-1737 (1984); Hock, R. A. et al., *Nature* 320:257 (1986); Miller, A. D. et al., *Molec. Cell. Biol.* 6:2895-2902 (1986). Newer packaging cell lines which are efficient an safe for gene transfer have also been described (Bank et al., U.S. Pat. No. 5,278,056.

This approach can be utilized in a site specific manner to deliver the retroviral vector to the tissue or organ of choice. Thus, for example, a catheter delivery system can be used label, E G et al., *Science* 244:1342 (1989)). Such methods, using either a retroviral vector or a liposome vector, are particularly useful to deliver the nucleic acid to be expressed to a blood vessel wall, or into the blood circulation of a tumor.

Other virus vectors may also be used, including recombinant adenoviruses (Horowitz, M S, In: *Virology*, Fields, B N et al., eds, Raven Press, NY, 1990, p. 1679; Berkner, K L, *Biotechniques* 6:616-29, 1988; Strauss, S E, In: *The Adenoviruses*, Ginsberg, H S, ed., Plenum Press, NY, 1984, chapter 11), herpes simplex virus (HSV) for neuron-specific delivery and persistence. Advantages of adenovirus vectors for human gene delivery include the fact that recombination is rare, no human malignancies are known to be associated with such viruses, the adenovirus genome is double stranded DNA which can be manipulated to accept foreign genes of up to 7.5 kb in size, and live adenovirus is a safe human vaccine organisms. Adeno-associated virus is also useful for human therapy (Samulski, R J et al., *EMBO J.* 10:3941, 1991) according to the present invention.

Another vector which can express the DNA molecule of the present invention, and is useful in the present therapeutic setting is vaccinia virus, which can be rendered non-replicating (U.S. Pat. Nos. 5,225,336; 5,204,243; 5,155,020; 4,769, 330; Sutter, G et al., *Proc Natl Acad Sci USA* 89:10847-51, 1992; Fuerst, T R et al., *Proc. Natl. Acad. Sci. USA* 86:2549-53, 1992; Falkner F G et al.; *Nucl. Acids Res* 15:7192, 1987; Chakrabarti, S et al., *Mol Cell Biol* 5:3403-9, 1985). Descriptions of recombinant vaccinia viruses and other viruses containing heterologous DNA and their uses in immunization and DNA therapy are reviewed in: Moss, B, *Curr Opin Genet Dev* 3:86-90, 1993; Moss, B, *Biotechnol.* 20:345-62, 1992); Moss, B, *Curr Top Microbiol Immunol* 158:25-38, 1992; Moss, B, *Science* 252:1662-7, 1991; Piccini, A et al., *Adv. Virus Res* 34:43-64, 1988; Moss, B et al., *Gene Amplif Anal* 3:201-13, 1983).

In addition to naked DNA or RNA, or viral vectors, engineered bacteria may be used as vectors. A number of bacterial strains including *Salmonella*, BCG and *Listeria monocytogenes*(LM) (Hoiseth et al., *Nature* 291:238-239, 1981; Poirier, T P et al., *J. Exp. Med.* 68:25-32, 1988); Sadoff, J C et al., *Science* 240:336-8, 1988; Stover, C K et al., *Nature* 351:456-60, 1991; Aldovini, A et al., *Nature* 351:479-82, 1991; Schafer, R, et al., *J Immunol* 149:53-9 (1992); Ikonomidis, G et al., *J Exp Med* 180:2209-18, 1994). These organisms display two promising characteristics for use as vaccine vectors: (1) enteric routes of infection, providing the possibility of oral vaccine delivery; and (2) infection of monocytes/macrophages thereby targeting antigens to professional APCs.

In addition to virus-mediated gene transfer in vivo, physical means well-known in the art can be used for direct transfer of DNA, including administration of plasmid DNA (Wolff et al., 1990, supra) and particle-bombardment mediated gene transfer (Yang, N-S, et al., *Proc Natl Acad Sci USA* 87:9568, 1990; Williams, R S et al., *Proc Natl Acad Sci USA* 88:2726, 1991; Zelenin, A V et al., *FEBS Lett* 280:94, 1991; Zelenin, A V et al., *FEBS Lett* 244:65, 1989); Johnston, S A et al., *In Vitro Cell Dev Biol* 27:11, 1991). Furthermore, electroporation, a well-known means to transfer genes into cell in vitro, can be used to transfer DNA molecules according to the present invention to tissues in vivo (Titomirov, A V et al., *Biochim Biophys Acta* 1088:131, 1991).

"Carrier mediated gene transfer" has also been described (Wu, C H et al., *J Biol Chem* 264:16985, 1989; Wu, G Y et al., *J Biol Chem* 263:14621, 1988; Soriano, P et al., *Proc Nat. Acad Sci USA* 80:7128, 1983; Wang, C-Y et al., *Pro. Natl Acad Sci USA* 84:7851, 1982; Wilson, J M et al., *J Biol Chem* 267:963, 1992). Preferred carriers are targeted liposomes (Nicolau, C et al., *Proc Natl Acad Sci USA* 80:1068, 1983; Soriano et al., supra) such as immunoliposomes, which can incorporate acylated mAbs into the lipid bilayer (Wang et al., supra). Polycations such as asialoglycoprotein/polylysine (Wu et al., 1989, supra) may be used, where the conjugate includes a target tissue-recognizing molecule (e.g., asialo-orosomucoid for liver) and a DNA binding compound to bind to the DNA to be transfected without causing damage, such as polylysine. This conjugate is then complexed with plasmid DNA of the present invention.

Plasmid DNA used for transfection or microinjection may be prepared using methods well-known in the art, for example using the Quiagen procedure (Quiagen), followed by DNA purification using known methods, such as the methods exemplified herein.

Having now generally described the invention, the same will be more readily understood through reference to the following examples which are provided by way of illustration, and are not intended to be limiting of the present invention, unless specified.

EXAMPLE 1

Materials and Methods

Plasmid DNA Constructs and DNA Preparation:

The production of the following vectors have been described: pcDNA3-E7, pcDNA3-Sig/E7/LAMP-1, pcDNA3-E7/HSP70, pcDNA3-CRT/E7, pDNA3-E7/GFP and pcDNA3-OVA (Kim T W et al., *J Clin Invest* 112: 109-117, 2003; Cheng W F et al., *J Clin Invest* 108: 669-678, 2001; Hung C F et al., *Cancer Res* 61: 3698-3703, 2001; Chen C H et al., *Cancer Res* 60: 1035-1042, 2000; see also U.S. Pat. No. 6,734,173 and published patent applications WO05/081716, WO05/047501, WO03/085085, WO02/12281C2, WO02/074920, WO02/061113, WO02/09645, and WO01/29233. The plasmid containing a sequence encoding influenza hemagglutinin (HA), pcDNA3-HA, was provided by Dr. Drew Pardoll, Johns Hopkins School of Medicine. The accuracy of these constructs was confirmed by DNA sequencing. DNA was amplified in *E. coli* DH5α and purified as described in Chen, C H et al., supra).

Preparation (Synthesis) of siRNAs and Transfection:

siRNAs were synthesized using 2'-O-ACE-RNA phosphoramides (Dharmacon, Lafayette, Colo.). The sense and anti-sense strands of siRNA were:

| Gene targeted | siRNA Sequence | SEQ ID NO: |
|---|---|---|
| Bak, beginning at nt 310, | 5'-UGCCUACGAACUCUUCACCdTdT-3' (sense) | 1 |
| | 5'-GGUGAAGAGUUCGUAGGCAdTdT-3' (antisense) | 2 |
| Bax, beginning at nt 217, | 5'-UAUGGAGCUGCAGAGGAUGdTdT-3' (sense) | 5 |
| | 5'-CAUCCUCUGCAGCUCCAUAdTdT-3' (antisense) | 6 |
| Non-specific ctrl siRNA | 5'-NNATTGTATGCGATCGCAGAC-3' | 45 |

RNAs were deprotected and annealed according to the manufacturer's instruction. Non-specific control siRNA was acquired from Dharmacon.

Dendritic cells—either DC-1 cells or bone marrow-derived DCs (BM-DCs) incubated for 6 days were transfected with Bak and Bax siRNA or control siRNA using Oligofectamine (Invitrogen, Carlsbad, Calif.). 24 to 48 hours later, the transfected cells were used.

Cells:

The HPV-16 E7-expressing murine tumor model, TC-1, has been described previously. In brief, HPV-16 E6, E7, and the ras oncogene were used to transform primary C57BL/6 mouse lung epithelial cells to generate TC-1.

DC-1 cells were generated from the dendritic cell line provided by Dr. Kenneth Rock, University of Massachusetts. With continued passage, subclones of DCs (DC-1) have been generated that can be easily transfected (Kim et al., 2004, supra).

Cells were maintained in RPMI medium (Invitrogen, Carlsbad, Calif.) supplemented with 2 mM glutamine, 1 mM sodium pyruvate, 100 μM non-essential amino acids, 20 mM HEPES, 50 μM β-mercaptoethanol, 100 IU/ml penicillin, 100 μg/ml streptomycin and 10% fetal bovine serum (Gemini Bio-Products, Woodland, Calif.).

An H-2 $D^b$-restricted HPV-16 E7-specific T cell line has also been described previously (Wang, T L et al., *Gene Ther*

7:726-733, 2000). These cell lines were stimulated weekly with irradiated TC-1 cells and 20 U/ml murine rIL-2 weekly.
Generation of Bone Marrow-Derived DCs (BM-DCs):

BM-DCs were generated from bone marrow (BM) progenitor cells generally as described by Inaba et al. (*J Exp Med* 176:1693-1702, 1992) with a modification. Briefly, BM cells were flushed from femurs and tibias of 5-8-wk old C57BL/6 mice. Cells were washed twice with RPMI-1640 after lysis of red blood cells, and were resuspended at a density of $10^6$/ml in RPMI-1640 medium supplemented as above, although with 5% fetal bovine serum, and further with 20 ng/ml recombinant murine GM-CSF (PeproTech, Rock Hill, N.J.). The cells were cultured in 24-well plates (1 ml/well) at 37° C. in 5% humidified $CO_2$. Wells were replenished on days 2 and 4 with fresh medium supplemented GM-CSF as above. Cells were harvested after 6 days and subjected to transfection with siRNA.

Western Blot Analysis:

$2\times10^5$ DC-1 cells were transfected with 300 pmol of the Bak+Bax siRNA or control siRNA in a final volume of 2 ml using Oligofectamine® (Invitrogen, Carlsbad, Calif.) according to vendor's instructions. Fluorescein-labeled siRNA was used to assess the transfection efficiency of DC-1 cells by flow cytometric analysis. Virtually 100% of DC-1 cells were successfully transfected with siRNA. The expression of Bak and Bax pro-apoptotic proteins in DC-1 cells transfected with Bak and/or Bax siRNA was characterized by Western blot analysis using 50 μg of cell lysate from transfected DC-1 cells and anti-Bak and/or anti-Bax mouse mAb (Cell Signaling Technology, Inc., Beverly, Mass.) using a protocol similar to that described previously (Hung et al., 2001, supra).

Measurement of Apoptotic Cells:

As described, $2\times10^5$ DC-1 cells were transfected with Bak+Bax siRNA or control siRNA. Two days after transfection, the cells were pulsed with 10 μg/ml E7 peptide (RAHYNIVTF; SEQ ID NO:46) or HA peptide (IYSTVASSL; SEQ ID NO:47) for 2 hours and subsequently incubated with an E7-specific CD8$^+$ T cell line (Wang T L et al., 2000, supra) at different E:T ratios (5, 1, 0.5 and 0.1) for 4 or 20 hrs. Apoptotic DC-1 cells were detected using PE-conjugated rabbit anti-active caspase-3 mAb (BD Pharmingen San Diego Calif.) according to the vendor's protocol. Briefly, cells were harvested and stained with FITC-conjugated anti-CD8 antibody as described previously. The cells were subsequently fixed and permeabilized using the Cytofix/Cytoperm™ Kit (BD Pharmingen) for 20 minutes at room temperature, and stained with PE-conjugated rabbit-anti-active caspase-3 monoclonal antibody using 20 μl per $10^6$ cells for 60 minutes at room temperature. Following incubation with the antibodies, the cells were washed, resuspended and analyzed by flow cytometric analysis. Analysis was performed on a Becton-Dickinson FACScan with CELLQuest software (Becton Dickinson Immunocytometry System, Mountain View, Calif.). CD8$^{neg}$ cells were gated and active caspase-3-positive DC-1 cells were analyzed to determine the percentage of apoptotic DC-1 cells.

Mice:

C57BL/6 mice (6- to 8-week-old) were purchased from the National Cancer Institute (Frederick, Md.) and maintained under specific pathogen-free conditions in the oncology animal facility of the Johns Hopkins Medical Institutions (Baltimore, Md.). All procedures were performed according to approved protocols and in accordance with recommendations for the proper use and care of laboratory animals.

DNA/siRNA Vaccination:

Gene gun particle-mediated DNA/siRNA vaccination was performed using a helium-driven gene gun (Bio-Rad, Hercules, Calif.) according to the protocol for RNA vaccination provided by the manufacturer, with a slight modification. Briefly, DNA/siRNA-coated gold particles were prepared by combining 25 mg of 1.6 μm gold microcarriers (Bio-Rad), 50 μg of plasmid DNA (50 μl), 5 μg of siRNA (50 μl), and 10 μl of 3M sodium acetate. Isopropyl alcohol (200 μl) was added to the mixture drop-wise while mixing by vortex. The mixture was allowed to precipitate at room temperature for 10 min. The suspension of microcarrier/DNA/siRNA was centrifuged 10,000 rpm for 30 s and washed 3 times in fresh absolute ethanol before resuspending in 3 ml of polyvinylpyrrolidone (0.1 mg/ml; Bio-Rad) in absolute ethanol. The solution was then loaded into 2.5 ft. of Gold-Coated™ tube (Bio Rad) and allowed to settle for 10 min. The ethanol was gently removed, and the microcarrier/DNA/siRNA suspension was evenly attached to the inside surface of the tube by rotation. The tube was then dried using flowing nitrogen gas at a rate of 0.4 liters/min. The dried tube coated with microcarrier/DNA/siRNA was then cut into 0.5 inch cartridges and stored in a capped dry bottle at 4° C. The DNA/siRNA-coated gold particles (1 μg of DNA and 0.1 μg of siRNA/bullet) were delivered to the shaved abdomens of mice using a helium-driven gene gun (supra) with a discharge pressure of 400 psi. Mice were immunized with 2 μg of the desired pcDNA3 plasmid, including those encoding E7, Sig/E7/LAMP-1, E7/HSP70, CRT/E7, HA, or OVA, mixed with 0.2 μg of Bak+Bax siRNA or control siRNA. The mice were boosted with the same dose 1 wk later.

To determine the effect of Bak+Bax siRNA and/or control siRNA administered during priming and/or boosting phases, mice were primed with 2 μg of pcDNA3-Sig/E7/LAMP-1 co-administrated with 0.2 μg of Bak+Bax siRNA or with control siRNA. Mice were then boosted with 2 μg of pcDNA3-Sig/E7/LAMP-1 co-administrated with 0.2 μg of Bak+Bax siRNA or control siRNA.

DC Immunization:

DC-1 cells or BM-DCs were transfected with the Bak+Bax siRNA or control siRNA as above. Two days later, DC-1 cells or BM-DCs transfected with Bak/Bax siRNA or with control siRNA were incubated with E7 aa49-57 peptide (RAHYNIVTF; SEQ ID NO:46) (10 μg/ml) at 37° C. for 2 hours. The cells were then washed with RPMI-1640/10% FCS and HBBS, and resuspended in HBBS at the final concentration of $5\times10^6$/ml (DC-1 cells) or $2\times10^6$/ml (BM-DCs). DC-1 cells or BM-DCs were injected s.c. into footpads of mice (100 μl/mouse). One week later, the mice were boosted once with the same dose and immunization regimen.

Intracellular Cytokine Staining (ICCS) and Flow Cytometric Analysis:

Spleen cells were harvested from mice one week after the last vaccination. Prior to ICCS, $4\times10^6$ (or $3.5\times10^5$) pooled spleen cells from each treatment group were incubated overnight or for about 16 hours with (a) 1 μg/ml of E7 peptide (RAHYNIVTF; SEQ ID NO:46), HA (IYSTVASSL; SEQ ID NO:47) (underscored in SEQ ID NO:23), or OVA peptide (SIINFEKL; SEQ ID NO:48), each of which includes an MHC class I epitope, to detect antigen-specific CD8$^+$ T cell precursors; or (b) 1 μg/ml of E7 peptide (aa 30-67) containing an MHC class II epitope—DSSEEEDEIDGPAGQAEPDRAHYNIVT-FCCKCDSTLRL (SEQ ID NO:49)—for detection of antigen-specific CD4+ T cell precursors. Intracellular IL-4 and IFN-γ staining and flow cytometric analysis were performed as described previously.

In studies of DC-1 or BM-DC vaccination, $3.5\times10^5$ pooled spleen cells from each group (see above) were used. Golgi-Plug (BD Pharmingen) was added to the culture, and incubated at 37° C. overnight. Cells were then washed once with FACScan® buffer and stained with phycoerythrin-conjugated monoclonal rat antimouse CD8a antibody (clone 53.6.7). Cells were subjected to ICCS using the Cytofix/Cytoperm kit according to the manufacturer's instructions (BD Pharmingen). Intracellular IFN-γ was stained with FITC-conjugated rat antimouse IFN-γ. Analysis of surface markers of untransfected or siRNA-transfected DCs was performed on FACS Calibur and analyzed using CellQuest software (BD Bioscience, San Jose, Calif.). FITC-conjugated mouse mAbs specific for the surface markers CD11c, CD40, CD86, I-A$^b$, or H-2 K$^b$/D$^b$ (BD Pharmingen) were used.

In Vivo Tumor Protection and Tumor Treatment Experiments:

For tumor protection studies, C57BL/6 mice (5/group) were challenged s.c., with $5\times10^4$ TC-1 tumor cells/mouse in the right leg one week after the last vaccination. Mice were monitored for evidence of tumor growth by palpation and inspection twice a week. To evaluate lymphocytes subsets responsible for antitumor effects, in vivo antibody depletion studies were performed using standard methods (e.g., Lin K Y et al., *Canc Res* 56:21-6, 1996).

For tumor therapy studies, mice were challenged with 1 or $5\times10^4$ TC-1 tumor cells/mouse i.v., in the tail vein to simulate hematogenous spread of tumors (Ji et al., supra). Mice were treated three days after tumor challenge with (a) DNA vaccine mixed with siRNA, boosted once after 1 wk and sacrificed on day 42 after the last vaccination or (b) $5\times10^5$ E7 peptide-pulsed siRNA-transfected DC-1, boosted once after 1 wk and sacrificed on day 28 after the last immunization. The mean number of pulmonary nodules in each mouse was evaluated by experimenters blinded to sample identity. In vivo tumor protection, antibody depletion, and tumor therapy experiments were performed at least two times to generate reproducible data.

Preparation of CD11c$^+$ Cells from Inguinal Lymph Nodes of Vaccinated Mice:

C57BL/6 mice (5/group) were first primed with pcDNA3-Sig/E7/LAMP1 or control pcDNA3 DNA via gene gun at a dose of 2 μg/mouse. Seven days later, mice received 16 inoculations of non-overlapping gene gun intradermal administration on their abdomens. Gold particles used for each inoculation were coated with 1 μg of pcDNA3-E7/GFP DNA mixed with 0.1 μg of Bak+Bax siRNA or control siRNA. pcDNA3 mixed with Bak+Bax siRNA was used as a negative control.

Inguinal lymph nodes (LN) draining the inoculation site were harvested from vaccinated mice 2 or 5 days after vaccination. CD11c$^+$ cells were enriched from a single cell suspension of isolated LN cells using CD11c (N418) microbeads (Miltenyi Biotec, Auburn, Calif.). Enriched CD11c$^+$ cells were analyzed by forward and side scatter and gated around a population of cells with size and granular characteristics of DCs. GFP$^+$ cells were analyzed by flow cytometry using a protocol described previously (Lappin M B et al., *Immunology* 98:181-8, 1999). Results are expressed as percent of GFP$^+$ CD11c$^+$ cells among gated monocytes. The percent of GFP$^+$ cells among the gated CD11c$^+$ cells was analyzed by flow cytometry.

In vivo antibody depletion studies were performed using conventional methods as noted above. Depletion was initiated 5 days after priming and terminated at time of LN harvest.

Adoptive Transfer of T Cells and Rapid DC Elimination Assay:

To create two distinctly labeled populations of BM-DCs, different concentrations of the dye carboxyfluorescein (CFSE) were used to label cells. E7-peptide-loaded BM-DCs transfected with either Bax/Bax siRNA or control siRNA were prepared using methods described above. The E7-peptide loaded BM-DCs transfected with control siRNA were labeled with 5 μM CFSE ("high-CFSE"), whereas Bak/Bax siRNA-transfected DCs were labeled with 10-fold lower concentration, 0.5 μM CFSE ("low-CFSE"). A 1:1 mixture of $2.5\times10^5$ low CFSE-labeled E7-peptide loaded BM-DCs and $2.5\times10^5$ high CFSE-labeled E7-peptide loaded BM-DCs was administered i.v. to C57BL/6 mice three days after adoptive transfer i.v. of $10^6$ E7-specific T cells into the mice. Sixteen hours later, single cell suspensions from the lung and spleen were prepared and analyzed for CFSE content by flow cytometry.

Statistical Analysis:

All results expressed as means±standard errors (SE) are representative of at least two experiments. Results of ICCS with flow cytometric analysis and tumor treatment experiments were evaluated by analysis of variance (ANOVA). Comparisons between individual data points were made using Student's t-test. In tumor protection experiments, the principal outcome of interest was time to tumor development. The event time distributions for different mice were compared using the Kaplan and Meier method and the log-rank statistic. All p values <0.05 were considered significant.

EXAMPLE 2

Figure 2:
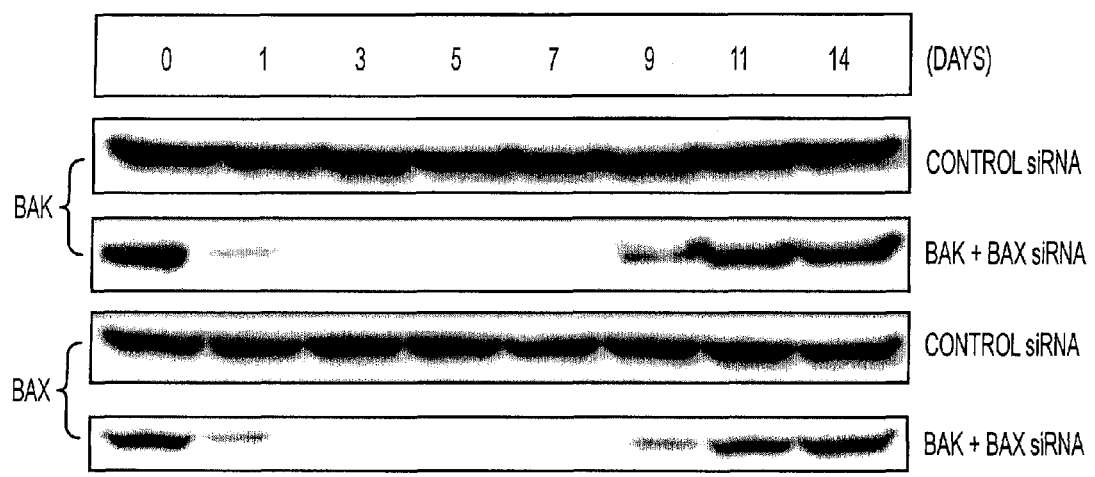

Transfection with Bak and/or Bax siRNA Leads to Downregulation of Bak and Bax, and Resistance to Apoptotic Cell Death To determine if the expression of Bak and/or Bax was downregulated in a DC cell line (DC-1) transfected with Bak and/or Bax siRNA, western blot analysis was performed using cell lysate from DC-1 cells, transfected with the various siRNAs. As shown in FIG. 1, the expression of Bak and/or Bax proteins was undetectable in DC-1 cells transfected with Bak and/or Bax siRNA. In contrast, expression of Bak and Bax proteins was detected in DC-1 cells after transfection with control siRNA, the levels of expression being similar to the levels in nontransfected DC-1 cells. The expression of β-actin protein was consistent among all DC-1 cell groups. The kinetics of inhibition of Bak and Bax protein expression by DC-1 cells transfected with Bak+Bax siRNA were examined. As shown in FIG. 2, significant downregulation of Bax and Bak expression was observed 1 day after transfection. No Bak or Bax expression was detectable at days 3, 5, and 7 and some expression was detected at by day 9 (below-normal levels). Expression returned to normal levels by day 11 after transfection.

To determine if DC-1 cells transfected with Bak and/or Bax siRNA could resist CTL-induced apoptosis, E7 peptide-loaded, siRNA-transfected DC-1 cells were incubated with an E7-specific CD8 T cell line and the percentages of apoptotic cells was measured. As shown in FIGS. 3A and 3B, 80-90% of E7 peptide-loaded DC-1 cells transfected with control siRNA were apoptotic by 20 hrs. In comparison, fewer DC-1 cells transfected with Bak+Bax siRNA were apoptotic, particularly at low E:T ratios (T cells to DC-1 cells).

These results show that transfection of DC-1 cells with Bak and/or Bax siRNA downregulates Bak and Bax protein expression, resulting in resistance to the apoptotic effects of activated, antigen-specific CD8$^+$ T cells on the DCs.

EXAMPLE 3

Figure 4:
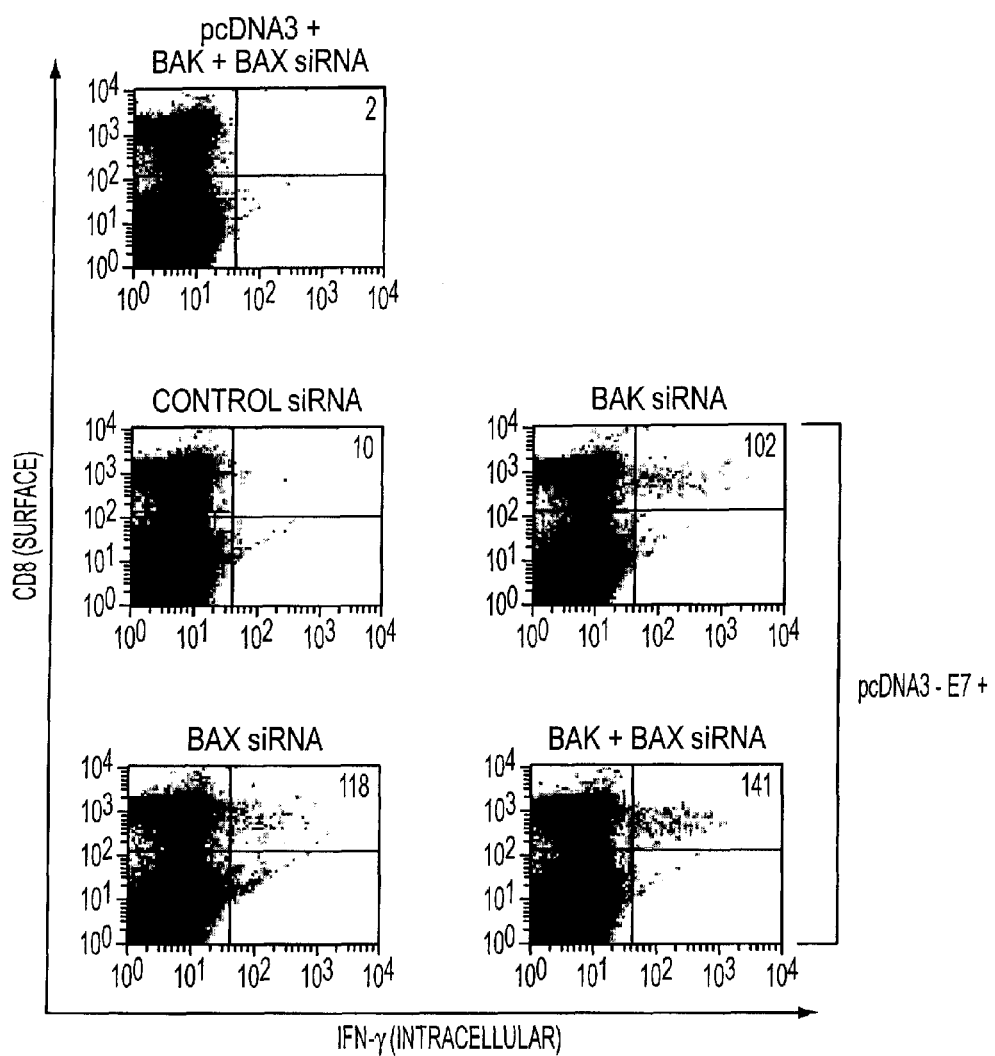
FIGS. 4-7. ICCS and flow cytometric analysis to determine the antigen-specific CD8+ T cell response to an immunogenic DNA vaccine coadministered with control or Bax and/or Bak siRNA.
Figure 5:
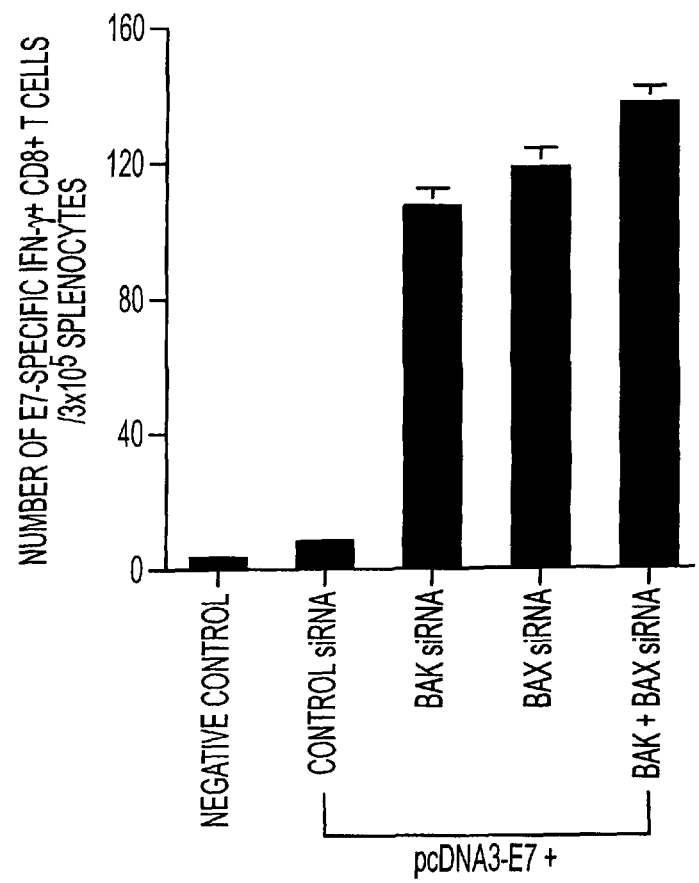

Coadministration of Bax+Bak siRNA with Antigen-Specific DNA Vaccines Significantly Enhances Numbers of Antigen-Specific CD8+ T Cell Precursors in Vaccinated Mice To determine if the anti-apoptotic action of Bak+Bax siRNA observed in DCs in vitro can be manifest in vivo, Bak+Bax siRNA was coadministered with pcDNA3-E7 intradermally via gene gun. As shown in FIGS. 4 and 5, coadministration of pcDNA3-E7 with Bak and/or Bax siRNA significantly enhanced the E7-specific CD8+ T cell response (by at least 10-fold) in vaccinated mice, compared to coadministration of pcDNA3-E7 with control siRNA.

Figure 6:
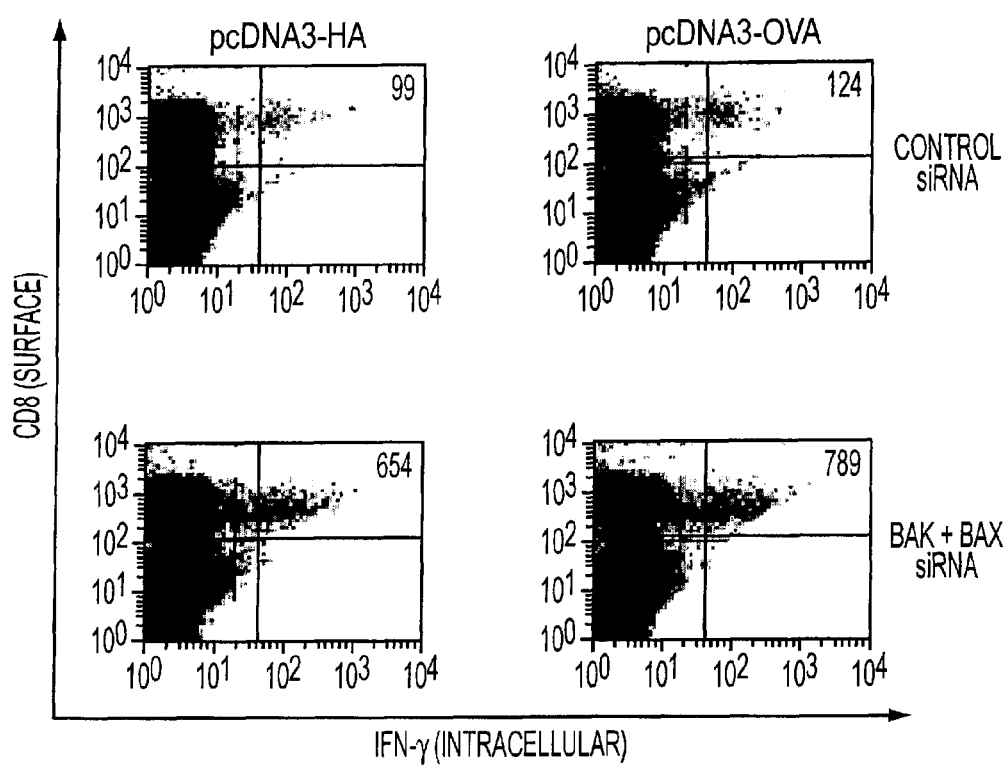
Figure 7:
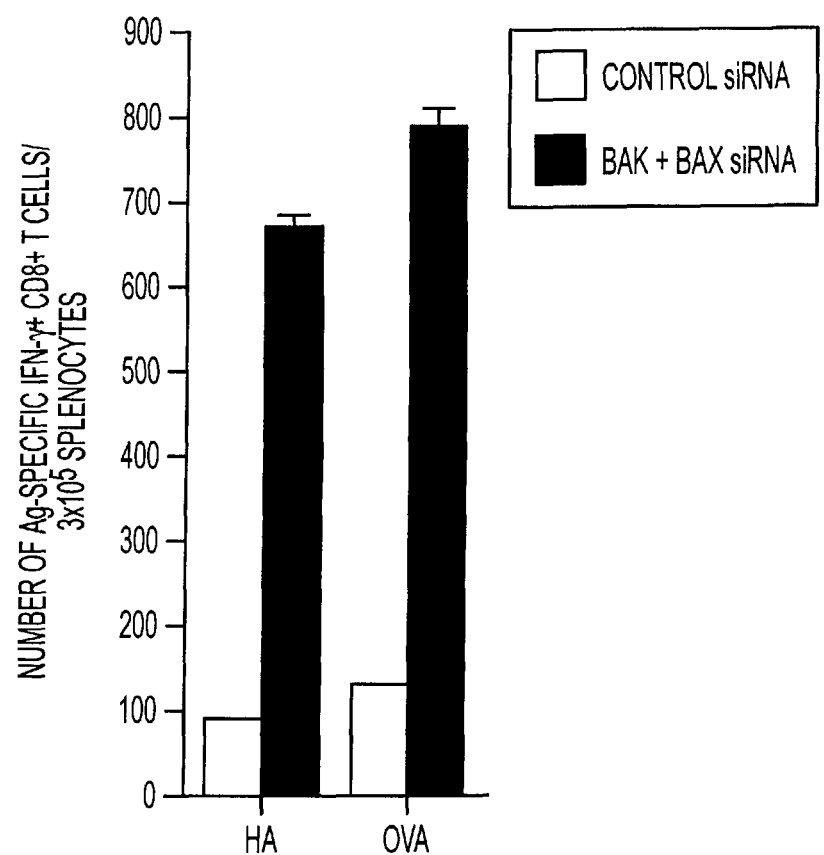

To determine if this result was obtained using other antigens, pcDNA3-HA and pcDNA3-OVA plasmids were coadministered with Bak+Bax siRNA. As shown in FIGS. 6-7, the coadministration of pcDNA3-HA or pcDNA3-OVA with Bak+Bax siRNA significantly enhanced the HA- and OVA-specific CD8+ T cell response in vaccinated mice, compared to coadministration of the antigen vectors with control siRNA. Thus Bak and/or Bax siRNA significantly enhance antigen-specific CD8+ T cell-mediated immune responses when coadministered with antigen-encoding DNA vaccines.

EXAMPLE 4

Figure 8:
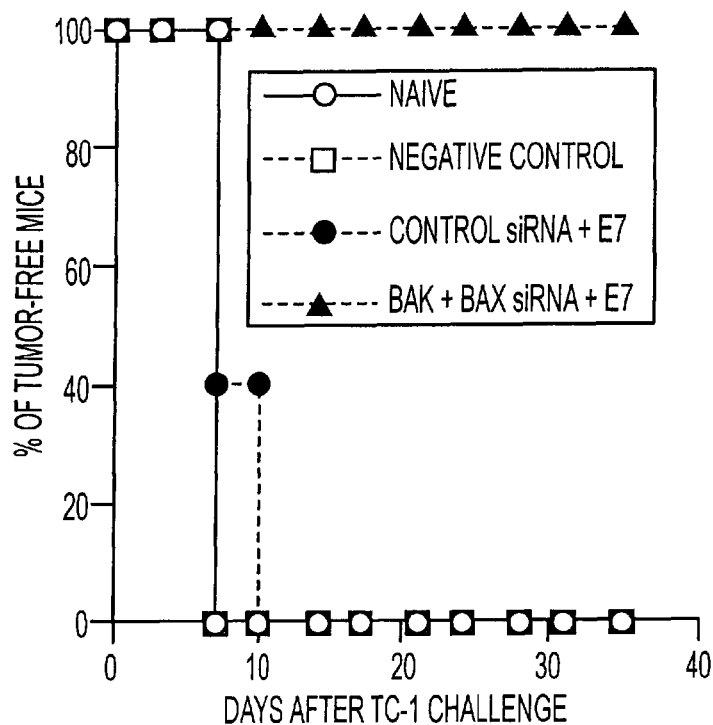
FIGS. 8-10. In vivo tumor protection and therapy studies using E7-expressing TC-1 Tumor cells.

Co-Administration of Bak+Bax siRNA with an E7-Specific DNA Vaccine Significantly Enhances Antitumor Effects Against an E7-Expressing Target Tumor Cell Line To determine if the observed enhancement of E7-specific T cell-mediated immunity described above can manifest itself in E7-specific antitumor effects, an in vivo tumor protection experiment was performed using E7-expressing TC-1 tumor cells. As shown in FIG. 8, all mice receiving E7 DNA mixed with Bak+Bax siRNA remained tumor-free for 35 days after TC-1 challenge. In contrast, all of the mice receiving E7 DNA with control siRNA or pcDNA3 (negative control for antigen) combined with Bak+Bax siRNA developed tumors by day 10.

Figure 9:
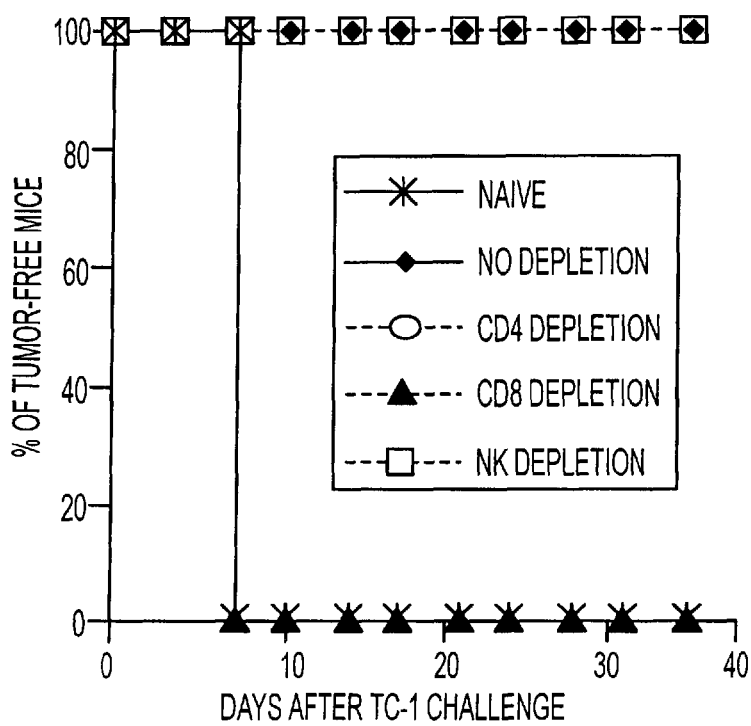

An in vivo antibody depletion experiment was conducted to determine which subsets of lymphocytes were responsible for the anti-tumor effects. As shown in FIG. 9, 100% of mice depleted of CD8+ T cells grew tumors within 10 days after TC-1 challenge. In contrast, 100% of the mice depleted of CD4+ T cells or NK cells remained tumor-free 35 days after TC-1 challenge (as with the "non-depleted mice discussed above). It was concluded that CD8+ T cells are needed for the antitumor effects induced by the combination of a DNA vaccine and Bak+Bax siRNA.

Figure 10:
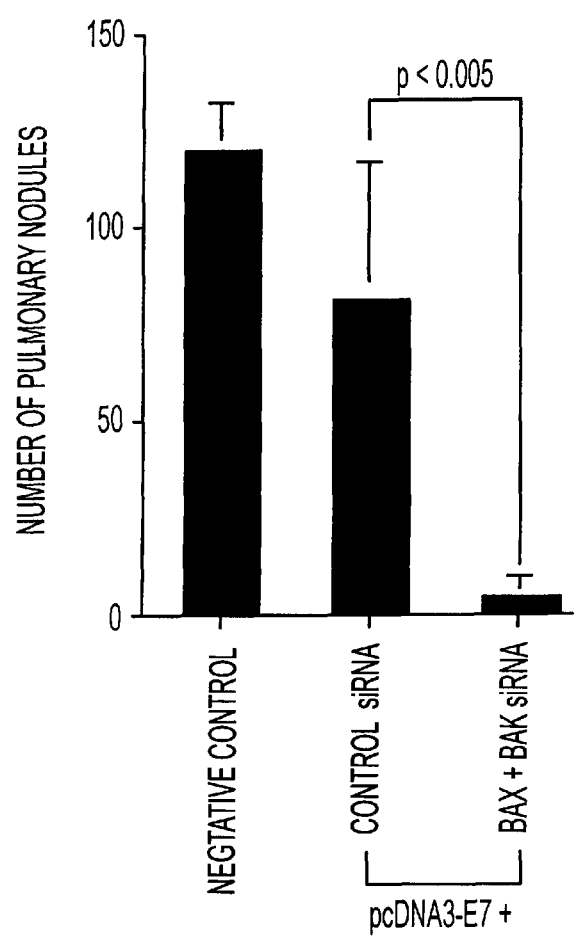

An in vivo tumor therapy experiment was performed using a model of hematogenous spread of tumors to the lungs (Ji et al., supra). As shown in FIG. 10, mice immunized with E7 DNA combined with Bak+Bax siRNA exhibited the fewest pulmonary tumor nodules ($p<0.005$) compared to mice vaccinated with E7 DNA combined with control siRNA, or pcDNA3 (no antigen) combined with Bak+Bax siRNA. Taken together, these results indicate that vaccination with the combination of E7 DNA with Bak+Bax siRNA leads to potent protective and therapeutic effects against E7-expressing TC-1 tumor cells.

EXAMPLE 5

Figure 11:
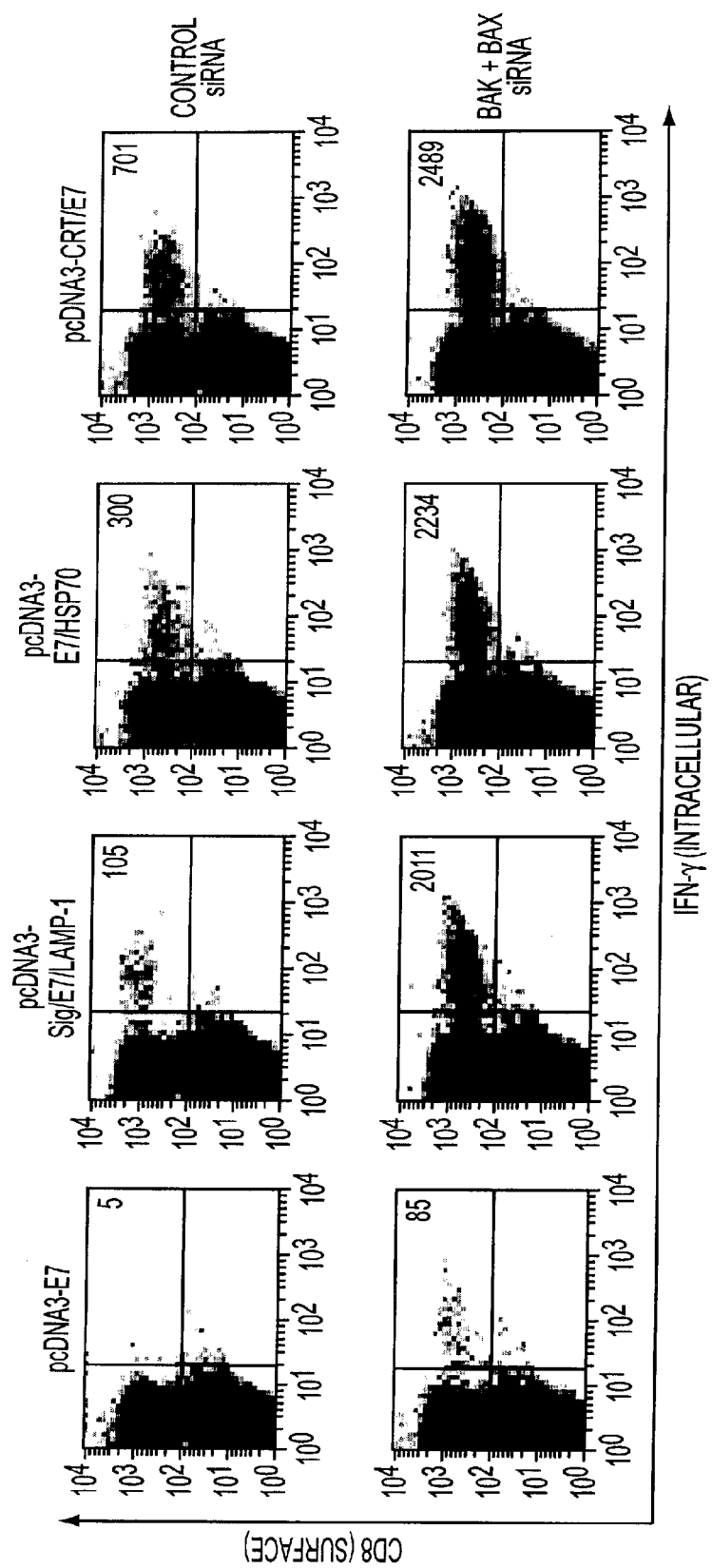
FIGS. 11-14. ICCS and flow cytometric analysis of E7-specific CD4+ or CD8+ T cell responses in mice vaccinated with a DNA vaccine employing intracellular targeting strategies and siRNA. In the experiments of FIGS. 11 and 12, mice were vaccinated with pcDNA3-E7, pcDNA3-Sig/E7/LAMP-1, pcDNA3-E7/HSP70, or pcDNA3-CRT/E7 combined with Bak+Bax siRNA or control siRNA. In the experiments of FIGS. 13 and 14, mice were vaccinated with pcDNA3-Sig/E7/LAMP-1 combined with Bak+Bax siRNA or control siRNA.
Figure 12:
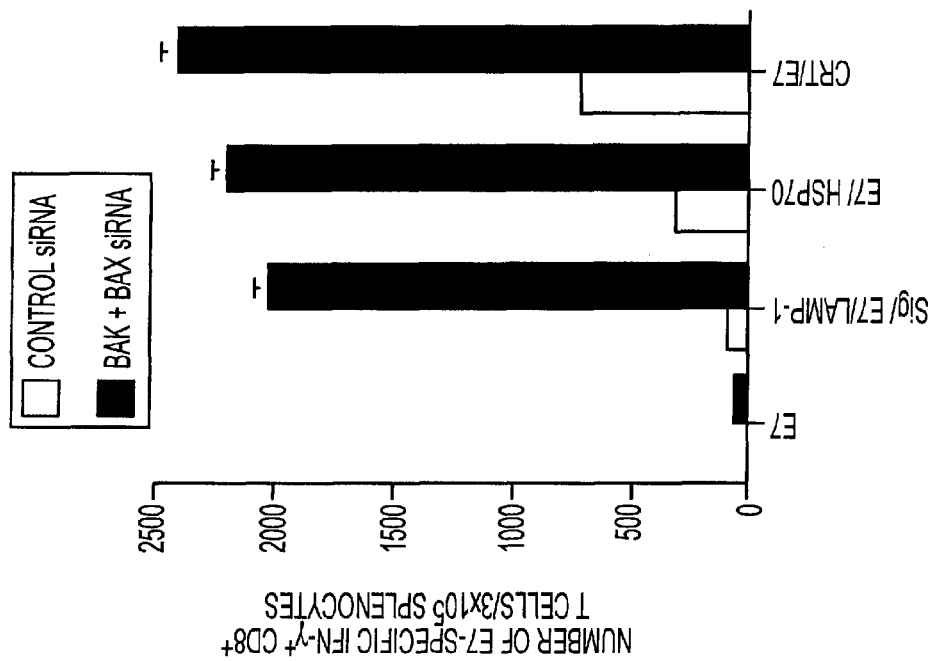

Combined Application of Anti-Apoptotic Bak+Bax SiRNA and an Intracellular Targeting Strategy Enhances Antigen-Specific T Cell-Mediated Immune Responses To assess the effect of coadministration of Bak+Bax siRNA with DNA encoding E7 linked to an DNA encoding an PP such as an intracellular targeting molecule, mice were vaccinated with either Sig/E7/LAMP-1 DNA, HSP70/E7 DNA, or CRT/E7 DNA each combined with either (i) Bak+Bax siRNA or (ii) control siRNA. As shown in FIGS. 11-12, coadministration of Bak+Bax siRNA with pcDNA3 encoding Sig/E7/LAMP-1, HSP70/E7, or CRT/E7 resulted in increased numbers of IFN-γ-expressing E7-specific CD8+ T cell precursors compared to coadministration of each of these three constructs with control siRNA. Among these intracellular targeting strategies, mice vaccinated with pcDNA3-Sig/E7/LAMP-1 combined with Bak+Bax siRNA displayed the greatest increase in the number E7-specific CD8+ T cell precursors (about a 19-fold). Thus, administration of Bak+Bax siRNA can be combined with any of the intracellular targeting strategies (using any IPP that itself can potentiate responses over those of DNA encoding antigen alone) to further enhance the potency of a DNA vaccine. Of the Antigen/IPP fusions tested, immunity was enhanced the most when pcDNA3-Sig/E7/LAMP-1 was combined with Bak+Bax siRNA.

Figure 13:
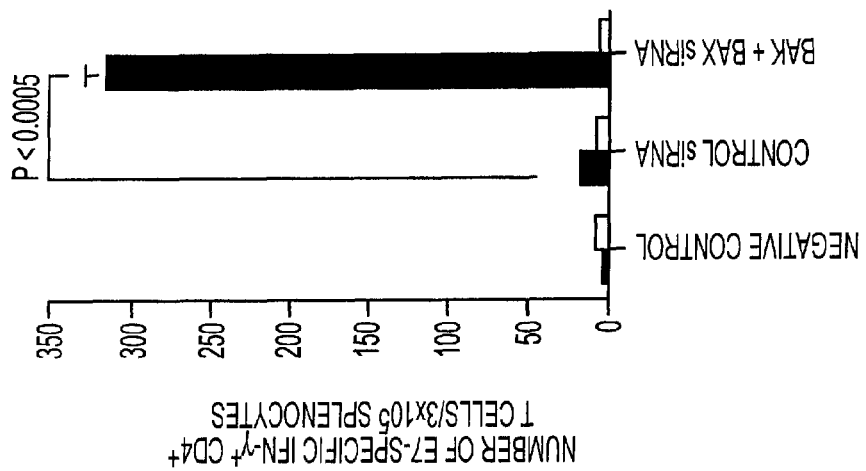
Figure 14:
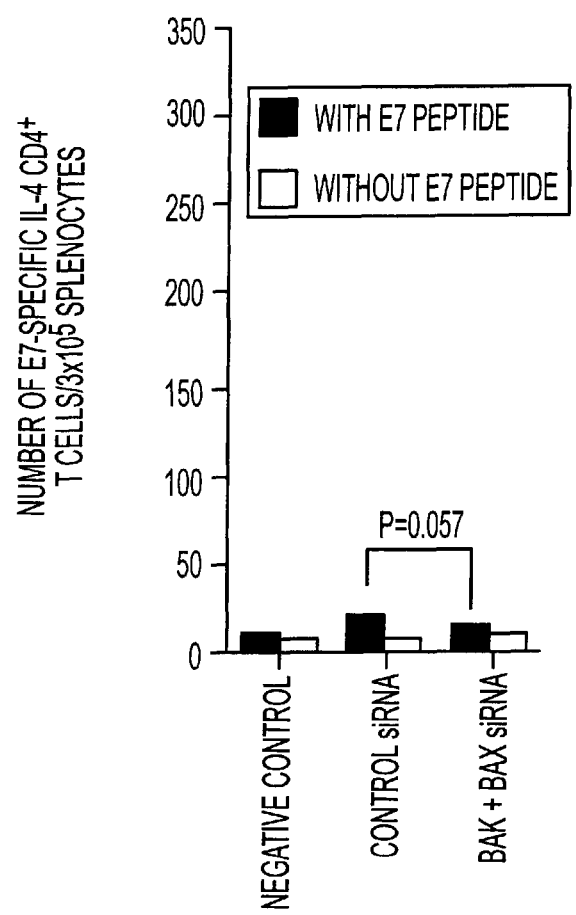

The ability of the Sig/E7/LAMP-1 targeting strategy to enhance antigen presentation to CD4+ T lymphocytes is achieved through targeting of expressed antigen to endosomal/lysosomal compartments, important loci for the MHC class II antigen presentation pathway (Wu T C et al., *Proc Natl Acad Sci USA* 92:11671-5, 1995). As shown in FIGS. 13-14, vaccination with pcDNA3-Sig/E7/LAMP-1 combined with Bak+Bax siRNA generated significantly more E7-specific CD4+ Th1 cells and similar numbers of E7-specific CD4+ Th2 cells when compared to vaccination with the same immunogen plus control siRNA. These results show that coadministration of Sig/E7/LAMP-1 DNA with Bak+Bax siRNA elicits an immune response mediated predominantly by E7-specific CD4+ Th1 cells.

EXAMPLE 6

Figure 15:
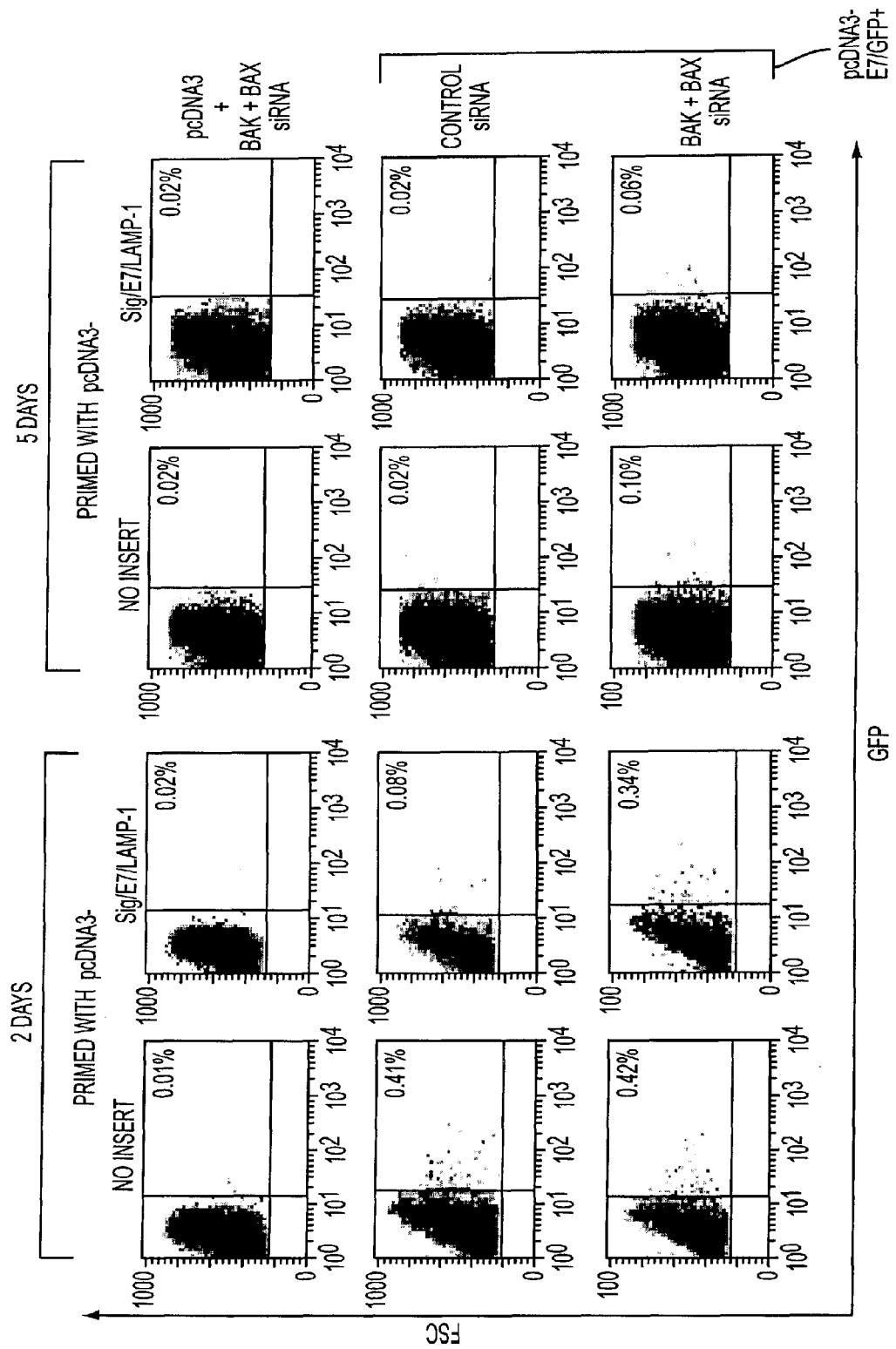
FIGS. 15-18. Flow cytometric analysis of GFP-expressing DCs in draining lymph nodes of mice vaccinated with E7/GFP DNA combined with Bak+Bax siRNA.
Figure 16:
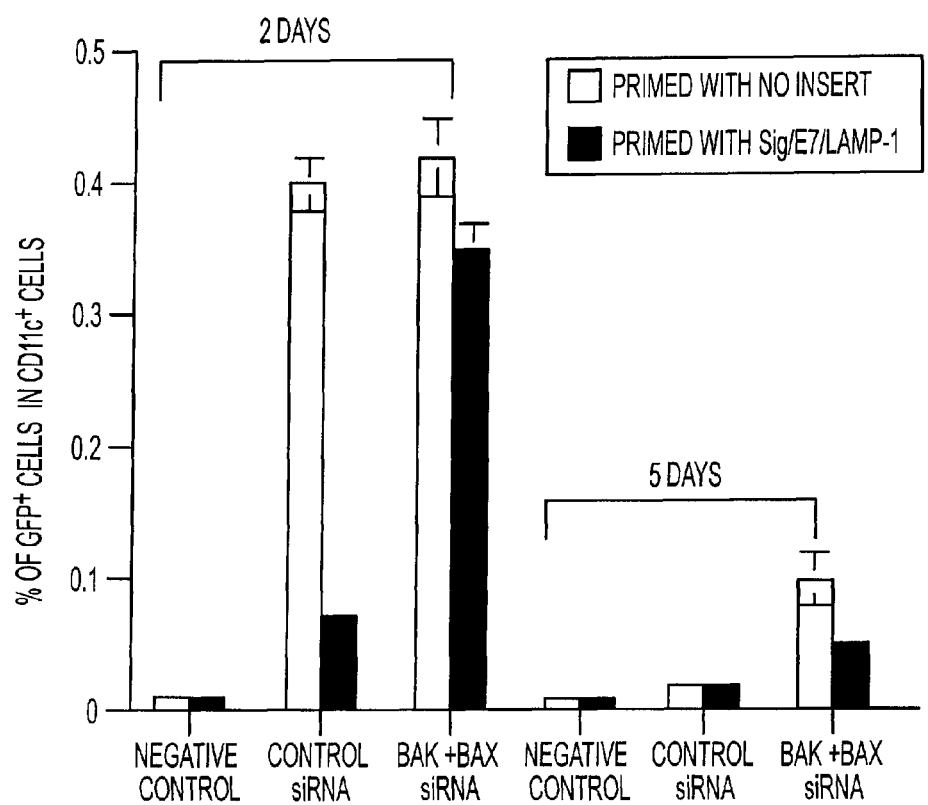

Co-Administration with Anti-Apoptotic Bax+Bak siRNA Improves Survival of DNA-Transfected DCs in Inguinal Lymph Nodes of Mice Vaccinated with E7/GFP DNA Mice were primed with pcDNA3-Sig/E7/LAMP-1 to generate sufficient E7-specific CD8+ T cells for testing of the anti-apoptotic ability of Bak+Bax siRNA in E7/GFP-expressing DCs. pcDNA3 (plasmid only) was the negative control. One week later, mice were treated via gene gun with pcDNA3-E7/GFP DNA plus either Bax+Bak siRNA or control siRNA. As shown in FIGS. 15-16, two days after vaccination. Control groups primed with pcDNA3 showed no significant difference in the percentages of GFP+ CD11c+ DCs between mice that received Bak+Bax siRNA and in that received siRNA. In comparison, in mice primed with the DNA immunogen pcDNA3-Sig/E7/LAMP-1, a significant decrease was observed in the percentage of GFP+ CD11c+ DCs detected in mice receiving control siRNA vs. the percentage of GFP CD11c+ DCs in mice administered Bak+Bax siRNA. Five days after vaccination with pcDNA3-E7/GFP, a similar, albeit weaker trend was observed in mice primed with Sig/E7/LAMP-1.

Assays for apoptotic GFP$^+$ CD11c$^+$ DCs were performed by staining cells for activated caspase-3 followed by flow cytometry. More than 90% of GFP$^+$ CD11c$^+$ DCs were caspase-3 negative, indicating that these cells were not apoptotic (not show). Thus, these results show that co-administration of anti-apoptotic Bak+Bax siRNA with the DNA immunogen E7/GFP protects DNA-transfected DCs from being killed by E7-specific CD8$^+$ T cells generated as a result of antigen-specific priming (by pcDNA3-Sig/E7/LAMP-1).

Figure 17:
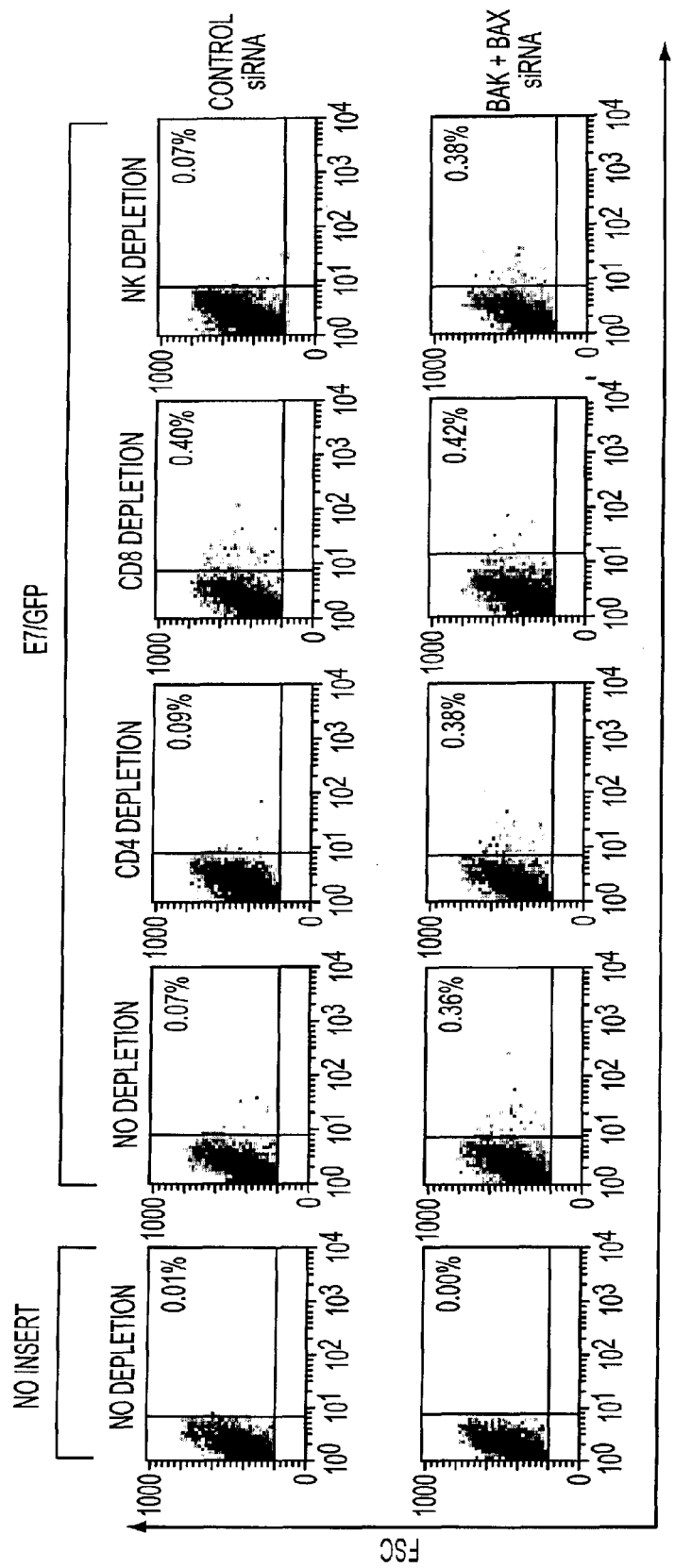
Figure 18:
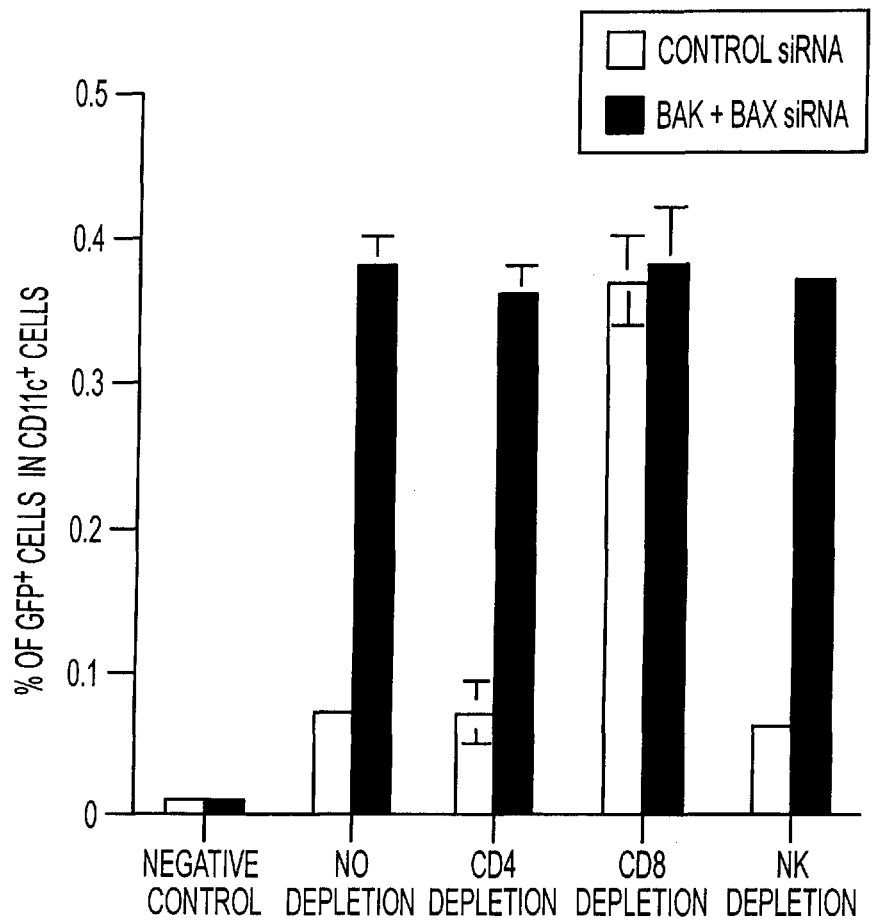

An antibody depletion experiment confirmed that CD8$^+$ T cells were responsible for the induction of apoptosis in GFP$^+$ CD11c$^+$ DCs. As shown in FIG. 17, the percentages of GFP$^+$ CD11$^+$ DCs in the inguinal LNs of mice depleted of CD8$^+$ T cells were similar in mice administered Bak+Bax siRNA compared to mice administered control siRNA. In comparison, percentages of GFP$^+$ CD11 cells in the inguinal LNs of mice depleted of CD4$^+$ T cells, NK cells, or control mice (no depletion) were significantly lower in mice receiving control siRNA compared to mice receiving Bak+Bax siRNA ($p<0.005$). Thus, CD8$^+$ T cells are responsible for the induction of apoptosis in antigen-expressing DCs in the draining LNs of vaccinated mice.

EXAMPLE 7

Co-Administration of Bak+Bax siRNA with DNA Vaccines During Boosting Elicits a Stronger Antigen-Specific CD8$^+$ T Cell Response than Co-Administration During Priming The results shown in FIGS. 15-18, indicate that the anti-apoptotic siRNA strategy is most critical for prolonging DC life when a pre-existing active antigen-specific CD8$^+$ T cell population is present; this occurs in the boosting phase of the DNA vaccination protocols used here.

Figure 19:
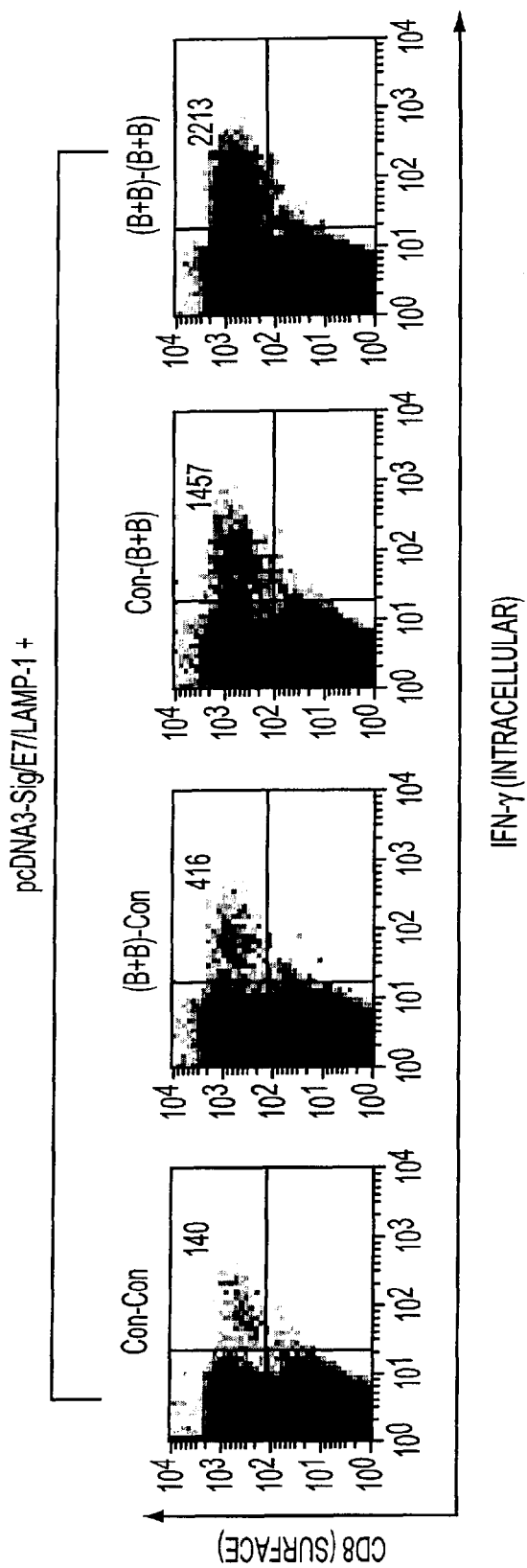
FIGS. 19-20. ICCS with flow cytometric analysis to determine the effect of co-administration of Bak+Bax siRNA during priming and/or boosting. Mice were vaccinated with pcDNA3-Sig/E7/LAMP-1 combined with Bak+Bax siRNA ("B+B") and/or control siRNA ("Con") in the priming phase and/or the boosting phase of the vaccination protocol.
Figure 20:
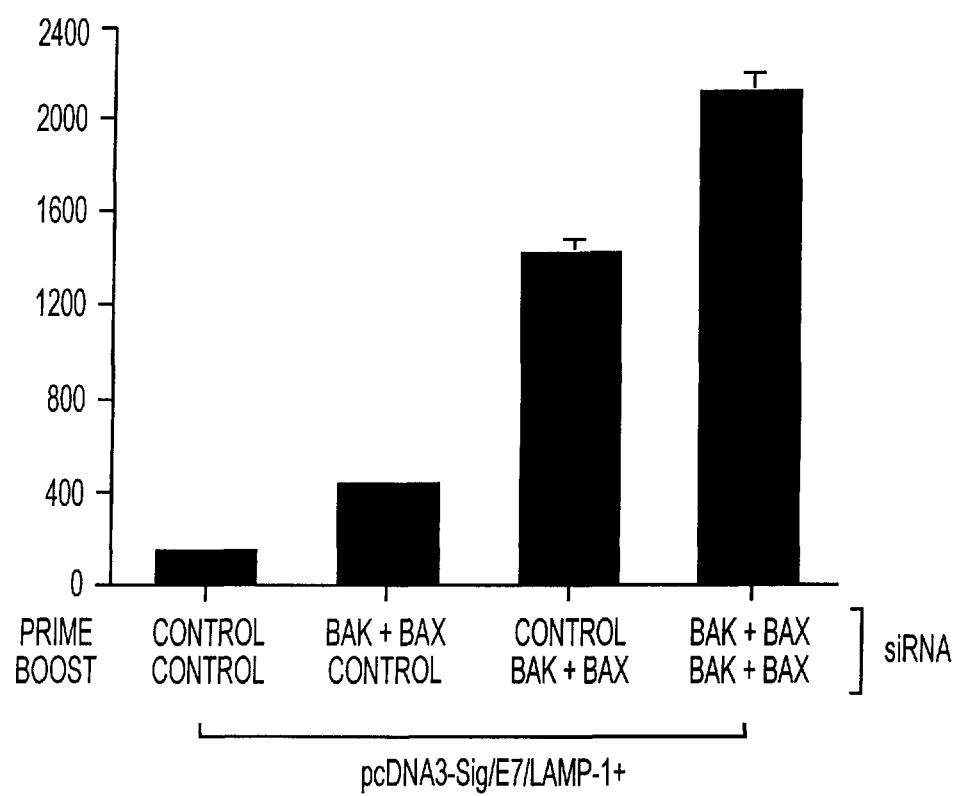

To determine whether prolonging the life of antigen-presenting DCs has more of an impact during the priming or the boosting phases of the vaccination process, pcDNA3-Sig/E7/LAMP-1 was co-administered with Bak+Bax siRNA or control siRNA during the priming or during the boosting phases. As shown in FIGS. 19-20, mice administered Bak+Bax siRNA during the priming and boosting phases generated the greatest number of E7-specific CD8$^+$ T cell precursors when compared to the other vaccination groups. Administration of Bak+Bax siRNA during the boosting phase resulted in a markedly higher number of E7-specific CD8$^+$ T cells than administration during the priming phase ($p=0.002$). These results show that prolonging the life of antigen-expressing DCs via administration of siRNA during the boosting phase has a greater impact on the (clonal) expansion of antigen-specific T cells.

EXAMPLE 8

Discussion of Examples 2-7

In vivo delivery of siRNA to target cells represents a significant challenge. Considerable endeavors have been devoted to efficient delivery of siRNA to specific cell types or organs in vivo (Song E et al., *Nat Med* 9:347-51, 2003). So far, these endeavors have met with only limited success (for a review, see Wall N R et al., *Lancet* 362:1401-3, 2003). The present inventors have shown that intradermal delivery to APCs via gene gun is an effective system for delivery of siRNA into professional antigen-presenting cells, allowing evaluation of siRNA-based strategies to modify DCs. Thus, the present work is the first to use intradermal delivery of siRNA to DCs and permits investigation of the properties of antigen-expressing DCs in vivo.

The encouraging results reported above indicate that modifying the function of DCs in vivo using siRNA technology targeting other key pro-apoptotic proteins, such as caspases 3, 6, 7, 8, or 9, should also enhance DNA vaccine potency. Furthermore, according to this invention, a combination of more than one type of siRNA targeting multiple pro-apoptotic proteins within the extrinsic and intrinsic apoptotic pathways is useful to induce even greater resistance to apoptotic stress in transfected DC-1 cells. This should result in greater numbers of viable, functional antigen-expressing DCs in the LNs draining a site of immunization in effectively primed mice. Other cell surface molecules such as PD-L1 and PD-L2 (Khoury S J et al., *Immunity* 20:529-38, 2004; Carreno B M et al., *Annu Rev Immunol* 20:29-53, 2002) and/or cytokines, such as IL4 and IL-10 (Li-Weber M et al., *Nat Rev Immunol* 3:534-43, 2003; Moore K W et al., *Annu Rev Immunol* 19 683-765, 2001) expressed by DCs cells suppress T cell responses. Expression of these molecules can be silenced by the siRNA technology to enhance antigen specific immune responses and the resultant antitumor effects.

Disclosed above is a significant increase in the number of GFP-positive DCs in the draining LNs of vaccinated mice after coadministration of pcDNA3-E7/GFP with Bak+Bax siRNA, compared to coadministration of pcDNA3-E7/GFP and control siRNA. This increase is likely due to enhanced DC survival mediated by Bak+Bax siRNA, rather than an influence on migration of DCs cells due to some nonspecific siRNA effect. This is so because coadministration of pcDNA3-E7/GFP with control siRNA did not produce similar effects. Previous observations by the present inventors and colleagues using DNA-encoding anti-apoptotic proteins (Kim T W et al., *J Clin Invest,* 2003, supra) support such a notion. DNA vaccines encoding antigen were coadministered with DNA encoding BCL-xL to prolong the lives of transfected DCs. While co-administration to mice of DNA encoding antigen with DNA encoding BCL-xL led yielded increased number of antigen-expressing DCs in the draining LNs, coadministration of the same immunogen with DNA encoding mutant BCL-xL with minimal mutations in a region critical to anti-apoptotic function, failed to lead to such an increase. Thus, the increase in GFP-positive DCs in the draining LNs after co-administration of Bak+Bax siRNA discussed above can be ascribed to changes in survival of DCs.

The increased number of antigen-expressing DCs in the LNs following the coadministration of Bak+Bax siRNA can contribute to increased numbers of E7-specific CD8$^+$ T cells through multiple mechanisms. Not only do antigen-expressing DCs provide signals to trigger proliferation and expansion of antigen-specific T cells, but they also can provide necessary signals that reduce T cell apoptotic death. Normally, DC death leads to decreasing interaction between APCs and lymphocytes, causing T cells to downregulate anti-apoptotic molecules and potentially upregulate pro-apoptotic molecules (Opferman et al., supra). This process would naturally lead to a decline in number of activated antigen-specific CD8$^+$ T cells. The continued survival of antigen-expressing DCs thanks to siRNA-mediated silencing of pro-apoptotic molecules would provide the necessary signals to prevent this decline. Other explanations for enhanced T cell responses include qualitative changes in antigen-expressing DCs as a result of vaccination together with Bak+Bax siRNA administration. The present inventors have observed that antigen-expressing DCs transfected with Bak+Bax siRNA could activate antigen-specific CD8+ T cells more efficiently than DCs transfected with control siRNA (not shown). Thus, the anti-apoptotic function mediated by Bak+Bax siRNA may modify the quantity and quality of DCs, thereby leading to enhanced T cell activation.

The present results show that prolonging the life of antigen-expressing DCs during the boosting phase is important for clonal expansion of antigen-specific T cells. Killing of antigen-expressing DCs is a natural process that regulates clonal expansion of antigen-specific CD8+ T cells. Pre-existing antigen-specific CD8+ T cells in draining LNs can lyse antigen-expressing DCs, limiting clonal expansion (Ritchie D S et al., *J Immunol Meth* 246:109-17, 2000; Hermans I F et al., *J Immunol* 164:3095-3101, 2000). Such CD8+ T cell-mediated lysis of DCs is more significant during the boosting phase of vaccination than during the priming phase, due to the increased number of antigen-specific CD8+ T cells that were elicited by the priming. Therefore, while prolonging the lives of antigen-expressing DCs during priming and boosting leads to the strongest clonal expansion of antigen-specific CD8+ T cells, it is during the boosting phase that this effect on DCs contributes most to T cell expansion.

The Bak and Bax siRNA technology can also be extended to the treatment of DCs ex vivo for subsequent in vivo use. As disclosed above, E7 peptide-pulsed DC-1 cells transfected with Bak+Bax siRNA were more resistant to killing by E7-specific CD8+ T cells than were DC-1 cells transfected with control siRNA.

Furthermore, as described in the Examples below, vaccination with E7 peptide-pulsed DC-1 cells transfected with Bak+Bax siRNA leads to significantly higher numbers of E7-specific CD8+ T cells compared to vaccination with antigen-pulsed DC-1 cells transfected with control siRNA. Thus, the potency of DC-based vaccines prepared ex vivo can be further enhanced by the specific targeting of key pro-apoptotic proteins, such as Bak and Bax, using siRNA.

In summary, the targeting of Bak+Bax siRNA with DNA vaccines (encoding antigen) to DCs in vivo represents an innovative approach to enhancing DNA vaccine potency. In addition, the use of siRNA alleviates safety concerns associated with the use of DNA vaccines encoding anti-apoptotic proteins. Not only does gene gun delivery of siRNA to DCs result in prolonged DC life, but it also avoids concerns for oncogenicity associated with DNA encoding anti-apoptotic proteins. Further safety is achieved by using detoxified (mutant) forms of the HPV antigens E7 or E6 as disclosed above. Indeed no gross anatomical or histological changes were observed in the vital organs of vaccinated mice compared to non-vaccinated mice, alleviating concerns about the induction of autoimmunity that as a sequela of prolonging DC life. Thus, the strategy of using siNA to silence pro-apoptotic proteins, as exemplified with siRNA targeting Bak+Bax useful in the clinical arena where enhanced DNA vaccine potency is a desirable goal in improving the immunologic control of cancer or infectious disease.

EXAMPLE 9

Examples 9-15 Incorporate by Reference Peng S et al., *Hum Gene Ther* 16:584-93 (2005 May)

Figure 21:
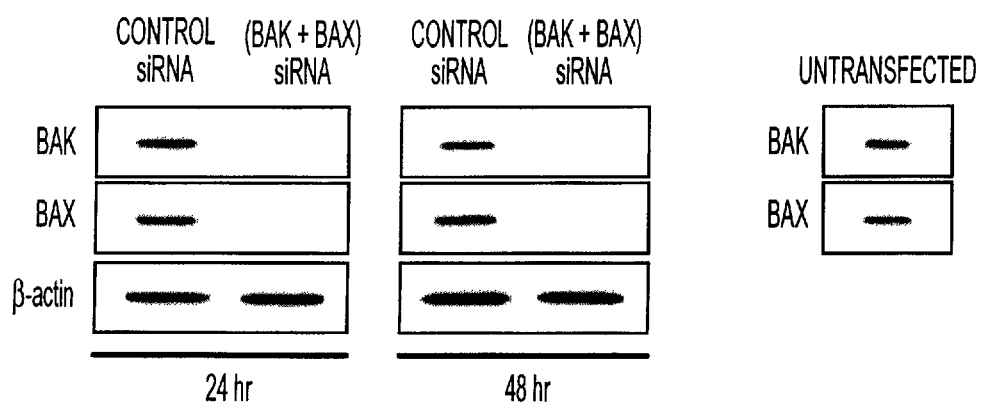
FIG. 21. Western blot analysis of the expression of Bak and Bax protein in DC-1 cells transfected with various siRNA constructs. DC-1 cells were transfected with either Bak/Bax siRNA or control siRNA. Western blot analysis was performed with 50 μg of cell lysates 24 and 48 hours after transfection. β-actin was used as a control for loading. Lysates of untransfected DC-1 cells were used as negative controls.

Transfected of Dendritic Cells with Bak/Bax siRNA Abolishes Expression of Bak and Bax Proteins Western blot analysis was performed to examine in DC-1 cells (a murine DC line) the effects of transfection with Bak/Bax siRNA on expression of Bak and Bax proteins. As shown in FIG. 21, lysates from DC-1 cells transfected with Bak/Bax siRNA showed significant reduction in the expression of Bak and Bax proteins 24 and 48 hrs after transfection. In contrast, when transfection with control siRNA was done, the expression of Bak and Bax did not differ from that in non-transfected DC-1 cells. Analysis of β-actin expression in transfected DCs confirmed that equal amounts of cell lysates had been loaded in all the Western blots. These results indicate that transfection of DC-1 cells with Bak/Bax siRNA abolishes Bak and Bax protein expression during the intervals examined.

DC-1 cells transfected with Bak and/or Bax siRNA can resist CTL-induced apoptosis. E7-loaded, siRNA-transfected, DC-1 cells were incubated with an E7-specific CD8+ T cell line. These DC-1 cells resisted killing by E7-specific CD8+ T cells in vitro. Taken together, these results show that transfection of DC-1 cells with Bak and/or Bax siRNA down-regulates Bak and Bax protein expression, a consequence of which is resistance to apoptosis caused by activated antigen-specific CD8+ T cells in DCs.

EXAMPLE 10

Figure 23:
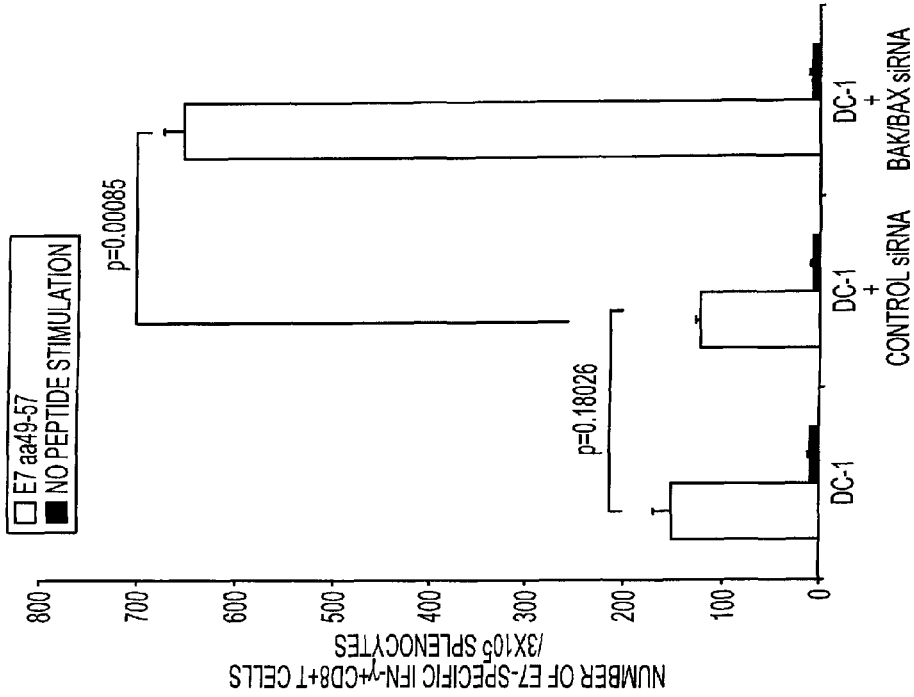
FIGS. 22-23. ICCS and flow cytometric analysis to determine the number of IFN-γ-producing E7-specific CD8+ T cells in mice after immunization with E7 peptide-pulsed DCs transfected with various siRNA constructs. Mice (5/group) were vaccinated with E7 peptide-loaded DCs transfected with (i) Bak/Bax siRNA or (ii) control siRNA. Mice vaccinated with E7 peptide-loaded DCs (no transfection) were additional controls.
Figure 22:
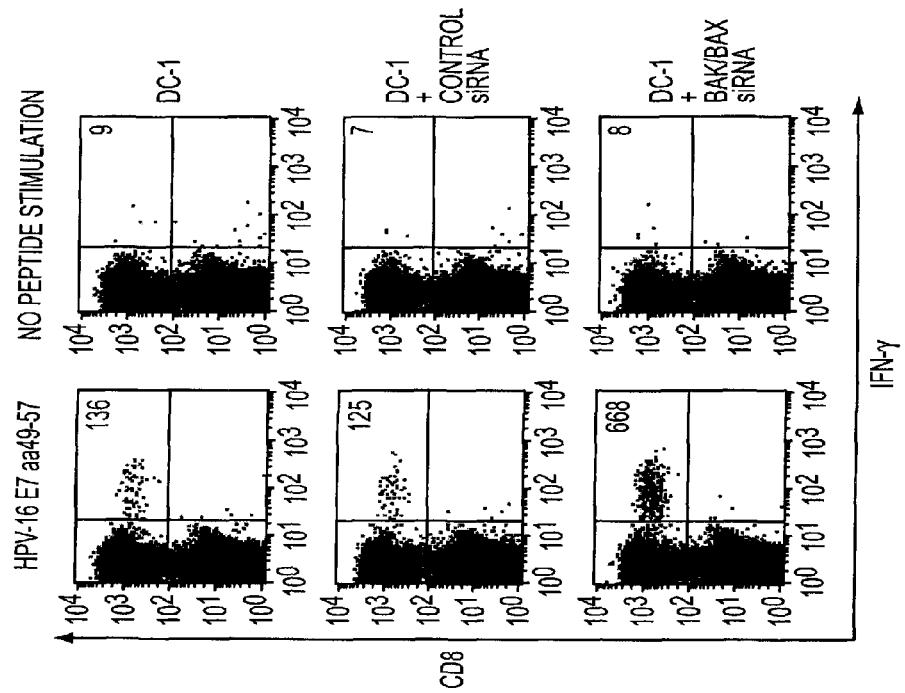

Vaccination with E7 Peptide-Loaded DCs Transfected with Bak/Bax siRNA Leads to a Significant Increase in E7-Specific IFN-γ+ CD8+ T Cell Precursors To determine whether vaccination with E7 peptide-loaded DCs transfected with Bak/Bax siRNA could enhance the generation of E7-specific IFN-γ+ CD8+ T cell precursors in mice, ICCS and flow-cytometry analysis was performed on spleen cells from mice vaccinated with the various DC-1 cells. As shown in FIGS. 22-23, mice vaccinated with E7-loaded DCs transfected with Bak/Bax siRNA exhibited an ~5.4-fold increase in the number of E7-specific IFN-γ+ CD8+ T cells (655±21) compared to mice vaccinated with E7-loaded DCs transfected with control siRNA (121±5) (which were similar to the number of E7-specific CD8+ T cells induced by E7-loaded DC-1 that remained untransfected). Thus, administration of DCs that are transfected with Bak/Bax siRNA is markedly more immunogenic than the use of control DCs when measured by the number of E7-specific IFN-γ+ CD8+ T cells that are generated in vivo.

EXAMPLE 11

Figure 25:
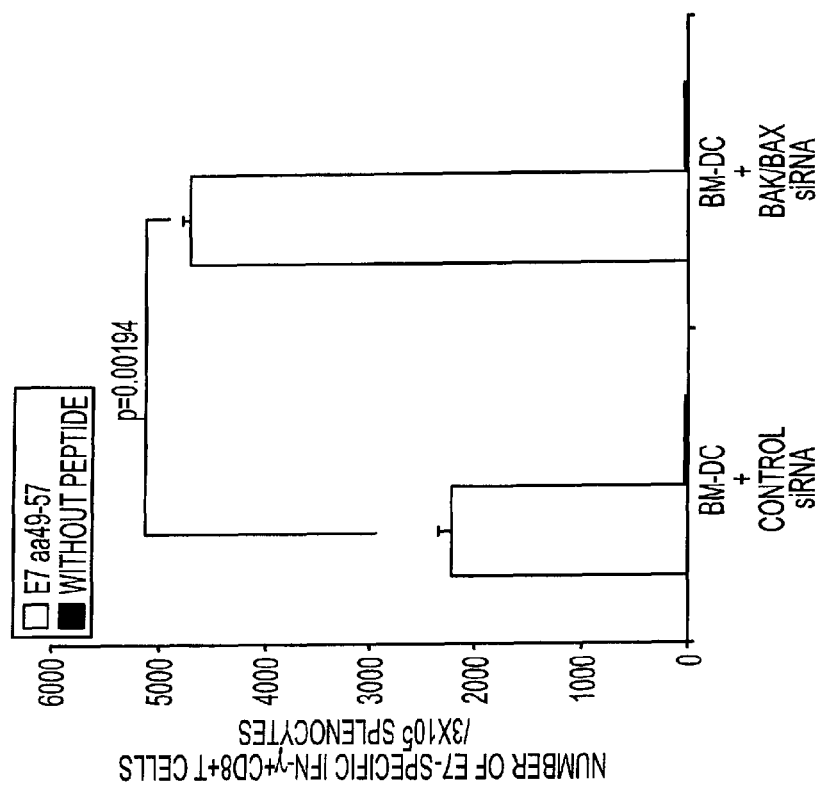
FIGS. 24-25. Flow cytometric analysis (FIG. 24) and ICCS (FIG. 25) of spleen cells from mice immunized with E7-pulsed bone marrow-derived DCs (BM-DCs) transfected with the various siRNA constructs. Mice (5/group) were vaccinated with E7 peptide-loaded BM-DCs transfected with (i) Bak/Bax siRNA or (ii) control siRNA.
Figure 24:
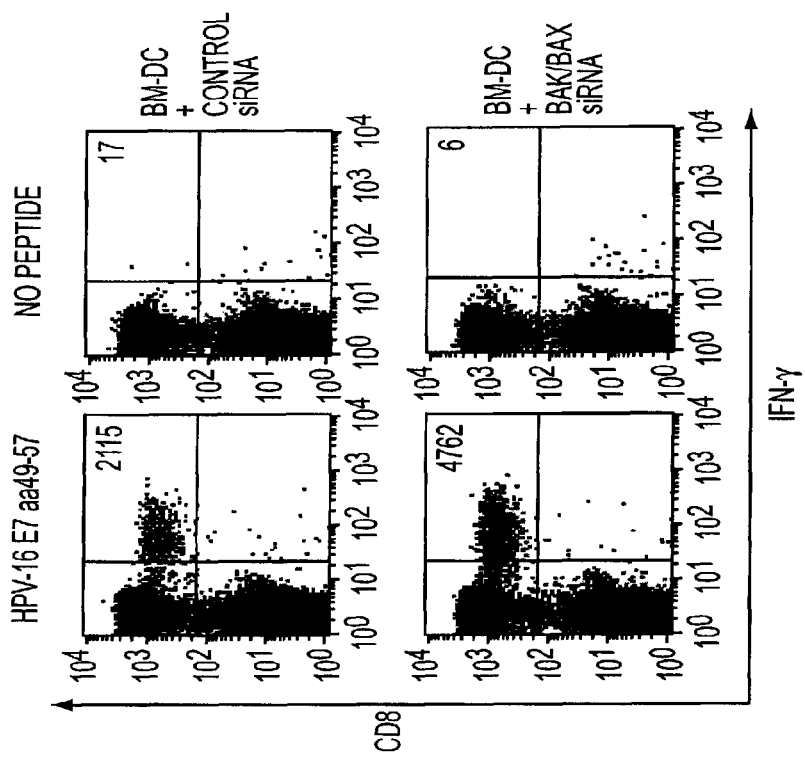

Vaccination with E7 Peptide-Loaded BM-DCs Transfected with Bak/Bax siRNA Increases E7-Specific IFN-γ+ CD8+ T Cell Precursors It was important to determine if the Bak/Bax siRNA technology also works with a more "physiological" source of DCs, not derived from an immortalized cell line, since the former would be a more appropriate source of cells for clinical use. For this purpose bone marrow-derived DCs (BM-DCs) were tested—after loading with E7 peptide and transfection with either Bak/Bax siRNA or control siRNA. To determine E7-specific CD8+ T cell precursors in vaccinated mice, ICCS followed by flow cytometry analysis was performed. As shown in FIGS. 24-25, mice vaccinated with E7-peptide-loaded BM-DCs transfected with Bak/Bax siRNA exhibited a ~2.2-fold increase in the number of E7-specific IFN-γ+ CD8+ T cells (4706±78.5) compared to mice vaccinated with E7 peptide-loaded DCs transfected with control siRNA (2210±134.3) (p≤0.002). Thus, the Bak/

Bax siRNA technology can also be applied to BM-DCs to enhance their potency as immunogens.

EXAMPLE 12

Figure 26:
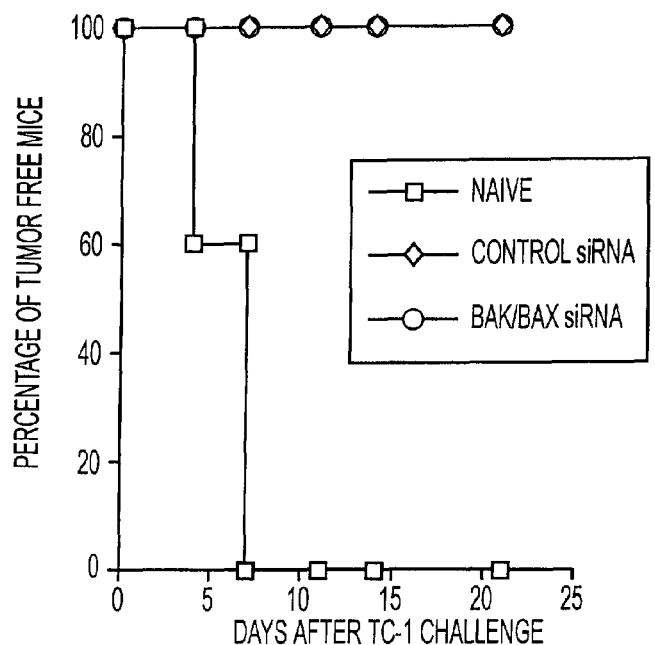
FIGS. 26-27. In vivo tumor protection and treatment experiments.

Vaccination with E7-Loaded DCs Transfected with Bak/Bax siRNA Generates Stronger Antitumor Effects than E7-Loaded DCs Transfected with Control siRNA To determine whether the observed increase in the number of E7-specific CD8+ T cell precursors translated into a stronger E7-specific antitumor effect, an in vivo tumor protection experiment was carried out using the TC-1 system (supra). As shown in FIG. 26, 100% of mice receiving E7 peptide-loaded DCs transfected with either control siRNA or Bak/Bax siRNA remained tumor-free for 30 days after a s.c. challenge with TC-1 cells, whereas non-vaccinated mice developed tumors within 10 days of tumor challenge. Therefore, vaccination with E7 peptide-loaded DC-1 transfected with either Bak/Bax siRNA or control siRNA elicited protective antitumor immunity against challenge by an E7-expressing tumor. The in vivo tumor protection model failed to distinguish between the use of Bak/Bax targeted and control siRNA.

Figure 27:
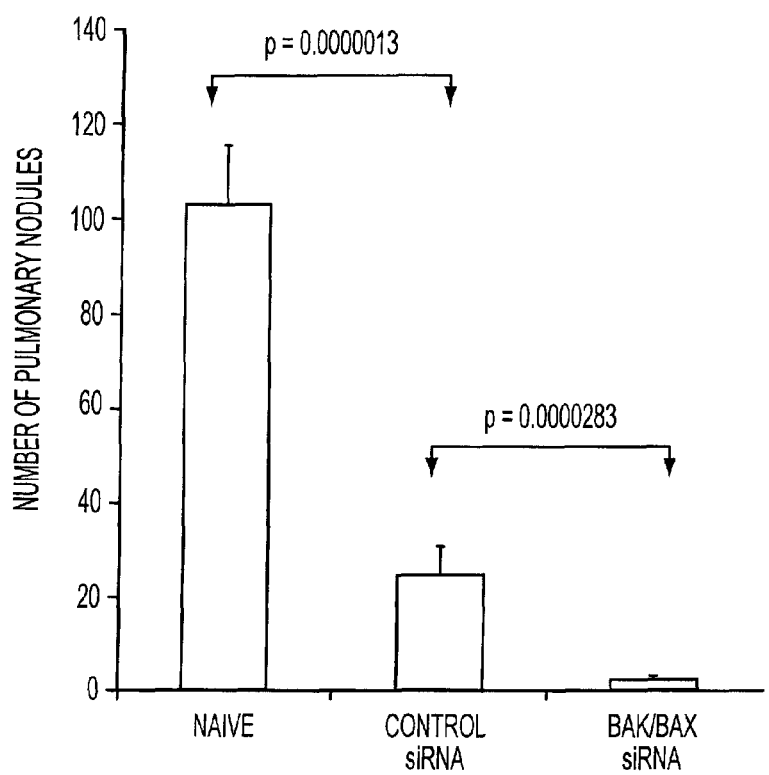

To extend the comparison, an in vivo tumor trial was performed using a more stringent lung tumor metastasis model in which TC-1 tumor cells were delivered i.v. Thus, mice were first challenged with the TC-1 tumor cells i.v. (tail vein) followed by treatment with E7-peptide loaded DC-1 cells transfected either with Bak/Bax siRNA or with control siRNA. Mice were sacrificed 28 days after the tumor challenge and the growth of pulmonary nodules was examined. As shown in FIG. 27, mice treated with E7-peptide loaded DCs transfected with Bak/Bax siRNA demonstrated the lowest number of pulmonary nodules (2.2±0.84) compared to mice treated with E7-peptide loaded DCs transfected with control siRNA (24.8±5.89), or the naïve control group (103±12.29; p<0.001; Student's t test). Thus, vaccination with E7-loaded DCs transfected with Bak/Bax siRNA generates a markedly better highly significant therapeutic effect than vaccination with E7-loaded DCs transfected with control siRNA.

EXAMPLE 13

Figure 28A:
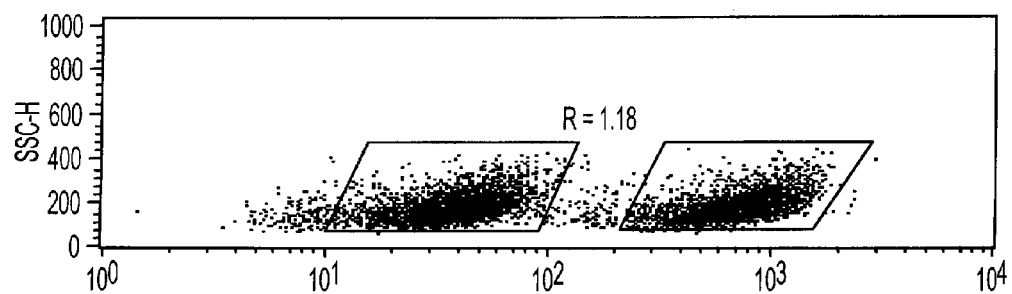
FIGS. 28A-28B. Survival of E7 peptide-loaded BM-DCs transfected with Bak/Bax siRNA or control siRNA after administration of E7-specific CD8+ T cells in vivo.
Figure 28B:
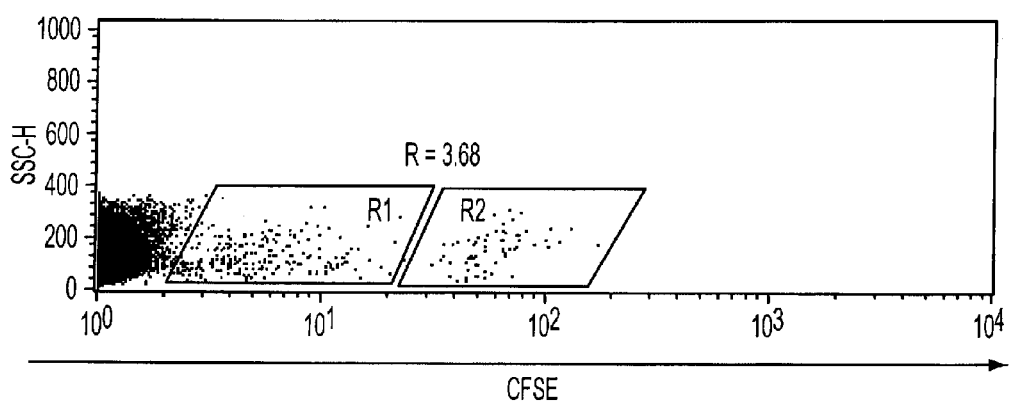

E7 Peptide-Loaded DCs Transfected with Bak/Bax siRNA Survive Longer In Vivo than E7 Peptide-Loaded DCs Transfected with Control siRNA To determine if transfection with Bak/Bax siRNA improves the survival of E7-peptide loaded DCs in vivo, two distinct groups of BM-DC cells loaded with carboxyfluorescein (CFSE)-labeled E7 peptide and transfected with different siRNAs were first created. E7 peptide-loaded BM-DCs transfected with control siRNA were labeled with a higher concentration of CFSE (5 μM), while Bak/Bax siRNA-transfected BM-DCs were labeled with a lower concentration of CFSE (0.5 μM). The relative levels of CFSE in these two distinctly CFSE-labeled E7 peptide-loaded BM-DCs were characterized by flow cytometry (FIG. 28A). Mice were then challenged with $10^6$ E7-specific T cells/mouse i.v. Three days later, a mixture of $2.5\times10^5$ low CFSE-labeled BM-DCs and $2.5\times10^5$ of high CFSE-labeled BM-DCs were injected i.v. into each challenged mouse. Sixteen hours later, flow-cytometry analysis was performed to characterize the ratio of low CFSE-labeled BM-DCs to high CFSE-labeled BM-DCs using cells collected from the spleen and lungs of challenged mice. As shown in FIG. 28B, a significantly higher number of low CFSE-labeled BM-DCs was observed (~3.7-fold), compared to the number of high-CFSE-labeled BM-DCs. These results show that transfection of E7 peptide-loaded BM-DCs with Bak/Bax siRNA can prolong DC life in vivo, and resulting in a higher number of E7-peptide loaded BM-DCs.

EXAMPLE 14

Figure 29:
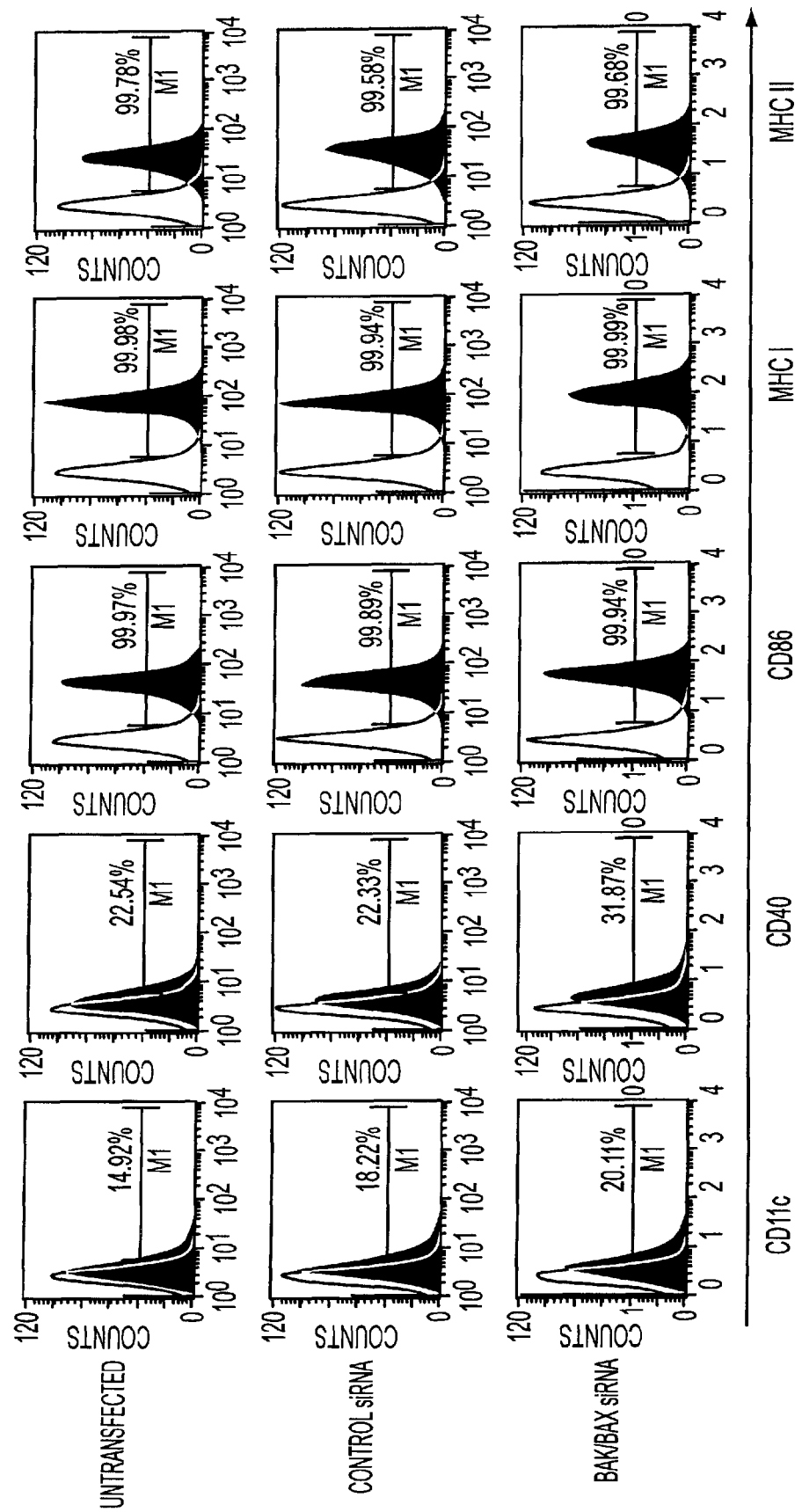
FIG. 29. Characterization of the surface molecules of E7 peptide-loaded DCs after transfection with Bak/Bax siRNA or control siRNA. Flow cytometry was used to determine the level of expression of CD11c, CD40, CD86, MHC I, and MHC II-molecules in E7 peptide-loaded murine DC-1 cells transfected with either (i) Bak/Bax siRNA or (ii) control siRNA. E7 peptide-loaded DCs that were not transfected at all served as negative controls.
Figure 30:
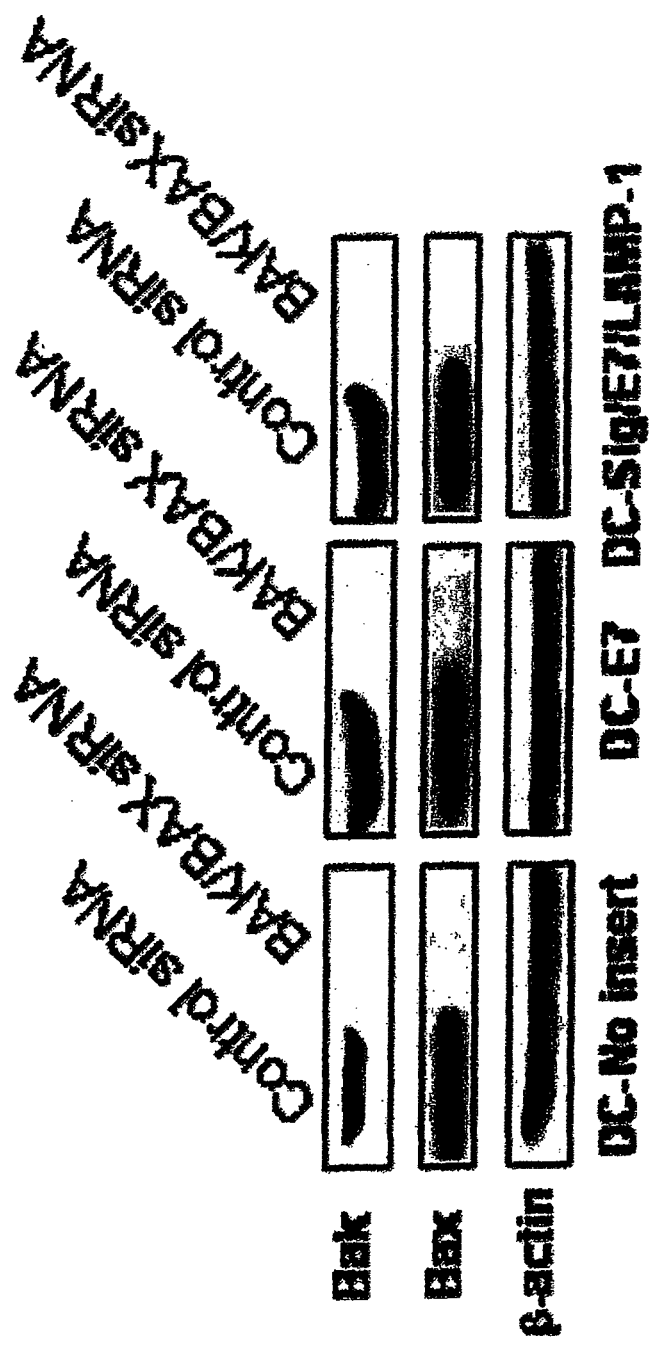
FIG. 30. Western blot analysis to detect expression of Bak and Bax protein in DCs transfected with the various siRNA constructs. Various DCs were transfected with control or BAK/BAX siRNAs. Equal amounts of protein (50 μg) were loaded and separated by SDS-PAGE using a 15% polyacrylamide gel. Western blot analysis was performed with 50 μg of the cell lysate and anti-BAK or BAX mouse monoclonal antibody 3 days after transfection. β-actin was used as a control to indicate that equal amounts of cell lysates were loaded.
Figure 31:
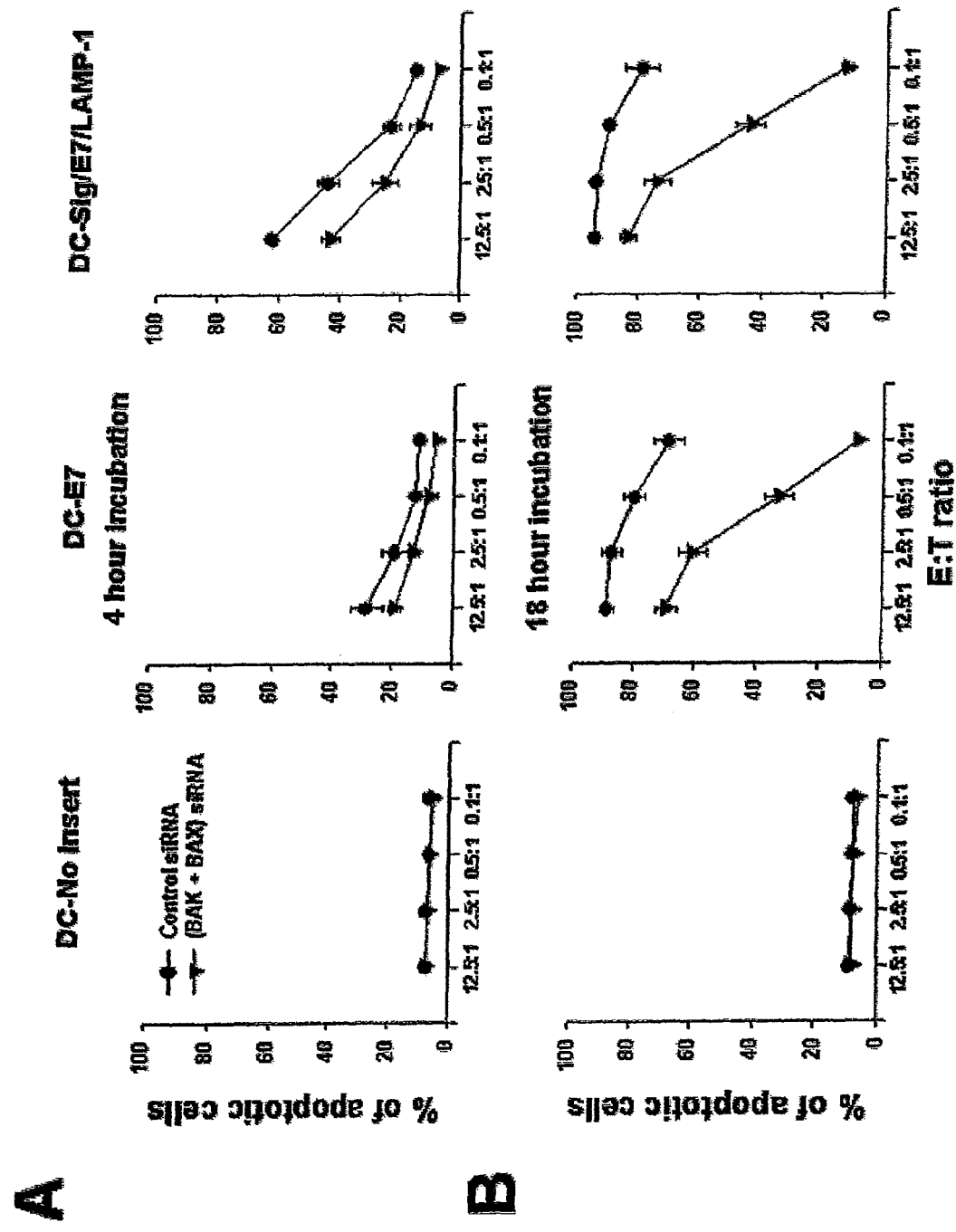
FIG. 31. In vitro resistance of the DCs transfected with the siRNAs to CD8 T cell-mediated CTL-killing. DCs were incubated with an E7-specific CD8+ T cell line at different E:T ratios (12.5:1, 2.5:1, 0.5:1 or 0.1:1) for 4 (A) or 18 hours (B). FITC-conjugated anti-CD8 antibody was used to stain for a CD8+ E7-specific T cell line, and then CD8-negative cells (DCs) were gated to identify the percentage of apoptotic dendritic cells. Detection of apoptotic cells in the DC cells was performed using PE-conjugated rabbit anti-active caspase-3 antibody (BD Bioscience). The percent of apoptotic cells was analyzed using flow cytometry.
Figure 32:
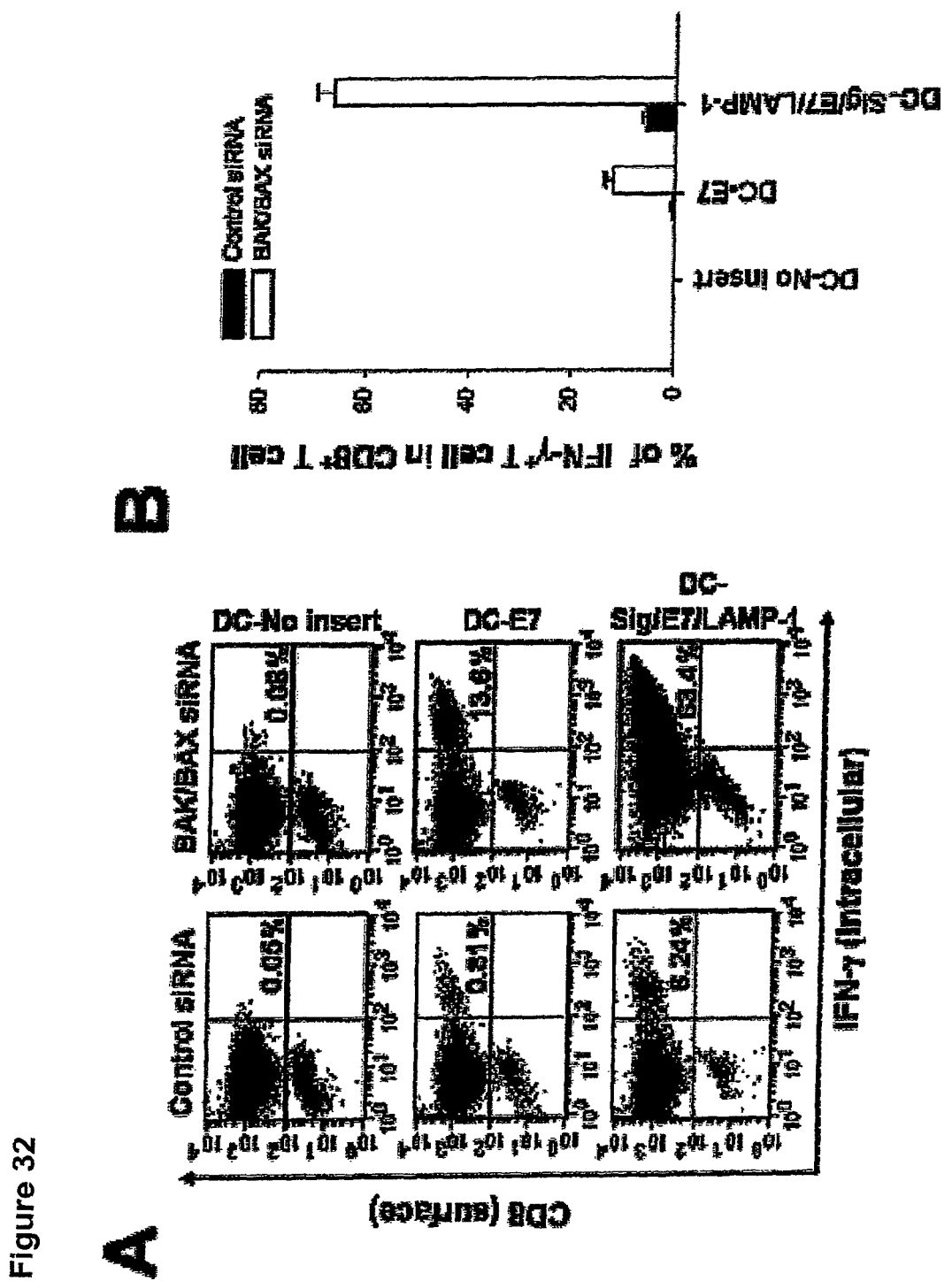
FIG. 32. Intracellular cytokine staining and flow cytometry analysis to demonstrate the in vitro activation of E7-specific T cells by DCs transfected with siRNAs. DCs expressing E7 or Sig/E7/LAMP-1, transfected with control or BAK/BAX siRNAs, were incubated with an E7-specific CD8+ T cell line at a 1:10 mixture of DC:T cell ratios for 18 hours. Intercellular cytokine staining assay was performed to count activated IFN-γ-secreting CD8+ T cells using flow cytometry. The data presented in this figure are from one representative experiment of three performed (A). Bar graph depicting the % of E7 specific CD8+ T cell (B).
Figure 33:
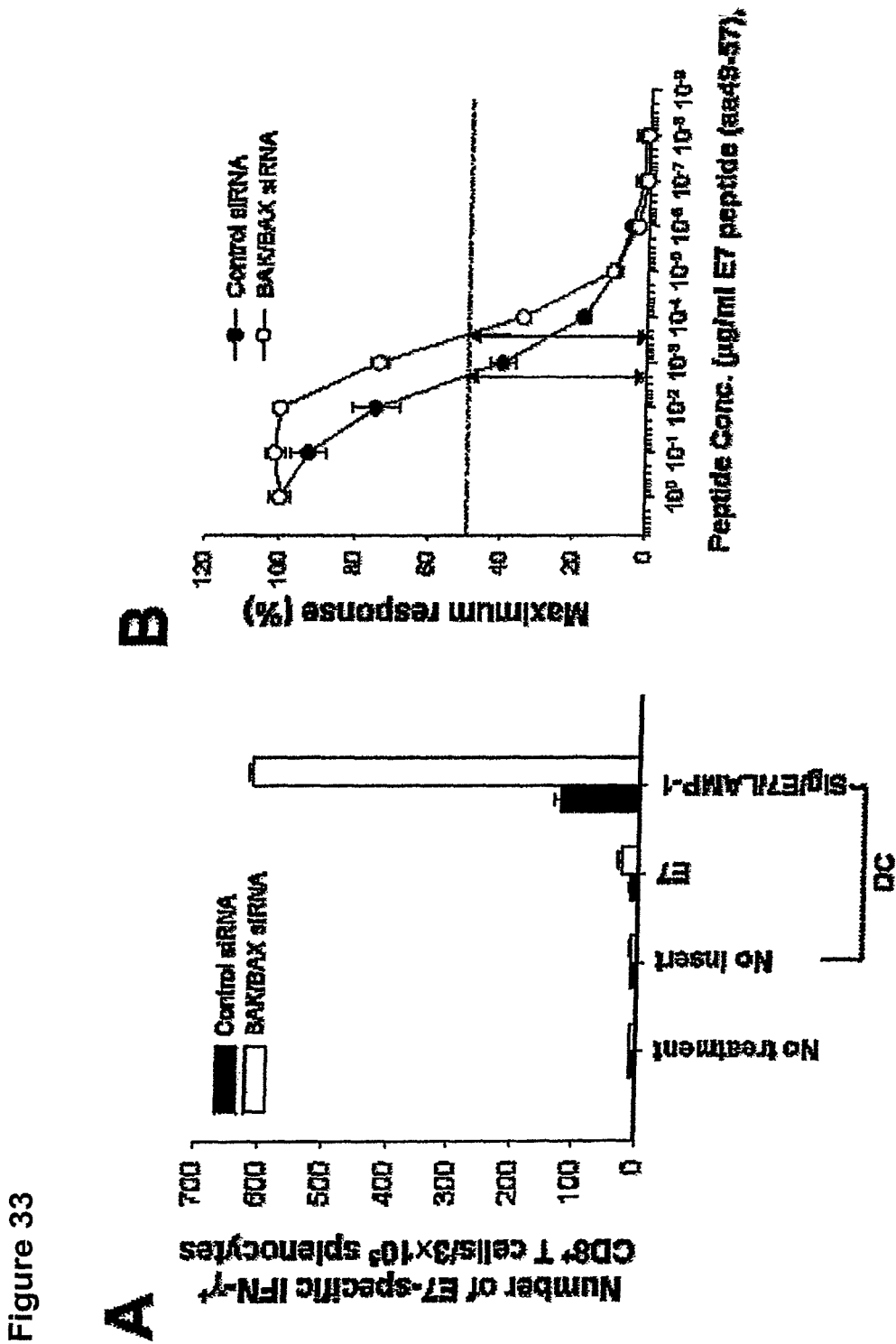
FIG. 33. Intracellular cytokine staining and flow cytometry analysis to determine the number (A) and functional avidity (B) of IFN-γ-producing E7-specific CD8+ T cells in mice after immunization with E7-expressing DCs transfected with various siRNA constructs. Mice (five per group) were vaccinated twice with E7-expressing DCs transfected with BAK/BAX siRNA or control siRNA. There was a 1-week interval between injections. Splenocytes were harvested one week after the last vaccination, stained for CD8+ and IFN-γ, and analyzed by flow cytometry to detect activated E7-specific CD8+ T cells. The bar graph depicts the number of IFN-γ-expressing E7-specific CD8+ T cells per 3×10⁵ splenocytes from vaccinated mice (mean±SD) (A). For the determination of the avidity of E7-specific CD8+ T cells, pooled splenocytes were incubated overnight with different concentrations of E7 peptide. The number of E7-specific IFN-γ-secreting CD8+ T cells was determined using intracellular cytokine staining and FACScan analysis as described above. We defined the number of IFN-γ-expressing CD8+ T cells stimulated with E7 peptide (amino acids 49-57; 10⁰ μ/ml) as the maximal response. The horizontal line allows comparison of E7 peptide concentrations needed for 50% of maximal E7-specific CD8+ T cell response in mice vaccinated using the two regimens. The data presented in this figure are from one representative experiment of two performed (B).
Figure 35:
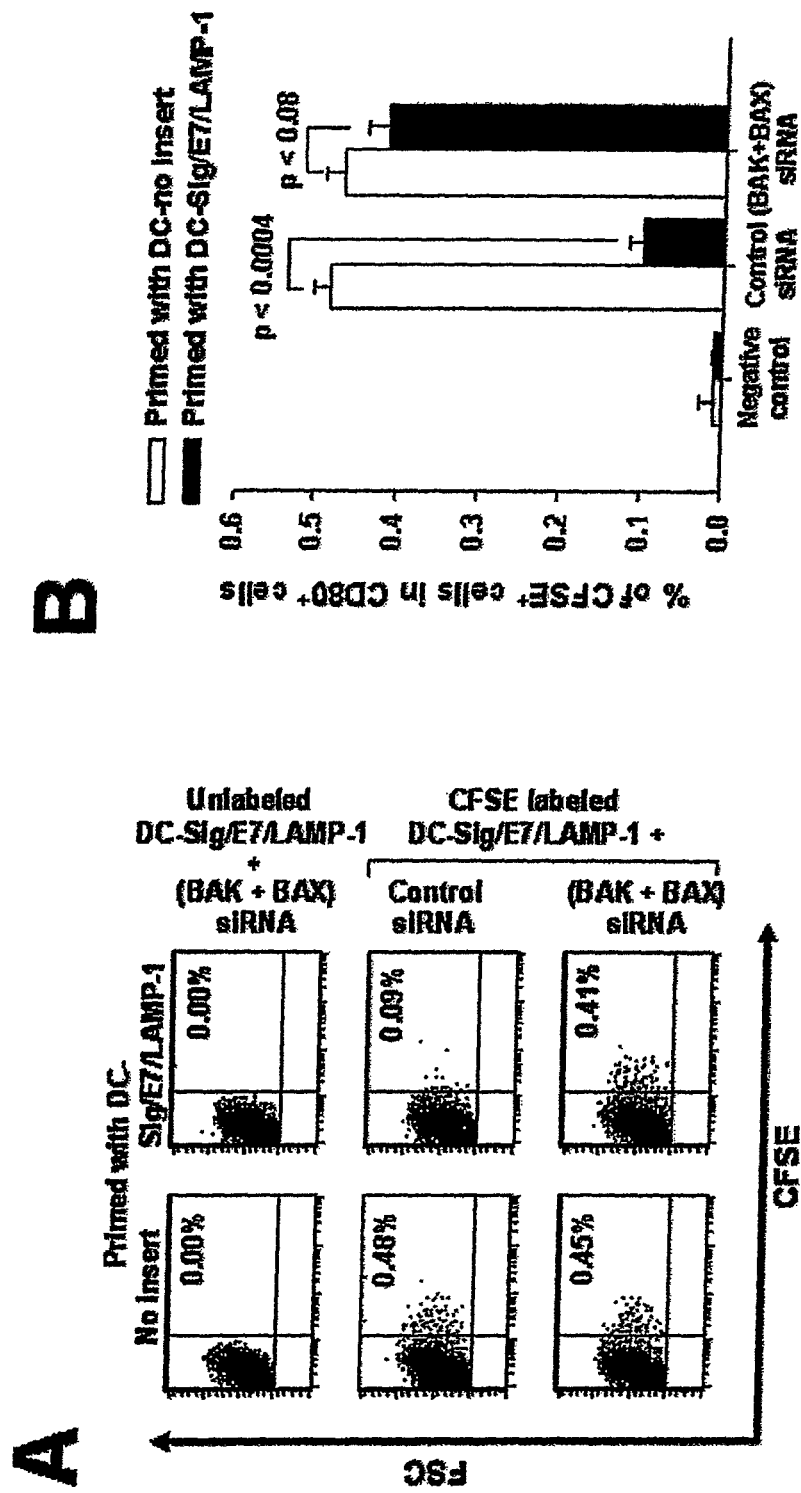
FIG. 35. Flow cytometry analysis to determine the survival of DC-Sig/E7/LAMP-1 transfected with control siRNA or BAK/BAX siRNA in draining lymph nodes. C57BL/6 mice (five per group) were first primed with DC-no insert or DC-Sig/E7/LAMP-1. Seven days later, the mice received CFSE-labeled DC-Sig/E7/LAMP-1 transfected with control siRNA or BAK/BAX siRNA. Unlabeled DCs transfected with BAK/BAX siRNA were used as a negative control. Two days after boosting with the DCs, popliteal lymph nodes were harvested and isolated lymphocytes were analyzed by flow cytometry. The monocyte-like cells with size and granular characteristics of DCs were gated. The percentage of CFSE+ cells among the gated CD80+ cells was analyzed. The data presented in this figure are from one representative experiment of two performed (A). Bar graph depicting percentages of CFSE-expressing cells out of total CD80+ cells (B).
Figure 38:
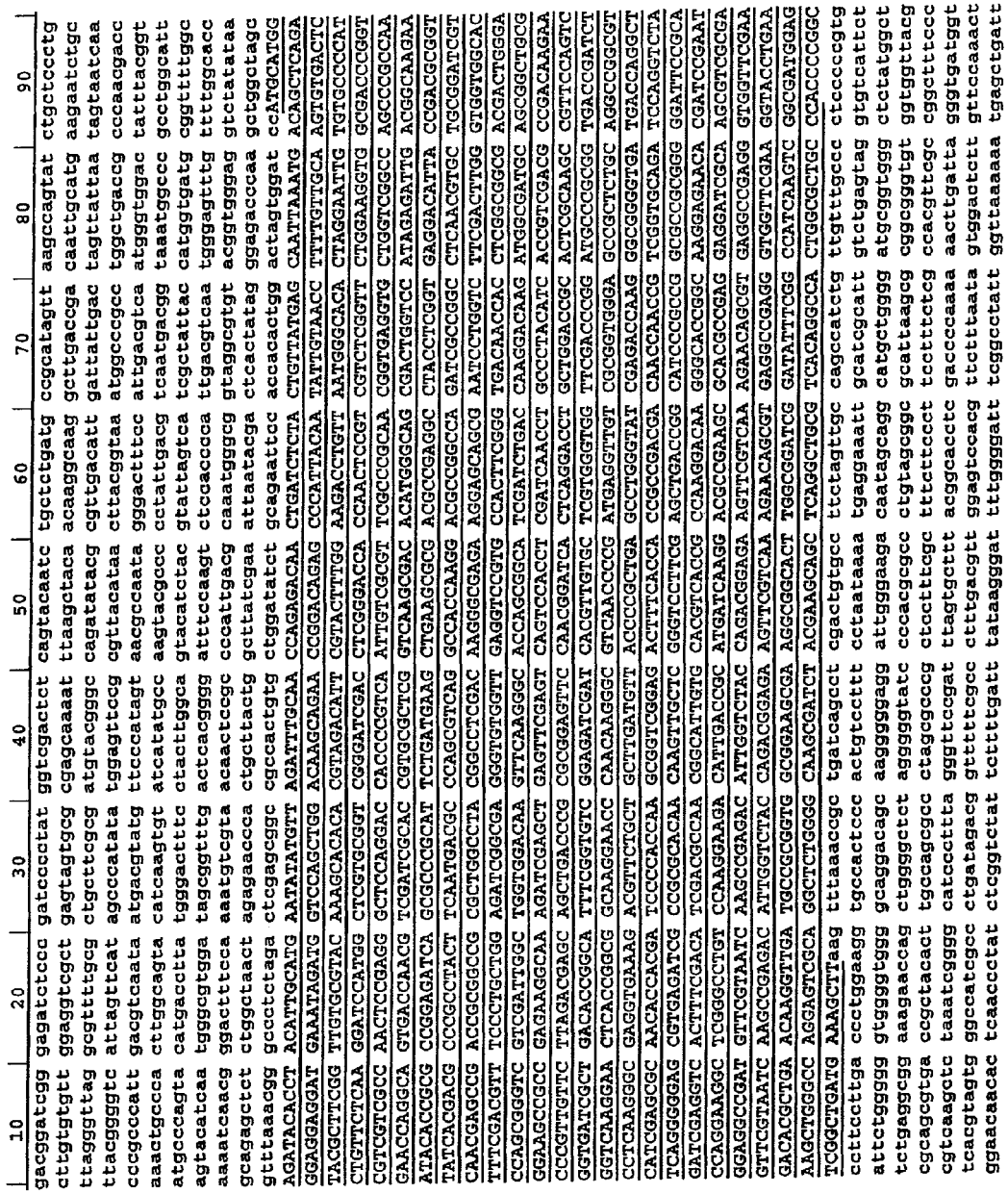
FIG. 38 shows the nucleotide sequence of the pcDNA3 vector encoding E7 and HSP70 (pcDNA3-E7-Hsp70) (SEQ ID NO:36). The E7-Hsp70 fusion sequence is shown in upper case, underscored. Plasmid sequences are in lower case.
Figure 39:
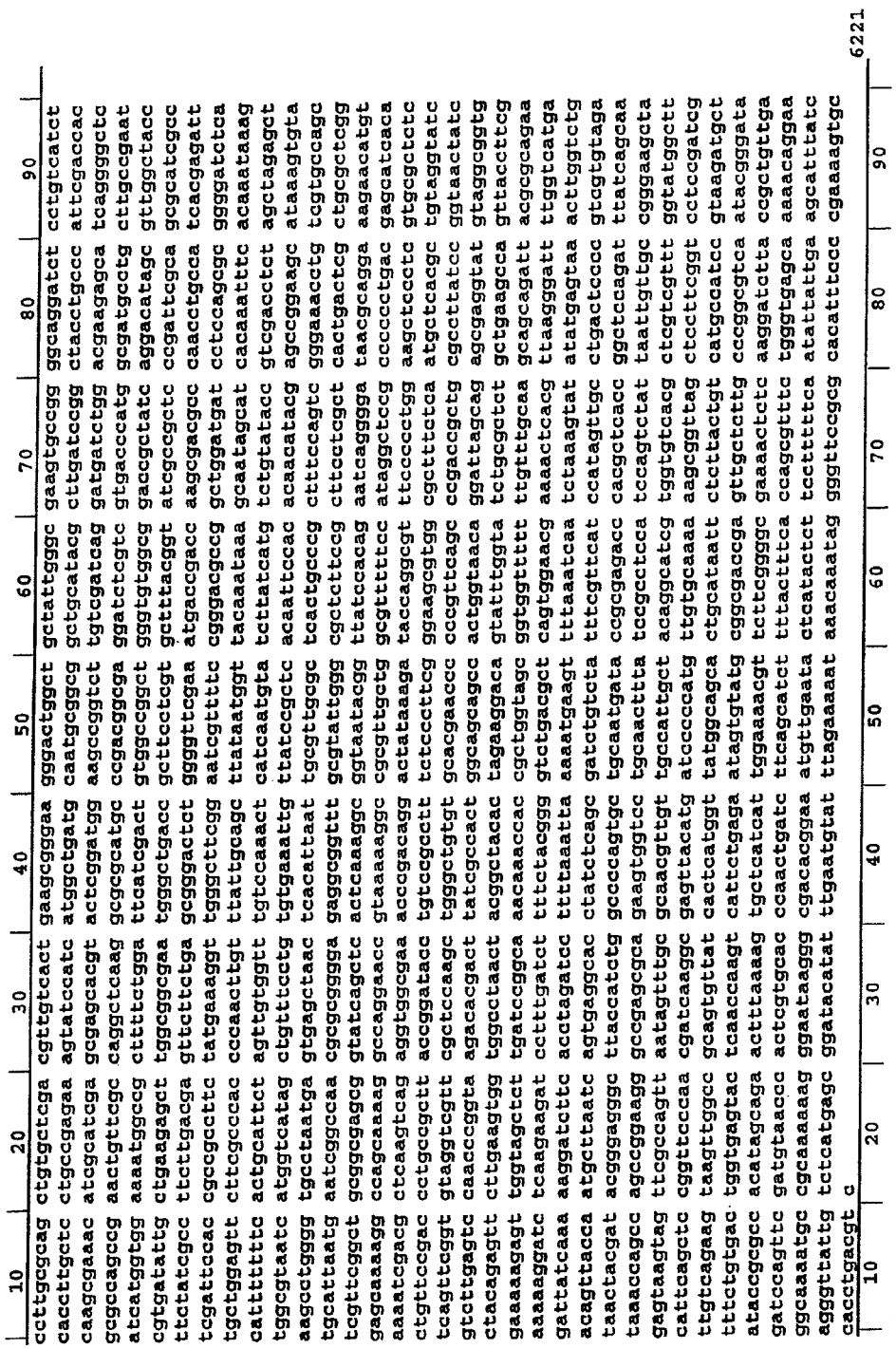
FIG. 39 shows the nucleic acid sequence of plasmid construct pcDNA3-ETA(dII)/E7 (SEQ ID NO:37). The nucleotides encoding ETA(dII)/E7 are shown in upper case and underscored. Plasmid sequence is lower case.

E7 Peptide-Loaded DC-1 Cells Transfected with Bak/Bax or Control siRNA Express Similar Levels of CD11c, CD40, CD86, MHC I and MHC II The significant therapeutic effect generated by vaccination with E7-peptide-loaded DCs transfected with Bak/Bax siRNA could have been due to changes in the expression of molecules important for antigen presentation in DCs, such as CD11c, CD40, CD86, MHC I, and MHC II. Flow cytometric analyses were done to determine the expression levels of these molecules in cells of an E7 peptide-loaded DC-1 cell line transfected with Bak/Bax siRNA, control siRNA or in non-transfected DC-1 cells. As shown in FIG. 29, there was no significant change in the expression of any of the cell surface molecules evaluated among the E7 peptide-loaded DC-1 cells. A similar study was done with BM-DCs. Again, no significant changes in the expression of these molecules were observed among the E7 peptide-loaded BM-DCs transfected with the various siRNA constructs (not shown). Taken together, these results indicated that the expression of CD11c, CD40, CD86, MHC class I, and MHC class II proteins on the surface of DCs that has been E7-peptide loaded were are not affected by Bak/Bax siRNA.

EXAMPLE 15

Discussion of Examples 9-14

This set of studies demonstrated that vaccination with E7 peptide-loaded DCs transfected with Bak/Bax siRNA generated enhanced E7-specific T cell-mediated immune responses and antitumor effects in vivo. Transfection of DCs with Bak/Bax siRNA inhibited apoptotic cell death of DCs mediated by T cells, leading to prolongation of DC survival and resulting in an improved DC-based vaccine.

Previous studies showed that DC life can be efficiently prolonged in vivo through transfection of DCs with DNA encoding antiapoptotic proteins (Kim, T W et al., *J Clin Invest* 112:109-17, 2003b). This technique, however, has raised concerns regarding potential oncogenic transformation as a result of overexpression of these antiapoptotic proteins. Antiapoptotic proteins such as the Bcl-2 family are known to be overexpressed in some cancers and therefore have been implicated as contributors to cellular immortalization (Lebedeva, I., *Cancer Res.* 60:6052-60, 2000). The modification of DCs using siRNA targeting Bak and Bax proteins alleviates many of these concerns. Due to the transient nature of siRNA-mediated silencing of target genes as well as the fact that RNA-based strategies carry no concerns for integration and permanent genetic change, transfection of DCs with Bak/Bax siRNA represent a potentially safe and effective method for enhancing DC-based vaccine potency by prolonging DC life without risk of DC immortalization.

Results employing this DC-based vaccine prepared ex vivo using siRNA technology targeting Bak and Bax are consistent with results of modifying DCs using Bak/Bax siRNA vaccination in vivo. Examples 2-8 describe intradermal gene-gun co-administration of DNA encoding antigen with Bak/Bax siRNA to prolong the life of antigen-expressing DCs in vivo. Mice vaccinated with DNA coadministered with Bak/Bax siRNA manifest significantly enhanced antigen-specific CD8+ T cell-mediated immune responses and antitumor effects compared to mice vaccinated with DNA coadministered with control siRNA. Taken together, these results indicate that siRNA technology as described herein can be used to modify DCs either ex vivo or in vivo to improve vaccine potency.

Modification of a DC-based vaccine with Bak/Bax siRNA as well as siRNA targeting other key pro-apoptotic proteins will further enhance DC-based vaccine potency. Since Bak/Bax siRNA only affects the intrinsic granzyme B/perforin-mediated apoptotic pathway, a combination of siRNAs targeting key pro-apoptotic proteins in the intrinsic granzyme B/perforin pathway along with siRNAs targeting other key pro-apoptotic proteins in the extrinsic Fas-mediated apoptotic pathway will likely result in stronger resistance to killing of the transfected DCs by T cells in vivo. As discussed above, caspase-8, a caspase that induces the proteolysis of a cascade of effector caspases leading to apoptotic cell death, is an excellent candidate protein to target for RNAi. Other caspases involved in cell apoptosis that could serve as targets for siRNA include caspase 9 and caspases 3, 6, and 7. Thus, a DC-based vaccination strategy employing siRNAs targeting key pro-apoptotic proteins in both the intrinsic and extrinsic apoptotic pathways, for example, antigen-loaded DCs transfected with Bak/Bax siRNA and caspase-8 siRNA, are expected to result in even greater enhancement of DC resistance to endogenous T cell-mediated killing, and this will result in improved T cell immune response and antitumor effects in vivo.

In the present study, antigen was loaded onto DCs by pulsing DCs with antigenic peptides. This Bak/Bax siRNA technology could also be applied to DCs prepared through other antigen-loading strategies, including viral vector-mediated, protein-mediated, RNA-mediated, and DNA-mediated transfection strategies. Viral vector-mediated strategies show highly efficient transfection of DCs, but have a limited "life expectancy", whereas DNA-mediated strategies are easily prepared but have a lower transfection efficiency in DCs. Thus, both viral vector-mediated and DNA-mediated strategies to deliver antigens to DCs benefit from the use of Bak/Bax siRNA technology. It will be possible to further enhance the potency of DC-based vaccines through the combined use of Bak/Bax siRNA as an antiapoptotic strategy with other vaccine enhancement strategies, such as the intracellular targeting of antigen inside DCs using various IPPs for more efficient intracellular processing. According to the present invention DNA-mediated strategies of DC-based vaccination employ DCs transfected with Bak/Bax siRNA co-administered with DNA plasmids comprising a DNA sequence encoding an antigen peptide linked to DNA encoding an IPP such as HSP70. The IPP targets the antigen for intracellular processing within the DCs, thereby resulting in increased expression/presentation of the antigen on the DC surface, while transfection by Bak/Bax siRNA would prolong the life of the DCs. The combination of these effects will increase T cell activation and result in an enhanced antigen-specific immune response.

In summary, antigen-loaded DCs transfected with Bak/Bax siRNA as a DC-based vaccine strategy offers an effective and potentially safer approach for prolonging the life of DCs and increasing the potency of DC-based vaccines than transfection of DCs in vivo with DNA encoding antiapoptotic proteins. Administering antigen-peptide loaded DCs transfected with Bak/Bax siRNA prolongs the life of transfected DCs and enhances antigen-specific CD8+ T cell activity, as well as eliciting strong antitumor effects in vivo. Thus, a DC-based vaccine strategy incorporating antigen-loaded DCs transfected with Bak/Bax siRNA shows potential is readily adaptable to clinical use with DC-based vaccines for the control of cancer and infectious disease.

EXAMPLE 15

Enhancing DC Vaccine Potency by Combining a BAK/BAX siRNA-Mediated Antiapoptotic Strategy to Prolong Dendritic Cell Life with an Intercellular Strategy to Target Antigen to Lysosomal Compartments (This Example incorporates by reference Kang et al. (January 2007) *Int. J. Cancer* 120:1696)

This study is the new vaccine strategy combining retrovirally-transduction of endogenously expressing Sig/E7/LAMP-1 and transfection with BAK/BAX siRNA in DCs. Our study may offer a promising strategy for improving DC vaccine potency.

Abstract

Dendritic cell (DC)-based vaccines have become important in immunotherapeutics as a measure for generating antitumor immune responses. We have previously demonstrated that linkage of the antigen gene to a lysosomal targeting signal, a sorting signal of the lysosome-associated membrane protein type 1 (LAMP-1), enhances the potency of DC-based vaccines. DCs have a limited life span, hindering their long-term ability to prime antigen-specific T cells. In this study, we attempted to further improve the potency of a DC vaccine that targets human papilloma virus 16 (HPV16) E7 to a lysosomal compartment (DC-Sig/E7/LAMP-1) by combining a strategy to prolong DC life. We show that small interfering RNA-targeting Bak and Bax proteins can be used to allow transfected DCs to resist being killed by T cells. This is done by downregulating these proapoptotic proteins, which have been known as so-called gate keepers in mitochondria-mediated apoptosis. DCs expressing intact E7 or Sig/E7/LAMP-1 became resistant to attack by CD8+ T cells after transfection with BAK/BAX siRNA, leading to enhanced E7-specific T cell activation in vitro and in vivo. More importantly, vaccination with E7-presenting DCs transfected with BAK/BAX siRNA generated a strong therapeutic effect against an E7-expressing tumor in vaccinated mice, compared to DCs transfected with control siRNA. Our data indicate that a combination of strategies to enhance intracellular Ag processing and to prolong DC life may offer a promising strategy for improving DC vaccine potency.

Introduction

Antigen presentation by dendritic cells (DCs) is a critical element in the induction of the cellular immune responses necessary for tumor immunotherapy. DCs have an intrinsic ability to prime immune responses.[1] Because of this, there has been a great deal of interest in the use of these cells for cancer therapy.[2-6] However, clinical results have not been very promising. One of the limitations in the use of DC vaccines for clinical applications is their low potency. In particular, the generation of cellular immunity using a DC vaccine against low immunogenic tumor-specific antigens, such as human papillomavirus (HPV) E7, has been difficult. This problem presents a major hurdle in the goal of controlling cervical cancer. In a previous study, we reported that only 60% of mice who received intramuscular immunization with DC-E7 survived following a challenge with a low number of E7-expressing tumor cells (TC-1) ($1 \times 10^4$/mouse).[7] The development of strategies for improvement of DC vaccine potency is indispensable if we are to use DC-mediated cancer immunotherapy. To compensate for the weak immune response generated by DCs expressing wild-type E7 antigen, we have developed intracellular targeting strategies which increase MHC class I and class II presentation of E7 antigen by DCs.[8-11] Recently, we found that linking the sorting signal of the lysosome-associated membrane protein 1 (Sig/LAMP-1)-targeted E7 to endosomal and lysosomal compartments enhanced MHC class I presentation to CD8$^+$ T cells, as well as MHC class II presentation of E7 to CD4$^+$ T cells.[12] More importantly, immunization of mice with DC-Sig/E7/LAMP-1 led to more effective anti-tumor protection and treatment against a TC-1 cervical tumor model than did DC-E7. Despite these efforts, the potency of DC-base vaccines still needs to be improved to treat a large tumor. After administration, the life span of antigen-presenting DCs is limited in various ways, which hinders their ability to prime the immune response.[13] A principal contributor to the short life of these DCs is cytotoxic cell-induced apoptosis.[14,15] After activation by DCs, cytotoxic T lymphocytes (CTLs) recognize antigens and kill the cells that express them via apoptosis.[16] Because DCs express MHC-I:antigen peptide complexes on their surface, newly primed CTLs can kill the very DCs that activated them.[17] From these observations, we reasoned that an intracellular targeting strategy, employing an approach to inhibit apoptosis and prolong the survival of antigen-expressing DCs in vivo, could work better. In previous reports, we also found that a variety of antiapoptotic factors can enhance DC survival and the antigen-specific CD8$^+$ T cell immune responses induced by various DNA vaccines.[15,17] Since antiapoptotic proteins, such as Bcl-xL, raise significant concerns related to oncogenicity, there are practical limitations in introducing them to DC-based vaccines for clinical trials. To overcome this problem, we have tried to introduce RNA interference (RNAi) technology to DC vaccine systems, using small interference RNA (siRNA) for targeting and silencing key pro-apoptotic proteins, such as Bax and Bak. They are members of the Bcl-2 family and play key gatekeeping roles in the mitochondria-mediated intrinsic apoptotic pathway.[18-21] By using siRNA, concerns related to biohazards are alleviated since RNA-based strategies avoid problems of integration and permanent genetic change. In this study, we show that the delivery of BAK and BAX siRNA to antigen-expressing DCs prolongs the lives of transfected DCs and DCs-Sig/E7/LAMP-1 transfected with BAK and BAX siRNA are capable of generating strong antigen-specific CD8$^+$ T cell immune responses and anti-tumor effects in vaccinated mice.

Materials and Methods

Preparation of siRNAs and Transfection siRNAs were synthesized using 2'-O-ACE-RNA phosphoramides (Dharmacon, Lafayette, Colo.). The sense and antisense strands of siRNA were: Bak, beginning at nt 310, 5'P-UGCCUACGAACUCUUCACCdTdT-3' (sense), 5'P-GGUGAAGAGUUCGUAGGCAdTdT-3' (antisense); Bax, beginning at nt 217, 5'P-UAUGGAGCUGCAGAG-GAUGdTdT-3' (sense), 5'P-CAUCCUCUGCAGCUCCAU AdTdT-3' (antisense); P represents 5' phosphate. RNAs were deprotected and annealed according to the manufacturer's instruction. Non-specific Control siRNA (Target: 5'-NNAT-TGTATGCGATCGCAGAC-3') was also acquired from Dharmacon (Lafayette, Colo.). Two hundred thousand recombinant DCs on a 6-well vessel were transfected with 300 pmol of the synthesized siRNAs using Oligofectamine (Invitrogen, Carlsbad, Calif.) according to the manufacturer's instructions. The transfected cells were used for subsequent experiments 3 days later. We used FITC-labeled siRNA to document transfection efficiency of the DCs, using flow cytometry analysis. Virtually 100% of the DCs were successfully transfected with siRNA (data not shown).

Construction of the DC Vaccines

The immortalized DC line, kindly provided by Dr. Kenneth Rock (University of Massachusetts, Worcester, Mass.), was genetically manipulated using a retroviral system.[22] Briefly, Bone marrow cells flushed from the femurs and tibias of C57BW6 mice were infected with a retrovirus encoding murine GM-CSF and myc and raf oncogene. This DC line was used for construction of the DC vaccines expressing no insert, E7, or Sig/E7/LAMP-1 as described previously.[12] For this, phoenix (φNX) packaging cells were transfected with a retroviral vector plasmid (pMSCV, pMSCV-E7, or pMSCV-Sig/E7/LAMP-1) using Lipofectamine 2000. Retroviral supernatant from the transfected phoenix cells was incubated with 50% confluent DC in the presence of polybrene (8 ug/ml; Sigma). Following transduction, the retroviral supernatants were removed, and DCs were grown in a culture medium containing 7.5 ug/ml of puromycin for selection. The expression of E7 antigens was confirmed by Western blot analysis.[12]

Western Blot Analysis

The expression of E7 and Sig/E7/LAMP-1 proteins in the DCs and the expression of Bak and Bax pro-apoptotic proteins in DC cells transfected with BAK and/or BAX siRNA was characterized by Western blot analysis as described previously.[23] Cells were lysed with protein extraction reagent (Pierce, Rockford, Ill.). Equal amounts of protein (50 μg) were loaded and separated by SDS-PAGE using a 15% polyacrylamide gel. The gels were electroblotted onto a polyvinylidene difluoride membrane (Bio-Rad, Hercules, Calif.). Blots were then blocked for 2 hr at room temperature with phosphate buffered saline (PBS)/0.05% Tween 20 (TTBS) containing 5% nonfat milk. Membranes were probed with E7-specific Ab (Zymed, San Francisco, Calif.) and anti-BAK or BAX mouse monoclonal antibody (Cell Signaling Technology, Inc., Beverly, Mass.), at 1:1000 dilution in TTBS for 2 hr. They were washed four times with TTBS, then incubated with goat anti-mouse IgG conjugated with horseradish peroxidase (Zymed, San Francisco, Calif.) in a 1:1000 dilution in TTBS containing 5% nonfat milk. Membranes were washed four times with TTBS and developed using Hyperfilm-enhanced chemiluminescence (Amersham, Piscataway, N.J.).

Determination of Apoptotic Cells after CTL Assay

DCs expressing no insert, E7, or Sig/E7/LAMP-1 transfected with control siRNA or Bak/Bax siRNA, were incubated for 4 or 18 hours with an E7-specific CD8$^+$ T cell line at different E:T ratios (12.5:1, 2.5:1, 0.5:1 or 0.1:1).[7] We used FITC-conjugated anti-CD8 antibody to stain for CD8$^+$ E7-specific T cells. We gated CD8-negative cells (DCs) for activated caspase-3 analysis in order to characterize the percentage of apoptotic dendritic cells. Detection of apoptotic cells in the DCs was accomplished using PE-conjugated rabbit anti-active Caspase-3 antibody (BD Bioscience, San Diego, Calif.) according to the manufacturer's instructions. The percent of apoptotic cells was analyzed using flow cytometry.

In Vitro Activation of E7-Specific CD8$^+$ T Cells by DCs

For assessing if the recombinant DCs transfected with the siRNAs were capable of presenting the E7 antigen to CD8$^+$ T cells, 5×10$^4$ DCs were incubated for 18 hours with 5×10$^5$ of the E7-specific CD8$^+$ T cell line.[7,24] Activated IFN-γ-secreting E7-specific CD8$^+$ T cells were identified by staining for both surface CD8$^+$ and intracellular IFN-γ, and analyzed by flow cytometry analysis as described above.

Immunization with DCs

Six- to eight-week-old female C57BL/6 mice were purchased from Daehan Biolink (Chungbuk, Korea). All animal procedures were performed according to approved protocols and in accordance with recommendations for the proper use and care of laboratory animals. For the obvious down-regulation of Bax and Bak expression, DCs transfected with BAK and/or BAX siRNA were used 3 days after transfection as described previously.[25] After two washes in phosphate-buffered saline, $1\times10^6$ of the retrovirus-transduced DCs in 0.1 ml of phosphate-buffered saline were injected intramuscularly into mice twice, with one week interval between the injections as described previously.[7]

Intracellular Cytokine Staining and Flow Cytometry Analysis

Splenocytes were harvested from mice (3 mice per group) one week after the last vaccination. Prior to intracellular cytokine staining, $4\times10^6$ pooled splenocytes from each vaccination group were incubated overnight with 1 μg/ml of E7 (RAHYNIVTF) peptide containing an MHC class I epitope (aa 49-57) for detection of E7-specific CD8$^+$ T cell precursors.[25] IFN-γ staining and flow cytometry analysis were performed as described previously. Analysis was performed on a Becton-Dickinson FACScan with CELLQuest software (Becton Dickinson Immunocytometry System, Mountain View, Calif.). For the determination of the avidity of E7-specific CD8$^+$ T cells in mice vaccinated with DC-Sig/E7/LAMP-1 transfected with the siRNAs, the pooled splenocytes were incubated overnight with different concentrations of E7 peptide (aa 49-57; 1, $10^{-1}$, $10^{-2}$, $10^{-3}$, $10^{-4}$, $10^{-5}$, $10^{-6}$, $10^{-7}$, or $10^{-8}$ μg/ml). The number of E7-specific IFN-γ-secreting CD8$^+$ T cells was determined using intracellular cytokine staining and FACScan analysis as described above.

In Vivo Tumor Treatment

The HPV-16 E7-expressing murine tumor model, TC-1, has been described previously.[11] In brief, HPV-16 E6, E7 and ras oncogene were used to transform primary C57BL/6 mouse lung epithelial cells to generate TC-1. Mice (5 per group) were challenged by intravenous injection of $5\times10^5$ TC-1 tumor cells/mouse into the tail, in order to simulate hematogenous spread.[11] Mice were treated with DCs three days after the tumor challenge. Mice were monitored twice a week and sacrificed on day 42 after the last vaccination. The mean number of pulmonary nodules in each mouse was evaluated by experimenters blinded as to sample identity. To study the subsets of lymphocytes that are important for the anti-tumor effects, a tumor protection experiment was performed, coupled with in vivo antibody depletion that used a protocol similar to one previously described.[11] Briefly, antibody depletion was initiated 1 week after the second vaccination and continued until sacrifice. mAb GK1.5 was used for CD4 depletion. mAb 2.43 was used for CD8 depletion. mAb PK136 was used for NK depletion. In vivo tumor treatment and antibody depletion experiments were performed at least twice to generate reproducible data.

In Vivo Clearance of DCs in the Primed Mouse

C57BL/6 mice (five per group) were first primed with DC-no insert or DC-Sig/E7/LAMP-1. Seven days later, the mice were boosted with carboxyfluorescein (CFSE)-labeled DC-Sig/E7/LAMP-1 transfected with control siRNA or BAK/BAX siRNA. To create CFSE positive DCs transfected with different siRNA, DCs were labeled with 5 μM CF SE for 10 min. Unlabeled DCs transfected with BAK/BAX siRNA were used as a negative control. Two days after boosting with the DCs, popliteal lymph nodes were harvested from the vaccinated mice. Isolated lymphocytes were analyzed by forward and side scatter and gated around a population of CD80 cells with the size and granular characteristics of DCs. The percentage of CFSE$^+$ cells among the gated CD80 cells was analyzed using a protocol described previously.[26]

Statistical Analysis

All data expressed as means ±standard deviation (S.D.) are representative of at least two different experiments. Data for intracellular cytokine staining with flow cytometry analysis and tumor treatment experiments were evaluated by analysis of variance (ANOVA). Comparisons between individual data points were made using Student's t-test. In the tumor protection experiment, the principal outcome of interest was time to tumor development. The event time distributions for different mice were compared using the method of Kaplan and Meier and the log-rank statistic. All p values <0.05 were considered significant.

Results

Transfection of DC Cell Lines with BAK/BAX siRNA Silences the Expression of Bak and Bax Proteins.

To examine if E7 proteins were translated in DCs, Western blot analysis was performed with an E7-specific antibody. In DC-E7 and DC-Sig/E7/LAMP-1, the bands of E7 and Sig/E7/LAMP-1 at their corresponding molecular weight were detected. In contrast, there was no band in the DC-no insert. This result is the same as that previously described.[12] We also performed Western blot analysis to determine whether transfection of recombinant DCs expressing no insert, E7 or Sig/E7/LAMP-1 with BAK/BAX siRNA would down-regulate the expression of Bak and Bax proteins in transfected cells. As shown in FIG. 1, the expression of Bak and Bax proteins was abolished 3 days after transfection in lysates from the DCs transfected with BAK/BAX siRNA. No expression of Bak or Bax was identified up to 7 days after transfection. Expression of Bak and Bax was detected at below-normal levels by day 9, and this expression returned to normal levels by day 11 after transfection as our previous report.[25] In contrast, expression of Bak and Bax proteins was detected in the DCs after transfection with control siRNA, and the levels of expression were similar to the expression of Bak and Bax proteins by non-siRNA-transfected DC cells (data not shown). We also analyzed β-actin expression in transfected DCs in order to demonstrate that equal amounts of cell lysates were loaded for Western blot analysis. These results indicate that BAK/BAX siRNA abolish Bak and Bax protein expression during the period of immune priming by the transfected DCs.

DCs Transfected with BAK/BAX siRNA are More Resistant to CTL Killing than Those with Control siRNA.

To determine if the DCs expressing E7 or Sig/E7/LAMP-1 transfected with BAK and BAX siRNA could resist a CTL-induced apoptosis, we incubated the DCs transfected with the siRNAs with an E7-specific CD8$^+$ T cell line and determined the percentages of apoptotic cells in DC populations 4 or 18 hours after incubation. DC-no insert was used as a negative control. As shown in FIG. 2, the significant difference in apoptotic cell percentages between the E7-presenting DCs transfected with control siRNA and those with BAK/BAX siRNA was observed 4 hours after incubation. The difference was greater at 18 hour. Although 80-90% of DC-E7 and DC-Sig/E7/LAMP-1 cells transfected with control siRNA were apoptotic, the DCs transfected with BAK/BAX siRNA generated less than 15% apoptotic cells 18 hours after incubation with the CD8$^+$ T cell line, particularly at low E:T ratios (0.1:1). These data suggest that transfection of DCs with BAK/BAX siRNA leads to down-regulation of BAK and BAX protein expression, resulting in resistance to apoptosis induced by antigen-specific CD8$^+$ T cells.

E7-Expressing DCs Transfected with BAK/BAX siRNA Increase the Number of Activated E7-Specific IFN-γ$^+$ CD8$^+$ T Cell Lines In Vitro.

Figure 3A:
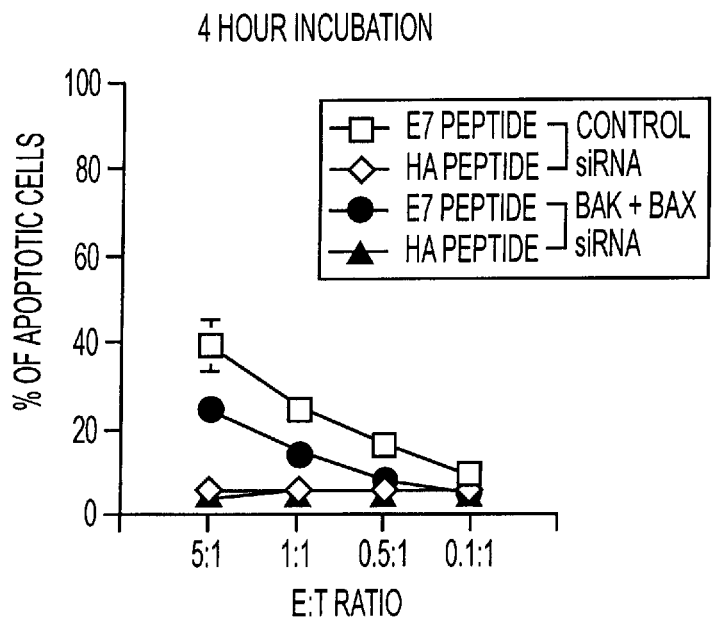
FIG. 3A-B is a graph showing the percentage of apoptotic cells in E7 peptide-pulsed DC1 cells (RAHYNIVTF, SEQ ID NO:46) transfected with either Bak+ Bax siRNA or with control siRNA, after incubation for 4 hrs (FIG. 3A) or 20 hrs (FIG. 3B)) with an E7-specific CD8+ T cell line. DC-1 cells pulsed with HA peptide (IYSTVASSL, SEQ ID NO:47) was used as a control.
Figure 3B:
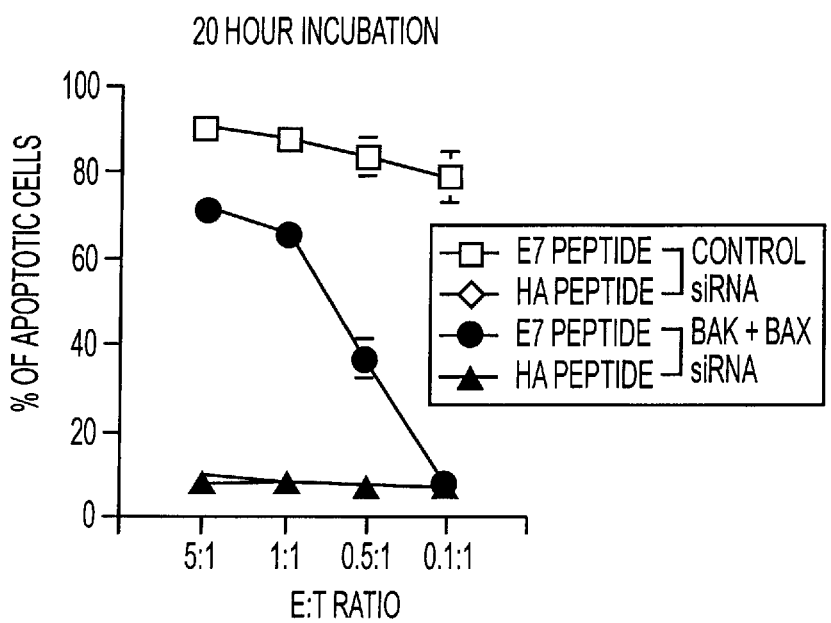

We determined whether the transfection of E7-expressing DCs with the siRNAs influenced the ability of the DCs to activate an E7-specific CD8+ T cell line in vitro. For this, the transfected DCs were co-cultured with an MHC class I-restricted E7-specific T cell line at a DC:T cell ratio of 1:10 in vitro.[24] As shown in FIG. 3, the DC-no insert transfected with control or BAK/BAX siRNAs failed to induce significant IFN-γ production in E7-specific CD8+ T cells. After 18 h, IFN-γ-secreting CD8+ T cells were counted using FACS analysis. FIGS. 3a and b demonstrate a more than 10 fold increase in the number of activated T cells following co-incubation of the E7-specific T cell line with the DCs transfected with BAK/BAX siRNA, when compared to DCs transfected with control siRNA. Taken together, these data suggest that the treatment of BAK/BAX siRNA may influence the ability of DCs to activate antigen-specific CD8+ T cells by prolonging DC life span during in vitro activation of an E7-specific IFN-γ+ CD8+ T cell line.

Vaccination with the E7-Expressing DCs Transfected with BAK/BAX siRNA Leads to a Significant Increase in the Number and Avidity of E7-Specific CD8+ T Cells in the Immune Response To determine whether vaccination with E7-expressing DCs transfected with the siRNAs could enhance the generation of E7-specific IFN-γ+ CD8+ T cell precursors in vaccinated mice, we performed an intracellular cytokine staining and flow-cytometry analysis using splenocytes from mice vaccinated with the various DCs. As shown in FIG. 4a, mice vaccinated with DC-Sig/E7/LAMP-1 cells transfected with Bak/Bax siRNA exhibited an approximately 5 fold increase in the number of E7-specific IFN-γ+ CD8+ T cells, compared with mice vaccinated with DCs transfected with control siRNA. DC-E7 cells transfected with BAK/BAX siRNA also generated more E7-specific T cell precursors than those with control siRNA. In contrast, the DC-no insert transfected with control or BAK/BAX siRNAs failed to induce significant IFN-γ production in E7-specific CD8+ T cells. Our results demonstrate that immunization with E7-expressing DCs transfected with BAK/BAX siRNA can significantly increase the number of E7-specific IFN-γ+ CD8+ T cells generated in vaccinated mice. In previous studies, the duration of dendritic cell and T cell interaction has been felt to be important for the generation of high avidity T cells.[27,28] In addition, we have shown that high-avidity CTLs provide better protection against a tumor challenge than low-avidity CTLs.[27] Therefore, we performed a functional avidity assay to determine the avidity of E7-specific CD8+ T cells generated by vaccination with DC-Sig/E7/LAMP-1 transfected with control or BAK/BAX siRNAs. We defined the number of IFN-γ-secreting CD8+ T cells stimulated by 1 μg/ml of E7 peptide (aa 49-57) as a maximum response and compared the functional avidity of T cells from mice vaccinated with DC-Sig/E7/LAMP-1 transfected with control or BAK/BAX siRNAs at 50% of the maximum. We found that the concentration of E7 peptide required to achieve 50% of the maximum IFN-γ+ CD8+ T cell response was about $8 \times 10^{-3}$ μg/ml for mice vaccinated with the DCs transfected with BAK/BAX siRNA, and about $9 \times 10^{-2}$ μg/ml for mice vaccinated with DCs transfected with control siRNA (FIG. 4b). Transfection of DC-Sig/E7/LAMP-1 with BAK/BAX siRNA generates higher avidity E7-specific CD8+ T cells in vaccinated mice than transfection of DC-Sig/E7/LAMP-1 with control siRNA.

Vaccination with DC-Sig/E7/LAMP-1 Cells Transfected with (BAK/BAX) siRNA Generates Better Anti-Tumor Effects than Controls.

To determine whether the observed increase in the number and functional avidity of E7-specific CD8+ T cell precursors could translate into a better E7-specific anti-tumor effect, we performed an in vivo tumor treatment experiment using a previously characterized E7-expressing tumor model, TC-1.[11] DC-Sig/E7/LAMP-1 cells, which exhibited better immunogenicity than DC-E7 cells in FIG. 4, were selected for this experiment. To compare the anti-tumor effects generated by vaccination with DC-Sig/E7/LAMP-1 transfected with Bak/Bax siRNA or control siRNA, we performed an in vivo tumor treatment experiment in a lung tumor metastasis model at a high lethal dose. In this experiment, $5 \times 10^5$ TC-1 cells were injected via the tail vein. This number was 50 times more TC-1 cells than that commonly used in our studies.[7-10-12,15,17,29] Mice were first challenged with the tumor cells, followed 3 days after tumor challenge by treatment with DC-Sig/E7/LAMP-1 cells transfected with control or BAK/BAX siRNAs. Mice were sacrificed 28 days after challenge, and the number of pulmonary tumor nodules was counted. As shown in FIG. 5a, mice treated with the DCs transfected with BAK/BAX siRNA demonstrated the lowest number of pulmonary nodules, compared to mice treated with the DCs transfected with control siRNA ($P<0.007$), or the naïve control group. These results show that vaccination with DCs transfected with BAK/BAX siRNA generates a significantly better therapeutic anti-tumor effect than vaccination with DCs transfected with control siRNA.

We also performed a tumor treatment experiment with antibody depletion to determine the subset of T lymphocytes responsible for the anti-tumor response. Mice were challenged with TC-1 and subsequently vaccinated with the DCs as described above. Antibody depletion was initiated 1 week after the booster vaccination and continued for 28 days following the challenge. Mice depleted of CD8+ T cells displayed nearly the same degree of tumor growth as naïve mice, and mice depleted of CD4+ T cells displayed slightly increased tumor growth compared to non-depleted mice. Mice depleted of NK cells did not generate a significantly different number of tumor nodules compared to mice with no depletion (FIG. 5b). These data suggest that CD8+ T cells are essential for the anti-tumor effect and that CD4+ T cells may also contribute to the observed anti-tumor effect, though not as strongly as CD8+ T cells.

E7 Peptide-Loaded DCs Transfected with BAK/BAX siRNA Survive Longer In Vivo than E7 Peptide-Loaded DCs Transfected with Control siRNA.

To determine if transfection with BAK/BAX siRNA improves the survival of DC-Sig/E7/LAMP-1 during in vivo conditions, mice were first primed with DC-no insert or DC-Sig/E7/LAMP-1. One week later, the mice were boosted with CFSE-labeled DC-Sig/E7/LAMP-1 transfected with control siRNA or BAK/BAX siRNA. Unlabeled DCs transfected with BAK/BAX siRNA were used as a negative control. Two days after boosting with the DCs, popliteal lymph nodes were harvested from the vaccinated mice. Isolated lymphocytes were further analyzed using flow cytometry. The percentage of CFSE+ cells among the gated CD80+ monocyte-like cells with size and granular characteristics of DC was measured, using a protocol described previously.[26] As shown in FIGS. 6a and b, at 2 days after vaccination with DC-no insert, there was no significant difference between the percentage of CFSE+ cells among the gated CD80+ monocyte-like cells in mice given BAK/BAX siRNA from mice given control siRNA. In comparison, in mice primed with DC-Sig/E7/LAMP-1, we detected a significant decrease in the percentage of CFSE+ CD80+ DCs in mice that received cells with control siRNA, compared to that of CFSE+ CD80+ DCs in mice that received cells with BAK/BAX siRNA. More than 90% of CFSE+ CD80+ DCs were caspase-3 negative, indicating that these cells were not apoptotic (data not shown). Our data suggest that transfection of E7-expressing DCs with BAK/BAX siRNA may protect DCs from being killed by E7-specific immunity, thus prolonging DC life in vivo.

Discussion

In this study, we have shown that vaccination with HPV16 E7-expressing DCs transfected with siRNA targeting BAK and BAX increased E7-specific anti-tumor immune responses. These siRNA transfected DCs were highly resistant to apoptotic cell death mediated by E7-specific CD8+ T cells, leading to prolonged DC survival. This resulted in a further increase in DC-mediated vaccine potency. In our previous studies, we demonstrated that retrovirally-transduced DCs endogenously expressing Sig/E7/LAMP-1 (the linkage of a Sig/LAMP-1 molecule to E7) increased the presentation of antigenic E7 peptides to E7-specific T cells in the context of MHC class I and class II, and enhanced the potency of DC vaccines.[12] This enhancement of dendritic cell-based vaccine potency might be explained by qualitative changes in antigen-expressing DCs that lead to enhanced activation of E7-specific T cells. DCs, however, have a limited life span that hinders their long-term ability to prime antigen-specific T cells. DCs that present the relevant MHC-peptide complexes qualify as potential targets and are at risk of being eliminated by the CTLs they have activated. This would seriously limit the capacity of DCs to prime CTL immunity.[14,25] During CTL-killing process, as shown in FIGS. 2 and 6, highly immunogenic DCs having more antigenic peptides on their surface such as DC-Sig/E7/LAMP-1 might be better targets for E7-specific CD8+ T cells, compared to less immunogenic DCs such as DC-E7. Thus, modulation of apoptosis in DCs using siRNA technology is necessary to prolong DC survival and further enhance the potency of DC-based vaccines.

The BAK and BAX siRNA technology can be extended to the preparation of antigen-specific T cells ex vivo. We have shown that E7-expressing DCs transfected with BAK/BAX siRNA were capable of resisting being killed by E7-specific CD8+ T cells, compared to DC cells transfected with control siRNA, leading to an increase in the number of activated CD8+ T cells (FIG. 3). It would be possible that the significant increase in activated CD8+ T cells might be due to change in the expression of molecules important for antigen presentation in DCs, such as CD11c, CD40, CD80, CD86, MHC I, and MHC II and pro-inflammatory cytokines, such as IFN-β, IFN-α, and TNF-α.[30,31] We therefore performed flow cytometry to determine the expression levels of them important for antigen presentation in DC-Sig/E7/LAMP-1 transfected with BAK/BAX siRNA or control siRNA in non-transfected DC cell line. There were no significant changes in the expression of the tested molecules among the DC cell lines. In our previous report, we observed a similar result in an E7 peptide-loaded DC cell line transfected with BAK/BAX siRNAs or control siRNA and in non-transfected DC cell line.[26] Recently, it has been reported that synthetic siRNAs complexed with liposomes can be potent inducers of pro-inflammatory cytokines.[30,31] To confirm the induction of the IFN-β, IFN-α, and TNF-α, we performed RT-PCR to determine the mRNA expression levels of them in these DC cell lines transfected with or without the BAK/BAX siRNA or control siRNA/Oligofectamine complexes. Unexpectedly, we found that there were no significant changes in the mRNA levels of the cytokines among these DC cell lines (data not shown). One of plausible explanations about this discrepancy may be a point of time to assess the level of cytokines. Most literatures have shown the induction of cytokines within 1 or 2 days after transfection. Notably, no expression of Bak or Bax was detected in the siRNA-treated DCs we used at days 3 after transfection. This silence of Bak and Bax was lasted by day 9, and the expression of them returned to normal levels by day 11 after transfection.[25] From this reason, in this study, the siRNA-treated DCs were used for in vitro and in vivo experiments 3 days after transfection. Similarly, the levels of the immune-modulating molecules were also determined 3 days after transfection of the DCs with the siRNAs. It would be possible that the pro-inflammatory molecules were induced within 1 day after transfection. Subsequently, the levels of the molecules could return to normal levels 3 days after treatment of siRNAs. We could not rule out, however, other possibility that transfection of DCs with siRNA/liposome complexes may affect immune-priming capacity of DCs through other cytokines we did not test such as IL-12, IL-6, IL-10 and INF-γ or other factors such as chemokines that influence DC homing to the draining lymph nodes. Despite a bundle of possible factors to affect DC capacity of priming an immune response, most important thing is that only difference between control siRNA and BAK/BAX siRNAs is a sequence. In some literatures, base sequence motifs including 5'-GUCCUUCAA-3', which can induce inflammatory cytokines, were identified.[31,32] It is worth to take a notice that the siRNAs we used do not contain these sequence motifs. Thus, the enhanced E7-specific T cell-mediated immune response may not be due to changes in the expression of the molecules important for antigen presentation in DCs and the pro-inflammatory cytokines in the DC cell lines transfected with BAK/BAX siRNA or control siRNA. Therefore, the increase in activated CD8+ T cells might be due to enhanced survival of dendritic cells mediated by BAK and BAX siRNA. Considering the difficulty in gathering blood from patients for ex vivo T cell preparation, the application of BAK/BAX siRNA technology might be promising for tumor immunotherapy using adoptive transfer of T cells.

We have shown DC survival can be prolonged by their transfection with DNA encoding antiapoptotic proteins.[17] Among them, the antiapoptotic Bcl-2 family, such BCL-xL and BCL-2, were most effective in increasing the life span of DCs transfected with a gene gun via an intradermal route. However, since these molecules have been implicated as contributors to oncogenic transformation, utilization of the antiapoptotic DNA encoding Bcl-2 family for clinical applications might be limited.[33] We have recently demonstrated that peptide-pulsed BM-DCs transfected with BAK/BAX siRNA were capable of resisting being killed by antigen-specific CD8+ T cells in vivo.[29] RNA interference (RNAi) using siRNA targeting proapoptotic proteins provided similar effects, while alleviating oncogenic concerns associated with the use of DNA encoding antiapoptotic proteins.

The discovery of defined tumor antigens and their application in therapeutic cancer vaccines has not yet resulted in a successful therapy for cancer patients. One of the reasons is most of tumor antigens are self ones. There are simple evidences in mouse and man that most cancers, similar to normal somatic cells, do not directly prime self-tumor-antigen-specific T cells very efficiently.[34-36] Like this, self tolerance that normally exists to prevent autoimmune disease may preclude the development of an adequate anti-tumor response and thwart the development of effective immune responses against tumors.[37] Thus, breaking tolerance in tumor-bearing hosts has been seen as a primary requirement for cancer immunotherapy. In this aspect, it is worth to notify that DCs expressing the baculoviral caspase inhibitor, p35, display defective apoptosis, resulting in their accumulation and, in turn, chronic lymphocyte activation and systemic autoimmune manifestations.[38] Considering the number of well characterized self-tumor antigens, it will be an interesting challenge to check whether antiapoptotic DCs that present a self tumor antigen break self-tolerance and induce a therapeutic immune response against various tumors. In this study, we further increased the potency of a Sig/E7/LAMP-1 expressing DC vaccine by prolonging DC life with BAK/BAX siRNAs. The DCs transfected with BAK/BAX siRNA enhanced E7-specific CD8+ T cell activation in vitro. They elicited stronger anti-tumor effects in vivo, compared with DCs transfected with control siRNA. Thus, a DC-based vaccine strategy incorporating Sig/E7/LAMP-1 DCs transfected with BAK/BAX siRNA may be a promising strategy for tumor immunotherapy.

REFERENCES

1. Cerundolo V, Hermans I F, Salio M. Dendritic cells: a journey from laboratory to clinic. Nat Immunol 2004; 5:7-10.
2. Engleman E G. Dendritic cell-based cancer immunotherapy. Semin Oncol 2003; 30: 23-9.
3. Gunzer M, Grabbe S. Dendritic cells in cancer immunotherapy. Crit Rev Immunol 2001; 21:133-45.
4. Schuler G, Schuler Thurner B, Steinman R M. The use of dendritic cells in cancer immunotherapy. Curr Opin Immunol 2003; 15:138-47.
5. Turtle C J, Hart D N. Dendritic cells in tumor immunology and immunotherapy. Curr Drug Targets 2004; 5:17-39.
6. Figdor C G, de VRIES I J, Lesterhuis W J, Melief C J. Dendritic cell immunotherapy: mapping the way. Nat Med 2004; 10:475-80.
7. Wang T L, Ling M, Shih I M, Pham T, Pai S I, Lu Z, Kurman R J, Pardoll D M, Wu T C. Intramuscular administration of E7-transfected dendritic cells generates the most potent E7-specific anti-tumor immunity. Gene Ther 2000; 7:726-33.
8. Moniz M, Ling M, Hung C F, Wu T C. HPV DNA vaccines. Frontiers Biosci 2003; 8: D55-68.
9. Wu T C, Guamieri F G, Staveley-O'Carroll K F, Viscidi R P, Levitsky H I, Hedrick L, Cho K R, August J T, Pardoll D M. Engineering an intracellular pathway for major histocompatibility complex class II presentation of antigens. Proc Natl Acad Sci USA 1995; 92:11671-5.
10. Cheng W F, Hung C F, Hsu K F, Chai C Y, He L, Ling M, Slater L A, Roden R B, Wu T C. Enhancement of sindbis virus self-replicating RNA vaccine potency by targeting antigen to endosomal/lysosomal compartments. Hum Gene Ther 2001; 12:235-52.
11. Lin K Y, Guamieri F G, Staveley-O'Carroll K F, Levitsky H I, August J T, Pardoll D M, Wu T C. Treatment of established tumors with a novel vaccine that enhances major histocompatibility class II presentation of tumor antigen. Cancer Res 1996; 56:21-6.
12. Kang T H, Lee J H, Bae H C, Noh K H, Kim J H, Song C K, Shin B C, Hung C F, Wu T C, Park J S, Kim T W. Enhancement of dendritic cell-based vaccine potency by targeting antigen to endosomal/lysosomal compartments. Immunol lett. In press.
13. Ronchese F, Hermans I F. Killing of dendritic cells: a life cut short or a purposeful death? J Exp Med 2001; 194:F23-6.
14. Medema J P, Schuurhuis D H, Rea D, Van Tongeren J, de Jong J, Bres S A, Laban S, Toes R F, Toebes M, Schumacher T N, Bladergroen B A, Ossendorp F, Kummer J A, Melief C J, Offring a R. Expression of the serpin serine protease inhibitor 6 protects dendritic cells from cytotoxic T lymphocyte-induced apoptosis: differential modulation by T helper type 1 and type 2 cells. J Exp Med 2001; 194:657-67.
15. Kim T W, Hung C F, Boyd D, Juang J, He L, Kim J W, Hardwick J M, Wu T C. Enhancing DNA vaccine potency by combining a strategy to prolong dendritic cell life with intracellular targeting strategies. Immunol 2003; 171:2970-6.
16. Russell J H, Ley T J. Lymphocyte-mediated cytotoxicity. Annu Rev Immunol 2002; 20:323-70.
17. Kim T W, Hung C F, Ling M, Juang J, He L, Hardwick J M, Kumar S, Wu T C. Enhancing DNA vaccine potency by coadministration of DNA encoding antiapoptotic proteins. J. Clin. Invest 2003; 112:109-17.
18. Jacotot E, Costantini P, Laboureau E, Zamzami N, Susin S A, Kroemer G. Mitochondrial membrane permeabilization during the apoptotic process. Ann NY Acad Sci 1999; 887:18-30.
19. Korsmeyer S J, Wei M C, Saito M, Weiler S, Oh K J, Schlesinger P H. Pro-apoptotic cascade activates BID, which oligomerizes BAK or BAX into pores that result in the release of cytochrome c. Cell Death Differ 2000; 7:1166-73.
20. Degli Esposti M, Dive C. Mitochondrial membrane permeabilisation by Bax/Bak. Biochem Biophys Res Commun 2003; 304:455-61.
21. Opferman J T, Korsmeyer S J. Apoptosis in the development and maintenance of the immune system. Nat Immunol 2003; 4:410-5.
22. Shen Z, Reznikoff G, Dranoff G, Rock K L. Cloned dendritic cells can present exogenous antigens on both MHC class I and class II molecules. J Immunol 1997; 158:2723-30.
23. Hung C F, Cheng W F, Hsu K F, Chai C Y, He L, Ling M, Wu T C. Cancer immunotherapy using a DNA vaccine encoding the translocation domain of a bacterial toxin linked to a tumor antigen. Cancer Res 2001; 61:3698-703.
24. Kim T W, Hung C F, Kim J W, Juang J, Chen P J, He L, Boyd D A, Wu T C. Vaccination with a DNA vaccine encoding herpes simplex virus type 1 VP22 linked to antigen generates long-term antigen-specific CD8-positive memory T cells and protective immunity. Hum Gene Ther 2004; 15:167-77.
25. Kim T W, Lee J H, He L, Boyd D A, Hardwick J M, Hung C F, Wu T C. Modification of professional antigen-presenting cells with small interfering RNA in vivo to enhance cancer vaccine potency. Cancer Res 2005; 65:309-16.
26. Peng S, Kim T W, Lee J H, Yang Hu, He L, Hung C F, Wu T C. Vaccination with Dendritic Cells Transfected with BAK and BAX siRNA Enhances Antigen-Specific Immune Responses by Prolonging Dendritic Cell Life. Human Gene Therapy 2005; 16: 584-93.
27. Cheng W F, Hung C F, Pai S I, Hsu K F, He L, Ling M, Wu T C. Repeated DNA vaccinations elicited qualitatively different cytotoxic T lymphocytes and improved protective antitumor effects. J Biomed Sci 2002; 9:675-87.
28. Langenkamp A, Casorati G, Garavaglia C, Dellabona P, Lanzavecchia A, Sallusto F. T cell priming by dendritic cells: thresholds for proliferation, differentiation and death and intraclonal functional diversification. Eur J Immunol 2002; 32:2046-54.
29. Ji H, Wang T L, Chen C H, Pai S I, Hung C F, Lin K Y, Kuman R J, Pardoll D M, Wu T C. Targeting human papillomavirus type 16 E7 to the endosomal/lysosomal compartment enhances the antitumor immunity of DNA vaccines against murine human papillomavirus type 16 E7-expressing tumors. Hum Gene Ther 1999; 10:2727-40.
30. Kariko K, Bhuyan P, Capodici J, Weissman D. Small interfering RNAs mediate sequence-independent gene suppression and induce immune activation by signaling through toll-like receptor 3. J Immunol 2004; 172:6545-9.
31. Judge A D, Sood V, Shaw J R, Fang D, McClintock K, MacLachlan I. Sequence-dependent stimulation of the mammalian innate immune response by synthetic siRNA. Nat Biotechnol 2005; 23:457-62.
32. Hornung V, Guenthner-Biller M, Bourquin C, Ablasser A, Schlee M, Uematsu S, Noronha A, Manoharan M, Akira S, de Fougerolles A, Endres S, Hartmann G. Sequence-specific potent induction of IFN-alpha by short interfering RNA in plasmacytoid dendritic cells through TLR7. Nat Med. 2005; 11:263-70
33. Lebedeva I, Rando R, Ojwang J, Cossum P, Stein C A. Bcl-xL in prostate cancer cells: Effects of overexpression and down-regulation on chemosensitivity. Cancer Res 2000; 60:6052-60.
34. van Mierlo G J, den Boer A T, Medema J P, van der Voort E I, Fransen M F, Offringa R, Melief C J, Toea R E. CD40 stimulation leads to effective therapy of CD40(−) tumors through induction of strong systemic cytotoxic T lymphocyte immunity. Proc Natl Acad Sci USA 2002; 99:5561-6.
35. Overwijk W W, Theoret M R, Finkelstein S E, Surman D R, De Jong L A, Vyth-Dreese F A, Dellemijn T A, Antony P A, Spiess P J, Palmer D C, Heimann D M, Klebanoff C A, Yu Z, Hwang L N, Feigenbaum L, Kruisbeek A M, Rosenberg S A, Restifo N P. Tumor Regression and Autoimmunity after Reversal of a Functionally Tolerant State of Self-reactive CD8$^+$ T Cells. J Exp Med 2003; 198:569-80.
36. Ochsenbein A F, Sierro S, Odermatt B, Pericin M, Karrer U, Hermans J, Hemmi S, Hengartner H, Zinkenagel R M. Roles of tumour localization, second signals and cross priming in cytotoxic T-cell induction. Nature 2001; 411: 1058-64.
37. Mapara M Y, Sykes M. Tolerance and cancer: mechanisms of tumor evasion and strategies for breaking tolerance. J Clin Oncol 2004; 22:1136-51.
38. Chen M, Wang Y H, Wang Y, Huang L, Sandoval H, Liu Y J, Wang J. Dendritic cell apoptosis in the maintenance of immune tolerance. Science 2006; 311:1160-4.

The references cited above are all incorporated herein by reference, whether specifically incorporated or not. All publications, patents, patent applications, GenBank sequences and ATCC deposits, cited herein are hereby expressly incorporated by reference for all purposes. When definitions of terms in documents that are incorporated by reference herein conflict with those used herein, the definitions used herein govern. Citation of the documents herein is not intended as an admission that any of them is pertinent prior art. All statements as to the date or representation as to the contents of these documents is based on the information available to the applicant and does not constitute any admission as to the correctness of the dates or contents of these documents. Having now fully described this invention, it will be appreciated by those skilled in the art that the same can be performed within a wide range of equivalent parameters, concentrations, and conditions without departing from the spirit and scope of the invention and without undue experimentation.

What is claimed is:

1. A nucleic acid composition useful as an immunogen, comprising a combination of:
   (a) a first nucleic acid molecule comprising a first sequence encoding an epitope of an antigenic polypeptide or peptide; and optionally, linked to the first sequence, directly or via a linker, a second sequence that encodes an immunogenicity-potentiating polypeptide (IPP); and
   (b) a second nucleic acid molecule the activity or expression of which stimulates development of an immune response to said epitope, which second nucleic molecule is (i) a siRNA or (ii) DNA that encodes said siRNA, wherein said siRNA has a sequence that is sufficiently complementary to and thus targets the sequence of mRNA that encodes a pro-apoptotic protein expressed in a dendritic cell (DC), such that the activity or expression of said siRNA in the cell results in inhibition of or loss of expression of said mRNA, resulting in inhibition of apoptosis and increased survival of DCs, wherein the first and second nucleic acid molecules are bound to particles comprising a material suitable for introduction into a cell or an animal by particle bombardment and wherein the development of said immune response is stimulated.

2. The composition of claim 1 that includes said second nucleic acid sequence encoding said IPP which is fused in frame to said first sequence such that said first and said second sequence encode a fusion protein comprising said antigenic epitope and said IPP.

3. The composition of claim 1, wherein the IPP acts in potentiating an immune response by promoting:
(a) processing of the linked antigenic polypeptide via the MHC class I pathway or targeting of a cellular compartment that increases said processing;
(b) development, accumulation or activity of antigen presenting cells or targeting of antigen to compartments of said antigen presenting cells leading to enhanced antigen presentation;
(c) intercellular transport and spreading of the antigen; or
(d) any combination of (a)-(c).

4. The composition of claim 3 wherein the IPP is:
(a) the sorting signal of the lysosome-associated membrane protein type 1 (Sig/LAMP-1)
(b) a mycobacterial HSP70 polypeptide, the C-terminal domain thereof, or a functional homologue or derivative of said polypeptide or domain;
(c) a viral intercellular spreading protein selected from the group of herpes simplex virus-1 VP22 protein, Marek's disease virus UL49 protein or a functional homologue or derivative thereof;
(d) an endoplasmic reticulum chaperone polypeptide selected from the group of calreticulin or a domain thereof, ER60, GRP94, gp96, or a functional homologue or derivative thereof
(e) domain II of *Pseudomonas* exotoxin ETA or a functional homologue or derivative thereof;
(f) a polypeptide that targets the centrosome compartment of a cell selected from γ-tubulin or a functional homologue or derivative thereof; or
(g) a polypeptide that stimulates DC precursors or activates DC activity selected from the group consisting of GM-CSF, Flt3-ligand extracellular domain, or a functional homologue or derivative thereof.

5. The composition of claim 1, wherein said pro-apoptotic protein is selected from the group consisting of one or more of (a) Bak, (b) Bax, (c) caspase-8, (d) caspase-9 and (e) caspase-3.

6. The composition of claim 1 wherein the antigenic polypeptide or peptide comprises an epitope that binds to and is presented on surfaces of antigen-presenting cells by MHC class I proteins.

7. The composition of claim 1, wherein the antigenic polypeptide or peptide:
(i) is derived from a pathogen selected from the group consisting of a mammalian cell, a microorganism or a virus;
(ii) cross-reacts with an antigen of the pathogen; or
(iii) is expressed on the surface of a pathogenic cell.

8. The composition of claim 7, wherein the antigenic polypeptide or peptide is derived from a human papilloma virus.

9. The composition of claim 7, wherein the antigen is an HPV-16 E7, E7(detox), E6 or E6(detox) polypeptide or peptide.

10. The composition of claim 7, wherein antigenic polypeptide or peptide cross-reacts with an antigen of a pathogen that is a bacterium.

11. The composition of claim 7, wherein the antigenic polypeptide or peptide is a tumor-specific or tumor-associated antigen.

12. The composition of claim 1 wherein the first nucleic acid molecule is an expression vector comprising a promoter operatively linked to said first and/or said second sequence.

13. The composition of claim 12, wherein the promoter is one which is expressed in an antigen presenting cell (APC).

14. The composition of claim 13, wherein the APC is a DC.

15. A combination of first and second particles each comprising a material that is suitable for introduction into a cell or an animal by particle bombardment, and to which particles is bound the composition of claim 1, wherein
(a) the first nucleic acid molecules are bound to said first particles; and
(b) the second nucleic acids are bound to said second particles.

16. The particle of claim 1, wherein the particles are gold particles.

17. A pharmaceutical composition capable of inducing or enhancing an antigen specific immune response, comprising the composition of claim 1 and a pharmaceutically acceptable carrier or excipient.

18. A pharmaceutical composition capable of inducing or enhancing an antigen specific immune response, comprising the particle of claim 1, and a pharmaceutically acceptable carrier or excipient.

19. A method of inducing or enhancing an antigen specific immune response in a subject comprising administering to the subject an effective amount of the composition of claim 1, thereby inducing or enhancing the antigen specific immune response.

20. A method of inducing or enhancing an antigen specific immune response in a subject, comprising administering to the subject an effective amount of the particle of claim 1, thereby inducing or enhancing the antigen specific immune response.

21. A method of inducing or enhancing an antigen specific immune response in a subject, comprising administering to the subject an effective amount of the particles of claim 15, thereby inducing or enhancing the antigen specific immune response.

22. The method of claim 19, wherein the composition is administered intradermally by particle bombardment, intratumorally or peritumorally.

23. A method of increasing the numbers of $CD8^+$ CTLs specific for a selected desired antigen in a subject comprising administering an effective amount of the composition of claim 1, wherein the antigenic peptide or polypeptide comprises an epitope that binds to and is presented on surfaces of antigen-presenting cells by MHC class I proteins, thereby increasing the numbers of antigen-specific $CD8^+$ CTLs.

24. A method of inhibiting the growth of a tumor in a subject comprising administering an effective amount of the composition of claim 1, wherein the antigenic epitopes are those expressed by the tumor or ones cross reactive with those expressed by the tumor, thereby inhibiting growth of the tumor.

25. A method of inhibiting the growth of a tumor in a subject comprising administering an effective amount of the particle of claim 1, wherein the antigenic epitopes are those expressed by the tumor or ones cross reactive with those expressed by the tumor, thereby inhibiting growth of the tumor.

26. An immunogenic cellular composition, comprising dendritic cells (DCs) which have been modified by:

(a) loading the DCs with an antigen so that the antigen is expressed on the DC surface, or transducing or transfecting the DCs with DNA that encodes an antigen fused to an IPP, wherein the DNA is bound to particles comprising a material suitable for introduction into a cell or an animal by particle bombardment; and (b) transfecting the DCs with a nucleic acid molecule that is (i) a siRNA or (ii) DNA that encodes said siRNA, wherein said siRNA has a sequence that is sufficiently complementary to and thus targets the sequence of mRNA that encodes a pro-apoptotic protein expressed in the DC and wherein the nucleic acid molecule is bound to particles comprising a material suitable for introduction into a cell or an animal by particle bombardment, such that expression or activity said siRNA in the cell results in diminution or loss of expression of said mRNA, resulting in inhibition of apoptosis and prolonged survival of the DC.

27. The composition of claim 26 wherein said pro-apoptotic protein is selected from the group consisting one or more of (a) Bak, (b) Bax, (c) caspase-8, (d) caspase-9 and (e) caspase-3.

28. A pharmaceutical composition capable of inducing or enhancing an antigen specific immune response, comprising the composition of claim 26 and a pharmaceutically acceptable carrier or excipient.

29. A method of inducing or enhancing an antigen specific immune response in a subject comprising administering to the subject an effective amount of the composition of claim 26, thereby inducing or enhancing the antigen specific immune response.

30. A method of increasing the numbers of $CD8^+$ CTLs specific for a selected desired antigen in a subject comprising administering an effective amount of the composition of claim 26 wherein the loaded antigen or the antigen expressed from said transduced DNA comprises an epitope that binds to and is presented on the DC surface by MHC class I proteins, thereby increasing the numbers of antigen-specific $CD8^+$ CTLs.

31. A method of inhibiting the growth of a tumor in a subject comprising administering an effective amount of the composition of claim 26, wherein the antigenic epitopes are those expressed by the tumor or ones cross reactive with those expressed by the tumor, thereby inhibiting growth of the tumor.

* * * * *

SEQUENCE LISTING

```
<160> NUMBER OF SEQ ID NOS: 49

<210> SEQ ID NO 1
<211> LENGTH: 21
<212> TYPE: DNA
<213> ORGANISM: Unknown
<220> FEATURE:
<223> OTHER INFORMATION: siNA
<220> FEATURE:
<221> NAME/KEY: misc_feature
<222> LOCATION: (20)..(21)
<223> OTHER INFORMATION: at positions 20 and 21, T is overhanging

<400> SEQUENCE: 1
ugccuacgaa cucuucacct t                                                     21

<210> SEQ ID NO 2
<211> LENGTH: 21
<212> TYPE: DNA
<213> ORGANISM: Unknown
<220> FEATURE:
<223> OTHER INFORMATION: siNA
<220> FEATURE:
<221> NAME/KEY: misc_feature
<222> LOCATION: (20)..(21)
<223> OTHER INFORMATION: at positions 20 and 21, T is overhanging

<400> SEQUENCE: 2
ggugaagagu ucguaggcat t                                                     21

<210> SEQ ID NO 3
<211> LENGTH: 627
<212> TYPE: DNA
<213> ORGANISM: Homo sapiens

<400> SEQUENCE: 3
```

```
atggcatctg acaaggacc aggtcccccg aaggtgggct gcgatgagtc cccgtccccct    60 tctgaacagc aggttgccca ggacacagag gaggtctttc gaagctacgt tttttacctc   120
caccagcagg aacaggagac ccaggggcgg ccgcctgcca accccgagat ggacaacttg   180
cccctggaac ccaacagcat cttgggtcag gtgggtcggc agcttgctct catcggagat   240
gatattaacc ggcgctacga cacagagttc cagaatttac tagaacagct tcagcccaca   300
gccgggaatg cctacgaact cttcaccaag atcgcctcca gcctatttaa gagtggcatc   360
agctggggcc gcgtggtggc tctcctgggc tttggctacc gtctggccct gtacgtctac   420
cagcgtggtt tgaccggctt cctgggccag gtgacctgct ttttggctga tatcatactg   480
catcattaca tcgccagatg gatcgcacag agaggcggtt gggtggcagc cctgaatttg   540
cgtagagacc ccatcctgac cgtaatggtg attttttggtg tggttctgtt gggccaattc   600
gtggtacaca gattcttcag atcatga                                        627
```

<210> SEQ ID NO 4
<211> LENGTH: 19
<212> TYPE: DNA
<213> ORGANISM: Homo sapiens

<400> SEQUENCE: 4

```
tgcctacgaa ctcttcacc                                                  19
```

<210> SEQ ID NO 5
<211> LENGTH: 21
<212> TYPE: DNA
<213> ORGANISM: Unknown
<220> FEATURE:
<223> OTHER INFORMATION: siNA
<220> FEATURE:
<221> NAME/KEY: misc_feature
<222> LOCATION: (20)..(21)
<223> OTHER INFORMATION: at positions 20 and 21, T is overhanging

<400> SEQUENCE: 5

```
uauggagcug cagaggaugt t                                               21
```

<210> SEQ ID NO 6
<211> LENGTH: 21
<212> TYPE: DNA
<213> ORGANISM: Unknown
<220> FEATURE:
<223> OTHER INFORMATION: siNA
<220> FEATURE:
<221> NAME/KEY: misc_feature
<222> LOCATION: (20)..(21)
<223> OTHER INFORMATION: at positions 20 and 21, T is overhanging

<400> SEQUENCE: 6

```
cauccucugc agcuccauat t                                               21
```

<210> SEQ ID NO 7
<211> LENGTH: 579
<212> TYPE: DNA
<213> ORGANISM: Homo sapiens

<400> SEQUENCE: 7

```
atggacgggt ccggggagca gcttgggagc ggcgggccca ccagctctga acagatcatg    60
aagacagggg cctttttgct acagggtttc atccaggatc gagcaggag atggctggg    120 gagacacctg agctgacctt ggagcagccg ccccaggatc gtccaccaa gaagctgagc   180 gagtgtctcc ggcgaattgg agatgaactg gatagcaata tggagctgca gaggatgatt   240
```

```
gctgacgtgg acacggactc cccccgagag gtcttcttcc gggtggcagc tgacatgttt    300
gctgatggca acttcaactg gggccgcgtg gttgccctct tctactttgc tagcaaactg    360
gtgctcaagg ccctgtgcac taaagtgccc gagctgatca gaaccatcat gggctggaca    420
ctggacttcc tccgtgagcg gctgcttgtc tggatccaag accagggtgg ctgggaaggc    480
ctcctctcct acttcgggac ccccacatgg cagacagtga ccatctttgt ggctggagtc    540
ctcaccgcct cgctcaccat ctggaagaag atgggctga                           579

<210> SEQ ID NO 8
<211> LENGTH: 19
<212> TYPE: DNA
<213> ORGANISM: Homo sapiens

<400> SEQUENCE: 8
tatggagctg cagaggatg                                                  19

<210> SEQ ID NO 9
<211> LENGTH: 1491
<212> TYPE: DNA
<213> ORGANISM: Homo sapiens

<400> SEQUENCE: 9
atggacttca gcagaaatct ttatgatatt ggggaacaac tggacagtga agatctggcc     60
tccctcaagt tcctgagcct ggactacatt ccgcaaagga agcaagaacc catcaaggat    120
gccttgatgt tattccagag actccaggaa aagagaatgt ggaggaaagg caatctgtcc    180
ttcctgaagg agctgctctt ccgaattaat agactggatt gctgattac  ctacctaaac    240 actagaaagg aggagatgga aagggaactt cagacaccag gcagggctca aatttctgcc    300
tacaggttcc acttctgccg catgagctgg gctgaagcaa acagccagtg ccagacacag    360 tctgtaccctt tctggcggag ggtcgatcat ctattaataa gggtcatgct ctatcagatt    420
tcagaagaag tgagcagatc agaattgagg tcttttaagt ttcttttgca agaggaaatc    480
tccaaatgca aactggatga tgacatgaac ctgctggata tttttcataga gatggagaag    540 agggtcatcc tgggagaagg aaagttggac atcctgaaaa gagtctgtgc ccaaatcaac    600
aagagcctgc tgaagataat caacgactat gaagaattca gcaaagggga ggagttgtgt    660
ggggtaatga caatctcgga ctctccaaga gaacaggata gtgaatcaca gacttttgac    720
aaagtttacc aaatgaaaag caaacctcgg ggatactgtc tgatcatcaa caatcacaat    780
tttgcaaaag cacgggagaa agtgcccaaa cttcacagca ttagggacag gaatggaaca    840
cacttggatg cagggggcttt gaccacgacc tttgaagagc ttcattttga gatcaagccc    900
cacgatgact gcacagtaga gcaaatctat gagattttga aaatctacca actcatggac    960
cacagtaaca tggactgctt catctgctgt atcctctccc atggagacaa gggcatcatc   1020
tatggcactg atggacagga ggcccccatc tatgagctga catctcagtt cactggtttg   1080 aagtgcccctt cccttgctgg aaaacccaaa gtgtttttta ttcaggcttg tcaggggat    1140 aactaccaga aagtatacc tgttgagact gattcagagg agcaaccta tttagaaatg     1200 gatttatcat cacctcaaac gagatatatc ccggatgagg ctgactttct gctgggatt    1260 gccactgtga ataactgtgt ttcctaccga aaccctgcag agggaacctg gtacatccag   1320
tcactttgcc agagcctgag agagcgatgt cctcgaggcg atgatattct caccatcctg   1380
actgaagtga actatgaagt aagcaacaag gatgacaaga aaaacatggg gaaacagatg   1440
```
cctcagccta ctttcacact aagaaaaaaa cttgtcttcc cttctgattg a       1491

<210> SEQ ID NO 10
<211> LENGTH: 23
<212> TYPE: DNA
<213> ORGANISM: Unknown
<220> FEATURE:
<223> OTHER INFORMATION: siNA
<220> FEATURE:
<221> NAME/KEY: misc_feature
<222> LOCATION: (22)..(23)
<223> OTHER INFORMATION: at positions 22 and 23, T is overhanging

<400> SEQUENCE: 10
aaccucgggg auacugucug att                                      23

<210> SEQ ID NO 11
<211> LENGTH: 23
<212> TYPE: DNA
<213> ORGANISM: Unknown
<220> FEATURE:
<223> OTHER INFORMATION: siNA
<220> FEATURE:
<221> NAME/KEY: misc_feature
<222> LOCATION: (22)..(23)
<223> OTHER INFORMATION: at positions 22 and 23, T is overhanging

<400> SEQUENCE: 11
ucagacagua uccccgaggu utt                                      23

<210> SEQ ID NO 12
<211> LENGTH: 1251
<212> TYPE: DNA
<213> ORGANISM: Homo sapiens

<400> SEQUENCE: 12
atggacgaag cggatcggcg gctcctgcgg cggtgccggc tgcggctggt ggaagagctg    60
caggtggacc agctctggga cgccctgctg agccgcgagc tgttcaggcc ccatatgatc   120
gaggacatcc agcgggcagg ctctggatct cggcgggatc aggccaggca gctgatcata   180
gatctggaga ctcgagggag tcaggctctt cctttgttca tctcctgctt agaggacaca   240
ggccaggaca tgctggcttc gtttctgcga actaacaggc aagcagcaaa gttgtcgaag   300
ccaaccctag aaaaccttac cccagtggtg ctcagaccag agattcgcaa accagaggtt   360
ctcagaccgg aaacacccag accagtggac attggttctg gaggatttgg tgatgtcggt   420
gctcttgaga gtttgagggg aaatgcagat ttggcttaca tcctgagcat ggagccctgt   480
ggccactgcc tcattatcaa caatgtgaac ttctgccgtg agtccgggct ccgcacccgc   540
actggctcca acatcgactg tgagaagttg cggcgtcgct tctcctcgct gcatttcatg   600
gtggaggtga agggcgacct gactgccaag aaaatggtgc tggcttttgct ggagctggcg   660 cagcaggacc acggtgctct ggactgctgc gtggtggtca ttctctctca cggctgtcag   720
gccagccacc tgcagttccc aggggctgtc tacggcacag atggatgccc tgtgtcggtc   780
gagaagattg tgaacatctt caatgggacc agctgcccca gcctgggagg gaagcccaag   840 ctcttttttca tccaggcctg tggtggggag cagaaagacc atgggtttga ggtggcctcc   900
acttcccctg aagacgagtc ccctggcagt aaccccgagc cagatgccac cccgttccag   960
gaaggtttga ggaccttcga ccagctggac gccatatcta gtttgcccac acccagtgac  1020
atctttgtgt cctactctac tttcccaggt tttgtttcct ggagggaccc caagagtggc  1080
tcctggtacg ttgagaccct ggacgacatc tttgagcagt gggctcactc tgaagacctg  1140

| | | |
|---|---|---|
| cagtccctcc tgcttagggt cgctaatgct gtttcggtga aagggattta taaacagatg | | 1200 |
| cctggttgct ttaatttcct ccggaaaaaa ctttctttta aacatcata a | | 1251 |

<210> SEQ ID NO 13
<211> LENGTH: 834
<212> TYPE: DNA
<213> ORGANISM: Homo sapiens

<400> SEQUENCE: 13

| | | |
|---|---|---|
| atggagaaca ctgaaaactc agtggattca aaatccatta aaatttggga accaaagatc | | 60 |
| atacatggaa gcgaatcaat ggactctgga atatccctgg acaacagtta taaaatggat | | 120 |
| tatcctgaga tgggtttatg tataataatt aataataaga attttcataa aagcactgga | | 180 |
| atgcatctc ggtctggtac agatgtcgat gcagcaaacc tcagggaaac attcagaaac | | 240 |
| ttgaaatatg aagtcaggaa taaaaatgat cttacacgtg aagaaattgt ggaattgatg | | 300 |
| cgtgatgttt ctaaagaaga tcacagcaaa aggagcagtt tgttttgtgt gcttctgagc | | 360 |
| catggtgaag aaggaataat ttttggaaca atggacctg ttgacctgaa aaaaataaca | | 420 |
| aacttttca gaggggatcg ttgtagaagt ctaactggaa acccaaaact tttcattatt | | 480 |
| caggcctgcc gtggtacaga actggactgt ggcattgaga cagacagtgg tgttgatgat | | 540 |
| gacatggcgt gtcataaaat accagtggag gccgacttct tgtatgcata ctccacagca | | 600 |
| cctggttatt attcttggcg aaattcaaag gatggctcct ggttcatcca gtcgctttgt | | 660 |
| gccatgctga acagtatgc cgacaagctt gaatttatgc acattcttac ccgggttaac | | 720 |
| cgaaaggtgg caacagaatt tgagtccttt tcctttgacg ctactttca tgcaaagaaa | | 780 |
| cagattccat gtattgtttc catgctcaca aaagaactct attttatca ctaa | | 834 |

<210> SEQ ID NO 14
<211> LENGTH: 5431
<212> TYPE: DNA
<213> ORGANISM: Plasmid pcDNA3

<400> SEQUENCE: 14

| | | |
|---|---|---|
| gacggatcgg gagatctccc gatccctat ggtcgactct cagtacaatc tgctctgatg | | 60 |
| ccgcatagtt aagccagtat ctgctccctg cttgtgtgtt ggaggtcgct gagtagtgcg | | 120 |
| cgagcaaaat ttaagctaca acaaggcaag cttgaccga caattgcatg aagaatctgc | | 180 |
| ttagggttag gcgttttgcg ctgcttcgcg atgtacgggc cagatatacg cgttgacatt | | 240 |
| gattattgac tagttattaa tagtaatcaa ttacggggtc attagttcat agcccatata | | 300 |
| tggagttccg cgttacataa cttacggtaa atggcccgcc tggctgaccg cccaacgacc | | 360 |
| cccgcccatt gacgtcaata atgacgtatg ttcccatagt aacgccaata gggactttcc | | 420 |
| attgacgtca tgggtggac tatttacggt aaactgccca cttggcagta catcaagtgt | | 480 |
| atcatatgcc aagtacgccc cctattgacg tcaatgacgg taaatggccc gcctggcatt | | 540 |
| atgcccagta catgacctta tgggactttc ctacttggca gtacatctac gtattagtca | | 600 |
| tcgctattac catggtgatg cggttttggc agtacatcaa tgggcgtgga tagcggtttg | | 660 |
| actcacgggg atttccaagt ctccacccca ttgacgtcaa tgggagtttg ttttggcacc | | 720 |
| aaaatcaacg ggactttcca aaatgtcgta acaactccgc cccattgacg caaatgggcg | | 780 |
| gtaggcgtgt acggtgggag gtctatataa gcagagctct ctggctaact agagaaccca | | 840 |
| ctgcttactg gcttatcgaa attaatacga ctcactatag ggagacccaa gctggctagc | | 900 |

-continued

```
gtttaaacgg gccctctaga ctcgagcggc cgccactgtg ctggatatct gcagaattcc    960
accacactgg actagtggat ccgagctcgg taccaagctt aagtttaaac cgctgatcag   1020
cctcgactgt gccttctagt tgccagccat ctgttgtttg cccctccccc gtgccttcct   1080
tgaccctgga aggtgccact cccactgtcc tttcctaata aaatgaggaa attgcatcgc   1140
attgtctgag taggtgtcat tctattctgg gggtggggt ggggcaggac agcaagggggg   1200
aggattggga agacaatagc aggcatgctg gggatgcgt gggctctatg gcttctgagg    1260
cggaaagaac cagctggggc tctaggggt atccccacgc gccctgtagc ggcgcattaa    1320
gcgcggcggt gtggtggtt acgcgcagcg tgaccgctac acttgccagc gccctagcgc    1380
ccgctccttt cgctttcttc ccttcctttc tcgccacgtt cgccggcttt ccccgtcaag   1440
ctctaaatcg gggcatccct ttagggttcc gatttagtgc tttacggcac ctcgacccca   1500
aaaaacttga ttagggtgat ggttcacgta gtgggccatc gccctgatag acggttttc    1560
gccctttgac gttggagtcc acgttcttta atagtggact cttgttccaa actggaacaa   1620
cactcaaccc tatctcggtc tattcttttg atttataagg gattttgggg atttcggcct   1680
attggttaaa aaatgagctg atttaacaaa aatttaacgc gaattaattc tgtggaatgt   1740
gtgtcagtta gggtgtggaa agtccccagg ctccccaggc aggcagaagt atgcaaagca   1800
tgcatctcaa ttagtcagca accaggtgtg gaaagtcccc aggctcccca gcaggcagaa   1860
gtatgcaaag catgcatctc aattagtcag caaccatagt cccgccccta actccgccca   1920
tcccgcccct aactccgccc agttccgccc attctccgcc ccatggctga ctaattttt    1980
ttatttatgc agaggccgag gccgcctctg cctctgagct attccagaag tagtgaggag   2040
gcttttttgg aggcctaggc ttttgcaaaa agctcccggg agcttgtata tccattttcg   2100
gatctgatca agagacagga tgaggatcgt ttcgcatgat tgaacaagat ggattgcacg   2160
caggttctcc ggccgcttgg gtggagaggc tattcggcta tgactgggca acagacaa    2220
tcggctgctc tgatgccgcc gtgttccggc tgtcagcgca ggggcgcccg gttctttttg   2280
tcaagaccga cctgtccggt gccctgaatg aactgcagga cgaggcagcg cggctatcgt   2340
ggctggccac gacgggcgtt ccttgcgcag ctgtgctcga cgttgtcact gaagcgggaa   2400
gggactggct gctattgggc gaagtgccgg ggcaggatct cctgtcatct caccttgctc   2460
ctgccgagaa agtatccatc atggctgatg caatgcggcg gctgcatacg cttgatccgg   2520
ctacctgccc attcgaccac caagcgaaac atcgcatcga gcgagcacgt actcggatgg   2580
aagccggtct tgtcgatcag gatgatctgg acgaagagca tcaggggctc gcgccagccg   2640
aactgttcgc caggctcaag gcgcgcatgc ccgacggcga ggatctcgtc gtgacccatg   2700
gcgatgcctg cttgccgaat atcatggtgg aaaatggccg cttttctgga ttcatcgact   2760
gtggccggct gggtgtggcg gaccgctatc aggacatagc gttggctacc cgtgatattg   2820
ctgaagagct tggcggcgaa tgggctgacc gcttcctcgt gctttacggt atcgccgctc   2880
ccgattcgca gcgcatcgcc ttctatcgcc ttcttgacga gttcttctga gcgggactct   2940
ggggttcgaa atgaccgacc aagcgacgcc caacctgcca tcacgagatt tcgattccac   3000
cgccgccttc tatgaaaggt tgggcttcgg aatcgttttc cgggacgccg gctgatgat    3060
cctccagcgc ggggatctca tgctggagtt cttcgcccac cccaacttgt ttattgcagc   3120
ttataatggt tacaaataaa gcaatagcat cacaaatttc acaaataaag catttttttc   3180
actgcattct agttgtggtt tgtccaaact catcaatgta tcttatcatg tctgtatacc   3240
gtcgacctct agctagagct tggcgtaatc atggtcatag ctgtttcctg tgtgaaattg   3300
```

-continued

```
ttatccgctc acaattccac acaacatacg agccggaagc ataaagtgta aagcctgggg    3360
tgcctaatga gtgagctaac tcacattaat tgcgttgcgc tcactgcccg ctttccagtc    3420
gggaaacctg tcgtgccagc tgcattaatg aatcggccaa cgcgcgggga gaggcggttt    3480
gcgtattggg cgctcttccg cttcctcgct cactgactcg ctgcgctcgg tcgttcggct    3540
gcggcgagcg gtatcagctc actcaaaggc ggtaatacgg ttatccacag aatcagggga    3600
taacgcagga aagaacatgt gagcaaaagg ccagcaaaag gccaggaacc gtaaaaaggc    3660
cgcgttgctg gcgtttttcc ataggctccg cccccctgac gagcatcaca aaaatcgacg    3720
ctcaagtcag aggtggcgaa acccgacagg actataaaga taccaggcgt ttccccctgg    3780
aagctccctc gtgcgctctc ctgttccgac cctgccgctt accggatacc tgtccgcctt    3840
tctcccttcg ggaagcgtgg cgctttctca atgctcacgc tgtaggtatc tcagttcggt    3900
gtaggtcgtt cgctccaagc tgggctgtgt gcacgaaccc cccgttcagc ccgaccgctg    3960
cgccttatcc ggtaactatc gtcttgagtc caacccggta agacacgact tatcgccact    4020
ggcagcagcc actggtaaca ggattagcag agcgaggtat gtaggcggtg ctacagagtt    4080
cttgaagtgg tggcctaact acggctacac tagaaggaca gtatttggta tctgcgctct    4140
gctgaagcca gttaccttcg gaaaaagagt tggtagctct tgatccggca aacaaaccac    4200
cgctggtagc ggtggttttt tgtttgcaa gcagcagatt acgcgcagaa aaaaggatc    4260 tcaagaagat cctttgatct tttctacggg gtctgacgct cagtggaacg aaaactcacg    4320
ttaagggatt ttggtcatga gattatcaaa aaggatcttc acctagatcc ttttaaatta    4380
aaaatgaagt tttaaatcaa tctaaagtat atatgagtaa acttggtctg acagttacca    4440
atgcttaatc agtgaggcac ctatctcagc gatctgtcta tttcgttcat ccatagttgc    4500
ctgactcccc gtcgtgtaga taactacgat acgggagggc ttaccatctg gccccagtgc    4560
tgcaatgata ccgcgagacc cacgctcacc ggctccagat ttatcagcaa taaaccagcc    4620
agccggaagg gccgagcgca gaagtggtcc tgcaacttta tccgcctcca tccagtctat    4680
taattgttgc cgggaagcta gagtaagtag ttcgccagtt aatagtttgc gcaacgttgt    4740
tgccattgct acaggcatcg tggtgtcacg ctcgtcgttt ggtatggctt cattcagctc    4800
cggttcccaa cgatcaaggc gagttacatg atcccccatg ttgtgcaaaa aagcggttag    4860
ctccttcggt cctccgatcg ttgtcagaag taagttggcc gcagtgttat cactcatggt    4920
tatggcagca ctgcataatt ctcttactgt catgccatcc gtaagatgct tttctgtgac    4980
tggtgagtac tcaaccaagt cattctgaga atagtgtatg cggcgaccga gttgctcttg    5040
cccggcgtca atacgggata ataccgcgcc acatagcaga actttaaaag tgctcatcat    5100
tggaaaacgt tcttcgggc gaaaactctc aaggatctta ccgctgttga tccagttc     5160 gatgtaaccc actcgtgcac ccaactgatc ttcagcatct tttactttca ccagcgtttc    5220
tgggtgagca aaaacaggaa ggcaaaatgc cgcaaaaaag ggaataaggg cgacacggaa    5280
atgttgaata ctcatactct ccttttttca atattattga agcatttatc agggttattg    5340
tctcatgagc ggatacatat ttgaatgtat ttagaaaaat aaacaaatag gggttccgcg    5400
cacatttccc cgaaaagtgc cacctgacgt c                                   5431
```

<210> SEQ ID NO 15
<211> LENGTH: 4479
<212> TYPE: DNA
<213> ORGANISM: Plasmid NGVA4a

```
<400> SEQUENCE: 15
tggccattgc atacgttgta tccatatcat aatatgtaca tttatattgg ctcatgtcca      60
acattaccgc catgttgaca ttgattattg actagttatt aatagtaatc aattacgggg     120
tcattagttc atagcccata tatggagttc cgcgttacat aacttacggt aaatggcccg     180
cctggctgac cgcccaacga cccccgccca ttgacgtcaa taatgacgta tgttcccata     240
gtaacgccaa tagggacttt ccattgacgt caatgggtgg agtatttacg gtaaactgcc     300
cacttggcag tacatcaagt gtatcatatg ccaagtacgc cccctattga cgtcaatgac     360
ggtaaatggc ccgcctggca ttatgccag tacatgacct tatgggactt cctacttgg      420
cagtacatct acgtattagt catcgctatt accatggtga tgcggttttg gcagtacatc     480
aatgggcgtg gatagcggtt tgactcacgg ggatttccaa gtctccaccc cattgacgtc     540
aatgggagtt tgttttggca ccaaaatcaa cgggactttc caaaatgtcg taacaactcc     600
gccccattga cgcaaatggg cggtaggcgt gtacggtggg aggtctatat aagcagagct     660
cgtttagtga accgtcagat cgcctggaga cgccatccac gctgttttga cctccataga     720
agacaccggg accgatccag cctccgcggc cgggaacggt gcattggaac gcggattccc     780
cgtgccaaga gtgacgtaag taccgcctat agagtctata ggcccacccc cttggcttct     840
tatgcatgct atactgtttt tggcttgggg tctatacacc cccgcttcct catgttatag     900
gtgatggtat agcttagcct ataggtgtgg gttattgacc attattgacc actccaacgg     960
tggagggcag tgtagtctga gcagtactcg ttgctgccgc gcgcgccacc agacataata    1020
gctgacagac taacagactg ttcctttcca tgggtctttt ctgcagtcac cgtcgtcgac    1080
ggtatcgata agcttgatat cgaattcacg tgggcccggt accgtatact ctagagcggc    1140
cgcggatcca gatcttttc cctcgccaaa aattatgggg acatcatgaa gccccttgag    1200
catctgactt ctggctaata aaggaaattt atttcattgc aatagtgtgt tggaattttt    1260
tgtgtctctc actcggaagg acatatggga gggcaaatca tttaaaacat cagaatcagt    1320
atttggttta gagtttggca acatatgcca ttcttccgct tcctcgctca ctgactcgct    1380
gcgctcggtc gttcggctgc ggcgagcggt atcagctcac tcaaaggcgg taatacggtt    1440
atccacagaa tcaggggata acgcaggaaa gaacatgtga gcaaaaggcc agcaaaaggc    1500
caggaaccgt aaaaaggccg cgttgctggc gtttttccat aggctccgcc ccctgacga     1560
gcatcacaaa aatcgacgct caagtcagag gtggcgaaac ccgacaggac tataaagata    1620
ccaggcgttt ccccctggaa gctccctcgt gcgctctcct gttccgaccc tgccgcttac    1680
cggatacctg tccgcctttc tcccttcggg aagcgtggcg ctttctcaat gctcacgctg    1740
taggtatctc agttcggtgt aggtcgttcg ctccaagctg ggctgtgtgc acgaaccccc    1800
cgttcagccc gaccgctgcg ccttatccgg taactatcgt cttgagtcca acccggtaag    1860
acacgactta tcgccactgg cagcagccac tggtaacagg attagcagag cgaggtatgt    1920
aggcggtgct acagagttct tgaagtggtg gcctaactac ggctacacta aaggacagt    1980
atttggtatc tgcgctctgc tgaagccagt taccttcgga aaagagttg gtagctcttg    2040
atccggcaaa caaccaccg ctggtagcgg tggttttttt gtttgcaagc agcagattac    2100
gcgcagaaaa aaaggatctc aagaagatcc tttgatcttt tctacggggt ctgacgctca    2160
gtggaacgaa aactcacgtt aagggatttt ggtcatgaga ttatcaaaaa ggatcttcac    2220
ctagatcctt ttaaattaaa aatgaagttt taaatcaatc taaagtatat atgagtaaac    2280
ttggtctgac agttaccaat gcttaatcag tgaggcacct atctcagcga tctgtctatt    2340
```

```
tcgttcatcc atagttgcct gactccgggg ggggggggcg ctgaggtctg cctcgtgaag    2400
aaggtgttgc tgactcatac cagggcaacg ttgttgccat tgctacaggc atcgtggtgt    2460
cacgctcgtc gtttggtatg gcttcattca gctccggttc ccaacgatca aggcgagtta    2520
catgatcccc catgttgtgc aaaaaagcgg ttagctcctt cggtcctccg atcgttgtca    2580
gaagtaagtt ggccgcagtg ttatcactca tggttatggc agcactgcat aattctctta    2640
ctgtcatgcc atccgtaaga tgcttttctg tgactggtga gtactcaacc aagtcattct    2700
gagaatagtg tatgcggcga ccgagttgct cttgcccggc gtcaatacgg ataataccg     2760 cgccacatag cagaacttta aaagtgctca tcattggaaa acgttcttcg gggcgaaaac    2820
tctcaaggat cttaccgctg ttgagatcca gttcgatgta acccactcgt gcacctgaat    2880
cgccccatca tccagccaga aagtgaggga gccacggttg atgagagctt tgttgtaggt    2940
ggaccagttg gtgattttga acttttgctt tgccacggaa cggtctgcgt tgtcgggaag    3000
atgcgtgatc tgatccttca actcagcaaa agttcgattt attcaacaaa gccgccgtcc    3060
cgtcaagtca gcgtaatgct ctgccagtgt acaaccaat taaccaattc tgattagaaa     3120
aactcatcga gcatcaaatg aaactgcaat ttattcatat caggattatc ataccatat     3180 ttttgaaaaa gccgtttctg taatgaagga gaaaactcac cgaggcagtt ccataggatg    3240
gcaagatcct ggtatcggtc tgcgattccg actcgtccaa catcaataca acctattaat    3300
ttcccctcgt caaaaataag gttatcaagt gagaaatcac catgagtgac gactgaatcc    3360
ggtgagaatg gcaaaagctt atgcatttct ttccagactt gttcaacagg ccagccatta    3420
cgctcgtcat caaaatcact cgcatcaacc aaaccgttat tcattcgtga ttgcgcctga    3480
gcgagacgaa atacgcgatc gctgttaaaa ggacaattac aaacaggaat cgaatgcaac    3540
cggcgcagga acactgccag cgcatcaaca atattttcac ctgaatcagg atattcttct    3600
aatacctgga atgctgtttt cccggggatc gcagtggtga gtaaccatgc atcatcagga    3660
gtacggataa aatgcttgat ggtcggaaga ggcataaatt ccgtcagcca gtttagtctg    3720
accatctcat ctgtaacatc attggcaacg ctaccttttgc catgtttcag aaacaactct    3780
ggcgcatcgg gcttcccata caatcgatag attgtcgcac ctgattgccc gacattatcg    3840
cgagcccatt tatcccata taaatcagca tccatgttgg aatttaatcg cggcctcgag    3900
caagacgttt cccgttgaat atggctcata cacccttg tattactgtt tatgtaagca      3960
gacagtttta ttgttcatga tgatatattt ttatcttgtg caatgtaaca tcagagattt    4020
tgagacacaa cgtggctttc ccccccccc cattattgaa gcatttatca gggttattgt      4080
ctcatgagcg gatacatatt tgaatgtatt tagaaaaata aacaaatagg ggttccgcgc    4140
acatttcccc gaaaagtgcc acctgacgtc taagaaacca ttattatcat gacattaacc    4200
tataaaaata ggcgtatcac gaggcccttt cgtcctcgcg cgtttcggtg atgacggtga    4260
aaacctctga cacatgcagc tcccggagac ggtcacagct tgtctgtaag cggatgccgg    4320
gagcagacaa gcccgtcagg gcgcgtcagc gggtgttggc gggtgtcggg gctggcttaa    4380
ctatgcggca tcagagcaga ttgtactgag agtgcaccat atgcggtgtg aaataccgca    4440
cagatgcgta aggagaaaat accgcatcag attggctat                           4479

<210> SEQ ID NO 16
<211> LENGTH: 297
<212> TYPE: DNA
<213> ORGANISM: Human papillomavirus type 16
<220> FEATURE:
```

<221> NAME/KEY: CDS
<222> LOCATION: (1)..(297)

<400> SEQUENCE: 16

```
atg cat gga gat aca cct aca ttg cat gaa tat atg tta gat ttg caa        48
Met His Gly Asp Thr Pro Thr Leu His Glu Tyr Met Leu Asp Leu Gln
1               5                   10                  15 cca gag aca act gat ctc tac tgt tat gag caa tta aat gac agc tca        96
Pro Glu Thr Thr Asp Leu Tyr Cys Tyr Glu Gln Leu Asn Asp Ser Ser
            20                  25                  30 gag gag gag gat gaa ata gat ggt cca gct gga caa gca gaa ccg gac       144
Glu Glu Glu Asp Glu Ile Asp Gly Pro Ala Gly Gln Ala Glu Pro Asp
        35                  40                  45 aga gcc cat tac aat att gta acc ttt tgt tgc aag tgt gac tct acg       192
Arg Ala His Tyr Asn Ile Val Thr Phe Cys Cys Lys Cys Asp Ser Thr
    50                  55                  60 ctt cgg ttg tgc gta caa agc aca cac gta gac att cgt act ttg gaa       240
Leu Arg Leu Cys Val Gln Ser Thr His Val Asp Ile Arg Thr Leu Glu
65                  70                  75                  80 gac ctg tta atg ggc aca cta gga att gtg tgc ccc atc tgt tct cag       288
Asp Leu Leu Met Gly Thr Leu Gly Ile Val Cys Pro Ile Cys Ser Gln
                85                  90                  95 gat aag ctt                                                           297
Asp Lys Leu
```

<210> SEQ ID NO 17
<211> LENGTH: 99
<212> TYPE: PRT
<213> ORGANISM: Human papillomavirus type 16

<400> SEQUENCE: 17

```
Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Asp Lys Leu
```

<210> SEQ ID NO 18
<211> LENGTH: 98
<212> TYPE: PRT
<213> ORGANISM: Human papillomavirus type 16

<400> SEQUENCE: 18

```
Met His Gly Asp Thr Pro Thr Leu His Glu Tyr Met Leu Asp Leu Gln
1               5                   10                  15

Pro Glu Thr Thr Asp Leu Tyr Gly Tyr Glu Gly Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60
```

```
Leu Arg Leu Cys Val Gln Ser Thr His Val Asp Ile Arg Thr Leu Glu
 65                  70                  75                  80

Asp Leu Leu Met Gly Thr Leu Gly Ile Val Cys Pro Ile Cys Ser Gln
                 85                  90                  95

Lys Pro

<210> SEQ ID NO 19
<211> LENGTH: 477
<212> TYPE: DNA
<213> ORGANISM: Human papillomavirus type 16
<220> FEATURE:
<221> NAME/KEY: CDS
<222> LOCATION: (1)..(477)

<400> SEQUENCE: 19 atg cac caa aag aga act gca atg ttt cag gac cca cag gag cga ccc      48
Met His Gln Lys Arg Thr Ala Met Phe Gln Asp Pro Gln Glu Arg Pro
 1               5                  10                  15 aga aag tta cca cag tta tgc aca gag ctg caa aca act ata cat gat      96
Arg Lys Leu Pro Gln Leu Cys Thr Glu Leu Gln Thr Thr Ile His Asp
             20                  25                  30 ata ata tta gaa tgt gtg tac tgc aag caa cag tta ctg cga cgt gag     144
Ile Ile Leu Glu Cys Val Tyr Cys Lys Gln Gln Leu Leu Arg Arg Glu
         35                  40                  45 gta tat gac ttt gct ttt cgg gat tta tgc ata gta tat aga gat ggg     192
Val Tyr Asp Phe Ala Phe Arg Asp Leu Cys Ile Val Tyr Arg Asp Gly
     50                  55                  60 aat cca tat gct gta tgt gat aaa tgt tta aag ttt tat tct aaa att     240
Asn Pro Tyr Ala Val Cys Asp Lys Cys Leu Lys Phe Tyr Ser Lys Ile
 65                  70                  75                  80 agt gag tat aga cat tat tgt tat agt ttg tat gga aca aca tta gaa     288
Ser Glu Tyr Arg His Tyr Cys Tyr Ser Leu Tyr Gly Thr Thr Leu Glu
                 85                  90                  95 cag caa tac aac aaa ccg ttg tgt gat ttg tta att agg tgt att aac     336
Gln Gln Tyr Asn Lys Pro Leu Cys Asp Leu Leu Ile Arg Cys Ile Asn
            100                 105                 110 tgt caa aag cca ctg tgt cct gaa gaa aag caa aga cat ctg gac aaa     384
Cys Gln Lys Pro Leu Cys Pro Glu Glu Lys Gln Arg His Leu Asp Lys
        115                 120                 125 aag caa aga ttc cat aat ata agg ggt cgg tgg acc ggt cga tgt atg     432
Lys Gln Arg Phe His Asn Ile Arg Gly Arg Trp Thr Gly Arg Cys Met
    130                 135                 140 tct tgt tgc aga tca tca aga aca cgt aga gaa acc cag ctg taa        477
Ser Cys Cys Arg Ser Ser Arg Thr Arg Arg Glu Thr Gln Leu
145                 150                 155

<210> SEQ ID NO 20
<211> LENGTH: 158
<212> TYPE: PRT
<213> ORGANISM: Human papillomavirus type 16

<400> SEQUENCE: 20

Met His Gln Lys Arg Thr Ala Met Phe Gln Asp Pro Gln Glu Arg Pro
 1               5                  10                  15

Arg Lys Leu Pro Gln Leu Cys Thr Glu Leu Gln Thr Thr Ile His Asp
             20                  25                  30

Ile Ile Leu Glu Cys Val Tyr Cys Lys Gln Gln Leu Leu Arg Arg Glu
         35                  40                  45

Val Tyr Asp Phe Ala Phe Arg Asp Leu Cys Ile Val Tyr Arg Asp Gly
     50                  55                  60
```

```
Asn Pro Tyr Ala Val Cys Asp Lys Cys Leu Lys Phe Tyr Ser Lys Ile
 65                  70                  75                  80

Ser Glu Tyr Arg His Tyr Cys Tyr Ser Leu Tyr Gly Thr Thr Leu Glu
                 85                  90                  95

Gln Gln Tyr Asn Lys Pro Leu Cys Asp Leu Leu Ile Arg Cys Ile Asn
            100                 105                 110

Cys Gln Lys Pro Leu Cys Pro Glu Glu Lys Gln Arg His Leu Asp Lys
        115                 120                 125

Lys Gln Arg Phe His Asn Ile Arg Gly Arg Trp Thr Gly Arg Cys Met
    130                 135                 140

Ser Cys Cys Arg Ser Ser Arg Thr Arg Arg Glu Thr Gln Leu
145                 150                 155

<210> SEQ ID NO 21
<211> LENGTH: 151
<212> TYPE: PRT
<213> ORGANISM: Human papillomavirus type 16

<400> SEQUENCE: 21

Met Phe Gln Asp Pro Gln Glu Arg Pro Arg Lys Leu Pro Gln Leu Cys
 1               5                  10                  15

Thr Glu Leu Gln Thr Thr Ile His Asp Ile Ile Leu Glu Cys Val Tyr
             20                  25                  30

Cys Lys Gln Gln Leu Leu Arg Arg Glu Val Tyr Asp Phe Ala Phe Arg
         35                  40                  45

Asp Leu Cys Ile Val Tyr Arg Asp Gly Asn Pro Tyr Ala Val Cys Asp
     50                  55                  60

Lys Cys Leu Lys Phe Tyr Ser Lys Ile Ser Glu Tyr Arg His Tyr Cys
 65                  70                  75                  80

Tyr Ser Leu Tyr Gly Thr Thr Leu Glu Gln Gln Tyr Asn Lys Pro Leu
                 85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
        115                 120                 125

Arg Gly Arg Trp Thr Gly Arg Cys Met Ser Cys Cys Arg Ser Ser Arg
    130                 135                 140

Thr Arg Arg Glu Thr Gln Leu
145                 150

<210> SEQ ID NO 22
<211> LENGTH: 1698
<212> TYPE: DNA
<213> ORGANISM: Homo sapiens

<400> SEQUENCE: 22
atgaaggcaa acctactggt cctgttaagt gcacttgcag ctgcagatgc agacacaata     60
tgtataggct accatgcgaa caattcaacc gacactgttg acacagtact cgagaagaat    120
gtgacagtga cacactctgt taacctgctc gaagacagcc acaacggaaa actatgtaga    180
ttaaaaggaa tagccccact acaattgggg aaatgtaaca tcgccggatg gctcttggga    240
aacccagaat gcgacccact gcttccagtg agatcatggt cctacattgt agaaacacca    300
aactctgaga tggaatatg ttatccagga gatttcatcg actatgagga gctgagggag    360
caattgagct cagtgtcatc attcgaaaga ttcgaaatat ttcccaaaga aagctcatgg    420
```

```
cccaaccaca acacaaacgg agtaacggca gcatgctccc atgaggggaa aagcagtttt    480
tacagaaatt tgctatggct gacggagaag gagggctcat acccaaagct gaaaaattct    540
tatgtgaaca aaaaagggaa agaagtcctt gtactgtggg gtattcatca cccgcctaac    600
agtaaggaac aacagaatat ctatcagaat gaaaatgctt atgtctctgt agtgacttca    660
aattataaca ggagatttac cccggaaata gcagaaagac ccaaagtaag agatcaagct    720
gggaggatga actattactg gaccttgcta aacccggag acacaataat atttgaggca    780
aatggaaatc taatagcacc aatgtatgct ttcgcactga gtagaggctt tgggtccggc    840
atcatcacct caaacgcatc aatgcatgag tgtaacacga agtgtcaaac accctggga    900 gctataaaca gcagtctccc ttaccagaat atacacccag tcacaatagg agagtgccca    960
aaatacgtca ggagtgccaa attgaggatg gttacaggac taaggaacac tccgtccatt    1020
caatccagag gtctatttgg agccattgcc ggttttattg aaggggatg gactggaatg    1080 atagatggat ggtatggtta tcatcatcag aatgaacagg gatcaggcta tgcagcggat    1140
caaaaaagca cacaaaatgc cattaacggg attacaaaca aggtgaacac tgttatcgag    1200
aaaatgaaca ttcaattcac agctgtgggt aaagaattca acaaattaga aaaaaggatg    1260
gaaaatttaa ataaaaagt tgatgatgga tttctggaca tttggacata taatgcagaa    1320
ttgttagttc tactggaaaa tgaaaggact ctggatttcc atgactcaaa tgtgaagaat    1380
ctgtatgaga agtaaaaag ccaattaaag aataatgcca agaaatcgg aaatggatgt    1440 tttgagttct accacaagtg tgacaatgaa tgcatggaaa gtgtaagaaa tgggacttat    1500
gattatccca aatattcaga agagtcaaag ttgaacaggg aaaggtaga tggagtgaaa    1560 ttggaatcaa tggggatcta tcagattctg gcgatctact caactgtcgc cagttcactg    1620
gtgcttttgg tctccctggg ggcaatcagt tctggatgt gttctaatgg atctttgcag    1680
tgcagaatat gcatctga                                                 1698
```

<210> SEQ ID NO 23
<211> LENGTH: 565
<212> TYPE: PRT
<213> ORGANISM: Homo sapiens

<400> SEQUENCE: 23

```
Met Lys Ala Asn Leu Leu Val Leu Leu Ser Ala Leu Ala Ala Ala Asp
1               5                   10                  15

Ala Asp Thr Ile Cys Ile Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Leu Leu Glu Asp Ser His Asn Gly Lys Leu Cys Arg Leu Lys Gly Ile
        50                  55                  60

Ala Pro Leu Gln Leu Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140
```

```
Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
            165                 170                 175

Leu Lys Asn Ser Tyr Val Asn Lys Lys Gly Lys Glu Val Leu Val Leu
        180                 185                 190

Trp Gly Ile His His Pro Pro Asn Ser Lys Glu Gln Gln Asn Ile Tyr
    195                 200                 205

Gln Asn Glu Asn Ala Tyr Val Ser Val Val Thr Ser Asn Tyr Asn Arg
210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
            245                 250                 255

Ile Phe Glu Ala Asn Gly Asn Leu Ile Ala Pro Met Tyr Ala Phe Ala
        260                 265                 270

Leu Ser Arg Gly Phe Gly Ser Gly Ile Ile Thr Ser Asn Ala Ser Met
    275                 280                 285

His Glu Cys Asn Thr Lys Cys Gln Thr Pro Leu Gly Ala Ile Asn Ser
290                 295                 300

Ser Leu Pro Tyr Gln Asn Ile His Pro Val Thr Ile Gly Glu Cys Pro
305                 310                 315                 320

Lys Tyr Val Arg Ser Ala Lys Leu Arg Met Val Thr Gly Leu Arg Asn
            325                 330                 335

Thr Pro Ser Ile Gln Ser Arg Gly Leu Phe Gly Ala Ile Ala Gly Phe
        340                 345                 350

Ile Glu Gly Gly Trp Thr Gly Met Ile Asp Gly Trp Tyr Gly Tyr His
    355                 360                 365

His Gln Asn Glu Gln Gly Ser Gly Tyr Ala Ala Asp Gln Lys Ser Thr
370                 375                 380

Gln Asn Ala Ile Asn Gly Ile Thr Asn Lys Val Asn Thr Val Ile Glu
385                 390                 395                 400

Lys Met Asn Ile Gln Phe Thr Ala Val Gly Lys Glu Phe Asn Lys Leu
            405                 410                 415

Glu Lys Arg Met Glu Asn Leu Asn Lys Lys Val Asp Asp Gly Phe Leu
        420                 425                 430

Asp Ile Trp Thr Tyr Asn Ala Glu Leu Leu Val Leu Leu Glu Asn Glu
    435                 440                 445

Arg Thr Leu Asp Phe His Asp Ser Asn Val Lys Asn Leu Tyr Glu Lys
450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asn Glu Cys Met Glu Ser Val Arg
            485                 490                 495

Asn Gly Thr Tyr Asp Tyr Pro Lys Tyr Ser Glu Glu Ser Lys Leu Asn
        500                 505                 510

Arg Glu Lys Val Asp Gly Val Lys Leu Glu Ser Met Gly Ile Tyr Gln
    515                 520                 525

Ile Leu Ala Ile Tyr Ser Thr Val Ala Ser Ser Leu Val Leu Leu Val
530                 535                 540

Ser Leu Gly Ala Ile Ser Phe Trp Met Cys Ser Asn Gly Ser Leu Gln
545                 550                 555                 560

Cys Arg Ile Cys Ile
```

<210> SEQ ID NO 24
<211> LENGTH: 501
<212> TYPE: DNA
<213> ORGANISM: Human papillomavirus type 16

<400> SEQUENCE: 24

```
atggcggccc ccggcgcccg gcggccgctg ctcctgctgc tgctggcagg ccttgcacat     60
ggcgcctcag cactctttga ggatctaatc atgcatggag atacacctac attgcatgaa    120
tatatgttag atttgcaacc agagacaact gatctctact gttatgagca attaaatgac    180
agctcagagg aggaggatga aatagatggt ccagctggac aagcagaacc ggacagagcc    240
cattacaata ttgttacctt ttgttgcaag tgtgactcta cgcttcggtt gtgcgtacaa    300
agcacacacg tagacattcg tactttggaa gacctgttaa tgggcacact aggaattgtg    360
tgccccatct gttctcagga tcttaacaac atgttgatcc ccattgctgt gggcggtgcc    420
ctggcagggc tggtcctcat cgtcctcatt gcctacctca ttggcaggaa gaggagtcac    480
gccggctatc agaccatcta g                                              501
```

<210> SEQ ID NO 25
<211> LENGTH: 166
<212> TYPE: PRT
<213> ORGANISM: Human papillomavirus type 16

<400> SEQUENCE: 25

```
Met Ala Ala Pro Gly Ala Arg Arg Pro Leu Leu Leu Leu Leu Leu Ala
  1               5                  10                  15

Gly Leu Ala His Gly Ala Ser Ala Leu Phe Glu Asp Leu Ile Met His
             20                  25                  30

Gly Asp Thr Pro Thr Leu His Glu Tyr Met Leu Asp Leu Gln Pro Glu
         35                  40                  45

Thr Thr Asp Leu Tyr Cys Tyr Glu Gln Leu Asn Asp Ser Ser Glu Glu
     50                  55                  60

Glu Asp Glu Ile Asp Gly Pro Ala Gly Gln Ala Glu Pro Asp Arg Ala
 65                  70                  75                  80

His Tyr Asn Ile Val Thr Phe Cys Cys Lys Cys Asp Ser Thr Leu Arg
                 85                  90                  95

Leu Cys Val Gln Ser Thr His Val Asp Ile Arg Thr Leu Glu Asp Leu
            100                 105                 110

Leu Met Gly Thr Leu Gly Ile Val Cys Pro Ile Cys Ser Gln Asp Leu
        115                 120                 125

Asn Asn Met Leu Ile Pro Ile Ala Val Gly Gly Ala Leu Ala Gly Leu
    130                 135                 140

Val Leu Ile Val Leu Ile Ala Tyr Leu Ile Gly Arg Lys Arg Ser His
145                 150                 155                 160

Ala Gly Tyr Gln Thr Ile
                165
```

<210> SEQ ID NO 26
<211> LENGTH: 5915
<212> TYPE: DNA
<213> ORGANISM: Artificial sequence
<220> FEATURE:
<223> OTHER INFORMATION: synthetic sequence

<400> SEQUENCE: 26

```
gacggatcgg gagatctccc gatccccta t ggtcgactct cagtacaatc tgctctgatg      60
ccgcatagtt aagccagtat ctgctccctg cttgtgtgtt ggaggtcgct gagtagtgcg     120
cgagcaaaat ttaagctaca caaggcaag gcttgaccga caattgcatg aagaatctgc      180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggac tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta acaactccgc cccattgacg caaatgggcg     780
gtaggcgtgt acggtgggag gtctatataa gcagagctct ctggctaact agagaaccca     840
ctgcttactg gcttatcgaa attaatacga ctcactatag ggagacccaa gctggctagc     900
gtttaaacgg gccctctaga ctcgagcggc cgccactgtg ctggatatct gcagaattca     960
tggcggcccc cggcgcccgg cggccgctgc tcctgctgct gctggcaggc cttgcacatg    1020
gcgcctcagc actctttgag gatctaatca tgcatggaga tacacctaca ttgcatgaat    1080
atatgttaga tttgcaacca gagacaactg atctctactg ttatgagcaa ttaaatgaca    1140
gctcagagga ggaggatgaa atagatggtc cagctggaca agcagaaccg gacagagccc    1200
attacaatat tgttaccttt tgttgcaagt gtgactctac gcttcggttg tgcgtacaaa    1260
gcacacacgt agacattcgt actttggaag acctgttaat gggcacacta ggaattgtgt    1320
gccccatctg ttctcaggat cttaacaaca tgttgatccc cattgctgtg ggcggtgccc    1380
tggcagggct ggtcctcatc gtcctcattg cctacctcat tggcaggaag aggagtcacg    1440
ccggctatca gaccatctag ggatccgagc tcggtaccaa gcttaagttt aaaccgctga    1500
tcagcctcga ctgtgccttc tagttgccag ccatctgttg tttgcccctc cccgtgcct     1560 tccttgaccc tggaaggtgc cactcccact gtcctttcct aataaaatga ggaaattgca    1620
tcgcattgtc tgagtaggtg tcattctatt ctggggggtg gggtggggca ggacagcaag    1680
ggggaggatt gggaagacaa tagcaggcat gctggggatg cggtgggctc tatggcttct    1740
gaggcggaaa gaaccagctg gggctctagg gggtatcccc acgcgccctg tagcggcgca    1800
ttaagcgcgg cgggtgtggt ggttacgcgc agcgtgaccg ctacacttgc cagcgcccta    1860
gcgcccgctc ctttcgcttt cttcccttcc tttctcgcca cgttcgccgg ctttccccgt    1920
caagctctaa atcggggcat ccctttaggg ttccgattta gtgctttacg gcacctcgac    1980
cccaaaaaac ttgattaggg tgatggttca cgtagtgggc catcgccctg atagacggtt    2040
tttcgccctt tgacgttgga gtccacgttc tttaatagtg gactcttgtt ccaaactgga    2100
acaacactca accctatctc ggtctattct tttgatttat aagggatttt ggggatttcg    2160
gcctattggt taaaaaatga gctgatttaa caaaaattta cgcgaatta attctgtgga    2220 atgtgtgtca gttagggtgt ggaaagtccc caggctcccc aggcaggcag aagtatgcaa    2280
agcatgcatc tcaattagtc agcaaccagg tgtggaaagt cccaggctc cccagcaggc    2340 agaagtatgc aaagcatgca tctcaattag tcagcaacca tagtcccgcc cctaactccg    2400
```

```
cccatcccgc ccctaactcc gcccagttcc gcccattctc cgccccatgg ctgactaatt    2460
ttttttattt atgcagaggc cgaggccgcc tctgcctctg agctattcca gaagtagtga    2520
ggaggctttt ttggaggcct aggcttttgc aaaaagctcc cgggagcttg tatatccatt    2580
ttcggatctg atcaagagac aggatgagga tcgtttcgca tgattgaaca agatggattg    2640
cacgcaggtt ctccggccgc ttgggtggag aggctattcg gctatgactg ggcacaacag    2700
acaatcggct gctctgatgc cgccgtgttc cggctgtcag cgcaggggcg cccgttctt     2760 tttgtcaaga ccgacctgtc cggtgccctg aatgaactgc aggacgaggc agcgcggcta    2820
tcgtggctgg ccacgacggg cgttccttgc gcagctgtgc tcgacgttgt cactgaagcg    2880
ggaagggact ggctgctatt gggcgaagtg ccggggcagg atctcctgtc atctcacctt    2940
gctcctgccg agaaagtatc catcatggct gatgcaatgc ggcggctgca tacgcttgat    3000
ccggctacct gcccattcga ccaccaagcg aaacatcgca tcgagcgagc acgtactcgg    3060
atggaagccg gtcttgtcga tcaggatgat ctggacgaag agcatcaggg gctcgcgcca    3120
gccgaactgt tcgccaggct caaggcgcgc atgcccgacg gcgaggatct cgtcgtgacc    3180
catggcgatg cctgcttgcc gaatatcatg gtggaaaatg gccgcttttc tggattcatc    3240
gactgtggcc ggctgggtgt ggcggaccgc tatcaggaca tagcgttggc tacccgtgat    3300
attgctgaag agcttggcgg cgaatgggct gaccgcttcc tcgtgcttta cggtatcgcc    3360
gctcccgatt cgcagcgcat cgccttctat cgccttcttg acgagttctt ctgagcggga    3420
ctctggggtt cgaaatgacc gaccaagcga cgcccaacct gccatcacga gatttcgatt    3480
ccaccgccgc cttctatgaa aggttgggct tcggaatcgt tttccgggac gccggctgga    3540
tgatcctcca gcgcgggat ctcatgctgg agttcttcgc ccaccccaac ttgtttattg    3600
cagcttataa tggttacaaa taagcaata gcatcacaaa tttcacaaat aaagcatttt    3660
tttcactgca ttctagttgt ggtttgtcca aactcatcaa tgtatcttat catgtctgta    3720
taccgtcgac ctctagctag agcttggcgt aatcatggtc atagctgttt cctgtgtgaa    3780
attgttatcc gctcacaatt ccacacaaca tacgagccgg aagcataaag tgtaaagcct    3840
ggggtgccta atgagtgagc taactcacat taattgcgtt cgctcactg cccgctttcc    3900 agtcgggaaa cctgtcgtgc cagctgcatt aatgaatcgg ccaacgcgcg gggagaggcg    3960
gtttgcgtat tgggcgctct tccgcttcct cgctcactga ctcgctgcgc tcggtcgttc    4020
ggctgcggcg agcggtatca gctcactcaa aggcggtaat acggttatcc acagaatcag    4080
gggataacgc aggaaagaac atgtgagcaa aaggccagca aaaggccagg aaccgtaaaa    4140
aggccgcgtt gctggcgttt ttccataggc tccgccccc tgacgagcat cacaaaaatc    4200
gacgctcaag tcagaggtgg cgaaacccga caggactata aagataccag gcgtttcccc    4260
ctggaagctc cctcgtgcgc tctcctgttc cgaccctgcc gcttaccgga tacctgtccg    4320
cctttctccc ttcgggaagc gtggcgcttt ctcaatgctc acgctgtagg tatctcagtt    4380
cggtgtaggt cgttcgctcc aagctgggct gtgtgcacga accccccgtt cagcccgacc    4440
gctgcgcctt atccggtaac tatcgtcttg agtccaaccc ggtaagacac gacttatcgc    4500
cactggcagc agccactggt aacaggatta gcagagcgag gtatgtaggc ggtgctacag    4560
agttcttgaa gtggtggcct aactacggct acactagaag gacagtattt ggtatctgcg    4620
ctctgctgaa gccagttacc ttcggaaaaa gagttggtag ctcttgatcc ggcaaacaaa    4680
ccaccgctgg tagcggtggt ttttttgttt gcaagcagca gattacgcgc agaaaaaaag    4740
```

-continued

```
gatctcaaga agatcctttg atcttttcta cggggtctga cgctcagtgg aacgaaaact      4800
cacgttaagg gattttggtc atgagattat caaaaaggat cttcacctag atccttttaa      4860
attaaaaatg aagttttaaa tcaatctaaa gtatatatga gtaaacttgg tctgacagtt      4920
accaatgctt aatcagtgag gcacctatct cagcgatctg tctatttcgt tcatccatag      4980
ttgcctgact ccccgtcgtg tagataacta cgatacggga gggcttacca tctggcccca      5040
gtgctgcaat gataccgcga gacccacgct caccggctcc agatttatca gcaataaacc      5100
agccagccgg aagggccgag cgcagaagtg gtcctgcaac tttatccgcc tccatccagt      5160
ctattaattg ttgccgggaa gctagagtaa gtagttcgcc agttaatagt ttgcgcaacg      5220
ttgttgccat tgctacaggc atcgtggtgt cacgctcgtc gtttggtatg gcttcattca      5280
gctccggttc ccaacgatca aggcgagtta catgatcccc catgttgtgc aaaaaagcgg      5340
ttagctcctt cggtcctccg atcgttgtca gaagtaagtt ggccgcagtg ttatcactca      5400
tggttatggc agcactgcat aattctctta ctgtcatgcc atccgtaaga tgcttttctg      5460
tgactggtga gtactcaacc aagtcattct gagaatagtg tatgcggcga ccgagttgct      5520
cttgcccggc gtcaatacgg gataataccg cgccacatag cagaacttta aaagtgctca      5580
tcattggaaa acgttcttcg gggcgaaaac tctcaaggat cttaccgctg ttgagatcca      5640
gttcgatgta acccactcgt gcacccaact gatcttcagc atctttact ttcaccagcg      5700
tttctgggtg agcaaaaaca ggaaggcaaa atgccgcaaa aaagggaata agggcgacac      5760
ggaaatgttg aatactcata ctcttccttt ttcaatatta ttgaagcatt tatcagggtt      5820
attgtctcat gagcggatac atatttgaat gtatttagaa aaataaacaa ataggggttc      5880
cgcgcacatt tccccgaaaa gtgccacctg acgtc                                 5915
```

```
<210> SEQ ID NO 27
<211> LENGTH: 1878
<212> TYPE: DNA
<213> ORGANISM: Mycobacterium tuberculosis
<400> SEQUENCE: 27
atggctcgtg cggtcgggat cgacctcggg accaccaact ccgtcgtctc ggttctggaa        60
ggtggcgacc cggtcgtcgt cgccaactcc gagggctcca ggaccacccc gtcaattgtc       120
gcgttcgccc gcaacggtga ggtgctggtc ggccagcccg ccaagaacca ggcagtgacc       180
aacgtcgatc gcaccgtgcg ctcggtcaag cgacacatgg gcagcgactg gtccatagag       240
attgacggca gaaatacacc cgcgccgag atcagcgccc gcattctgat gaagctgaag        300
cgcgacgccg aggcctacct cggtgaggac attaccgacg cggttatcac gacgcccgcc       360
tacttcaatg acgcccagcg tcaggccacc aaggacgccg ccagatcgc cggcctcaac        420
gtgctgcgga tcgtcaacga gccgaccgcg gccgcgctgg cctacggcct cgacaagggc       480
gagaaggagc agcgaatcct ggtcttcgac ttgggtggtg gcactttcga cgtttccctg       540
ctggagatcg gcgagggtgt ggttgaggtc cgtgccactt cgggtgacaa ccacctcggc       600
ggcgacgact gggaccagcg ggtcgtcgat ggctggtgg acaagttcaa gggcaccagc       660
ggcatcgatc tgaccaagga caagatgcg atgcagcggc tgcgggaagc cgccgagaag        720
gcaaagatcg agctgagttc gagtcagtcc acctcgatca acctgccctta catcaccgtc      780
gacgccgaca gaacccgtt gttcttagac gagcagctga cccgcgcgga gttccaacgg        840
atcactcagg acctgctgga ccgcactcgc aagccgttcc agtcggtgat cgctgacacc       900
ggcatttcgg tgtcggagat cgatcacgtt gtgctcgtgg gtggttcgac ccggatgccc       960
```

-continued

```
gcggtgaccg atctggtcaa ggaactcacc ggcggcaagg aacccaacaa gggcgtcaac    1020
cccgatgagg ttgtcgcggt gggagccgct ctgcaggccg cgtcctcaa gggcgaggtg     1080 aaagacgttc tgctgcttga tgttacccg ctgagcctgg gtatcgagac caagggcggg     1140
gtgatgacca ggctcatcga gcgcaacacc acgatcccca ccaagcggtc ggagactttc    1200
accaccgccg acgacaacca accgtcggtg cagatccagg tctatcaggg ggagcgtgag    1260
atcgccgcgc acaacaagtt gctcgggtcc ttcgagctga ccggcatccc gccggcgccg    1320
cgggggattc cgcagatcga ggtcactttc gacatcgacg ccaacggcat tgtgcacgtc    1380
accgccaagg acaagggcac cggcaaggag aacacgatcc gaatccagga aggctcgggc    1440
ctgtccaagg aagacattga ccgcatgatc aaggacgccg aagcgcacgc cgaggaggat    1500
cgcaagcgtc gcgaggaggc cgatgttcgt aatcaagccg agacattggt ctaccagacg    1560
gagaagttcg tcaaagaaca gcgtgaggcc gagggtggtt cgaaggtacc tgaagacacg    1620
ctgaacaagg ttgatgccgc ggtggcggaa gcgaaggcgg cacttggcgg atcggatatt    1680
tcggccatca agtcggcgat ggagaagctg gccaggagt cgcaggctct ggggcaagcg     1740
atctacgaag cagctcaggc tgcgtcacag gccactggcg ctgcccaccc cggcggcgag    1800
ccgggcggtg cccaccccgg ctcggctgat gacgttgtgg acgcggaggt ggtcgacgac    1860
ggccgggagg ccaagtga                                                  1878
```

```
<210> SEQ ID NO 28
<211> LENGTH: 625
<212> TYPE: PRT
<213> ORGANISM: Mycobacterium tuberculosis

<400> SEQUENCE: 28

Met Ala Arg Ala Val Gly Ile Asp Leu Gly Thr Thr Asn Ser Val Val
1               5                   10                  15

Ser Val Leu Glu Gly Gly Asp Pro Val Val Ala Asn Ser Glu Gly
            20                  25                  30

Ser Arg Thr Thr Pro Ser Ile Val Ala Phe Ala Arg Asn Gly Glu Val
        35                  40                  45

Leu Val Gly Gln Pro Ala Lys Asn Gln Ala Val Thr Asn Val Asp Arg
    50                  55                  60

Thr Val Arg Ser Val Lys Arg His Met Gly Ser Asp Trp Ser Ile Glu
65                  70                  75                  80

Ile Asp Gly Lys Lys Tyr Thr Ala Pro Glu Ile Ser Ala Arg Ile Leu
                85                  90                  95

Met Lys Leu Lys Arg Asp Ala Glu Ala Tyr Leu Gly Glu Asp Ile Thr
            100                 105                 110

Asp Ala Val Ile Thr Thr Pro Ala Tyr Phe Asn Asp Ala Gln Arg Gln
        115                 120                 125

Ala Thr Lys Asp Ala Gly Gln Ile Ala Gly Leu Asn Val Leu Arg Ile
    130                 135                 140

Val Asn Glu Pro Thr Ala Ala Ala Leu Ala Tyr Gly Leu Asp Lys Gly
145                 150                 155                 160

Glu Lys Glu Gln Arg Ile Leu Val Phe Asp Leu Gly Gly Gly Thr Phe
                165                 170                 175

Asp Val Ser Leu Leu Glu Ile Gly Glu Gly Val Val Glu Val Arg Ala
            180                 185                 190

Thr Ser Gly Asp Asn His Leu Gly Gly Asp Asp Trp Asp Gln Arg Val
        195                 200                 205
```

```
Val Asp Trp Leu Val Asp Lys Phe Lys Gly Thr Ser Gly Ile Asp Leu
    210                 215                 220

Thr Lys Asp Lys Met Ala Met Gln Arg Leu Arg Glu Ala Ala Glu Lys
225                 230                 235                 240

Ala Lys Ile Glu Leu Ser Ser Ser Gln Ser Thr Ser Ile Asn Leu Pro
                    245                 250                 255

Tyr Ile Thr Val Asp Ala Asp Lys Asn Pro Leu Phe Leu Asp Glu Gln
                260                 265                 270

Leu Thr Arg Ala Glu Phe Gln Arg Ile Thr Gln Asp Leu Leu Asp Arg
            275                 280                 285

Thr Arg Lys Pro Phe Gln Ser Val Ile Ala Asp Thr Gly Ile Ser Val
        290                 295                 300

Ser Glu Ile Asp His Val Val Leu Val Gly Gly Ser Thr Arg Met Pro
305                 310                 315                 320

Ala Val Thr Asp Leu Val Lys Glu Leu Thr Gly Gly Lys Glu Pro Asn
                    325                 330                 335

Lys Gly Val Asn Pro Asp Glu Val Val Ala Val Gly Ala Ala Leu Gln
                340                 345                 350

Ala Gly Val Leu Lys Gly Glu Val Lys Asp Val Leu Leu Leu Asp Val
            355                 360                 365

Thr Pro Leu Ser Leu Gly Ile Glu Thr Lys Gly Gly Val Met Thr Arg
        370                 375                 380

Leu Ile Glu Arg Asn Thr Thr Ile Pro Thr Lys Arg Ser Glu Thr Phe
385                 390                 395                 400

Thr Thr Ala Asp Asp Asn Gln Pro Ser Val Gln Ile Gln Val Tyr Gln
                    405                 410                 415

Gly Glu Arg Glu Ile Ala Ala His Asn Lys Leu Leu Gly Ser Phe Glu
                420                 425                 430

Leu Thr Gly Ile Pro Pro Ala Pro Arg Gly Ile Pro Gln Ile Glu Val
            435                 440                 445

Thr Phe Asp Ile Asp Ala Asn Gly Ile Val His Val Thr Ala Lys Asp
        450                 455                 460

Lys Gly Thr Gly Lys Glu Asn Thr Ile Arg Ile Gln Glu Gly Ser Gly
465                 470                 475                 480

Leu Ser Lys Glu Asp Ile Asp Arg Met Ile Lys Asp Ala Glu Ala His
                    485                 490                 495

Ala Glu Glu Asp Arg Lys Arg Glu Glu Ala Asp Val Arg Asn Gln
                500                 505                 510

Ala Glu Thr Leu Val Tyr Gln Thr Glu Lys Phe Val Lys Glu Gln Arg
            515                 520                 525

Glu Ala Glu Gly Gly Ser Lys Val Pro Glu Asp Thr Leu Asn Lys Val
        530                 535                 540

Asp Ala Ala Val Ala Glu Ala Lys Ala Ala Leu Gly Gly Ser Asp Ile
545                 550                 555                 560

Ser Ala Ile Lys Ser Ala Met Glu Lys Leu Gly Gln Glu Ser Gln Ala
                    565                 570                 575

Leu Gly Gln Ala Ile Tyr Glu Ala Ala Gln Ala Ser Gln Ala Thr
                580                 585                 590

Gly Ala Ala His Pro Gly Gly Glu Pro Gly Gly Ala His Pro Gly Ser
            595                 600                 605

Ala Asp Asp Val Val Asp Ala Glu Val Val Asp Gly Arg Glu Ala
        610                 615                 620
```

Lys
625

<210> SEQ ID NO 29
<211> LENGTH: 2104
<212> TYPE: DNA
<213> ORGANISM: Artificial sequence
<220> FEATURE:
<223> OTHER INFORMATION: synthetic sequence
<220> FEATURE:
<221> NAME/KEY: CDS
<222> LOCATION: (1)..(2103)

<400> SEQUENCE: 29

```
atg cat gga gat aca cct aca ttg cat gaa tat atg tta gat ttg caa      48
Met His Gly Asp Thr Pro Thr Leu His Glu Tyr Met Leu Asp Leu Gln
1               5                   10                  15 cca gag aca act gat ctc tac tgt tat gag caa tta aat gac agc tca      96
Pro Glu Thr Thr Asp Leu Tyr Cys Tyr Glu Gln Leu Asn Asp Ser Ser
            20                  25                  30 gag gag gag gat gaa ata gat ggt cca gct gga caa gca gaa ccg gac     144
Glu Glu Glu Asp Glu Ile Asp Gly Pro Ala Gly Gln Ala Glu Pro Asp
        35                  40                  45 aga gcc cat tac aat att gta acc ttt tgt tgc aag tgt gac tct acg     192
Arg Ala His Tyr Asn Ile Val Thr Phe Cys Cys Lys Cys Asp Ser Thr
    50                  55                  60 ctt cgg ttg tgc gta caa agc aca cac gta gac att cgt act ttg gaa     240
Leu Arg Leu Cys Val Gln Ser Thr His Val Asp Ile Arg Thr Leu Glu
65                  70                  75                  80 gac ctg tta atg ggc aca cta gga att gtg tgc ccc atc tgt tct caa     288
Asp Leu Leu Met Gly Thr Leu Gly Ile Val Cys Pro Ile Cys Ser Gln
                85                  90                  95 gga tcc atg gct cgt gcg gtc ggg atc gac ctc ggg acc acc aac tcc     336
Gly Ser Met Ala Arg Ala Val Gly Ile Asp Leu Gly Thr Thr Asn Ser
            100                 105                 110 gtc gtc tcg gtt ctg gaa ggt ggc gac ccg gtc gtc gtc gcc aac tcc     384
Val Val Ser Val Leu Glu Gly Gly Asp Pro Val Val Val Ala Asn Ser
        115                 120                 125 gag ggc tcc agg acc acc ccg tca att gtc gcg ttc gcc cgc aac ggt     432
Glu Gly Ser Arg Thr Thr Pro Ser Ile Val Ala Phe Ala Arg Asn Gly
    130                 135                 140 gag gtg ctg gtc ggc cag ccc gcc aag aac cag gca gtg acc aac gtc     480
Glu Val Leu Val Gly Gln Pro Ala Lys Asn Gln Ala Val Thr Asn Val
145                 150                 155                 160 gat cgc acc gtg cgc tcg gtc aag cga cac atg ggc agc gac tgg tcc     528
Asp Arg Thr Val Arg Ser Val Lys Arg His Met Gly Ser Asp Trp Ser
                165                 170                 175 ata gag att gac ggc aag aaa tac acc gcg ccg gag atc agc gcc cgc     576
Ile Glu Ile Asp Gly Lys Lys Tyr Thr Ala Pro Glu Ile Ser Ala Arg
            180                 185                 190 att ctg atg aag ctg aag cgc gac gcc gag gcc tac ctc ggt gag gac     624
Ile Leu Met Lys Leu Lys Arg Asp Ala Glu Ala Tyr Leu Gly Glu Asp
        195                 200                 205 att acc gac gcg gtt atc acg acg ccc gcc tac ttc aat gac gcc cag     672
Ile Thr Asp Ala Val Ile Thr Thr Pro Ala Tyr Phe Asn Asp Ala Gln
    210                 215                 220 cgt cag gcc acc aag gac gcc ggc cag atc gcc ggc ctc aac gtg ctg     720
Arg Gln Ala Thr Lys Asp Ala Gly Gln Ile Ala Gly Leu Asn Val Leu
225                 230                 235                 240 cgg atc gtc aac gag ccg acc gcg gcc gcg ctg gcc tac ggc ctc gac     768
Arg Ile Val Asn Glu Pro Thr Ala Ala Ala Leu Ala Tyr Gly Leu Asp
                245                 250                 255
```

-continued

| | | |
|---|---|---|
| aag ggc gag aag gag cag cga atc ctg gtc ttc gac ttg ggt ggt ggc<br>Lys Gly Glu Lys Glu Gln Arg Ile Leu Val Phe Asp Leu Gly Gly Gly<br>260                          265                     270 | 816 | |
| act ttc gac gtt tcc ctg ctg gag atc ggc gag ggt gtg gtt gag gtc<br>Thr Phe Asp Val Ser Leu Leu Glu Ile Gly Glu Gly Val Val Glu Val<br>275                         280                     285 | 864 | |
| cgt gcc act tcg ggt gac aac cac ctc ggc ggc gac gac tgg gac cag<br>Arg Ala Thr Ser Gly Asp Asn His Leu Gly Gly Asp Asp Trp Asp Gln<br>290                         295                     300 | 912 | |
| cgg gtc gtc gat tgg ctg gtg gac aag ttc aag ggc acc agc ggc atc<br>Arg Val Val Asp Trp Leu Val Asp Lys Phe Lys Gly Thr Ser Gly Ile<br>305                   310                     315                     320 | 960 | |
| gat ctg acc aag gac aag atg gcg atg cag cgg ctg cgg gaa gcc gcc<br>Asp Leu Thr Lys Asp Lys Met Ala Met Gln Arg Leu Arg Glu Ala Ala<br>                     325                     330                     335 | 1008 | |
| gag aag gca aag atc gag ctg agt tcg agt cag tcc acc tcg atc aac<br>Glu Lys Ala Lys Ile Glu Leu Ser Ser Ser Gln Ser Thr Ser Ile Asn<br>                 340                     345                     350 | 1056 | |
| ctg ccc tac atc acc gtc gac gcc gac aag aac ccg ttg ttc tta gac<br>Leu Pro Tyr Ile Thr Val Asp Ala Asp Lys Asn Pro Leu Phe Leu Asp<br>                     355                     360                     365 | 1104 | |
| gag cag ctg acc cgc gcg gag ttc caa cgg atc act cag gac ctg ctg<br>Glu Gln Leu Thr Arg Ala Glu Phe Gln Arg Ile Thr Gln Asp Leu Leu<br>370                         375                     380 | 1152 | |
| gac cgc act cgc aag ccg ttc cag tcg gtg atc gct gac acc ggc att<br>Asp Arg Thr Arg Lys Pro Phe Gln Ser Val Ile Ala Asp Thr Gly Ile<br>385                   390                     395                     400 | 1200 | |
| tcg gtg tcg gag atc gat cac gtt gtg ctc gtg ggt ggt tcg acc cgg<br>Ser Val Ser Glu Ile Asp His Val Val Leu Val Gly Gly Ser Thr Arg<br>                     405                     410                     415 | 1248 | |
| atg ccc gcg gtg acc gat ctg gtc aag gaa ctc acc ggc ggc aag gaa<br>Met Pro Ala Val Thr Asp Leu Val Lys Glu Leu Thr Gly Gly Lys Glu<br>                 420                     425                     430 | 1296 | |
| ccc aac aag ggc gtc aac ccc gat gag gtt gtc gcg gtg gga gcc gct<br>Pro Asn Lys Gly Val Asn Pro Asp Glu Val Val Ala Val Gly Ala Ala<br>                 435                     440                     445 | 1344 | |
| ctg cag gcc ggc gtc ctc aag ggc gag gtg aaa gac gtt ctg ctg ctt<br>Leu Gln Ala Gly Val Leu Lys Gly Glu Val Lys Asp Val Leu Leu Leu<br>450                         455                     460 | 1392 | |
| gat gtt acc ccg ctg agc ctg ggt atc gag acc aag ggc ggg gtg atg<br>Asp Val Thr Pro Leu Ser Leu Gly Ile Glu Thr Lys Gly Gly Val Met<br>465                   470                     475                     480 | 1440 | |
| acc agg ctc atc gag cgc aac acc acg atc ccc acc aag cgg tcg gag<br>Thr Arg Leu Ile Glu Arg Asn Thr Thr Ile Pro Thr Lys Arg Ser Glu<br>                     485                     490                     495 | 1488 | |
| act ttc acc acc gcc gac gac aac caa ccg tcg gtg cag atc cag gtc<br>Thr Phe Thr Thr Ala Asp Asp Asn Gln Pro Ser Val Gln Ile Gln Val<br>                 500                     505                     510 | 1536 | |
| tat cag ggg gag cgt gag atc gcc gcg cac aac aag ttg ctc ggg tcc<br>Tyr Gln Gly Glu Arg Glu Ile Ala Ala His Asn Lys Leu Leu Gly Ser<br>                 515                     520                     525 | 1584 | |
| ttc gag ctg acc ggc atc ccg ccg gcg ccg cgg ggg att ccg cag atc<br>Phe Glu Leu Thr Gly Ile Pro Pro Ala Pro Arg Gly Ile Pro Gln Ile<br>530                         535                     540 | 1632 | |
| gag gtc act ttc gac atc gac gcc aac ggc att gtg cac gtc acc gcc<br>Glu Val Thr Phe Asp Ile Asp Ala Asn Gly Ile Val His Val Thr Ala<br>545                   550                     555                     560 | 1680 | |
| aag gac aag ggc acc ggc aag gag aac acg atc cga atc cag gaa ggc<br>Lys Asp Lys Gly Thr Gly Lys Glu Asn Thr Ile Arg Ile Gln Glu Gly | 1728 | |

```
                    565                    570                     575
tcg ggc ctg tcc aag gaa gac att gac cgc atg atc aag gac gcc gaa      1776
Ser Gly Leu Ser Lys Glu Asp Ile Asp Arg Met Ile Lys Asp Ala Glu
            580                     585                     590 gcg cac gcc gag gag gat cgc aag cgt cgc gag gag gcc gat gtt cgt      1824
Ala His Ala Glu Glu Asp Arg Lys Arg Arg Glu Glu Ala Asp Val Arg
        595                     600                     605 aat caa gcc gag aca ttg gtc tac cag acg gag aag ttc gtc aaa gaa      1872
Asn Gln Ala Glu Thr Leu Val Tyr Gln Thr Glu Lys Phe Val Lys Glu
    610                     615                     620 cag cgt gag gcc gag ggt ggt tcg aag gta cct gaa gac acg ctg aac      1920
Gln Arg Glu Ala Glu Gly Gly Ser Lys Val Pro Glu Asp Thr Leu Asn
625                     630                     635                 640 aag gtt gat gcc gcg gtg gcg gaa gcg aag gcg gca ctt ggc gga tcg      1968
Lys Val Asp Ala Ala Val Ala Glu Ala Lys Ala Ala Leu Gly Gly Ser
                645                     650                     655 gat att tcg gcc atc aag tcg gcg atg gag aag ctg ggc cag gag tcg      2016
Asp Ile Ser Ala Ile Lys Ser Ala Met Glu Lys Leu Gly Gln Glu Ser
            660                     665                     670 cag gct ctg ggg caa gcg atc tac gaa gca gct cag gct gcg tca cag      2064
Gln Ala Leu Gly Gln Ala Ile Tyr Glu Ala Ala Gln Ala Ala Ser Gln
        675                     680                     685 gcc act ggc gct gcc cac ccc ggc tcg gct gat gaa agc a                2104
Ala Thr Gly Ala Ala His Pro Gly Ser Ala Asp Glu Ser
    690                     695                     700

<210> SEQ ID NO 30
<211> LENGTH: 701
<212> TYPE: PRT
<213> ORGANISM: Artificial sequence
<220> FEATURE:
<223> OTHER INFORMATION: Synthetic Construct

<400> SEQUENCE: 30

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Gly Ser Met Ala Arg Ala Val Gly Ile Asp Leu Gly Thr Thr Asn Ser
            100                 105                 110

Val Val Ser Val Leu Glu Gly Gly Asp Pro Val Val Ala Asn Ser
        115                 120                 125

Glu Gly Ser Arg Thr Thr Pro Ser Ile Val Ala Phe Ala Arg Asn Gly
    130                 135                 140

Glu Val Leu Val Gly Gln Pro Ala Lys Asn Gln Ala Val Thr Asn Val
145                 150                 155                 160

Asp Arg Thr Val Arg Ser Val Lys Arg His Met Gly Ser Asp Trp Ser
                165                 170                 175

Ile Glu Ile Asp Gly Lys Lys Tyr Thr Ala Pro Glu Ile Ser Ala Arg
            180                 185                 190
```

```
Ile Leu Met Lys Leu Lys Arg Asp Ala Glu Ala Tyr Leu Gly Glu Asp
        195                 200                 205

Ile Thr Asp Ala Val Ile Thr Thr Pro Ala Tyr Phe Asn Asp Ala Gln
210                     215                 220

Arg Gln Ala Thr Lys Asp Ala Gly Gln Ile Ala Gly Leu Asn Val Leu
225                 230                 235                 240

Arg Ile Val Asn Glu Pro Thr Ala Ala Leu Ala Tyr Gly Leu Asp
                245                 250                 255

Lys Gly Glu Lys Glu Gln Arg Ile Leu Val Phe Asp Leu Gly Gly Gly
                260                 265                 270

Thr Phe Asp Val Ser Leu Leu Glu Ile Gly Glu Gly Val Val Glu Val
        275                 280                 285

Arg Ala Thr Ser Gly Asp Asn His Leu Gly Gly Asp Asp Trp Asp Gln
290                 295                 300

Arg Val Val Asp Trp Leu Val Asp Lys Phe Lys Gly Thr Ser Gly Ile
305                 310                 315                 320

Asp Leu Thr Lys Asp Lys Met Ala Met Gln Arg Leu Arg Glu Ala Ala
                325                 330                 335

Glu Lys Ala Lys Ile Glu Leu Ser Ser Ser Gln Ser Thr Ser Ile Asn
        340                 345                 350

Leu Pro Tyr Ile Thr Val Asp Ala Asp Lys Asn Pro Leu Phe Leu Asp
        355                 360                 365

Glu Gln Leu Thr Arg Ala Glu Phe Gln Arg Ile Thr Gln Asp Leu Leu
        370                 375                 380

Asp Arg Thr Arg Lys Pro Phe Gln Ser Val Ile Ala Asp Thr Gly Ile
385                 390                 395                 400

Ser Val Ser Glu Ile Asp His Val Val Leu Val Gly Gly Ser Thr Arg
                405                 410                 415

Met Pro Ala Val Thr Asp Leu Val Lys Glu Leu Thr Gly Gly Lys Glu
                420                 425                 430

Pro Asn Lys Gly Val Asn Pro Asp Glu Val Val Ala Val Gly Ala Ala
        435                 440                 445

Leu Gln Ala Gly Val Leu Lys Gly Glu Val Lys Asp Val Leu Leu Leu
        450                 455                 460

Asp Val Thr Pro Leu Ser Leu Gly Ile Glu Thr Lys Gly Gly Val Met
465                 470                 475                 480

Thr Arg Leu Ile Glu Arg Asn Thr Thr Ile Pro Thr Lys Arg Ser Glu
                485                 490                 495

Thr Phe Thr Thr Ala Asp Asp Asn Gln Pro Ser Val Gln Ile Gln Val
                500                 505                 510

Tyr Gln Gly Glu Arg Glu Ile Ala Ala His Asn Lys Leu Leu Gly Ser
        515                 520                 525

Phe Glu Leu Thr Gly Ile Pro Pro Ala Pro Arg Gly Ile Pro Gln Ile
530                 535                 540

Glu Val Thr Phe Asp Ile Asp Ala Asn Gly Ile Val His Val Thr Ala
545                 550                 555                 560

Lys Asp Lys Gly Thr Gly Lys Glu Asn Thr Ile Arg Ile Gln Glu Gly
                565                 570                 575

Ser Gly Leu Ser Lys Glu Asp Ile Asp Arg Met Ile Lys Asp Ala Glu
                580                 585                 590

Ala His Ala Glu Glu Asp Arg Lys Arg Glu Glu Ala Asp Val Arg
        595                 600                 605
```

```
Asn Gln Ala Glu Thr Leu Val Tyr Gln Thr Glu Lys Phe Val Lys Glu
        610                 615                 620

Gln Arg Glu Ala Glu Gly Gly Ser Lys Val Pro Glu Asp Thr Leu Asn
625                 630                 635                 640

Lys Val Asp Ala Val Ala Glu Ala Lys Ala Leu Gly Gly Ser
                645                 650                 655

Asp Ile Ser Ala Ile Lys Ser Ala Met Glu Lys Leu Gly Gln Glu Ser
                660                 665                 670

Gln Ala Leu Gly Gln Ala Ile Tyr Glu Ala Ala Gln Ala Ser Gln
        675                 680                 685

Ala Thr Gly Ala Ala His Pro Gly Ser Ala Asp Glu Ser
690                 695                 700
```

<210> SEQ ID NO 31
<211> LENGTH: 2760
<212> TYPE: DNA
<213> ORGANISM: Pseudomonas aeruginosa

<400> SEQUENCE: 31

```
ctgcagctgg tcaggccgtt tccgcaacgc ttgaagtcct ggccgatata ccggcagggc        60
cagccatcgt tcgacgaata aagccacctc agccatgatg cccttttccat ccccagcgga      120
accccgacat ggacgccaaa gccctgctcc tcggcagcct ctgcctggcc gccccattcg       180
ccgacgcggc gacgctcgac aatgctctct ccgcctgcct cgccgcccgg ctcggtgcac       240
cgcacacggc ggagggccag ttgcacctgc cactcaccct tgaggcccgg cgctccaccg       300
gcgaatgcgg ctgtacctcg gcgctggtgc gatatcggct gctggccagg gcgccagcg       360
ccgacagcct cgtgcttcaa gagggctgct cgatagtcgc caggacacgc gcgcacgct       420
gaccctggcg gcggacgccg gcttggcgag cggccgcgaa ctggtcgtca ccctgggttg       480
tcaggcgcct gactgacagg ccgggctgcc accaccaggc cgagatggac gccctgcatg       540
tatcctccga tcgcaagcc tcccgttcgc acattcacca ctctgcaatc cagttcataa       600
atcccataaa agccctcttc cgctccccgc cagcctcccc gcatcccgca ccctagacgc       660
cccgccgctc tccgccggct cgcccgacaa gaaaaaccaa ccgctcgatc agcctcatcc       720
ttcacccatc acaggagcca tcgcgatgca cctgataccc cattggatcc ccctggtcgc       780
cagcctcggc ctgctcgcg gcggctcgtc gcgtccgcc gccgaggaag ccttcgacct       840
ctggaacgaa tgcgccaaag cctgcgtgct cgacctcaag gacggcgtgc gttccagccg       900
catgagcgtc gacccggcca tcgccgacac caacggccag ggcgtgctgc actactccat       960
ggtcctggag ggcggcaacg acgcgctcaa gctggccatc gacaacgccc tcagcatcac      1020
cagcgacggc ctgaccatcc gcctcgaagg cggcgtcgag ccgaacaagc cggtgcgcta      1080
cagctacacg cgccaggcgc gcggcagttg gtcgctgaac tggctggtac cgatcggcca      1140
cgagaagccc tcgaacatca aggtgttcat ccacgaactg aacgccggca accagctcag      1200
ccacatgtcg ccgatctaca ccatcgagat gggcgacgag ttgctggcga agctggcgcg      1260
cgatgccacc ttcttcgtca gggcgcacga gagcaacgag atgcagccga cgctcgccat      1320
cagccatgcc ggggtcagcg tggtcatggc ccagacccag ccgcgccggg aaaagcgctg      1380
gagcgaatgg gccagcggca aggtgttgtg cctgctcgac ccgctggacg gggtctacaa      1440
ctacctcgcc cagcaacgct gcaacctcga cgatacctgg aaggcaaga tctaccgggt      1500
gctcgccgg aaccccggcga agcatgacct ggacatcaaa cccacggtca tcagtcatcg      1560
cctgcacttt cccgagggcg gcagcctggc cgcgctgacc gcgcaccagg cttgccacct      1620
```

-continued

```
gccgctggag actttcaccc gtcatcgcca gccgcgcggc tgggaacaac tggagcagtg   1680
cggctatccg gtgcagcggc tggtcgccct ctacctggcg gcgcggctgt cgtggaacca   1740
ggtcgaccag gtgatccgca acgccctggc cagccccggc agcggcggcg acctgggcga   1800
agcgatccgc gagcagccgg agcaggcccg tctggccctg accctggccg ccgccgagag   1860
cgagcgcttc gtccggcagg gcaccggcaa cgacgaggcc ggcgcggcca acgccgacgt   1920
ggtgagcctg acctgcccgg tcgccgccgg tgaatgcgcg ggcccggcgg acagcggcga   1980
cgccctgctg gagcgcaact atcccactgg cgcggagttc ctcggcgacg gcggcgacgt   2040
cagcttcagc acccgcggca cgcagaactg gacggtggag cggctgctcc aggcgcaccg   2100
ccaactggag gagcgcggct atgtgttcgt cggctaccac ggcaccttcc tcgaagcggc   2160
gcaaagcatc gtcttcggcg gggtgcgcgc gcgcagccag gacctcgacg cgatctggcg   2220
cggtttctat atcgccggcg atccggcgct ggcctacggc tacgcccagg accaggaacc   2280
cgacgcacgc ggccggatcc gcaacggtgc cctgctgcgg gtctatgtgc cgcgctcgag   2340
cctgccgggc ttctaccgca ccagcctgac cctggccgcg ccggaggcgg cgggcgaggt   2400
cgaacggctg atcggccatc cgctgccgct gcgcctggac gccatcaccg gccccgagga   2460
ggaaggcggg cgcctggaga ccattctcgg ctggccgctg gccgagcgca ccgtggtgat   2520
tccctcggcg atccccaccg acccgcgcaa cgtcggcggc gacctcgacc cgtccagcat   2580
ccccgacaag gaacaggcga tcagcgccct gccggactac gccagccagc ccggcaaacc   2640
gccgcgcgag gacctgaagt aactgccgcg accggccggc tcccttcgca ggagccggcc   2700
ttctcggggc ctggccatac atcaggtttt cctgatgcca gcccaatcga atatgaattc   2760
```

<210> SEQ ID NO 32
<211> LENGTH: 638
<212> TYPE: PRT
<213> ORGANISM: Pseudomonas aeruginosa

<400> SEQUENCE: 32

```
Met His Leu Ile Pro His Trp Ile Pro Leu Val Ala Ser Leu Gly Leu
1               5                   10                  15

Leu Ala Gly Gly Ser Ser Ala Ser Ala Ala Glu Glu Ala Phe Asp Leu
            20                  25                  30

Trp Asn Glu Cys Ala Lys Ala Cys Val Leu Asp Leu Lys Asp Gly Val
        35                  40                  45

Arg Ser Ser Arg Met Ser Val Asp Pro Ala Ile Ala Asp Thr Asn Gly
    50                  55                  60

Gln Gly Val Leu His Tyr Ser Met Val Leu Glu Gly Gly Asn Asp Ala
65                  70                  75                  80

Leu Lys Leu Ala Ile Asp Asn Ala Leu Ser Ile Thr Ser Asp Gly Leu
                85                  90                  95

Thr Ile Arg Leu Glu Gly Gly Val Glu Pro Asn Lys Pro Val Arg Tyr
            100                 105                 110

Ser Tyr Thr Arg Gln Ala Arg Gly Ser Trp Ser Leu Asn Trp Leu Val
        115                 120                 125

Pro Ile Gly His Glu Lys Pro Ser Asn Ile Lys Val Phe Ile His Glu
    130                 135                 140

Leu Asn Ala Gly Asn Gln Leu Ser His Met Ser Pro Ile Tyr Thr Ile
145                 150                 155                 160

Glu Met Gly Asp Glu Leu Leu Ala Lys Leu Ala Arg Asp Ala Thr Phe
                165                 170                 175
```

```
Phe Val Arg Ala His Glu Ser Asn Glu Met Gln Pro Thr Leu Ala Ile
                180                 185                 190

Ser His Ala Gly Val Ser Val Met Ala Gln Thr Gln Pro Arg Arg
            195                 200                 205

Glu Lys Arg Trp Ser Glu Trp Ala Ser Gly Lys Val Leu Cys Leu Leu
        210                 215                 220

Asp Pro Leu Asp Gly Val Tyr Asn Tyr Leu Ala Gln Gln Arg Cys Asn
225                 230                 235                 240

Leu Asp Asp Thr Trp Glu Gly Lys Ile Tyr Arg Val Leu Ala Gly Asn
                245                 250                 255

Pro Ala Lys His Asp Leu Asp Ile Lys Pro Thr Val Ile Ser His Arg
            260                 265                 270

Leu His Phe Pro Glu Gly Gly Ser Leu Ala Ala Leu Thr Ala His Gln
        275                 280                 285

Ala Cys His Leu Pro Leu Glu Thr Phe Thr Arg His Arg Gln Pro Arg
    290                 295                 300

Gly Trp Glu Gln Leu Glu Gln Cys Gly Tyr Pro Val Gln Arg Leu Val
305                 310                 315                 320

Ala Leu Tyr Leu Ala Ala Arg Leu Ser Trp Asn Gln Val Asp Gln Val
                325                 330                 335

Ile Arg Asn Ala Leu Ala Ser Pro Gly Ser Gly Gly Asp Leu Gly Glu
            340                 345                 350

Ala Ile Arg Glu Gln Pro Glu Gln Ala Arg Leu Ala Leu Thr Leu Ala
        355                 360                 365

Ala Ala Glu Ser Glu Arg Phe Val Arg Gln Gly Thr Gly Asn Asp Glu
370                 375                 380

Ala Gly Ala Ala Asn Ala Asp Val Val Ser Leu Thr Cys Pro Val Ala
385                 390                 395                 400

Ala Gly Glu Cys Ala Gly Pro Ala Asp Ser Gly Asp Ala Leu Leu Glu
                405                 410                 415

Arg Asn Tyr Pro Thr Gly Ala Glu Phe Leu Gly Asp Gly Asp Val
            420                 425                 430

Ser Phe Ser Thr Arg Gly Thr Gln Asn Trp Thr Val Glu Arg Leu Leu
        435                 440                 445

Gln Ala His Arg Gln Leu Glu Glu Arg Gly Tyr Val Phe Val Gly Tyr
    450                 455                 460

His Gly Thr Phe Leu Glu Ala Ala Gln Ser Ile Val Phe Gly Gly Val
465                 470                 475                 480

Arg Ala Arg Ser Gln Asp Leu Asp Ala Ile Trp Arg Gly Phe Tyr Ile
                485                 490                 495

Ala Gly Asp Pro Ala Leu Ala Tyr Gly Tyr Ala Gln Asp Gln Glu Pro
            500                 505                 510

Asp Ala Arg Gly Arg Ile Arg Asn Gly Ala Leu Leu Arg Val Tyr Val
        515                 520                 525

Pro Arg Ser Ser Leu Pro Gly Phe Tyr Arg Thr Ser Leu Thr Leu Ala
    530                 535                 540

Ala Pro Glu Ala Ala Gly Glu Val Glu Arg Leu Ile Gly His Pro Leu
545                 550                 555                 560

Pro Leu Arg Leu Asp Ala Ile Thr Gly Pro Glu Glu Gly Gly Arg
            565                 570                 575

Leu Glu Thr Ile Leu Gly Trp Pro Leu Ala Glu Arg Thr Val Val Ile
                580                 585                 590
```

Pro Ser Ala Ile Pro Thr Asp Pro Arg Asn Val Gly Asp Leu Asp
            595                 600                 605

Pro Ser Ser Ile Pro Asp Lys Glu Gln Ala Ile Ser Ala Leu Pro Asp
    610                 615                 620

Tyr Ala Ser Gln Pro Gly Lys Pro Arg Glu Asp Leu Lys
625                 630                 635

<210> SEQ ID NO 33
<211> LENGTH: 171
<212> TYPE: PRT
<213> ORGANISM: Pseudomonas aeruginosa

<400> SEQUENCE: 33

Arg Leu His Phe Pro Glu Gly Gly Ser Leu Ala Ala Leu Thr Ala His
1               5                   10                  15

Gln Ala Cys His Leu Pro Leu Glu Thr Phe Thr Arg His Arg Gln Pro
            20                  25                  30

Arg Gly Trp Glu Gln Leu Glu Gln Cys Gly Tyr Pro Val Gln Arg Leu
        35                  40                  45

Val Ala Leu Tyr Leu Ala Ala Arg Leu Ser Trp Asn Gln Val Asp Gln
    50                  55                  60

Val Ile Arg Asn Ala Leu Ala Ser Pro Gly Ser Gly Gly Asp Leu Gly
65                  70                  75                  80

Glu Ala Ile Arg Glu Gln Pro Glu Gln Ala Arg Leu Ala Leu Thr Leu
                85                  90                  95

Ala Ala Ala Glu Ser Glu Arg Phe Val Arg Gln Gly Thr Gly Asn Asp
            100                 105                 110

Glu Ala Gly Ala Ala Asn Ala Asp Val Val Ser Leu Thr Cys Pro Val
        115                 120                 125

Ala Ala Gly Glu Cys Ala Gly Pro Ala Asp Ser Gly Asp Ala Leu Leu
    130                 135                 140

Glu Arg Asn Tyr Pro Thr Gly Ala Glu Phe Leu Gly Asp Gly Gly Asp
145                 150                 155                 160

Val Ser Phe Ser Thr Arg Gly Thr Gln Asn Trp
                165                 170

<210> SEQ ID NO 34
<211> LENGTH: 870
<212> TYPE: DNA
<213> ORGANISM: Artificial sequence
<220> FEATURE:
<223> OTHER INFORMATION: synthetic sequence
<220> FEATURE:
<221> NAME/KEY: CDS
<222> LOCATION: (1)..(870)

<400> SEQUENCE: 34 atg cgc ctg cac ttt ccc gag ggc ggc agc ctg gcc gcg ctg acc gcg         48
Met Arg Leu His Phe Pro Glu Gly Gly Ser Leu Ala Ala Leu Thr Ala
1               5                   10                  15 cac cag gct tgc cac ctg ccg ctg gag act ttc acc cgt cat cgc cag         96
His Gln Ala Cys His Leu Pro Leu Glu Thr Phe Thr Arg His Arg Gln
            20                  25                  30 ccg cgc ggc tgg gaa caa ctg gag cag tgc ggc tat ccg gtg cag cgg        144
Pro Arg Gly Trp Glu Gln Leu Glu Gln Cys Gly Tyr Pro Val Gln Arg
        35                  40                  45 ctg gtc gcc ctc tac ctg gcg gcg cgg ctg tcg tgg aac cag gtc gac        192
Leu Val Ala Leu Tyr Leu Ala Ala Arg Leu Ser Trp Asn Gln Val Asp
    50                  55                  60

```
cag gtg atc cgc aac gcc ctg gcc agc ccc ggc agc ggc ggc gac ctg      240
Gln Val Ile Arg Asn Ala Leu Ala Ser Pro Gly Ser Gly Gly Asp Leu
 65              70                  75                  80 ggc gaa gcg atc cgc gag cag ccg gag cag gcc cgt ctg gcc ctg acc      288
Gly Glu Ala Ile Arg Glu Gln Pro Glu Gln Ala Arg Leu Ala Leu Thr
                 85                  90                  95 ctg gcc gcc gcc gag agc gag cgc ttc gtc cgg cag ggc acc ggc aac      336
Leu Ala Ala Ala Glu Ser Glu Arg Phe Val Arg Gln Gly Thr Gly Asn
            100                 105                 110 gac gag gcc ggc gcg gcc aac gcc gac gtg gtg agc ctg acc tgc ccg      384
Asp Glu Ala Gly Ala Ala Asn Ala Asp Val Val Ser Leu Thr Cys Pro
        115                 120                 125 gtc gcc gcc ggt gaa tgc gcg ggc ccg gcg gac agc ggc gac gcc ctg      432
Val Ala Ala Gly Glu Cys Ala Gly Pro Ala Asp Ser Gly Asp Ala Leu
    130                 135                 140 ctg gag cgc aac tat ccc act ggc gcg gag ttc ctc ggc gac ggc ggc      480
Leu Glu Arg Asn Tyr Pro Thr Gly Ala Glu Phe Leu Gly Asp Gly Gly
145                 150                 155                 160 gac gtc agc ttc agc acc cgc ggc acg cag aac gaa ttc atg cat gga      528
Asp Val Ser Phe Ser Thr Arg Gly Thr Gln Asn Glu Phe Met His Gly
                165                 170                 175 gat aca cct aca ttg cat gaa tat atg tta gat ttg caa cca gag aca      576
Asp Thr Pro Thr Leu His Glu Tyr Met Leu Asp Leu Gln Pro Glu Thr
            180                 185                 190 act gat ctc tac tgt tat gag caa tta aat gac agc tca gag gag gag      624
Thr Asp Leu Tyr Cys Tyr Glu Gln Leu Asn Asp Ser Ser Glu Glu Glu
        195                 200                 205 gat gaa ata gat ggt cca gct gga caa gca gaa ccg gac aga gcc cat      672
Asp Glu Ile Asp Gly Pro Ala Gly Gln Ala Glu Pro Asp Arg Ala His
    210                 215                 220 tac aat att gta acc ttt tgt tgc aag tgt gac tct acg ctt cgg ttg      720
Tyr Asn Ile Val Thr Phe Cys Cys Lys Cys Asp Ser Thr Leu Arg Leu
225                 230                 235                 240 tgc gta caa agc aca cac gta gac att cgt act ttg gaa gac ctg tta      768
Cys Val Gln Ser Thr His Val Asp Ile Arg Thr Leu Glu Asp Leu Leu
                245                 250                 255 atg ggc aca cta gga att gtg tgc ccc atc tgt tct caa gga tcc gag      816
Met Gly Thr Leu Gly Ile Val Cys Pro Ile Cys Ser Gln Gly Ser Glu
            260                 265                 270 ctc ggt acc aag ctt aag ttt aaa ccg ctg atc agc ctc gac tgt gcc      864
Leu Gly Thr Lys Leu Lys Phe Lys Pro Leu Ile Ser Leu Asp Cys Ala
        275                 280                 285 ttc tag                                                              870
Phe

<210> SEQ ID NO 35
<211> LENGTH: 289
<212> TYPE: PRT
<213> ORGANISM: Artificial sequence
<220> FEATURE:
<223> OTHER INFORMATION: Synthetic Construct

<400> SEQUENCE: 35

Met Arg Leu His Phe Pro Glu Gly Gly Ser Leu Ala Ala Leu Thr Ala
 1               5                  10                  15

His Gln Ala Cys His Leu Pro Leu Glu Thr Phe Thr Arg His Arg Gln
                 20                  25                  30

Pro Arg Gly Trp Glu Gln Leu Glu Gln Cys Gly Tyr Pro Val Gln Arg
             35                  40                  45

Leu Val Ala Leu Tyr Leu Ala Ala Arg Leu Ser Trp Asn Gln Val Asp
```

```
                50                  55                  60
Gln Val Ile Arg Asn Ala Leu Ala Ser Pro Gly Ser Gly Gly Asp Leu
 65                  70                  75                  80

Gly Glu Ala Ile Arg Glu Gln Pro Glu Gln Ala Arg Leu Ala Leu Thr
                 85                  90                  95

Leu Ala Ala Ala Glu Ser Glu Arg Phe Val Arg Gln Gly Thr Gly Asn
                100                 105                 110

Asp Glu Ala Gly Ala Ala Asn Ala Asp Val Val Ser Leu Thr Cys Pro
                115                 120                 125

Val Ala Ala Gly Glu Cys Ala Gly Pro Ala Asp Ser Gly Asp Ala Leu
                130                 135                 140

Leu Glu Arg Asn Tyr Pro Thr Gly Ala Glu Phe Leu Gly Asp Gly Gly
145                 150                 155                 160

Asp Val Ser Phe Ser Thr Arg Gly Thr Gln Asn Glu Phe Met His Gly
                165                 170                 175

Asp Thr Pro Thr Leu His Glu Tyr Met Leu Asp Leu Gln Pro Glu Thr
                180                 185                 190

Thr Asp Leu Tyr Cys Tyr Glu Gln Leu Asn Asp Ser Ser Glu Glu Glu
                195                 200                 205

Asp Glu Ile Asp Gly Pro Ala Gly Gln Ala Glu Pro Asp Arg Ala His
                210                 215                 220

Tyr Asn Ile Val Thr Phe Cys Cys Lys Cys Asp Ser Thr Leu Arg Leu
225                 230                 235                 240

Cys Val Gln Ser Thr His Val Asp Ile Arg Thr Leu Glu Asp Leu Leu
                245                 250                 255

Met Gly Thr Leu Gly Ile Val Cys Pro Ile Cys Ser Gln Gly Ser Glu
                260                 265                 270

Leu Gly Thr Lys Leu Lys Phe Lys Pro Leu Ile Ser Leu Asp Cys Ala
                275                 280                 285

Phe

<210> SEQ ID NO 36
<211> LENGTH: 7648
<212> TYPE: DNA
<213> ORGANISM: Artificial sequence
<220> FEATURE:
<223> OTHER INFORMATION: synthetic sequence

<400> SEQUENCE: 36
gacggatcgg gagatctccc gatccctat ggtcgactct cagtacaatc tgctctgatg    60
ccgcatagtt aagccagtat ctgctccctg cttgtgtgtt ggaggtcgct gagtagtgcg   120
cgagcaaaat ttaagctaca acaaggcaag gcttgaccga caattgcatg aagaatctgc   180
ttagggttag gcgttttgcg ctgcttcgcg atgtacgggc cagatatacg cgttgacatt   240
gattattgac tagttattaa tagtaatcaa ttacggggtc attagttcat agcccatata   300
tggagttccg cgttacataa cttacggtaa atggcccgcc tggctgaccg cccaacgacc   360
cccgcccatt gacgtcaata atgacgtatg ttcccatagt aacgccaata gggactttcc   420
attgacgtca atgggtggac tatttacggt aaactgccca cttggcagta catcaagtgt   480
atcatatgcc aagtacgccc cctattgacg tcaatgacgg taaatggccc gcctggcatt   540
atgcccagta catgacctta tgggactttc ctacttggca gtacatctac gtattagtca   600
tcgctattac catggtgatg cggttttggc agtacatcaa tgggcgtgga tagcggtttg   660
actcacgggg atttccaagt ctccacccca ttgacgtcaa tgggagtttg ttttggcacc   720
```

-continued

```
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaacgg gccctctaga ctcgagcggc cgccactgtg ctggatatct gcagaattcc    960
accacactgg actagtggat ccatgcatgg agatacacct acattgcatg aatatatgtt   1020
agatttgcaa ccagagacaa ctgatctcta ctgttatgag caattaaatg acagctcaga   1080
ggaggaggat gaaatagatg gtccagctgg acaagcagaa ccggacagag cccattacaa   1140
tattgtaacc ttttgttgca agtgtgactc tacgcttcgg ttgtgcgtac aaagcacaca   1200
cgtagacatt cgtactttgg aagacctgtt aatgggcaca ctaggaattg tgtgcccat    1260 ctgttctcaa ggatccatgg ctcgtgcggt cgggatcgac ctcgggacca ccaactccgt   1320
cgtctcggtt ctggaaggtg gcgacccggt cgtcgtcgcc aactccgagg ctccaggac    1380 caccccgtca attgtcgcgt tcgcccgcaa cggtgaggtg ctggtcggcc agcccgccaa   1440
gaaccaggca gtgaccaacg tcgatcgcac cgtgcgctcg gtcaagcgac acatgggcag   1500
cgactggtcc atagagattg acggcaagaa atacaccgcg ccggagatca cgcccgcat    1560 tctgatgaag ctgaagcgcg acgccgaggc ctacctcggt gaggacatta ccgacgcggt   1620
tatcacgacg cccgcctact tcaatgacgc ccagcgtcag gccaccaagg acgccggcca   1680
gatcgccggc ctcaacgtgc tgcggatcgt caacgagccg accgcggccg cgctggccta   1740
cggcctcgac aagggcgaga aggagcagcg aatcctggtc ttcgacttgg gtggtggcac   1800
tttcgacgtt tccctgctgg agatcggcga gggtgtggtt gaggtccgtg ccacttcggg   1860
tgacaaccac ctcggcggcg acgactggga ccagcgggtc gtcgattggc tggtggacaa   1920
gttcaagggc accagcggca tcgatctgac caaggacaag atggcgatgc agcggctgcg   1980
ggaagccgcc gagaaggcaa agatcgagct gagttcgagt cagtccaccct cgatcaacct   2040 gccctacatc accgtcgacg ccgacaagaa cccgttgttc ttagacgagc agctgacccg   2100
cgcggagttc caacggatca ctcaggacct gctggaccgc actcgcaagc cgttccagtc   2160
ggtgatcgct gacaccggca tttcggtgtc ggagatcgat cacgttgtgc tcgtgggtgg   2220 ttcgaccccgg atgcccgcgg tgaccgatct ggtcaaggaa ctcaccggcg gcaaggaacc   2280
caacaagggc gtcaaccccg atgaggttgt cgcggtggga gccgctctgc aggccggcgt   2340
cctcaagggc gaggtgaaag acgttctgct gcttgatgtt accccgctga gcctgggtat   2400
cgagaccaag ggcggggtga tgaccaggct catcgagcgc aacaccacga tccccaccaa   2460
gcggtcggag actttcacca ccgccgacga caaccaaccg tcggtgcaga tccaggtcta   2520 tcaggggag cgtgagatcg ccgcgcacaa caagttgctc gggtccttcg agctgaccgg   2580
catcccgccg gcgccgcggg ggattccgca gatcgaggtc actttcgaca tcgacgccaa   2640
cggcattgtg cacgtcaccg ccaaggacaa gggcaccggc aaggagaaca cgatccgaat   2700
ccaggaaggc tcgggcctgt ccaaggaaga cattgaccgc atgatcaagg acgccgaagc   2760
gcacgccgag gaggatcgca agcgtcgcga ggaggccgat gttcgtaatc aagccgagac   2820
attggtctac cagacggaga agttcgtcaa agaaacgcgt gaggccgagg gtggttcgaa   2880
gttcgtaatc aagccgagac attggtctac cagacggaga agttcgtcaa agaacagcgt   2940
gaggccgagg gtggttcgaa ggtacctgaa gacacgctga acaaggttga tgccgcggtg   3000
gcggaagcga aggcggcact tggcggatcg gatatttcgg ccatcaagtc ggcgatggag   3060
```

```
aagctgggcc aggagtcgca ggctctgggg caagcgatct acgaagcagc tcaggctgcg    3120
tcacaggcca ctggcgctgc ccaccccggc tcggctgatg aaagcttaag tttaaaccgc    3180
tgatcagcct cgactgtgcc ttctagttgc cagccatctg ttgtttgccc ctccccgtg    3240 ccttccttga ccctggaagg tgccactccc actgtccttt cctaataaaa tgaggaaatt    3300
gcatcgcatt gtctgagtag gtgtcattct attctggggg gtggggtggg gcaggacagc    3360 aaggggagg attgggaaga caatagcagg catgctgggg atgcggtggg ctctatggct     3420
tctgaggcgg aaagaaccag ctggggctct aggggtatc cccacgcgcc ctgtagcggc     3480
gcattaagcg cggcgggtgt ggtggttacg cgcagcgtga ccgctacact tgccagcgcc    3540
ctagcgcccg ctcctttcgc tttcttccct tcctttctcg ccacgttcgc cggctttccc    3600
cgtcaagctc taaatcgggg catcccttta gggttccgat ttagtgcttt acggcacctc    3660
gaccccaaaa aacttgatta gggtgatggt tcacgtagtg gccatcgcc ctgatagacg     3720 gttttcgcc ctttgacgtt ggagtccacg ttctttaata gtggactctt gttccaaact    3780
ggaacaacac tcaaccctat ctcggtctat tcttttgatt tataagggat tttggggatt    3840
tcggcctatt ggttaaaaaa tgagctgatt taacaaaaat ttaacgcgaa ttaattctgt    3900
ggaatgtgtg tcagttaggg tgtggaaagt ccccaggctc cccaggcagg cagaagtatg    3960
caaagcatgc atctcaatta gtcagcaacc aggtgtggaa agtccccagg ctccccagca    4020
ggcagaagta tgcaaagcat gcatctcaat tagtcagcaa ccatagtccc gcccctaact    4080
ccgcccatcc cgcccctaac tccgcccagt tccgcccatt ctccgcccca tggctgacta    4140 attttttta tttatgcaga ggccgaggcc gcctctgcct ctgagctatt ccagaagtag    4200
tgaggaggct ttttggagg cctaggcttt tgcaaaaagc tcccgggagc ttgtatatcc     4260
attttcggat ctgatcaaga gacaggatga ggatcgtttc gcatgattga acaagatgga    4320
ttgcacgcag gttctccggc cgcttgggtg gagaggctat tcggctatga ctgggcacaa    4380
cagacaatcg gctgctctga tgccgccgtg ttccggctgt cagcgcaggg gcgcccggtt    4440 cttttgtca agaccgacct gtccggtgcc ctgaatgaac tgcaggacga ggcagcgcgg    4500
ctatcgtggc tggccacgac gggcgttcct tgcgcagctg tgctcgacgt tgtcactgaa    4560
tgcaggacga ggcagcgcgg ctatcgtggc tggccacgac gggcgttcct tgcgcagctg    4620
tgctcgacgt tgtcactgaa gcgggaaggg actggctgct attgggcgaa gtgccggggc    4680
aggatctcct gtcatctcac cttgctcctg ccgagaaagt atccatcatg gctgatgcaa    4740
tgcggcggct gcatacgctt gatccggcta cctgcccatt cgaccaccaa gcgaaacatc    4800
gcatcgagcg agcacgtact cggatggaag ccggtcttgt cgatcaggat gatctggacg    4860
aagagcatca ggggctcgcg ccagccgaac tgttcgccag gctcaaggcg cgcatgcccg    4920
acggcgagga tctcgtcgtg acccatggcg atgcctgctt gccgaatatc atggtggaaa    4980
atggccgctt ttctggattc atcgactgtg gccggctggg tgtggcggac cgctatcagg    5040
acatagcgtt ggctacccgt gatattgctg aagagcttgg cggcgaatgg gctgaccgct    5100
tcctcgtgct ttacggtatc gccgctcccg attcgcagcg catcgccttc tatcgccttc    5160
ttgacgagtt cttctgagcg ggactctggg gttcgaaatg accgaccaag cgacgcccaa    5220
cctgccatca cgagatttcg attccaccgc cgccttctat gaaaggttgg gcttcggaat    5280
cgttttccgg gacgccggct ggatgatcct ccagcgcggg gatctcatgc tggagttctt    5340
cgcccacccc aacttgttta ttgcagctta taatggttac aaataaagca atagcatcac    5400
aaatttcaca aataaagcat ttttttcact gcattctagt tgtggtttgt ccaaactcat    5460
```

-continued

```
caatgtatct tatcatgtct gtataccgtc gacctctagc tagagcttgg cgtaatcatg    5520
gtcatagctg tttcctgtgt gaaattgtta tccgctcaca attccacaca acatacgagc    5580
cggaagcata agtgtaaag cctggggtgc ctaatgagtg agctaactca cattaattgc     5640
gttgcgctca ctgcccgctt tccagtcggg aaacctgtcg tgccagctgc attaatgaat    5700
cggccaacgc gcggggagag gcggtttgcg tattgggcgc tcttccgctt cctcgctcac    5760
tgactcgctg cgctcggtcg ttcggctgcg gcgagcggta tcagctcact caaaggcggt    5820
aatacggtta tccacagaat caggggataa cgcaggaaag aacatgtgag caaaaggcca    5880
gcaaaaggcc aggaaccgta aaaaggccgc gttgctggcg catcacaaaa atcgacgctc    5940
aagtcagagg tggcgaaacc cgacaggact ataaagatac caggcgtttc ccctggaag     6000 ctccctcgtg cgctctcctg ttccgaccct gccgcttacc ggatacctgt ccgcctttct    6060
cccttcggga agcgtggcgc tttctcaatg ctcacgctgt aggtatctca gttcggtgta    6120
ggtcgttcgc tccaagctgg gctgtgtgca cgaaccccc gttcagcccg accgctgcgc     6180
cttatccggt aactatcgtc ttgagtccaa cccggtaaga cacgacttat cgccactggc    6240
agcagccact ggtaacagga ttagcagagc gaggtatgta ggcggtgcta cagagttctt    6300
gaagtggtgg cctaactacg gctacactag aaggacagta tttggtatct gcgctctgct    6360
gaagccagtt accttcggaa aaagagttgg tagctcttga tccggcaaac aaaccaccgc    6420
tggtagcggt ggtttttttg tttgcaagca gcagattacg cgcagaaaaa aaggatctca    6480
agaagatcct ttgatctttt ctacggggtc tgacgctcag tggaacgaaa actcacgtta    6540
agggattttg gtcatgagat tatcaaaaag gatcttcacc tagatccttt taaattaaaa    6600
atgaagtttt aaatcaatct aaagtatata tgagtaaact tggtctgaca gttaccaatg    6660
cttaatcagt gaggcaccta tctcagcgat ctgtctattt cgttcatcca tagttgcctg    6720
actccccgtc gtgtagataa ctacgatacg ggagggctta ccatctggcc ccagtgctgc    6780
aatgataccg cgagacccac gctcaccggc tccagattta tcagcaataa accagccagc    6840
cggaagggcc gagcgcagaa gtggtcctgc aactttatcc gcctccatcc agtctattaa    6900
ttgttgccgg gaagctagag taagtagttc gccagttaat agtttgcgca acgttgttgc    6960
cattgctaca ggcatcgtgg tgtcacgctc gtcgtttggt atggcttcat tcagctccgg    7020
ttcccaacga tcaaggcgag ttacatgatc ccccatgttg tgcaaaaaag cggttagctc    7080
cttcggtcct ccgatcgttg tcagaagtaa gttggccgca gtgttatcac tcatggttat    7140
ggcagcactg cataattctc ttactgtcat gccatccgta agatgctttt ctgtgactgg    7200
tgagtactca accaagtcat tctgagaata gtgtatgcgg cgaccgagtt gctcttgccc    7260
ggcgtcaata cgggataata ccgcgccaca tagcagaact ttaaaagtgc tcatcattgg    7320
aaaacgttct cggggcgaaa actctcaag gatcttaccg ctgttgagat ccagttcgat     7380
gtaacccact cgtgcaccca actgatcttc agcatctttt actttcacca gcgtttctgg    7440
gtgagcaaaa acaggaaggc aaaatgccgc aaaaaaggga ataagggcga cacggaaatg    7500
ttgaatactc atactcttcc tttttcaata ttattgaagc atttatcagg gttattgtct    7560
catgagcgga tacatatttg aatgtattta gaaaaataaa caaatagggg ttccgcgcac    7620
atttccccga aaagtgccac ctgacgtc                                       7648
```

<210> SEQ ID NO 37
<211> LENGTH: 6221
<212> TYPE: DNA

<213> ORGANISM: Artificial sequence
<220> FEATURE:
<223> OTHER INFORMATION: synthetic sequence

<400> SEQUENCE: 37

| | | | | | |
|---|---|---|---|---|---|
| gacggatcgg | gagatctccc | gatccctat | ggtcgactct | cagtacaatc | tgctctgatg | 60 |
| ccgcatagtt | aagccagtat | ctgctccctg | cttgtgtgtt | ggaggtcgct | gagtagtgcg | 120 |
| cgagcaaaat | ttaagctaca | acaaggcaag | gcttgaccga | caattgcatg | aagaatctgc | 180 |
| ttagggttag | gcgttttgcg | ctgcttcgcg | atgtacgggc | cagatatacg | cgttgacatt | 240 |
| gattattgac | tagttattaa | tagtaatcaa | ttacggggtc | attagttcat | agcccatata | 300 |
| tggagttccg | cgttacataa | cttacggtaa | atggcccgcc | tggctgaccg | cccaacgacc | 360 |
| cccgcccatt | gacgtcaata | atgacgtatg | ttcccatagt | aacgccaata | gggactttcc | 420 |
| attgacgtca | atgggtggac | tatttacggt | aaactgccca | cttggcagta | catcaagtgt | 480 |
| atcatatgcc | aagtacgccc | cctattgacg | tcaatgacgg | taaatggccc | gcctggcatt | 540 |
| atgcccagta | catgacctta | tgggactttc | ctacttggca | gtacatctac | gtattagtca | 600 |
| tcgctattac | catggtgatg | cggttttggc | agtacatcaa | tgggcgtgga | tagcggtttg | 660 |
| actcacgggg | atttccaagt | ctccacccca | ttgacgtcaa | tgggagtttg | ttttggcacc | 720 |
| aaaatcaacg | ggactttcca | aaatgtcgta | acaactccgc | cccattgacg | caaatgggcg | 780 |
| gtaggcgtgt | acggtgggag | gtctatataa | gcagagctct | ctggctaact | agagaaccca | 840 |
| ctgcttactg | gcttatcgaa | attaatacga | ctcactatag | ggagacccaa | gctggctagc | 900 |
| gtttaaacgg | gccctctaga | ctcgagcggc | cgccactgtg | ctggatatct | gcagaattca | 960 |
| tgcgcctgca | ctttcccgag | ggcggcagcc | tggccgcgct | gaccgcgcac | caggcttgcc | 1020 |
| acctgccgct | ggagactttc | acccgtcatc | gccagccgcg | cggctgggaa | caactggagc | 1080 |
| agtgcggcta | tccggtgcag | cggctggtcg | ccctctacct | ggcggcgcgg | ctgtcgtgga | 1140 |
| accaggtcga | ccaggtgatc | cgcaacgccc | tggccagccc | cggcagcggc | ggcgacctgg | 1200 |
| gcgaagcgat | ccgcgagcag | ccggagcagg | cccgtctggc | cctgaccctg | ccgccgccg | 1260 |
| agagcgagcg | cttcgtccgg | cagggcaccg | gcaacgacga | ggccggcgcg | gccaacgccg | 1320 |
| acgtggtgag | cctgacctgc | ccggtcgccg | ccggtgaatg | cgcgggcccg | gcggacagcg | 1380 |
| gcgacgccct | gctggagcgc | aactatccca | ctggcgcgga | gttcctcggc | gacgcggcg | 1440 |
| acgtcagctt | cagcacccgc | ggcacgcaga | acgaattcat | gcatggagat | acacctacat | 1500 |
| tgcatgaata | tatgttagat | ttgcaaccag | agacaactga | tctctactgt | tatgagcaat | 1560 |
| taaatgacag | ctcagaggag | gaggatgaaa | tagatggtcc | agctggacaa | gcagaaccgg | 1620 |
| acagagccca | ttacaatatt | gtaaccttt | gttgcaagtg | tgactctacg | cttcggttgt | 1680 |
| gcgtacaaag | cacacacgta | gacattcgta | ctttggaaga | cctgttaatg | ggcacactag | 1740 |
| gaattgtgtg | ccccatctgt | tctcaaggat | ccgagctcgg | taccaagctt | aagtttaaac | 1800 |
| cgctgatcag | cctcgactgt | gccttctagt | tgccagccat | ctgttgtttg | cccctccccc | 1860 |
| gtgccttcct | tgaccctgga | aggtgccact | cccactgtcc | tttcctaata | aaatgaggaa | 1920 |
| attgcatcgc | attgtctgag | taggtgtcat | tctattctgg | ggggtggggt | ggggcaggac | 1980 |
| agcaagggg | aggattggga | agacaatagc | aggcatgctg | gggatgcggt | gggctctatg | 2040 |
| gcttctgagg | cggaaagaac | cagctggggc | tctaggggt | atccccacgc | gccctgtagc | 2100 |
| ggcgcattaa | gcgcggcggg | tgtggtggtt | acgcgcagcg | tgaccgctac | acttgccagc | 2160 |
| gccctagcgc | ccgctccttt | cgctttcttc | ccttcctttc | tcgccacgtt | cgccggcttt | 2220 |

```
cccgtcaag ctctaaatcg gggcatccct ttagggttcc gatttagtgc tttacggcac   2280
ctcgacccca aaaaacttga ttagggtgat ggttcacgta gtgggccatc gccctgatag   2340
acggttttc gcccttgac gttggagtcc acgttcttta atagtggact cttgttccaa    2400
actggaacaa cactcaaccc tatctcggtc tattctttg atttataagg gattttggg    2460
atttcggcct attggttaaa aaatgagctg atttaacaaa aatttaacgc gaattaattc   2520
tgtggaatgt gtgtcagtta gggtgtggaa agtcccagg ctccccaggc aggcagaagt    2580
atgcaaagca tgcatctcaa ttagtcagca accaggtgtg aaagtcccc aggctcccca    2640
gcaggcagaa gtatgcaaag catgcatctc aattagtcag caaccatagt cccgccccta   2700
actccgccca tcccgcccct aactccgccc agttccgccc attctccgcc ccatggctga   2760
ctaattttt ttatttatgc agaggccgag gccgcctctg cctctgagct attccagaag   2820
tagtgaggag cttttttgg aggcctaggc ttttgcaaaa agctcccggg agcttgtata   2880
tccattttcg gatctgatca agagacagga tgaggatcgt ttcgcatgat tgaacaagat   2940
ggattgcacg caggttctcc ggccgcttgg gtggagaggc tattcggcta tgactgggca   3000
caacagacaa tcggctgctc tgatgccgcc gtgttccggc tgtcagcgca ggggcgcccg   3060
gttcttttg tcaagaccga cctgtccggt gccctgaatg aactgcagga cgaggcagcg   3120
cggctatcgt ggctggccac gacgggcgtt ccttgcgcag ctgtgctcga cgttgtcact   3180
gaagcgggaa gggactggct gctattgggc gaagtgccgg ggcaggatct cctgtcatct   3240
caccttgctc ctgccgagaa agtatccatc atggctgatg caatgcggcg gctgcatacg   3300
cttgatccgg ctacctgccc attcgaccac caagcgaaac atcgcatcga gcgagcacgt   3360
actcggatgg aagccggtct gtcgatcag gatgatctgg acgaagagca tcagggctc    3420
gcgccagccg aactgttcgc caggctcaag gcgcgcatgc ccgacggcga ggatctcgtc   3480
gtgacccatg gcgatgcctg cttgccgaat atcatggtgg aaaatggccg cttttctgga   3540
ttcatcgact gtggccggct gggtgtggcg gaccgctatc aggacatagc gttggctacc   3600
cgtgatattg ctgaagagct tggcggcgaa tgggctgacc gcttcctcgt gctttacggt   3660
atcgccgctc ccgattcgca gcgcatcgcc ttctatcgcc ttcttgacga gttcttctga   3720
gcgggactct ggggttcgaa atgaccgacc aagcgacgcc caacctgcca tcacgagatt   3780
tcgattccac cgccgccttc tatgaaaggt tgggcttcgg aatcgttttc cgggacgccg   3840
gctggatgat cctccagcgc ggggatctca tgctggagtt cttcgcccac cccaacttgt   3900
ttattgcagc ttataatggt tacaaataaa gcaatagcat cacaaatttc acaaataaag   3960
catttttttc actgcattct agttgtggtt tgtccaaact catcaatgta tcttatcatg   4020
tctgtatacc gtcgacctct agctagagct tggcgtaatc atggtcatag ctgtttcctg   4080
tgtgaaattg ttatccgctc acaattccac acaacatacg agccggaagc ataaagtgta   4140
aagcctgggg tgcctaatga gtgagctaac tcacattaat tgcgttgcgc tcactgcccg   4200
ctttccagtc gggaaacctg tcgtgccagc tgcattaatg aatcggccaa cgcgcgggga   4260
gaggcggttt gcgtattggg cgctcttccg cttcctcgct cactgactcg ctgcgctcgg   4320
tcgttcggct gcggcgagcg gtatcagctc actcaaaggc ggtaatacgg ttatccacag   4380
aatcagggga taacgcagga aagaacatgt gagcaaaagg ccagcaaaag gccaggaacc   4440
gtaaaaaggc cgcgttgctg gcgtttttcc ataggctccg cccccctgac gagcatcaca   4500
aaaatcgacg ctcaagtcag aggtggcgaa acccgacagg actataaaga taccaggcgt   4560
```

| | |
|---|---|
| ttcccctgg aagctccctc gtgcgctctc ctgttccgac cctgccgctt accggatacc | 4620 |
| tgtccgcctt tctcccttcg ggaagcgtgg cgctttctca atgctcacgc tgtaggtatc | 4680 |
| tcagttcggt gtaggtcgtt cgctccaagc tgggctgtgt gcacgaaccc cccgttcagc | 4740 |
| ccgaccgctg cgccttatcc ggtaactatc gtcttgagtc caacccggta agacacgact | 4800 |
| tatcgccact ggcagcagcc actggtaaca ggattagcag agcgaggtat gtaggcggtg | 4860 |
| ctacagagtt cttgaagtgg tggcctaact acggctacac tagaaggaca gtatttggta | 4920 |
| tctgcgctct gctgaagcca gttaccttcg gaaaagagt tggtagctct tgatccggca | 4980 |
| aacaaaccac cgctggtagc ggtggttttt tgtttgcaa gcagcagatt acgcgcagaa | 5040 |
| aaaaggatc tcaagaagat cctttgatct tttctacggg gtctgacgct cagtggaacg | 5100 |
| aaaactcacg ttaagggatt ttggtcatga gattatcaaa aaggatcttc acctagatcc | 5160 |
| ttttaaatta aaaatgaagt tttaaatcaa tctaaagtat atatgagtaa acttggtctg | 5220 |
| acagttacca atgcttaatc agtgaggcac ctatctcagc gatctgtcta tttcgttcat | 5280 |
| ccatagttgc ctgactcccc gtcgtgtaga taactacgat acgggagggc ttaccatctg | 5340 |
| gccccagtgc tgcaatgata ccgcgagacc cacgctcacc ggctccagat ttatcagcaa | 5400 |
| taaaccagcc agccggaagg gccgagcgca gaagtggtcc tgcaacttta tccgcctcca | 5460 |
| tccagtctat taattgttgc cgggaagcta gagtaagtag ttcgccagtt aatagtttgc | 5520 |
| gcaacgttgt tgccattgct acaggcatcg tggtgtcacg ctcgtcgttt ggtatggctt | 5580 |
| cattcagctc cggttcccaa cgatcaaggc gagttacatg atcccccatg ttgtgcaaaa | 5640 |
| aagcggttag ctccttcggt cctccgatcg ttgtcagaag taagttggcc gcagtgttat | 5700 |
| cactcatggt tatggcagca ctgcataatt ctcttactgt catgccatcc gtaagatgct | 5760 |
| tttctgtgac tggtgagtac tcaaccaagt cattctgaga atagtgtatg cggcgaccga | 5820 |
| gttgctcttg cccggcgtca atacgggata ataccgcgcc acatagcaga actttaaaag | 5880 |
| tgctcatcat tggaaaacgt tcttcggggc gaaaactctc aaggatctta ccgctgttga | 5940 |
| gatccagttc gatgtaaccc actcgtgcac ccaactgatc ttcagcatct tttactttca | 6000 |
| ccagcgtttc tgggtgagca aaaacaggaa ggcaaaatgc cgcaaaaaag ggaataaggg | 6060 |
| cgacacggaa atgttgaata ctcatactct tcctttttca atattattga gcatttatc | 6120 |
| agggttattg tctcatgagc ggatacatat ttgaatgtat ttagaaaaat aaacaaatag | 6180 |
| gggttccgcg cacatttccc cgaaaagtgc cacctgacgt c | 6221 |

<210> SEQ ID NO 38
<211> LENGTH: 1899
<212> TYPE: DNA
<213> ORGANISM: Homo sapiens

<400> SEQUENCE: 38

| | |
|---|---|
| gtccgtactg cagagccgct gccggagggt cgttttaaag ggccgcgttg ccgcccctc | 60 |
| ggcccgccat gctgctatcc gtgccgctgc tgctcggcct cctcggcctg gccgtcgccg | 120 |
| agcccgccgt ctacttcaag gagcagtttc tggacggaga cgggtggact tcccgctgga | 180 |
| tcgaatccaa acacaagtca gatttttggca aattcgttct cagttccggc aagttctacg | 240 |
| gtgacgagga gaaagataaa ggtttgcaga caagccagga tgcacgcttt tatgctctgt | 300 |
| cggccagttt cgagcctttc agcaacaaag ccagacgct ggtggtgcag ttcacggtga | 360 |
| aacatgagca gaacatcgac tgtggggggcg gctatgtgaa gctgtttcct aatagtttgg | 420 |
| accagacaga catgcacgga gactcagaat acaacatcat gtttggtccc gacatctgtg | 480 |

```
gccctggcac caagaaggtt catgtcatct tcaactacaa gggcaagaac gtgctgatca    540
acaaggacat ccgttgcaag gatgatgagt ttacacacct gtacacactg attgtgcggc    600
cagacaacac ctatgaggtg aagattgaca cagccaggt ggagtccggc tccttggaag     660
acgattggga cttcctgcca cccaagaaga taaaggatcc tgatgcttca aaaccggaag    720
actgggatga gcgggccaag atcgatgatc ccacagactc caagcctgag gactgggaca    780
agcccgagca tatccctgac cctgatgcta agaagcccga ggactgggat gaagagatgg    840
acggagagtg ggaaccccca gtgattcaga accctgagta caagggtgag tggaagcccc    900
ggcagatcga caacccagat tacaagggca cttggatcca cccagaaatt gacaaccccg    960
agtattctcc cgatcccagt atctatgcct atgataactt tggcgtgctg ggcctggacc   1020
tctggcaggt caagtctggc accatctttg caacttcct catcaccaac gatgaggcat    1080
acgctgagga gtttggcaac gagacgtggg gcgtaacaaa ggcagcagag aaacaaatga   1140
aggacaaaca ggacgaggag cagaggctta aggaggagga agaagacaag aaacgcaaag   1200
aggaggagga ggcagaggac aaggaggatg atgaggacaa agatgaggat gaggaggatg   1260
aggaggacaa ggaggaagat gaggaggaag atgtccccgg ccaggccaag gacgagctgt   1320
agagaggcct gcctccaggg ctggactgag gcctgagcgc tcctgccgca gagcttgccg   1380
cgccaaataa tgtctctgtg agactcgaga actttcattt ttttccaggc tggttcggat   1440
ttggggtgga ttttggtttt gttcccctcc tccactctcc cccaccccct cccgcccctt   1500 ttttttttt ttttaaact ggtattttat cctttgattc tccttcagcc ctcacccctg     1560
gttctcatct ttcttgatca acatcttttc ttgcctctgt gccccttctc tcatctctta   1620
gctcccctcc aacctggggg gcagtggtgt ggagaagcca caggcctgag atttcatctg   1680
ctctccttcc tggagcccag aggagggcag cagaaggggg tggtgtctcc aacccccag    1740 cactgaggaa gaacgggggct cttctcattt caccccttccc tttctcccct gccccagga  1800 ctgggccact tctgggtggg gcagtgggtc ccagattggc tcacactgag aatgtaagaa   1860
ctacaaacaa aatttctatt aaattaaatt ttgtgtctc                          1899
```

<210> SEQ ID NO 39
<211> LENGTH: 417
<212> TYPE: PRT
<213> ORGANISM: Homo sapiens

<400> SEQUENCE: 39

```
Met Leu Leu Ser Val Pro Leu Leu Leu Gly Leu Leu Gly Leu Ala Val
1               5                  10                  15

Ala Glu Pro Ala Val Tyr Phe Lys Glu Gln Phe Leu Asp Gly Asp Gly
            20                  25                  30

Trp Thr Ser Arg Trp Ile Glu Ser Lys His Lys Ser Asp Phe Gly Lys
        35                  40                  45

Phe Val Leu Ser Ser Gly Lys Phe Tyr Gly Asp Glu Glu Lys Asp Lys
    50                  55                  60 ly Leu Gln Thr Ser Gln Asp Ala Arg Phe Tyr Ala Leu Ser Ala Ser 65                  70                  75                  80

Phe Glu Pro Phe Ser Asn Lys Gly Gln Thr Leu Val Val Gln Phe Thr
                85                  90                  95

Val Lys His Glu Gln Asn Ile Asp Cys Gly Gly Gly Tyr Val Lys Leu
            100                 105                 110
```

-continued

```
Phe Pro Asn Ser Leu Asp Gln Thr Asp Met His Gly Asp Ser Glu Tyr
            115                 120                 125

Asn Ile Met Phe Gly Pro Asp Ile Cys Gly Pro Gly Thr Lys Lys Val
130                 135                 140

His Val Ile Phe Asn Tyr Lys Gly Lys Asn Val Leu Ile Asn Lys Asp
145                 150                 155                 160

Ile Arg Cys Lys Asp Asp Glu Phe Thr His Leu Tyr Thr Leu Ile Val
                165                 170                 175

Arg Pro Asp Asn Thr Tyr Glu Val Lys Ile Asp Asn Ser Gln Val Glu
            180                 185                 190

Ser Gly Ser Leu Glu Asp Asp Trp Asp Phe Leu Pro Pro Lys Lys Ile
        195                 200                 205

Lys Asp Pro Asp Ala Ser Lys Pro Glu Asp Trp Asp Glu Arg Ala Lys
210                 215                 220

Ile Asp Asp Pro Thr Asp Ser Lys Pro Glu Asp Trp Asp Lys Pro Glu
225                 230                 235                 240

His Ile Pro Asp Pro Asp Ala Lys Lys Pro Glu Asp Trp Asp Glu Glu
                245                 250                 255

Met Asp Gly Glu Trp Glu Pro Pro Val Ile Gln Asn Pro Glu Tyr Lys
            260                 265                 270

Gly Glu Trp Lys Pro Arg Gln Ile Asp Asn Pro Asp Tyr Lys Gly Thr
        275                 280                 285

Trp Ile His Pro Glu Ile Asp Asn Pro Glu Tyr Ser Pro Asp Pro Ser
            290                 295                 300

Ile Tyr Ala Tyr Asp Asn Phe Gly Val Leu Gly Leu Asp Leu Trp Gln
305                 310                 315                 320

Val Lys Ser Gly Thr Ile Phe Asp Asn Phe Leu Ile Thr Asn Asp Glu
                325                 330                 335

Ala Tyr Ala Glu Glu Phe Gly Asn Glu Thr Trp Gly Val Thr Lys Ala
            340                 345                 350

Ala Glu Lys Gln Met Lys Asp Lys Gln Asp Glu Glu Gln Arg Leu Lys
        355                 360                 365

Glu Glu Glu Glu Asp Lys Lys Arg Lys Glu Glu Glu Glu Ala Glu Asp
370                 375                 380

Lys Glu Asp Asp Glu Asp Lys Asp Glu Asp Glu Asp Glu Glu Asp
385                 390                 395                 400

Lys Glu Glu Asp Glu Glu Asp Val Pro Gly Gln Ala Lys Asp Glu
                405                 410                 415

Leu

<210> SEQ ID NO 40
<211> LENGTH: 30
<212> TYPE: DNA
<213> ORGANISM: Artificial sequence
<220> FEATURE:
<223> OTHER INFORMATION: primer

<400> SEQUENCE: 40
ccggtctaga atgctgctcc ctgtgccgct                                      30

<210> SEQ ID NO 41
<211> LENGTH: 30
<212> TYPE: DNA
<213> ORGANISM: Artificial sequence
<220> FEATURE:
<223> OTHER INFORMATION: primer
```

```
<400> SEQUENCE: 41
ccggagatct cagctcgtcc ttggcctggc                                      30

<210> SEQ ID NO 42
<211> LENGTH: 24
<212> TYPE: DNA
<213> ORGANISM: Artificial sequence
<220> FEATURE:
<223> OTHER INFORMATION: primer

<400> SEQUENCE: 42
ggggaattca tggagataca ccta                                            24

<210> SEQ ID NO 43
<211> LENGTH: 23
<212> TYPE: DNA
<213> ORGANISM: Artificial sequence
<220> FEATURE:
<223> OTHER INFORMATION: primer

<400> SEQUENCE: 43
ggtggatcct tgagaacaga tgg                                             23

<210> SEQ ID NO 44
<211> LENGTH: 5970
<212> TYPE: DNA
<213> ORGANISM: Artificial sequence
<220> FEATURE:
<223> OTHER INFORMATION: synthetic sequence

<400> SEQUENCE: 44
gctccgcccc cctgacgagc atcacaaaaa tcgacgctca agtcagaggt ggcgaaaccc      60
gacaggacta taaagatacc aggcgtttcc ccctggaagc tccctcgtgc gctctcctgt     120
tccgaccctg ccgcttaccg gatacctgtc cgcctttctc ccttcgggaa gcgtggcgct     180
ttctcatagc tcacgctgta ggtatctcag ttcggtgtag gtcgttcgct ccaagctggg     240
ctgtgtgcac gaaccccccg ttcagcccga ccgctgcgcc ttatccggta actatcgtct     300
tgagtccaac ccggtaagac acgacttatc gccactggca gcagccactg gtaacaggat     360
tagcagagcg aggtatgtag gcggtgctac agagttcttg aagtggtggc ctaactacgg     420
ctacactaga agaacagtat ttggtatctg cgctctgctg aagccagtta ccttcggaaa     480
aagagttggt agctcttgat ccggcaaaca aaccaccgct ggtagcggtg gtttttttgt     540
ttgcaagcag cagattacgc gcagaaaaaa aggatctcaa gaagatcctt tgatcttttc     600
tacggggtct gacgctcagt ggaacgaaaa ctcacgttaa gggattttgg tcatgagatt     660
atcaaaaagg atcttcacct agatcctttt aaattaaaaa tgaagtttta atcaatcta     720 aagtatatat gagtaaactt ggtctgacag ttaccaatgc ttaatcagtg aggcaccat     780 ctcagcgatc tgtctatttc gttcatccat agttgcctga ctcgggggg ggggcgctg     840 aggtctgcct cgtgaagaag gtgttgctga ctcataccag ggcaacgttg ttgccattgc     900
tacaggcatc gtggtgtcac gctcgtcgtt tggtatggct tcattcagct ccggttccca     960
acgatcaagg cgagttacat gatccccat gttgtgcaaa aaagcggtta gctccttcgg    1020
tcctccgatc gttgtcagaa gtaagttggc cgcagtgtta tcactcatgg ttatggcagc    1080
actgcataat tctcttactg tcatgccatc cgtaagatgc ttttctgtga ctggtgagta    1140
ctcaaccaag tcattctgag aatagtgtat gcggcgaccg agttgctctt gcccggcgtc    1200
aatacgggat aataccgcgc cacatagcag aactttaaaa gtgctcatca ttggaaaacg    1260
```

```
ttcttcgggg cgaaaactct caaggatctt accgctgttg agatccagtt cgatgtaacc    1320
cactcgtgca cctgaatcgc cccatcatcc agccagaaag tgagggagcc acggttgatg    1380
agagctttgt tgtaggtgga ccagttggtg attttgaact tttgctttgc cacggaacgg    1440
tctgcgttgt cggaagatg cgtgatctga tccttcaact cagcaaaagt tcgatttatt    1500
caacaaagcc gccgtcccgt caagtcagcg taatgctctg ccagtgttac aaccaattaa    1560
ccaattctga ttagaaaaac tcatcgagca tcaaatgaaa ctgcaattta ttcatatcag    1620
gattatcaat accatatttt tgaaaagcc gtttctgtaa tgaaggagaa aactcaccga    1680
ggcagttcca taggatggca agatcctggt atcggtctgc gattccgact cgtccaacat    1740
caatacaacc tattaatttc ccctcgtcaa aaataaggtt atcaagtgag aaatcaccat    1800
gagtgacgac tgaatccggt gagaatggca aaagcttatg catttctttc cagacttgtt    1860
caacaggcca gccattacgc tcgtcatcaa aatcactcgc atcaaccaaa ccgttattca    1920
ttcgtgattg cgcctgagcg agacgaaata cgcgatcgct gttaaaagga caattacaaa    1980
caggaatcga atgcaaccgg cgcaggaaca ctgccagcgc atcaacaata ttttcacctg    2040
aatcaggata ttcttctaat acctggaatg ctgttttccc ggggatcgca gtggtgagta    2100
accatgcatc atcaggagta cggataaaat gcttgatggt cggaagaggc ataaattccg    2160
tcagccagtt tagtctgacc atctcatctg taacatcatt ggcaacgcta cctttgccat    2220
gtttcagaaa caactctggc gcatcgggct tcccatacaa tcgatagatt gtcgcacctg    2280
attgcccgac attatcgcga gcccatttat acccatataa atcagcatcc atgttggaat    2340
ttaatcgcgg cctcgagcaa gacgtttccc gttgaatatg gctcataaca ccccttgtat    2400
tactgtttat gtaagcagac agttttattg ttcatgatga tatattttta tcttgtgcaa    2460
tgtaacatca gagattttga gacacaacgt ggctttcccc cccccccat tattgaagca    2520 tttatcaggg ttattgtctc atgagcggat acatatttga atgtatttag aaaaataaac    2580
aaataggggt tccgcgcaca tttccccgaa aagtgccacc tgacgtctaa gaaaccatta    2640
ttatcatgac attaacctat aaaaataggc gtatcacgag gccctttcgt ctcgcgcgtt    2700
tcggtgatga cggtgaaaac ctctgacaca tgcagctccc ggagacggtc acagcttgtc    2760
tgtaagcgga tgccgggagc agacaagccc gtcagggcgc gtcagcgggt gttggcgggt    2820 gtcgggctg gcttaactat gcggcatcag agcagattgt actgagagtg caccatatgc    2880
ggtgtgaaat accgcacaga tgcgtaagga gaaaataccg catcagattg gctattggcc    2940
attgcatacg ttgtatccat atcataatat gtacatttat attggctcat gtccaacatt    3000
accgccatgt tgacattgat tattgactag ttattaatag taatcaatta cggggtcatt    3060
agttcatagc ccatatatgg agttccgcgt tacataactt acggtaaatg gcccgcctgg    3120
ctgaccgccc aacgaccccc gcccattgac gtcaataatg acgtatgttc ccatagtaac    3180 gccaatagg actttccatt gacgtcaatg ggtggagtat ttacggtaaa ctgcccactt    3240
ggcagtacat caagtgtatc atatgccaag tacgcccct attgacgtca tgacggtaa    3300 atggcccgcc tggcattatg cccagtacat gaccttatgg actttcct cttggcagta    3360 catctacgta ttagtcatcg ctattaccat ggtgatgcgg ttttggcagt acatcaatgg    3420
gcgtggatag cggtttgact cacggggatt tccaagtctc caccccattg acgtcaatgg    3480
gagtttgttt tggcaccaaa atcaacggga ctttccaaaa tgtcgtaaca actccgcccc    3540
attgacgcaa atgggcggta ggcgtgtacg gtgggaggtc tatataagca gagctcgttt    3600
```

```
agtgaaccgt cagatcgcct ggagacgcca tccacgctgt tttgacctcc atagaagaca    3660
ccgggaccga tccagcctcc gcggccggga acggtgcatt ggaacgcgga ttccccgtgc    3720
caagagtgac gtaagtaccg cctatagact ctataggcac accccttttgg ctcttatgca   3780
tgctatactg tttttggctt ggggcctata caccccgct tccttatgct ataggtgatg     3840
gtatagctta gcctataggt gtgggttatt gaccattatt gaccactcca acggtggagg    3900
gcagtgtagt ctgagcagta ctcgttgctg ccgcgcgcgc caccagacat aatagctgac    3960
agactaacag actgttcctt tccatgggtc tttttctgcag tcaccgtcgt cgacatgctg   4020
ctatccgtgc cgctgctgct cggcctcctc ggcctggccg tcgccgagcc tgccgtctac    4080
ttcaaggagc agtttctgga cggggacggg tggacttccc gctggatcga atccaaacac    4140
aagtcagatt ttggcaaatt cgttctcagt tccggcaagt tctacggtga cgaggagaaa    4200
gataaaggtt tgcagacaag ccaggatgca cgcttttatg ctctgtcggc cagtttcgag    4260
cctttcagca acaaaggcca gacgctggtg gtgcagttca cggtgaaaca tgagcagaac    4320
atcgactgtg ggggcggcta tgtgaagctg tttcctaata gtttgaccga gacagacatg    4380
cacggagact cagaatacaa catcatgttt ggtcccgaca tctgtggccc tggcaccaag    4440
aaggttcatg tcatcttcaa ctacaagggc aagaacgtgc tgatcaacaa ggacatccgt    4500
tgcaaggatg atgagtttac acacctgtac acactgattg tgcggccaga caacacctat    4560
gaggtgaaga ttgacaacag ccaggtggag tccggctcct ggaagacga tttgggactc    4620
ctgccaccca agaagataaa ggatcctgat gcttcaaaac cggaagactg ggatgagcgg    4680
gccaagatcg atgatcccac agactccaag cctgaggact gggacaagcc cgagcatatc    4740
cctgaccctg atgctaagaa gcccgaggac tgggatgaag agatggacgg agagtgggaa    4800
cccccagtga ttcagaaccc tgagtacaag ggtgagtgga gccccggca gatcgacaac    4860
ccagattaca agggcacttg gatccaccca gaaattgaca accccgagta ttctcccgat    4920
cccagtatct atgcctatga taactttggc gtgctgggcc tggacctctg gcaggtcaag    4980
tctggcacca tctttgacaa cttcctcatc accaacgatg aggcatacgc tgaggagttt    5040
ggcaacgaga cgtggggcgt aacaaaggca gcagagaaac aaatgaagga caaacaggac    5100
gaggagcaga ggcttaagga ggaggaagaa gacaagaaac gcaaagagga ggaggaggca    5160
gaggacaagg aggatgatga ggacaaagat gaggatgagg aggatgagga ggacaaggag    5220
gaagatgagg aggaagatgt ccccggccag gccaaggacg agctggaatt catgcatgga    5280
gatacaccta cattgcatga atatatgtta gatttgcaac cagagacaac tgatctctac    5340
ggttatgggc aattaaatga cagctcagag gaggaggatg aaatagatgg tccagctgga    5400
caagcagaac cggacagagc ccattacaat attgtaacct tttgttgcaa gtgtgactct    5460
acgcttcggt tgtgcgtaca agcacacac gtagacattc gtactttgga agacctgtta    5520
atgggcacac taggaattgt gtgccccatc tgttctcaga accataagg atccagatct    5580
ttttccctct gccaaaaatt atgggacat catgaagccc cttgagcatc tgacttctgg    5640
ctaataaagg aaatttattt tcattgcaat agtgtgttgg aatttttttgt gtctctcact   5700
cggaaggaca tatgggaggg caaatcattt aaaacatcag aatgagtatt tggtttagag    5760
tttggcaaca tatgcccatt cttccgcttc ctcgctcact gactcgctgc gctcggtcgt    5820
tcggctgcgg cgagcggtat cagctcactc aaaggcggta atacggttat ccacagaatc    5880
aggggataac gcaggaaaga acatgtgagc aaaaggccag caaaaggcca ggaaccgtaa    5940
aaaggccgcg ttgctggcgt ttttccatag                                     5970
```

```
<210> SEQ ID NO 45
<211> LENGTH: 21
<212> TYPE: DNA
<213> ORGANISM: Unknown
<220> FEATURE:
<223> OTHER INFORMATION: siNA
<220> FEATURE:
<221> NAME/KEY: misc_feature
<222> LOCATION: (1)..(2)
<223> OTHER INFORMATION: n is a, c, g, t or u

<400> SEQUENCE: 45
nnattgtatg cgatcgcaga c                                             21

<210> SEQ ID NO 46
<211> LENGTH: 9
<212> TYPE: PRT
<213> ORGANISM: Homo sapiens

<400> SEQUENCE: 46

Arg Ala His Tyr Asn Ile Val Thr Phe
1               5

<210> SEQ ID NO 47
<211> LENGTH: 9
<212> TYPE: PRT
<213> ORGANISM: Homo sapiens

<400> SEQUENCE: 47

Ile Tyr Ser Thr Val Ala Ser Ser Leu
1               5

<210> SEQ ID NO 48
<211> LENGTH: 8
<212> TYPE: PRT
<213> ORGANISM: Homo sapiens

<400> SEQUENCE: 48

Ser Ile Ile Asn Phe Glu Lys Leu
1               5

<210> SEQ ID NO 49
<211> LENGTH: 38
<212> TYPE: PRT
<213> ORGANISM: Homo sapiens

<400> SEQUENCE: 49

Asp Ser Ser Glu Glu Glu Asp Glu Ile Asp Gly Pro Ala Gly Gln Ala
1               5                   10                  15

Glu Pro Asp Arg Ala His Tyr Asn Ile Val Thr Phe Cys Cys Lys Cys
            20                  25                  30

Asp Ser Thr Leu Arg Leu
            35
```